United States Patent [19]
Lowder et al.

[11] Patent Number: 6,136,983
[45] Date of Patent: Oct. 24, 2000

[54] PESTICIDAL SULFUR COMPOUNDS

[75] Inventors: Patrick Doyle Lowder, Raleigh; David Treadway Manning, Cary; Jennifer Lantz Phillips, Apex; Michael Thomas Pilato, Cary; Tai-Teh Wu, Chapel Hill, all of N.C.

[73] Assignee: Rhone-Poulenc Agrochimie, Lyons, France

[21] Appl. No.: 08/973,520

[22] PCT Filed: May 31, 1996

[86] PCT No.: PCT/EP96/02363

§ 371 Date: Jun. 16, 1998

§ 102(e) Date: Jun. 16, 1998

[87] PCT Pub. No.: WO96/39389

PCT Pub. Date: Dec. 12, 1996

Related U.S. Application Data

[63] Continuation-in-part of application No. 08/588,839, Jan. 19, 1996, abandoned, which is a continuation of application No. 08/464,372, Jun. 5, 1995, abandoned.

[51] Int. Cl.[7] .......................... A01N 43/56; C07D 231/44
[52] U.S. Cl. .................. 548/367.4; 514/404; 514/407; 546/279; 548/119; 548/323.5; 548/324.5; 548/366.7; 548/368.4; 548/369.1; 548/370.1; 548/541; 548/544
[58] Field of Search ............................. 548/367.4, 369.1; 514/404

[56] References Cited

U.S. PATENT DOCUMENTS

| | | |
|---|---|---|
| 4,614,533 | 9/1986 | Schallner et al. . |
| 4,804,675 | 2/1989 | Jensen-Korte et al. . |
| 4,810,720 | 3/1989 | Jensen-Korte et al. . |
| 4,945,165 | 7/1990 | Jensen-Korte et al. . |
| 5,047,550 | 9/1991 | D'Silva et al. . |
| 5,079,370 | 1/1992 | D'Silva et al. . |
| 5,104,994 | 4/1992 | Roberts et al. . |
| 5,187,185 | 2/1993 | Outcalt et al. . |
| 5,223,525 | 6/1993 | Wu et al. . |
| 5,232,940 | 8/1993 | Hatton et al. . |
| 5,306,694 | 4/1994 | Phillips et al. . |

FOREIGN PATENT DOCUMENTS

| | | |
|---|---|---|
| 0201852 | 11/1986 | European Pat. Off. . |
| 0352944 | 1/1990 | European Pat. Off. . |
| 0403309 | 12/1990 | European Pat. Off. . |
| 0418016 | 3/1991 | European Pat. Off. . |
| 1603122 | 11/1981 | United Kingdom . |
| 93/06089 | 4/1993 | WIPO . |
| 94/21606 | 9/1994 | WIPO . |

OTHER PUBLICATIONS

Hatton et al, *Chemical Abstracts*, vol. 120 (1994), abstract No. 298625p.

*Primary Examiner*—Robert W. Ramsuer
*Attorney, Agent, or Firm*—Burns, Doane, Swecker & Mathis, L.L.P.

[57] ABSTRACT

Pyrazole, pyrrole and imidazole derivatives having formula (I) or (II):

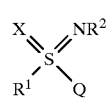

(I)

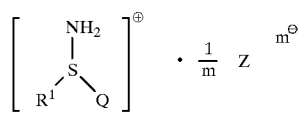

(II)

wherein $=X$ is $=NR^3$, $=O$ or an electron pair and Q comprises certain pyrazole, pyrrole and imidazole structures which, together with the remaining substituents, are defined in the description, are useful for controlling arthropod, nematodes, helminth or protozoan pests.

40 Claims, No Drawings

PESTICIDAL SULFUR COMPOUNDS

This application is the U.S. national stage of International Application No. PCT/EP96/02363, filed May 31, 1996 and designating the United States, which is a continuation-in-part of U.S. patent application Ser. No. 08/588,839, filed Jan. 19, 1996 and now abandoned, which is in turn a continuation of U.S. patent application Ser. No. 08/464,372, filed Jun. 5, 1995 and now abandoned.

The present invention relates to new sulfur compounds, including sulfilimines and sulfoximines intermediates thereto, and processes to prepare the compounds. The invention further pertains to compositions of said compounds and methods, using said compounds, for the control of arthropod, nematode, helminth or protozoan pests. In particular, it pertains to the application of compounds or compositions thereof in agricultural methods of use, particularly as pesticides.

In the instant specification, the word sulfilimine is used to name compounds comprising the group

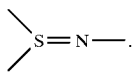

In the instant specification, the word sulfoximine is used to name compounds comprising

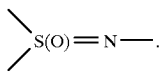

Various pesticidal pyrazoles, pyrroles, and imidazoles have been disclosed: European Patent Publication No 418016; European Patent Publication No 403309; U.S. Pat. No. 5,104,994; European Patent Publication No 352944; U.S. Pat. No. 5,079,370; U.S. Pat. No. 5,047,550; U.S. Pat. No. 5,232,940; U.S. Pat. No. 4,810,720; U.S. Pat. No. 4,804,675; U.S. Pat. No. 5,306,694; U.S. Pat. No. 4,614,533; WPO Publication No. WO 93/06089; and WPO Publication No. WO 94/21606 describe pesticidal (4-pyrazolyl) sulfides, sulfoxides and sulfones. U.S. Pat. No. 5,187,185 describes 4-pyrrolyl sulfides, sulfoxides and sulfones. U.S. Pat. No. 5,223,525 describes pesticidal 4-imidazolyl sulfides, sulfoxides and sulfones.

Due to the many existing pests and crops and conditions of attacks of crops by pests, there is a need for further novel pesticidal compounds.

In one aspect, the present invention provides compounds for use in controlling arthropod, nematode, helminth and protozoan pests, said compounds having the general formula:

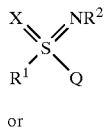

(I)

or

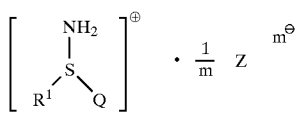

(II)

wherein:

=X is =NR$^3$, =O or an electron pair (it being understood that, in this situation, another way to represent Formula (I) is to delete =X);

R$^1$ is C$_1$–C$_6$ alkyl, C$_3$–C$_6$ cycloalkyl, or C$_4$–C$_8$ (cycloalkyl)alkyl, each of which is optionally substituted by one or more halogen;

R$^2$ and R$^3$ are independently selected from H; C$_1$–C$_6$ alkyl; C$_1$–C$_6$ haloalkyl; COR$^4$; S(O)$_p$R$^4$; CN; NO$_2$; COOR$^4$; CONR$^4$R$^5$; C(O)SR$^4$; C(S)OR$^4$; SO$_2$NR$^4$R$^5$; P(O)$_q$(R$^4$)(R$^5$); P(O)$_q$(OR$^4$)(R$^5$); P(O)$_q$(OR$^4$)(OR$^5$); C=(NR$^4$)NR$^5$R$^6$; CH=NR$^4$; C=(NR$^4$)(OR$^5$); C(S)N(R$^4$)(R$^5$); C(O)C(O)R$^4$; C(O)C(O)OR$^4$; C(O)C(O)NR$^4$R$^5$; and CONR$^4$SO$_2$R$^5$;

m is 1 or 2;

p is 0, 1 or 2;

q is 0 or 1;

R$^4$, R$^5$ and R$^6$ are independently selected from H; NO$_2$; CN; CHO; R$^{14}$; phenyl optionally substituted by one or more of R$^{14}$, halogen, CN, NO$_2$, OR$^{14}$, SR$^{14}$, COR$^{14}$, COOR$^{14}$, or OR$^{14}$; halogen; COR$^{14}$; COOR$^{14}$; CHO; and OH;

Q is Q-1, Q-2 or Q-3, as designated below:

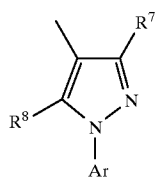

Q-1

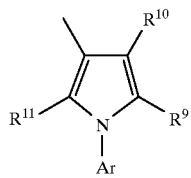

Q-2

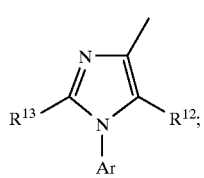

Q-3

R$^7$ is CN, NO$_2$, H, C$_1$–C$_4$ alkyl, C$_1$–C$_4$ haloalkyl, halogen, CHO, or COR$^{20}$, R$^7$;

R$^8$ is H, halogen, CN, S(O)$_p$R$^{14}$, OR$^4$, NR$^{16}$R$^{17}$, N(R$^{16}$)CON(R$^{17}$)(R$^{18}$), N$_3$ or NH(C$_1$–C$_5$ alkyl) substituted by one or more OH, OR$^{14}$, S(O)$_p$R$^{14}$, CN, NO$_2$, COOR$^{14}$ or CON(R$^{16}$)(R$^{17}$);

R$^9$ and R$^{11}$ are independently selected from H, halogen, OR$^{14}$, SR$^{14}$ and R$^{14}$;

$R^{10}$ is CN;

$R^{12}$ is H, halogen, $R^{14}$, $OR^{14}$, $S(O)_p R^{14}$ or

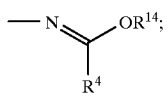

$R^{13}$ is H, halogen or $R^{14}$;

Ar is phenyl, optionally bearing one or more substituents selected from the group consisting of halogen, $R^{15}$, $OR^{15}$, $SF_5$ and $S(O)_p R^{15}$; or Ar is 2-pyridyl, optionally bearing one or more substituents selected from the group consisting of halogen, $R^{15}$, $OR^{15}$, $SF_5$ and $S(O)_p R^{14}$;

$R^{14}$ and $R^{19}$ are independently selected from $C_1$–$C_6$ alkyl, $C_3$–$C_6$ cycloalkyl, and $C_4$–$C_8$ (cycloalkyl)alkyl, each of which is optionally substituted by one or more halogen;

$R^{15}$ is $C_1$–$C_6$ alkyl, optionally substituted by one or more halogen;

$R^{16}$, $R^{17}$ and $R^{18}$ are independently selected from H, $NO_2$, CN, CHO, $R^{19}$, $COR^{19}$, and $COOR^{19}$;

$R^{20}$ is selected from $C_1$–$C_6$ alkyl, optionally substituted by one or more halogen; and Z is an anionic counter ion, such as Cl$^-$, Br$^-$, I$^-$, F$^-$, $OSO_2R^{4-}$, $ClO_4^-$, $OCOR^{4-}$, $BF_4^-$, $SbF_6^-$, $SO_3^-$ or $HSO_4^-$, a phosphate anion or a hydrogenophosphate anion or other agriculturally acceptable anion.

The stereoisomers, e.g. diastereomers and optical isomers, having the Formula (I) or (II) are included in the invention as well.

Preferred compounds of the present invention include one or more of the following features:

(1) $R^1$ is optionally halogenated $C_1$–$C_6$ alkyl, preferably methyl or ethyl; and/or (2) $R^2$ is H, $COOR^4$, $S(O)_p R^4$, $CONR^4 R^5$, CN, $COR^4$, $P(O)_q(OR^4)(OR^5)$ or $P(O)_q(R^4)(R^5)$; more preferably $R^2$ is H; or CN; or $COOR^4$ (in which $R^4$ is $C_1$–$C_6$ alkyl); or $R^2$ is $S(O)_p R^4$ (in which p is two and $R^4$ is $C_1$–$C_6$ alkyl or optionally substituted phenyl); or $R^2$ is $CONR^4 R^5$ (in which $R^4$ is H or $C_1$–$C_6$ alkyl and $R^5$ is $C_1$–$C_6$ alkyl, or in which $R^4$ is H and $R^5$ is $COR^{14}$ in which $R^{14}$ is optionally halogenated $C_1$–$C_6$ alkyl); or $R^2$ is $COR^4$ (in which $R^4$ is H or $C_1$–$C_6$ alkyl); or $R^2$ is $P(O)_q(OR^4)(OR^5)$ or $P(O)_q(R^4)(R^5)$ (in which q is one and $R^4$ and $R^5$ are each $C_1$–$C_6$ alkyl); and/or (3) Q is Q-1, preferably wherein $R^7$ is CN or H, or $C_1$–$C_4$ alkyl and/or when $R^8$ is $N(R^{16})(R^{17})$, most preferably when $R^8$ is $NH_2$; and/or (4) Ar is phenyl substituted in the 2 and 6 positions by halogen and in the 4 position by halogenated $C_1$–$C_6$ alkyl or $SF_5$ or $OR^{15}$, preferably when Ar is 2,6-dichloro-4-trifluoromethylphenyl; or Ar is 2-pyridyl substituted in the 3 position by halogen and in the 5 position by halogenated $C_1$–$C_6$ alkyl or $SF_5$ or $OR^{15}$, preferably when Ar is 3-chloro-5-trifluoromethylpyrid-2-yl.

In another aspect, the present invention provides a pesticidal composition (ie. an arthropodicidal, nematocidal, anti-helminth or anti-protozoal composition) comprising a pesticidally effective amount (i.e. an arthropodicidally effective amount, a nematocidally effective amount, an effective anti-helminth amount or an effective anti-protozoal amount) of a compound of formula (I) or (II) and an agriculturally acceptable inert carrier therefor. The expression "a compound of formula (I) or (II)" used here and throughout this application includes within its ambit the various stereoisomeric forms of the compounds of formulas (I) and (II) and salts thereof.

In yet another aspect, the invention provides a method for controlling arthropod, nematode, helminths or protozoan pests at a locus, said method comprising applying to said locus a pesticidically effective amount (i.e. an arthropodicidally or nematocidally effective amount or an effective anti-helminth or anti-protozoal amount) of a compound of formula (I) or (II) or of a pesticidal composition as defined above.

Compounds of Formula (I) wherein X is O and $R^2$ is not H are prepared from compounds of Formula (I) wherein X is an electron pair and $R^2$ is not H said compounds of Formula (I) also being part of the invention] by oxidation of a sulfur atom into a sulfoximine group according to any method known per se by those skilled in the art. Such transformations can be made by various oxidizing reagents, including, but not limited to, potassium permanganate, sodium periodate and ruthenium tetroxide. This transformation can take place in common solvents such as water, ethers e.g. dioxane, nitriles e.g. acetonitrile, or halohydrocarbons such as dichloromethane, chloroform, carbontetrachloride and the like, at temperatures between about –100° C. and about 100° C., preferably between about 0° C. and about 50° C. Such chemistry can be similar to that found in *Tetrahedron*, 1975, 31, 505.

Compounds of Formula (I) in which X is an electron pair and $R^2$ is other than H can be prepared from compounds of Formula (II) by reaction of an appropriate electrophile $R^2$-L in the presence of a base. $R^2$ has the hereinabove-given meaning except that it is not H, and L is a leaving group. Examples of leaving groups L are halides, acetate, phenyl sulfonates, alkyl sulfonates and phenoxy groups. Examples of bases which can be used in the reaction are sodium hydride, triethylamine and potassium tert-butoxide.

Such reactions can take place in a variety of common solvents, such as, but not limited to, ethers such as tetrahydrofuran or dioxane; water; halohydrocarbons such as dichloromethane or chloroform; nitriles such as acetonitrile; and the like. Such reactions can take place at temperatures between about –100° C. and about 100° C., but preferably between about 0° C. and the boiling temperature of the solvent.

Compounds of Formula (I) in which X is an electron pair and in which $R^2$ is H can be prepared from the corresponding compounds of Formula (I) in which $R^2$ is an ester grouping $COOR^{14}$, by conventional hydrolysis.

Compounds of Formula (II) can be prepared from compounds of Formula (III) by amination according to a reaction known per se to those skilled in the art.

(III)

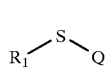

Such chemistry can occur upon mixing a sulfide of Formula (III) with an aminating reagent such as, but not limited to, an O-benzoylhydroxylamine, e.g. O-(2,4,6-trimethylbenzoyl) hydroxylamine or O-(3-chlorobenzoyl)hydroxylamine; an O-sulfonylhydroxylamines such as, but not limited to, hydroxylamine sulfonic acid or O-(2,4,6-triisopropylbenzenesulfonyl)hydroxylamine; or an O-phosphinic hydroxylamine, such as O-(diphenylphosphinyl)hydroxylamine. This can take place in a variety of solvents, including, but not limited to, water, halogenated hydrocarbons such as dichloromethane, chloroform, dichloroethane and the like, and aromatic solvents like benzene, toluene, xylenes and the like, and can take place at a temperature between about −100° C. and about 100° C., 0° C. to the boiling point of the solvent being preferred. Such chemistry may be similar to that found in *Aldrichimica Acta*, 1980, 13(1)3.

Compounds of Formula (I) wherein X is NH and $R^2$ is H can be prepared from compounds of Formula (III) by reaction with chloramine [*Tetrahedron*, 1970, 51, 4449]. Such a reaction can take place in ammonia at a temperature between about −100° C. and −33° C.

Compounds of Formula (I) wherein =X is =NR$^3$ (wherein $R^3$ is as defined above except that it is not hydrogen) and wherein $R^2$ is H, can be derived from compounds of Formula (I) wherein =X is NH and $R^2$ is H, by reaction of an appropriate electrophile $R^3$-L in the presence of a base. $R^3$ is as defined above except that it is not H, and L is a leaving group. Examples of leaving groups L are halides, acetate, phenyl sulfonates, alkyl sulfonates and phenoxy groups. Examples of bases which can be used in the reaction are sodium hydride, triethylamine and potassium tert-butoxide.

Such reactions can take place in a variety of common solvents, such as, but not limited to, ethers such as tetrahydrofuran or dioxane; water; halohydrocarbons such as dichloromethane or chloroform; nitriles such as acetonitrile; and the like. Such reactions can take place at temperatures between about −100° C. and about 100° C., but preferably between about 0° C. and the boiling temperature of the solvent. Similar reactions are found in *Chem. Ber.*, 1984, 117, 2779.

Compounds of Formula (I) wherein =X is =NR$^3$ wherein $R^2$ and $R^3$ are the same and neither is hydrogen can be derived from compounds of Formula (I) wherein $R^2$ is H and X is NH by reaction with at least two equivalents of an appropriate electrophile $R^3$-L in the presence of a base. $R^3$ has the hereinabove-given meaning except that it is not H, and L is a leaving group. Examples of leaving groups L are halides, acetate, phenyl sulfonates, alkyl sulfonates and phenoxy groups. Examples of bases which can be used in the reaction are sodium hydride, triethylamine and potassium tert-butoxide.

Such reactions can take place in a variety of common solvents, such as, but not limited to, ethers such as tetrahydrofuran or dioxane; water; halohydrocarbons such as dichloromethane or chloroform; nitriles such as acetonitrile; and the like. Such reactions can take place at temperatures between about −100° C. and about 100° C., but preferably between about 0° C. and the boiling temperature of the solvent. Similar reactions are found in *Lieb. Ann. Chem.*, 1972,759,107.

Compounds of Formula (III) are known in the art. For example, those wherein Q is Q-1 are described in European Patent Publication No 418016; European Patent Publication No 403309; U.S. Pat. No. 5,104,994; European Patent Publication No 352944; U.S. Pat. No. 5,079,370; U.S. Pat. No. 5,047,550; U.S. Pat. No. 5,232,940; U.S. Pat. No. 4,810,720; U.S. Pat. No. 4,804,675; U.S. Pat. No. 5,306,694; U.S. Pat. No. 4,614,533; WPO Publication No. 93/06089 and WPO Publication No. 94/21606. The compounds of Formula (III) wherein Q is Q-2 are described in U.S. Pat. No. 5,187,185. Compounds of Formula (III) wherein Q is Q-3 are described in U.S. Pat. No. 5,223,525.

In the many transformations hereinabove described, it is apparent that selected substituents may occasionally interfere in the contemplated reactions. Such undesired effects can be avoided by using appropriate protecting groups to prevent the unwanted side reactions. It is also possible to use reagents that do not affect functional groups other than those desired to be changed. The particular choice of the appropriate protecting groups and reagents will be easily understood by those skilled in the art. The use of Chemical Abstracts is considered and suggested as part of the knowledge of the person skilled in the art.

In order to further illustrate the present invention and the advantages thereof, the following specific examples are given, it being understood that these examples are for the purpose of illustration only and in no way limit the scope of the invention.

EXAMPLE 1

2,4,6-Trimethylbenzenesulfonic acid, compound with S4-[5-amino-3-cyano-1-(2,6-dichloro-4-trifluoromethyl)phenyl]pyrazolyl-S-ethylsulfilimine Ethyl O-mesitylene sulfonylacetohydroxamate (10 g, 0.035 mol) was dissolved in dioxane (10 mL) and cooled to 0° C. 70% Perchloric acid (3.3 mL, 0.038 mol) was added and the mixture was stirred for 10 minutes. Water (200 mL) was added and the remaining solid was filtered, washed with water, then dissolved in methylene chloride (50 mL) and separated from the aqueous phase.

5-Amino-3-cyano- 1-(2,6-dichloro-4-trifluoromethyl) phenyl-4-ethylthiopyrazole (10.7 g, 0.028 mol) was dissolved in methylene chloride (50 mL) and the resulting solution was cooled to 0° C. The solution from above was added. After stirring for 1 hr at 0° C. and then at room temperature, methylene chloride was removed and diethyl ether was added (200 mL). The resulting solid was filtered to provide the title compound as a white solid (12.45 g, 75%), m.p. about 193° C.

In a similar manner, the following were prepared: 2,4,6-Trimethylbenzene-sulfonic acid, compound with S4-[5-amino-3-cyano-1-(2,6-dichloro4-trifluoromethyl)phenyl]pyrazolyl-S-methylsulfilimine, m.p. about 180° C. hereinafter know as EXAMPLE 1a; 2,4,6-Trimethylbenzenesulfonic acid, compound with S4-[5-amino-1-(2,6-dichloro4-trifluoromethyl)phenyl]pyrazolyl-S-methylsulfilimine, m.p. about 187° C. hereinafter know as EXAMPLE 1b.

The following two compounds were also prepared by the above method, but were not isolated, but used as in EXAMPLE 2: 2,4,6-Trimethylbenzenesulfonic acid, compound with S-4-[5-amino-1-(2,6-dichloro4-trifluoromethyl) phenyl-3-methyl]pyrazolyl-S-ethylsulfilimine and 2,4,6-Trimethylbenzenesulfonic acid, compound with S4-[5-amino-1-(2,6-dichloro4-trifluoromethyl)phenyl-3-ethyl] pyrazolyl-S-ethylsulfilimine.

EXAMPLE 2

S-{[5-Amino-3-cyano-1-(2,6-dichloro4-trifluoromethyl)pheny]4-(1H-pyrazolyl)}-S-ethyl-N-(tert-butoxycarbonyl)sulfilimine The product of EXAMPLE 1 (1.0 g, 1.7 mmol) was stirred in methylene chloride (10 mL), cooled to 0° C., and triethylamine (1.2 mL, 8.5 mmol) was added. Di-tert-butyldicarbonate (0.6 mL, 2.6 mmol) was added and the reaction was stirred 50 minutes. The mixture was diluted with diethyl ether and washed with water (3×50 mL) and saturated aqueous sodium chloride solution (75 mL). The organic layer was dried, filtered and concentrated. The resulting oil was mixed with cold pentane and the precipitate was filtered. The solid was recombined with the filtrate and solvent was removed and the oil filtered through silica gel using 2:3 ethyl acetate:hexane as eluent. After removal of solvent, precipitation from diethyl ether/pentane provided the title compound as a white solid (0.36 g, 43%), m.p. about 191° C.

In a similar manner, the following compounds were prepared (TABLE 1).

TABLE 1

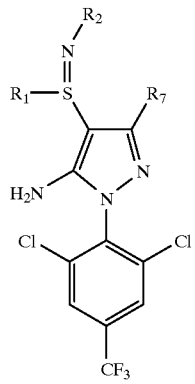

| EXAMPLE # | $R^1$ | $R^2$ | $R^7$ | m.p. |
|---|---|---|---|---|
| 3 | Et | COMe | CN | about 163° C. |
| 4 | Et | COOMe | CN | about 200° C. |
| 5 | Et | $SO_2Me$ | CN | about 191° C. |
| 6 | Et | CONHMe | CN | about 187° C. |
| 7 | Et | CN | CN | about 175° C. |
| 8 | Et | CHO | CN | about 181° C. |
| 9 | Me | COMe | CN | about 159° C. |
| 10 | Et | $PO(OEt)_2$ | CN | gum |
| 11 | Et | $CON(Me)_2$ | CN | about 173° C. |
| 12 | Et | $PO(Me)_2$ | CN | about 150° C. |
| 13 | Et | $CONHCOCCl_3$ | CN | about 116° C. |
| 14 | Et | $CONHCOCH_2Cl$ | CN | about 159° C. |
| 15 | Et | C(S)NHMe | CN | about 90° C. |
| 16 | Et | $CONHCH_2COOEt$ | CN | about 91° C. |
| 17 | Me | C(S)NHMe | CN | about 95° C. |
| 18 | Et | CONHCOOEt | CN | about 167° C. |
| 19 | Me | CHO | CN | about 160° C. |
| 20 | Me | CN | CN | about 181° C. |
| 21 | Me | C(O)C(O)Me | CN | about 204° C. |
| 22 | Me | $COO^tBu$ | CN | about 196° C. |
| 23 | Me | CHO | H | about 199° C. |
| 24 | Me | COMe | H | about 181° C. |
| 25 | Me | CN | H | about 182° C. |
| 26 | Et | CHO | Me | about 159° C. |
| 27 | Et | CN | Me | about 67° C. |
| 28 | Et | CHO | Et | gum |
| 29 | Et | CN | Et | about 64° C. |

EXAMPLE 30

N-(tert-Butoxycarbonyl)-S4-[5-amino-3-cyano-1-(2, 6-dichloro-4-trifluoromethyl)phenylpyrazolyl]-S-ethylsulfoximine The product of EXAMPLE 2 (1.55 g, 31 mmol) was dissolved in a 1:1 mixture of acetonitrile:carbon tetrachloride (19 mL). Sodium metaperiodate (2.7 g, 12.4 mmol) was added as a solution in water (19 mL). Ruthenium (III) chloride hydrate (20 mg; used to make the tetroxide in situ) and acetonitrile (25 mL) were added. After 2 hours, more sodium periodate (1.8 g, 8.2 mmol) and ruthenium (III) chloride hydrate (15 mg; forming the oxide in situ) were added and the reaction was stirred for 30 minutes. Then water (100 mL) and diethyl ether (100 mL) and isopropanol (2 mL) were successively added and mixed. Separation of the organic phase was followed by washes with water (100 mL) and saturated aqueous sodium chloride solution (100 mL). After drying over magnesium sulfate, the mixture was filtered and the solvent was removed to provide an oily residue which was triturated with cold diethyl ether and methylene chloride to provide the title compound as a brown, gummy solid (0.94 g, 60%). The proton nuclear magnetic resonance spectrum made in $CDCl_3$ has the following chemical shifts: 7.81 (m, 2H); 5.57 (brs, 2H); 3.7–3.5 (m, 2H); 1.44 (s, 9H); 1.39 (t, 3H).

In a similar manner, N-Acetyl-S4-[5-amino-3-cyano-1-(2, 6-dichloro-4-trifluoromethyl)phenylpyrazolyl]-S-ethylsulfoximine (m.p. about 217° C.) was prepared, hereinafter known as EXAMPLE 30a.

EXAMPLE 31

S-4-[5-Amino-3-cyano-1-(2,6-dichloro-4-trifluoromethyl)phenylpyrazolyl]-S-ethylsulfoximine The product of EXAMPLE 30 (0.1 g, 0.2 mmol) was dissolved in 2 mL of acetonitrile. Powdered molecular sieves (0.1 g), sodium iodide (0.07 g, 0.46 mmol) and chlorotrimethylsilane (0.06 mL, 0.46 mmol) were combined in 2 mL acetonitrile and the above solution added to it. After 25 minutes, the mixture was diluted with diethyl ether (7 mL) and sequentially washed with water, 10% aqueous hydrochloric acid solution and saturated aqueous sodium chloride solution. The organic phase was dried over sodium sulfate, filtered and concentrated under reduced pressure. The residual oil was triturated with cold pentane and dichloromethane to leave the desired product as a yellow solid (46 mg) having a melting point of about 86° C.

EXAMPLE 32

S-[5-Amino-3-cyano-1-(2,6-dichloro-4-trifluoromethyl)phenyl-4-(1H-pyrazolyl)]-S-methyl-N-[(4-methylphenyl)sulfonyl]sulfilimine To a stirred solution of 5-amino-1-(2,6-dichloro-4-trifluoromethyl)phenyl-4-methylthio-1H-pyrazole-3-carbonitrile (0.99 g, 2.7 mmol) in acetonitrile (25 mL) was added an aqueous solution of N-chloro-p-toluenesulfonamide, sodium salt, hydrate (Chloramine-T hydrate) (0.61 g, 2.7 mmol) in water (5 mL), over a 2-minute interval. Stirring under ambient conditions was continued for approximately 2 hours and the mixture then heated to boiling on a steam bath for 1 hour. Volatiles were removed under reduced pressure and the residue chromatographed on silica gel, eluting with 3:1 ethyl acetate/hexane, to give 0.81 g of the title compound as a solid having a melting point of about 197° C.

EXAMPLE 33

S-4-[5-Amino-3-cyano-1-(2-(3-chloro-5-trifluoromethyl)pyridyl)pyrazolyl]-S-ethylsulfoxide Ethyl O-mesitylene sulfonylacetohydroxamate (0.47 g, 1.64 mmol) was dissolved in dioxane (1 mL) and cooled to 0° C. 70% Perchloric acid (0.5 mL) was added and the mixture was stirred for 10 minutes. Water was added and the remaining solid was filtered, washed with water, then dissolved in methylene chloride and separated from the aqueous phase.

5-Amino-3-cyano- 1-(2-(3-chloro-5-trifluoromethyl) pyridyl)4-ethylsulfinylpyrazole (0.5 g, 1.37 mmol) was dissolved in methylene chloride (25 mL) and the resulting solution was cooled to 0° C. The solution from above was added. After one month, the mixture was concentrated to a solid and washed repeatedly until no starting pyrazole remained. This provided the title compound as a white solid, m.p. around 193° C.

Further illustrative specific compounds of the invention are set forth below in TABLES 2–5 below. Throughout these tables, the notation "··" is used to indicate a lone electron pair.

TABLE 2

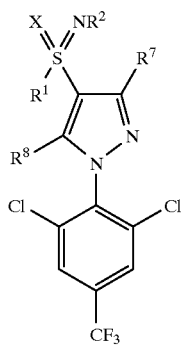

| R¹ | R⁷ | R⁸ | NR² | X |
|---|---|---|---|---|
| Me | CN | NH₂ | NCOEt | ·· |
| Me | CN | NH₂ | NCOPr | ·· |
| Me | CN | NH₂ | NCOiPr | ·· |
| Me | CN | NH₂ | NCOtBu | ·· |
| Me | CN | NH₂ | NCOPh | ·· |
| Me | CN | NH₂ | NSO₂Et | xx |
| Me | CN | NH₂ | NSO₂Ph | ·· |
| Me | CN | NH₂ | NSO₂Pr | ·· |
| Me | CN | NH₂ | NSO₂iPr | ·· |
| Me | CN | NH₂ | NNO₂ | ·· |
| Me | CN | NH₂ | NCOOEt | ·· |
| Me | CN | NH₂ | NCOOPh | ·· |
| Me | CN | NH₂ | NCOOPr | ·· |
| Me | CN | NH₂ | NCOOiPr | ·· |
| Me | CN | NH₂ | NCONHEt | ·· |
| Me | CN | NH₂ | NCONHPr | ·· |
| Me | CN | NH₂ | NCONHiPr | ·· |
| Me | CN | NH₂ | NCOSMe | ·· |
| Me | CN | NH₂ | NCOSEt | ·· |
| Me | CN | NH₂ | NCSOMe | ·· |
| Me | CN | NH₂ | NCSOEt | ·· |
| Me | CN | NH₂ | NCSOPr | ·· |
| Me | CN | NH₂ | NSO₂NH₂ | ·· |
| Me | CN | NH₂ | NSO₂NHMe | ·· |
| Me | CN | NH₂ | NSO₂NMe₂ | ·· |
| Me | CN | NH₂ | NP(O)(OMe)₂ | ·· |
| Me | CN | NH₂ | NP(O)(OMe)(OMe) | ·· |
| Me | CN | NH₂ | NP(O)(OPr)₂ | ·· |
| Me | CN | NH₂ | NP(O)(Et)₂ | ·· |
| Me | CN | NH₂ | NC(O)C(O)H | ·· |
| Me | CN | NH₂ | NC(O)C(O)Me | ·· |
| Me | CN | NH₂ | NC(O)C(O)OMe | ·· |
| Me | CN | NH₂ | NC(O)C(O)OEt | ·· |
| Me | CN | NH₂ | NC(O)C(O)NH₂ | ·· |
| Me | CN | NH₂ | NC(O)C(O)OH | ·· |
| Me | CN | NH₂ | NC(NH)NH₂ | ·· |
| Me | CN | NH₂ | NC(NOH)NH₂ | ·· |
| Me | CN | NH₂ | NC(NH)NHMe | ·· |
| Me | CN | NH₂ | NC(NH)NMe₂ | ·· |
| Me | CN | NH₂ | NC(NH)OMe | ·· |
| Me | CN | NH₂ | NC(NH)OEt | ·· |
| Et | CN | NH₂ | NCOEt | ·· |
| Et | CN | NH₂ | NCOPr | ·· |
| Et | CN | NH₂ | NCOiPr | ·· |

TABLE 2-continued

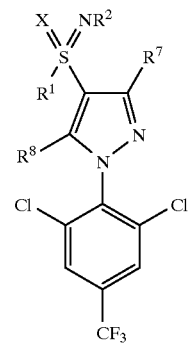

| R¹ | R⁷ | R⁸ | NR² | X |
|---|---|---|---|---|
| Et | CN | NH₂ | NCOtBu | ·· |
| Et | CN | NH₂ | NCOPh | ·· |
| Et | CN | NH₂ | NSO₂Et | ·· |
| Et | CN | NH₂ | NSO₂Ph | ·· |
| Et | CN | NH₂ | NSO₂Pr | ·· |
| Et | CN | NH₂ | NSO₂iPr | ·· |
| Et | CN | NH₂ | NNO₂ | ·· |
| Et | CN | NH₂ | NCOOEt | ·· |
| Et | CN | NH₂ | NCOOPh | ·· |
| Et | CN | NH₂ | NCOOPr | ·· |
| Et | CN | NH₂ | NCOOiPr | ·· |
| Et | CN | NH₂ | NCONHEt | ·· |
| Et | CN | NH₂ | NCONHPr | ·· |
| Et | CN | NH₂ | NCONHiPr | ·· |
| Et | CN | NH₂ | NCOSMe | ·· |
| Et | CN | NH₂ | NCOSEt | ·· |
| Et | CN | NH₂ | NCSOMe | ·· |
| Et | CN | NH₂ | NCSOEt | ·· |
| Et | CN | NH₂ | NCSOPr | ·· |
| Et | CN | NH₂ | NSO₂NH₂ | ·· |
| Et | CN | NH₂ | NSO₂NHMe | ·· |
| Et | CN | NH₂ | NSO₂NMe₂ | ·· |
| Et | CN | NH₂ | NP(O)(OMe)₂ | ·· |
| Et | CN | NH₂ | NP(O)(OMe)(OMe) | ·· |
| Et | CN | NH₂ | NP(O)(OPr)₂ | ·· |
| Et | CN | NH₂ | NP(O)(Et)₂ | ·· |
| Et | CN | NH₂ | NC(O)C(O)H | ·· |
| Et | CN | NH₂ | NC(O)C(O)Me | ·· |
| Et | CN | NH₂ | NC(O)C(O)OMe | ·· |
| Et | CN | NH₂ | NC(O)C(O)OEt | ·· |
| Et | CN | NH₂ | NC(O)C(O)NH₂ | ·· |
| Et | CN | NH₂ | NC(O)C(O)OH | ·· |
| Et | CN | NH₂ | NC(NH)NH₂ | ·· |
| Et | CN | NH₂ | NC(NOH)NH₂ | ·· |
| Et | CN | NH₂ | NC(NH)NHMe | ·· |
| Et | CN | NH₂ | NC(NH)NMe₂ | ·· |
| Et | CN | NH₂ | NC(NH)OMe | ·· |
| Et | CN | NH₂ | NC(NH)OEt | ·· |
| Me | CN | NHMe | NCOMe | ·· |
| Me | CN | NHMe | NCOEt | ·· |
| Me | CN | NHMe | NCOPr | ·· |
| Me | CN | NHMe | NCHO | ·· |
| Me | CN | NHMe | NCOiPr | ·· |
| Me | CN | NHMe | NCOtBu | ·· |
| Me | CN | NHMe | NCOPh | ·· |
| Me | CN | NHMe | NSO₂Me | ·· |
| Me | CN | NHMe | NSO₂Et | ·· |
| Me | CN | NHMe | NSO₂Pr | ·· |
| Me | CN | NHMe | NSO₂Ph | ·· |
| Me | CN | NHMe | NSO₂iPr | ·· |
| Me | CN | NHMe | NNO₂ | ·· |
| Me | CN | NHMe | NCOOMe | ·· |
| Me | CN | NHMe | NCOOEt | ·· |
| Me | CN | NHMe | NCOOPr | ·· |
| Me | CN | NHMe | NCOOiPr | ·· |
| Me | CN | NHMe | NCONHEt | ·· |
| Me | CN | NHMe | NCONHPr | ·· |
| Me | CN | NHMe | NCONH₂ | ·· |
| Me | CN | NHMe | NCONHMe | ·· |

TABLE 2-continued

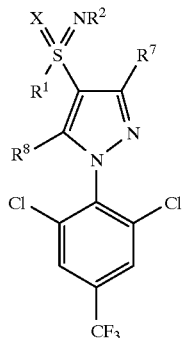

| R$^1$ | R$^7$ | R$^8$ | NR$^2$ | X |
|---|---|---|---|---|
| Me | CN | NHMe | NCN | " |
| Me | CN | NHMe | NCOSMe | " |
| Me | CN | NHMe | NCOSEt | " |
| Me | CN | NHMe | NCSOMe | " |
| Me | CN | NHMe | NCSOEt | " |
| Me | CN | NHMe | NCSOPr | " |
| Me | CN | NHMe | NSO$_2$NH$_2$ | " |
| Me | CN | NHMe | NSO$_2$NHMe | " |
| Me | CN | NHMe | NSO$_2$NMe$_2$ | " |
| Me | CN | NHMe | NP(O)(OMe)$_2$ | " |
| Me | CN | NHMe | NP(O)(OEt)2 | " |
| Me | CN | NHMe | NP(O)Me$_2$ | " |
| Me | CN | NHMe | NP(O)Et$_2$ | " |
| Me | CN | NHMe | NP(O)Me(OMe) | " |
| Me | CN | NHMe | NP(O)(OPr)$_2$ | " |
| Me | CN | NHMe | NC(O)C(O)H | " |
| Me | CN | NHMe | NC(O)C(O)Me | " |
| Me | CN | NHMe | NC(O)C(O)OMe | " |
| Me | CN | NHMe | NC(O)C(O)OEt | " |
| Me | CN | NHMe | NC(O)C(O)NH$_2$ | " |
| Me | CN | NHMe | NC(O)C(O)OH | " |
| Me | CN | NHMe | NC(NH)NH$_2$ | " |
| Me | CN | NHMe | NC(NOH)NH$_2$ | " |
| Me | CN | NHMe | NC(NH)NHMe | " |
| Me | CN | NHMe | NC(NH)NMe$_2$ | " |
| Me | CN | NHMe | NC(NH)OMe | " |
| Me | CN | NHMe | NC(NH)OEt | " |
| Me | CN | NHEt | NCOMe | " |
| Me | CN | NHEt | NCOEt | " |
| Me | CN | NHEt | NCOPr | " |
| Me | CN | NHEt | NCHO | " |
| Me | CN | NHEt | NCOiPr | " |
| Me | CN | NHEt | NCOtBu | " |
| Me | CN | NHEt | NCOPh | " |
| Me | CN | NHEt | NSO$_2$Me | " |
| Me | CN | NHEt | NSO$_2$Et | " |
| Me | CN | NHEt | NSO$_2$Pr | " |
| Me | CN | NHEt | NSO$_2$Ph | " |
| Me | CN | NHEt | NSO$_2$iPr | " |
| Me | CN | NHEt | NNO$_2$ | " |
| Me | CN | NHEt | NCOOMe | " |
| Me | CN | NHEt | NCOOEt | " |
| Me | CN | NHEt | NCOOPr | " |
| Me | CN | NHEt | NCOOiPr | " |
| Me | CN | NHEt | NCONHEt | " |
| Me | CN | NHEt | NCONHPr | " |
| Me | CN | NHEt | NCONH$_2$ | " |
| Me | CN | NHEt | NCONHMe | " |
| Me | CN | NHEt | NCN | " |
| Me | CN | NHEt | NCOSMe | " |
| Me | CN | NHEt | NCOSEt | " |
| Me | CN | NHEt | NCSOMe | " |
| Me | CN | NHEt | NCSOEt | " |
| Me | CN | NHEt | NCSOPr | " |
| Me | CN | NHEt | NSO$_2$NH$_2$ | " |
| Me | CN | NHEt | NSO$_2$NHMe | " |
| Me | CN | NHEt | NSO$_2$NMe$_2$ | " |
| Me | CN | NHEt | NP(O)(OMe)$_2$ | " |
| Me | CN | NHEt | NP(O)(OEt)2 | " |

TABLE 2-continued

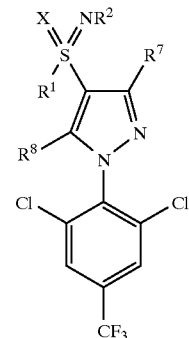

| R$^1$ | R$^7$ | R$^8$ | NR$^2$ | X |
|---|---|---|---|---|
| Me | CN | NHEt | NP(O)Me$_2$ | " |
| Me | CN | NHEt | NP(O)Et$_2$ | " |
| Me | CN | NHEt | NP(O)Me(OMe) | " |
| Me | CN | NHEt | NP(O)(OPr)$_2$ | " |
| Me | CN | NHEt | NC(O)C(O)H | " |
| Me | CN | NHEt | NC(O)C(O)Me | " |
| Me | CN | NHEt | NC(O)C(O)OMe | " |
| Me | CN | NHEt | NC(O)C(O)OEt | " |
| Me | CN | NHEt | NC(O)C(O)NH$_2$ | " |
| Me | CN | NHEt | NC(O)C(O)OH | " |
| Me | CN | NHEt | NC(NH)NH$_2$ | " |
| Me | CN | NHEt | NC(NOH)NH$_2$ | " |
| Me | CN | NHEt | NC(NH)NHMe | " |
| Me | CN | NHEt | NC(NH)NMe$_2$ | " |
| Me | CN | NHEt | NC(NH)OMe | " |
| Me | CN | NHEt | NC(NH)OEt | " |
| Me | CN | NHPr | NCOMe | " |
| Me | CN | NHPr | NCOEt | " |
| Me | CN | NHPr | NCOPr | " |
| Me | CN | NHPr | NCHO | " |
| Me | CN | NHPr | NCOiPr | " |
| Me | CN | NHPr | NCOtBu | " |
| Me | CN | NHPr | NCOPh | " |
| Me | CN | NHPr | NSO$_2$Me | " |
| Me | CN | NHPr | NSO$_2$Et | " |
| Me | CN | NHPr | NSO$_2$Pr | " |
| Me | CN | NHPr | NSO$_2$Ph | " |
| Me | CN | NHPr | NSO$_2$iPr | " |
| Me | CN | NHPr | NNO$_2$ | " |
| Me | CN | NHPr | NCOOMe | " |
| Me | CN | NHPr | NCOOEt | " |
| Me | CN | NHPr | NCOOPr | " |
| Me | CN | NHPr | NCOOiPr | " |
| Me | CN | NHPr | NCONHEt | " |
| Me | CN | NHPr | NCONHPr | " |
| Me | CN | NHPr | NCONH$_2$ | " |
| Me | CN | NHPr | NCONHMe | " |
| Me | CN | NHPr | NCN | " |
| Me | CN | NHPr | NCOSMe | " |
| Me | CN | NHPr | NCOSEt | " |
| Me | CN | NHPr | NCSOMe | " |
| Me | CN | NHPr | NCSOEt | " |
| Me | CN | NHPr | NCSOPr | " |
| Me | CN | NHPr | NSO$_2$NH$_2$ | " |
| Me | CN | NHPr | NSO$_2$NHMe | " |
| Me | CN | NHPr | NSO$_2$NMe$_2$ | " |
| Me | CN | NHPr | NP(O)(OMe)$_2$ | " |
| Me | CN | NHPr | NP(O)(OEt)2 | " |
| Me | CN | NHPr | NP(O)Me$_2$ | " |
| Me | CN | NHPr | NP(O)Et$_2$ | " |
| Me | CN | NHPr | NP(O)Me(OMe) | " |
| Me | CN | NHPr | NP(O)(OPr)$_2$ | " |
| Me | CN | NHPr | NC(O)C(O)H | " |
| Me | CN | NHPr | NC(O)C(O)Me | " |
| Me | CN | NHPr | NC(O)C(O)OMe | " |
| Me | CN | NHPr | NC(O)C(O)OEt | " |
| Me | CN | NHPr | NC(O)C(O)NH$_2$ | " |
| Me | CN | NHPr | NC(O)C(O)OH | " |
| Me | CN | NHPr | NC(NH)NH$_2$ | " |

TABLE 2-continued

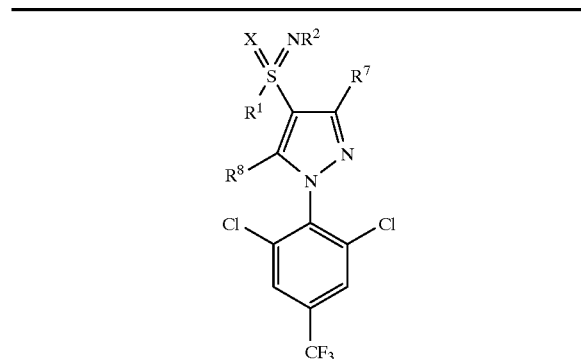

| R¹ | R⁷ | R⁸ | NR² | X |
|---|---|---|---|---|
| Me | CN | NHPr | NC(NOH)NH₂ | " |
| Me | CN | NHPr | NC(NH)NHMe | " |
| Me | CN | NHPr | NC(NH)NMe₂ | " |
| Me | CN | NHPr | NC(NH)OMe | " |
| Me | CN | NHPr | NC(NH)OEt | " |
| Et | CN | NHMe | NCOMe | " |
| Et | CN | NHMe | NCOEt | " |
| Et | CN | NHMe | NCOPr | " |
| Et | CN | NHMe | NCHO | " |
| Et | CN | NHMe | NCOiPr | " |
| Et | CN | NHMe | NCOtBu | " |
| Et | CN | NHMe | NCOPh | " |
| Et | CN | NHMe | NSO₂Me | " |
| Et | CN | NHMe | NSO₂Et | " |
| Et | CN | NHMe | NSO₂Pr | " |
| Et | CN | NHMe | NSO₂Ph | " |
| Et | CN | NHMe | NSO₂iPr | " |
| Et | CN | NHMe | NNO₂ | " |
| Et | CN | NHMe | NCOOMe | " |
| Et | CN | NHMe | NCOOEt | " |
| Et | CN | NHMe | NCOOPr | " |
| Et | CN | NHMe | NCOOiPr | " |
| Et | CN | NHMe | NCONHEt | " |
| Et | CN | NHMe | NCONHPr | " |
| Et | CN | NHMe | NCONH₂ | " |
| Et | CN | NHMe | NCONHMe | " |
| Et | CN | NHMe | NCN | " |
| Et | CN | NHMe | NCOSMe | " |
| Et | CN | NHMe | NCOSEt | " |
| Et | CN | NHMe | NCSOMe | " |
| Et | CN | NHMe | NCSOEt | " |
| Et | CN | NHMe | NCSOPr | " |
| Et | CN | NHMe | NSO₂NH₂ | " |
| Et | CN | NHMe | NSO₂NHMe | " |
| Et | CN | NHMe | NSO₂NMe₂ | " |
| Et | CN | NHMe | NP(O)(OMe)₂ | " |
| Et | CN | NHMe | NP(O)(OEt)2 | " |
| Et | CN | NHMe | NP(O)Me₂ | " |
| Et | CN | NHMe | NP(O)Et₂ | " |
| Et | CN | NHMe | NP(O)Me(OMe) | " |
| Et | CN | NHMe | NP(O)(OPr)₂ | " |
| Et | CN | NHMe | NC(O)C(O)H | " |
| Et | CN | NHMe | NC(O)C(O)Me | " |
| Et | CN | NHMe | NC(O)C(O)OMe | " |
| Et | CN | NHMe | NC(O)C(O)OEt | " |
| Et | CN | NHMe | NC(O)C(O)NH₂ | " |
| Et | CN | NHMe | NC(O)C(O)OH | " |
| Et | CN | NHMe | NC(NH)NH₂ | " |
| Et | CN | NHMe | NC(NOH)NH₂ | " |
| Et | CN | NHMe | NC(NH)NHMe | " |
| Et | CN | NHMe | NC(NH)NMe₂ | " |
| Et | CN | NHMe | NC(NH)OMe | " |
| Et | CN | NHMe | NC(NH)OEt | " |
| Et | CN | NHEt | NCOMe | " |
| Et | CN | NHEt | NCOEt | " |
| Et | CN | NHEt | NCOPr | " |
| Et | CN | NHEt | NCHO | " |
| Et | CN | NHEt | NCOiPr | " |
| Et | CN | NHEt | NCOtBu | " |
| Et | CN | NHEt | NCOPh | " |
| Et | CN | NHEt | NSO₂Me | " |
| Et | CN | NHEt | NSO₂Et | " |
| Et | CN | NHEt | NSO₂Pr | " |
| Et | CN | NHEt | NSO₂Ph | " |
| Et | CN | NHEt | NSO₂iPr | " |
| Et | CN | NHEt | NNO₂ | " |
| Et | CN | NHEt | NCOOMe | " |
| Et | CN | NHEt | NCOOEt | " |
| Et | CN | NHEt | NCOOPr | " |
| Et | CN | NHEt | NCOOiPr | " |
| Et | CN | NHEt | NCONHEt | " |
| Et | CN | NHEt | NCONHPr | " |
| Et | CN | NHEt | NCONH₂ | " |
| Et | CN | NHEt | NCONHMe | " |
| Et | CN | NHEt | NCN | " |
| Et | CN | NHEt | NCOSMe | " |
| Et | CN | NHEt | NCOSEt | " |
| Et | CN | NHEt | NCSOMe | " |
| Et | CN | NHEt | NCSOEt | " |
| Et | CN | NHEt | NCSOPr | " |
| Et | CN | NHEt | NSO₂NH₂ | " |
| Et | CN | NHEt | NSO₂NHMe | " |
| Et | CN | NHEt | NSO₂NMe₂ | " |
| Et | CN | NHEt | NP(O)(OMe)₂ | " |
| Et | CN | NHEt | NP(O)(OEt)₂ | " |
| Et | CN | NHEt | NP(O)Me₂ | " |
| Et | CN | NHEt | NP(O)Et₂ | " |
| Et | CN | NHEt | NP(O)Me(OMe) | " |
| Et | CN | NHEt | NP(O)(OPr)₂ | " |
| Et | CN | NHEt | NC(O)C(O)H | " |
| Et | CN | NHEt | NC(O)C(O)Me | " |
| Et | CN | NHEt | NC(O)C(O)OMe | " |
| Et | CN | NHEt | NC(O)C(O)OEt | " |
| Et | CN | NHEt | NC(O)C(O)NH₂ | " |
| Et | CN | NHEt | NC(O)C(O)OH | " |
| Et | CN | NHEt | NC(NH)NH₂ | " |
| Et | CN | NHEt | NC(NOH)NH₂ | " |
| Et | CN | NHEt | NC(NH)NHMe | " |
| Et | CN | NHEt | NC(NH)NMe₂ | " |
| Et | CN | NHEt | NC(NH)OMe | " |
| Et | CN | NHEt | NC(NH)OEt | " |
| Et | CN | NHPr | NCOMe | " |
| Et | CN | NHPr | NCOEt | " |
| Et | CN | NHPr | NCOPr | " |
| Et | CN | NHPr | NCHO | " |
| Et | CN | NHPr | NCOiPr | " |
| Et | CN | NHPr | NCOtBu | " |
| Et | CN | NHPr | NCOPh | " |
| Et | CN | NHPr | NSO₂Me | " |
| Et | CN | NHPr | NSO₂Et | " |
| Et | CN | NHPr | NSO₂Pr | " |
| Et | CN | NHPr | NSO₂Ph | " |
| Et | CN | NHPr | NSO₂iPr | " |
| Et | CN | NHPr | NNO₂ | " |
| Et | CN | NHPr | NCOOMe | " |
| Et | CN | NHPr | NCOOEt | " |
| Et | CN | NHPr | NCOOPr | " |
| Et | CN | NHPr | NCOOiPr | " |

TABLE 2-continued

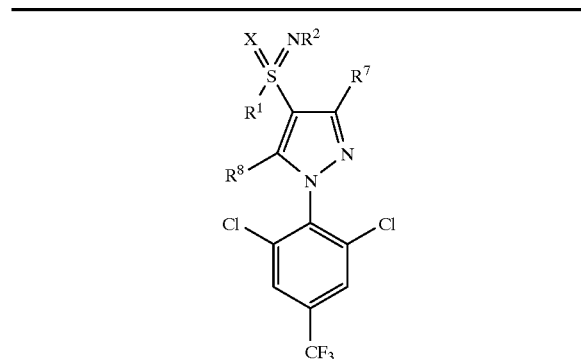

| R¹ | R⁷ | R⁸ | NR² | X |
|---|---|---|---|---|
| Et | CN | NHPr | NCONHEt | " |
| Et | CN | NHPr | NCONHPr | " |
| Et | CN | NHPr | NCONH₂ | " |
| Et | CN | NHPr | NCONHMe | " |
| Et | CN | NHPr | NCN | " |
| Et | CN | NHPr | NCOSMe | " |
| Et | CN | NHPr | NCOSEt | " |
| Et | CN | NHPr | NCSOMe | " |
| Et | CN | NHPr | NCSOEt | " |
| Et | CN | NHPr | NCSOPr | " |
| Et | CN | NHPr | NSO₂NH₂ | " |
| Et | CN | NHPr | NSO₂NHMe | " |
| Et | CN | NHPr | NSO₂NMe₂ | " |
| Et | CN | NHPr | NP(O)(OMe)₂ | " |
| Et | CN | NHPr | NP(O)(OEt)₂ | " |
| Et | CN | NHPr | NP(O)Me₂ | " |
| Et | CN | NHPr | NP(O)Et₂ | " |
| Et | CN | NHPr | NP(O)Me(OMe) | " |
| Et | CN | NHPr | NP(O)(OPr)₂ | " |
| Et | CN | NHPr | NC(O)C(O)H | " |
| Et | CN | NHPr | NC(O)C(O)Me | " |
| Et | CN | NHPr | NC(O)C(O)OMe | " |
| Et | CN | NHPr | NC(O)C(O)OEt | " |
| Et | CN | NHPr | NC(O)C(O)NH₂ | " |
| Et | CN | NHPr | NC(O)C(O)OH | " |
| Et | CN | NHPr | NC(NH)NH₂ | " |
| Et | CN | NHPr | NC(NOH)NH₂ | " |
| Et | CN | NHPr | NC(NH)NHMe | " |
| Et | CN | NHPr | NC(NH)NMe₂ | " |
| Et | CN | NHPr | NC(NH)OMe | " |
| Et | CN | NHPr | NC(NH)OEt | " |
| Me | CN | NH₂ | NCOMe | O |
| Me | CN | NH₂ | NCOEt | O |
| Me | CN | NH₂ | NCOPr | O |
| Me | CN | NH₂ | NCHO | O |
| Me | CN | NH₂ | NCOiPr | O |
| Me | CN | NH₂ | NCOtBu | O |
| Me | CN | NH₂ | NCOPh | O |
| Me | CN | NH₂ | NSO₂Me | O |
| Me | CN | NH₂ | NSO₂Et | O |
| Me | CN | NH₂ | NSO₂Pr | O |
| Me | CN | NH₂ | NSO₂Ph | O |
| Me | CN | NH₂ | NSO₂iPr | O |
| Me | CN | NH₂ | NNO₂ | O |
| Me | CN | NH₂ | NCOOMe | O |
| Me | CN | NH₂ | NCOOEt | O |
| Me | CN | NH₂ | NCOOPr | O |
| Me | CN | NH₂ | NCOOiPr | O |
| Me | CN | NH₂ | NCONHEt | O |
| Me | CN | NH₂ | NCONHPr | O |
| Me | CN | NH₂ | NCONH₂ | O |
| Me | CN | NH₂ | NCONHMe | O |
| Me | CN | NH₂ | NCN | O |
| Me | CN | NH₂ | NCOSMe | O |
| Me | CN | NH₂ | NCOSEt | O |
| Me | CN | NH₂ | NCSOMe | O |
| Me | CN | NH₂ | NCSOEt | O |
| Me | CN | NH₂ | NCSOPr | O |
| Me | CN | NH₂ | NSO₂NH₂ | O |
| Me | CN | NH₂ | NSO₂NHMe | O |
| Me | CN | NH₂ | NSO₂NMe₂ | O |
| Me | CN | NH₂ | NP(O)(OMe)₂ | O |
| Me | CN | NH₂ | NP(O)(OEt)2 | O |
| Me | CN | NH₂ | NP(O)Me₂ | O |
| Me | CN | NH₂ | NP(O)Et₂ | O |
| Me | CN | NH₂ | NP(O)Me(OMe) | O |
| Me | CN | NH₂ | NP(O)(OPr)₂ | O |
| Me | CN | NH₂ | NC(O)C(O)H | O |
| Me | CN | NH₂ | NC(O)C(O)Me | O |
| Me | CN | NH₂ | NC(O)C(O)OMe | O |
| Me | CN | NH₂ | NC(O)C(O)OEt | O |
| Me | CN | NH₂ | NC(O)C(O)NH₂ | O |
| Me | CN | NH₂ | NC(O)C(O)OH | O |
| Me | CN | NH₂ | NC(NH)NH₂ | O |
| Me | CN | NH₂ | NC(NOH)NH₂ | O |
| Me | CN | NH₂ | NC(NH)NHMe | O |
| Me | CN | NH₂ | NC(NH)NMe₂ | O |
| Me | CN | NH₂ | NC(NH)OMe | O |
| Me | CN | NH₂ | NC(NH)OEt | O |
| Me | CN | NH₂ | NH | O |
| Me | CN | NHMe | NCOMe | O |
| Me | CN | NHMe | NCOEt | O |
| Me | CN | NHMe | NCOPr | O |
| Me | CN | NHMe | NCHO | O |
| Me | CN | NHMe | NCOiPr | O |
| Me | CN | NHMe | NCOtBu | O |
| Me | CN | NHMe | NCOPh | O |
| Me | CN | NHMe | NSO₂Me | O |
| Me | CN | NHMe | NSO₂Et | O |
| Me | CN | NHMe | NSO₂Pr | O |
| Me | CN | NHMe | NSO₂Ph | O |
| Me | CN | NHMe | NSO₂iPr | O |
| Me | CN | NHMe | NNO₂ | O |
| Me | CN | NHMe | NCOOMe | O |
| Me | CN | NHMe | NCOOEt | O |
| Me | CN | NHMe | NCOOPr | O |
| Me | CN | NHMe | NCOOiPr | O |
| Me | CN | NHMe | NCONHEt | O |
| Me | CN | NHMe | NCONHPr | O |
| Me | CN | NHMe | NCONH₂ | O |
| Me | CN | NHMe | NCONHMe | O |
| Me | CN | NHMe | NCN | O |
| Me | CN | NHMe | NCOSMe | O |
| Me | CN | NHMe | NCOSEt | O |
| Me | CN | NHMe | NCSOMe | O |
| Me | CN | NHMe | NCSOEt | O |
| Me | CN | NHMe | NCSOPr | O |
| Me | CN | NHMe | NSO₂NH₂ | O |
| Me | CN | NHMe | NSO₂NHMe | O |
| Me | CN | NHMe | NSO₂NMe₂ | O |
| Me | CN | NHMe | NP(O)(OMe)₂ | O |
| Me | CN | NHMe | NP(O)(OEt)2 | O |
| Me | CN | NHMe | NP(O)Me₂ | O |
| Me | CN | NHMe | NP(O)Et₂ | O |
| Me | CN | NHMe | NP(O)Me(OMe) | O |
| Me | CN | NHMe | NP(O)(OPr)₂ | O |
| Me | CN | NHMe | NC(O)C(O)H | O |
| Me | CN | NHMe | NC(O)C(O)Me | O |

TABLE 2-continued

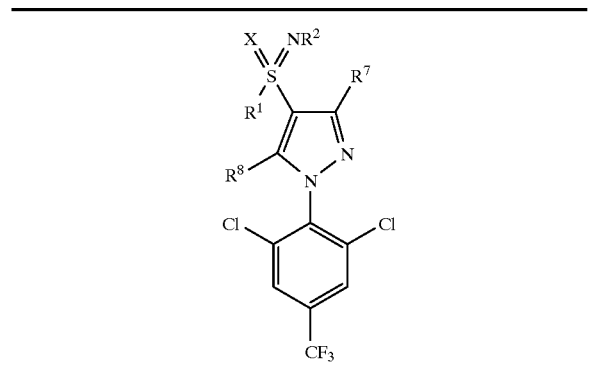

| R¹ | R⁷ | R⁸ | NR² | X |
|----|----|----|-----|---|
| Me | CN | NHMe | NC(O)C(O)OMe | O |
| Me | CN | NHMe | NC(O)C(O)OEt | O |
| Me | CN | NHMe | NC(O)C(O)NH₂ | O |
| Me | CN | NHMe | NC(O)C(O)OH | O |
| Me | CN | NHMe | NC(NH)NH₂ | O |
| Me | CN | NHMe | NC(NOH)NH₂ | O |
| Me | CN | NHMe | NC(NH)NHMe | O |
| Me | CN | NHMe | NC(NH)NMe₂ | O |
| Me | CN | NHMe | NC(NH)OMe | O |
| Me | CN | NHMe | NC(NH)OEt | O |
| Me | CN | NHEt | NCOMe | O |
| Me | CN | NHEt | NCOEt | O |
| Me | CN | NHEt | NCOPr | O |
| Me | CN | NHEt | NCHO | O |
| Me | CN | NHEt | NCOiPr | O |
| Me | CN | NHEt | NCOtBu | O |
| Me | CN | NHEt | NCOPh | O |
| Me | CN | NHEt | NSO₂Me | O |
| Me | CN | NHEt | NSO₂Et | O |
| Me | CN | NHEt | NSO₂Pr | O |
| Me | CN | NHEt | NSO₂Ph | O |
| Me | CN | NHEt | NSO₂iPr | O |
| Me | CN | NHEt | NNO₂ | O |
| Me | CN | NHEt | NCOOMe | O |
| Me | CN | NHEt | NCOOEt | O |
| Me | CN | NHEt | NCOOPr | O |
| Me | CN | NHEt | NCOOiPr | O |
| Me | CN | NHEt | NCONHEt | O |
| Me | CN | NHEt | NCONHPr | O |
| Me | CN | NHEt | NCONH₂ | O |
| Me | CN | NHEt | NCONHMe | O |
| Me | CN | NHEt | NCN | O |
| Me | CN | NHEt | NCOSMe | O |
| Me | CN | NHEt | NCOSEt | O |
| Me | CN | NHEt | NCSOMe | O |
| Me | CN | NHEt | NCSOEt | O |
| Me | CN | NHEt | NCSOPr | O |
| Me | CN | NHEt | NSO₂NH₂ | O |
| Me | CN | NHEt | NSO₂NHMe | O |
| Me | CN | NHEt | NSO₂NMe₂ | O |
| Me | CN | NHEt | NP(O)(OMe)₂ | O |
| Me | CN | NHEt | NP(O)(OEt)₂ | O |
| Me | CN | NHEt | NP(O)Me₂ | O |
| Me | CN | NHEt | NP(O)Et₂ | O |
| Me | CN | NHEt | NP(O)Me(OMe) | O |
| Me | CN | NHEt | NP(O)(OPr)₂ | O |
| Me | CN | NHEt | NC(O)C(O)H | O |
| Me | CN | NHEt | NC(O)C(O)Me | O |
| Me | CN | NHEt | NC(O)C(O)OMe | O |
| Me | CN | NHEt | NC(O)C(O)OEt | O |
| Me | CN | NHEt | NC(O)C(O)NH₂ | O |
| Me | CN | NHEt | NC(O)C(O)OH | O |
| Me | CN | NHEt | NC(NH)NH₂ | O |
| Me | CN | NHEt | NC(NOH)NH₂ | O |
| Me | CN | NHEt | NC(NH)NHMe | O |
| Me | CN | NHEt | NC(NH)NMe₂ | O |
| Me | CN | NHEt | NC(NH)OMe | O |
| Me | CN | NHEt | NC(NH)OEt | O |
| Et | CN | NH₂ | NCOEt | O |
| Et | CN | NH₂ | NCOPr | O |
| Et | CN | NH₂ | NCHO | O |
| Et | CN | NH₂ | NCOiPr | O |
| Et | CN | NH₂ | NCOtBu | O |
| Et | CN | NH₂ | NCOPh | O |
| Et | CN | NH₂ | NSO₂Me | O |
| Et | CN | NH₂ | NSO₂Et | O |
| Et | CN | NH₂ | NSO₂Pr | O |
| Et | CN | NH₂ | NSO₂Ph | O |
| Et | CN | NH₂ | NSO₂iPr | O |
| Et | CN | NH₂ | NNO₂ | O |
| Et | CN | NH₂ | NCOOMe | O |
| Et | CN | NH₂ | NCOOEt | O |
| Et | CN | NH₂ | NCOOPr | O |
| Et | CN | NH₂ | NCOOiPr | O |
| Et | CN | NH₂ | NCONHEt | O |
| Et | CN | NH₂ | NCONHPr | O |
| Et | CN | NH₂ | NCONH₂ | O |
| Et | CN | NH₂ | NCONHMe | O |
| Et | CN | NH₂ | NCN | O |
| Et | CN | NH₂ | NCOSMe | O |
| Et | CN | NH₂ | NCOSEt | O |
| Et | CN | NH₂ | NCSOMe | O |
| Et | CN | NH₂ | NCSOEt | O |
| Et | CN | NH₂ | NCSOPr | O |
| Et | CN | NH₂ | NSO₂NH₂ | O |
| Et | CN | NH₂ | NSO₂NHMe | O |
| Et | CN | NH₂ | NSO₂NMe₂ | O |
| Et | CN | NH₂ | NP(O)(OMe)₂ | O |
| Et | CN | NH₂ | NP(O)(OEt)₂ | O |
| Et | CN | NH₂ | NP(O)Me₂ | O |
| Et | CN | NH₂ | NP(O)Et₂ | O |
| Et | CN | NH₂ | NP(O)Me(OMe) | O |
| Et | CN | NH₂ | NP(O)(OPr)₂ | O |
| Et | CN | NH₂ | NC(O)C(O)H | O |
| Et | CN | NH₂ | NC(O)C(O)Me | O |
| Et | CN | NH₂ | NC(O)C(O)OMe | O |
| Et | CN | NH₂ | NC(O)C(O)OEt | O |
| Et | CN | NH₂ | NC(O)C(O)NH₂ | O |
| Et | CN | NH₂ | NC(O)C(O)OH | O |
| Et | CN | NH₂ | NC(NH)NH₂ | O |
| Et | CN | NH₂ | NC(NOH)NH₂ | O |
| Et | CN | NH₂ | NC(NH)NHMe | O |
| Et | CN | NH₂ | NC(NH)NMe₂ | O |
| Et | CN | NH₂ | NC(NH)OMe | O |
| Et | CN | NH₂ | NC(NH)OEt | O |
| Et | CN | NHMe | NH | O |
| Et | CN | NHMe | NCOMe | O |
| Et | CN | NHMe | NCOEt | O |
| Et | CN | NHMe | NCOPr | O |
| Et | CN | NHMe | NCHO | O |
| Et | CN | NHMe | NCOiPr | O |
| Et | CN | NHMe | NCOtBu | O |
| Et | CN | NHMe | NCOPh | O |
| Et | CN | NHMe | NSO₂Me | O |
| Et | CN | NHMe | NSO₂Et | O |
| Et | CN | NHMe | NSO₂Pr | O |
| Et | CN | NHMe | NSO₂Ph | O |
| Et | CN | NHMe | NSO₂iPr | O |

TABLE 2-continued

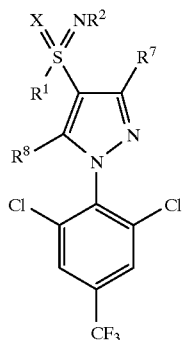

| R¹ | R⁷ | R⁸ | NR² | X |
|---|---|---|---|---|
| Et | CN | NHMe | NNO₂ | O |
| Et | CN | NHMe | NCOOMe | O |
| Et | CN | NHMe | NCOOEt | O |
| Et | CN | NHMe | NCOOPr | O |
| Et | CN | NHMe | NCOOiPr | O |
| Et | CN | NHMe | NCONHEt | O |
| Et | CN | NHMe | NCONHPr | O |
| Et | CN | NHMe | NCONH₂ | O |
| Et | CN | NHMe | NCONHMe | O |
| Et | CN | NHMe | NCN | O |
| Et | CN | NHMe | NCOSMe | O |
| Et | CN | NHMe | NCOSEt | O |
| Et | CN | NHMe | NCSOMe | O |
| Et | CN | NHMe | NCSOEt | O |
| Et | CN | NHMe | NCSOPr | O |
| Et | CN | NHMe | NSO₂NH₂ | O |
| Et | CN | NHMe | NSO₂NHMe | O |
| Et | CN | NHMe | NSO₂NMe₂ | O |
| Et | CN | NHMe | NP(O)(OMe)₂ | O |
| Et | CN | NHMe | NP(O)(OEt)₂ | O |
| Et | CN | NHMe | NP(O)Me₂ | O |
| Et | CN | NHMe | NP(O)Et₂ | O |
| Et | CN | NHMe | NP(O)Me(OMe) | O |
| Et | CN | NHMe | NP(O)(OPr)₂ | O |
| Et | CN | NHMe | NC(O)C(O)H | O |
| Et | CN | NHMe | NC(O)C(O)Me | O |
| Et | CN | NHMe | NC(O)C(O)OMe | O |
| Et | CN | NHMe | NC(O)C(O)OEt | O |
| Et | CN | NHMe | NC(O)C(O)NH₂ | O |
| Et | CN | NHMe | NC(O)C(O)OH | O |
| Et | CN | NHMe | NC(NH)NH₂ | O |
| Et | CN | NHMe | NC(NOH)NH₂ | O |
| Et | CN | NHMe | NC(NH)NHMe | O |
| Et | CN | NHMe | NC(NH)NMe₂ | O |
| Et | CN | NHMe | NC(NH)OMe | O |
| Et | CN | NHMe | NC(NH)OEt | O |
| Et | CN | NHEt | NCOMe | O |
| Et | CN | NHEt | NCOEt | O |
| Et | CN | NHEt | NCOPr | O |
| Et | CN | NHEt | NCHO | O |
| Et | CN | NHEt | NCOiPr | O |
| Et | CN | NHEt | NCOtBu | O |
| Et | CN | NHEt | NCOPh | O |
| Et | CN | NHEt | NSO₂Me | O |
| Et | CN | NHEt | NSO₂Et | O |
| Et | CN | NHEt | NSO₂Pr | O |
| Et | CN | NHEt | NSO₂Ph | O |
| Et | CN | NHEt | NSO₂iPr | O |
| Et | CN | NHEt | NNO₂ | O |
| Et | CN | NHEt | NCOOMe | O |
| Ft | CN | NHEt | NCOOEt | O |
| Et | CN | NHEt | NCOOPr | O |
| Et | CN | NHEt | NCOOiPr | O |
| Et | CN | NHEt | NCONHEt | O |
| Et | CN | NHEt | NCONHPr | O |
| Et | CN | NHEt | NCONH₂ | O |
| Et | CN | NHEt | NCONHMe | O |
| Et | CN | NHEt | NCN | O |
| Et | CN | NHEt | NCOSMe | O |

TABLE 2-continued

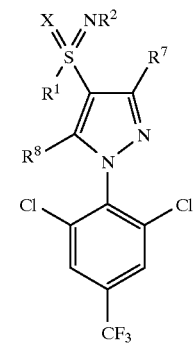

| R¹ | R⁷ | R⁸ | NR² | X |
|---|---|---|---|---|
| Et | CN | NHEt | NCOSEt | O |
| Et | CN | NHEt | NCSOMe | O |
| Et | CN | NHEt | NCSOEt | O |
| Et | CN | NHEt | NCSOPr | O |
| Et | CN | NHEt | NSO₂NH₂ | O |
| Et | CN | NHEt | NSO₂NHMe | O |
| Et | CN | NHEt | NSO₂NMe₂ | O |
| Et | CN | NHEt | NP(O)(OMe)₂ | O |
| Et | CN | NHEt | NP(O)(OEt)₂ | O |
| Et | CN | NHEt | NP(O)Me₂ | O |
| Et | CN | NHEt | NP(O)Et₂ | O |
| Et | CN | NHEt | NP(O)Me(OMe) | O |
| Et | CN | NHEt | NP(O)(OPr)₂ | O |
| Et | CN | NHEt | NC(O)C(O)H | O |
| Et | CN | NHEt | NC(O)C(O)Me | O |
| Et | CN | NHEt | NC(O)C(O)OMe | O |
| Et | CN | NHEt | NC(O)C(O)OEt | O |
| Et | CN | NHEt | NC(O)C(O)NH₂ | O |
| Et | CN | NHEt | NC(O)C(O)OH | O |
| Et | CN | NHEt | NC(NH)NH₂ | O |
| Et | CN | NHEt | NC(NOH)NH₂ | O |
| Et | CN | NHEt | NC(NH)NHMe | O |
| Et | CN | NHEt | NC(NH)NMe₂ | O |
| Et | CN | NHEt | NC(NH)OMe | O |
| Et | CN | NHEt | NC(NH)OEt | O |
| Me | CN | NHCOMe | NCOMe | " |
| Me | CN | NHCOMe | NCOEt | " |
| Me | CN | NHCOMe | NCOPr | " |
| Me | CN | NHCOMe | NCHO | " |
| Me | CN | NHCOMe | NCOiPr | " |
| Me | CN | NHCOMe | NCOtBu | " |
| Me | CN | NHCOMe | NCOPh | " |
| Me | CN | NHCOMe | NSO₂Me | " |
| Me | CN | NHCOMe | NSO₂Et | " |
| Me | CN | NHCOMe | NSO₂Pr | " |
| Me | CN | NHCOMe | NSO₂Ph | " |
| Me | CN | NHCOMe | NSO₂iPr | " |
| Me | CN | NHCOMe | NNO₂ | " |
| Me | CN | NHCOMe | NCOOMe | " |
| Me | CN | NHCOMe | NCOOEt | " |
| Me | CN | NHCOMe | NCOOPr | " |
| Me | CN | NHCOMe | NCOOiPr | " |
| Me | CN | NHCOMe | NCONHEt | " |
| Me | CN | NHCOMe | NCONHPr | " |
| Me | CN | NHCOMe | NCONH₂ | " |
| Me | CN | NHCOMe | NCONHMe | " |
| Me | CN | NHCOMe | NCN | " |
| Me | CN | NHCOMe | NCOSMe | " |
| Me | CN | NHCOMe | NCOSEt | " |
| Me | CN | NHCOMe | NCSOMe | " |
| Me | CN | NHCOMe | NCSOEt | " |
| Me | CN | NHCOMe | NCSOPr | " |
| Me | CN | NHCOMe | NSO₂NH₂ | " |
| Me | CN | NHCOMe | NSO₂NHMe | " |
| Me | CN | NHCOMe | NSO₂NMe₂ | " |
| Me | CN | NHCOMe | NP(O)(OMe)₂ | " |
| Me | CN | NHCOMe | NP(O)(OEt)₂ | " |
| Me | CN | NHCOMe | NP(O)Me₂ | " |
| Me | CN | NHCOMe | NP(O)Et₂ | " |

TABLE 2-continued

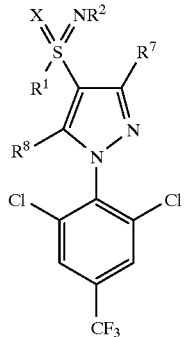

| R¹ | R⁷ | R⁸ | NR² | X |
|---|---|---|---|---|
| Me | CN | NHCOMe | NP(O)Me(OMe) | " |
| Me | CN | NHCOMe | NP(O)(OPr)$_2$ | " |
| Me | CN | NHCOMe | NC(O)C(O)H | " |
| Me | CN | NHCOMe | NC(O)C(O)Me | " |
| Me | CN | NHCOMe | NC(O)C(O)OMe | " |
| Me | CN | NHCOMe | NC(O)C(O)OEt | " |
| Me | CN | NHCOMe | NC(O)C(O)NH$_2$ | " |
| Me | CN | NHCOMe | NC(O)C(O)OH | " |
| Me | CN | NHCOMe | NC(NH)NH$_2$ | " |
| Me | CN | NHCOMe | NC(NOH)NH$_2$ | " |
| Me | CN | NHCOMe | NC(NH)NHMe | " |
| Me | CN | NHCOMe | NC(NH)NMe$_2$ | " |
| Me | CN | NHCOMe | NC(NH)OMe | " |
| Me | CN | NHCOMe | NC(NH)OEt | " |
| Et | CN | NHCOMe | NCOMe | " |
| Et | CN | NHCOMe | NCOEt | " |
| Et | CN | NHCOMe | NCOPr | " |
| Et | CN | NHCOMe | NCHO | " |
| Et | CN | NHCOMe | NCOiPr | " |
| Et | CN | NHCOMe | NCOtBu | " |
| Et | CN | NHCOMe | NCOPh | " |
| Et | CN | NHCOMe | NSO$_2$Me | " |
| Et | CN | NHCOMe | NSO$_2$Et | " |
| Et | CN | NHCOMe | NSO$_2$Pr | " |
| Et | CN | NHCOMe | NSO$_2$Ph | " |
| Et | CN | NHCOMe | NSO$_2$iPr | " |
| Et | CN | NHCOMe | NNO$_2$ | " |
| Et | CN | NHCOMe | NCOOMe | " |
| Et | CN | NHCOMe | NCOOEt | " |
| Et | CN | NHCOMe | NCOOPr | " |
| Et | CN | NHCOMe | NCOOiPr | " |
| Et | CN | NHCOMe | NCONHEt | " |
| Et | CN | NHCOMe | NCONHPr | " |
| Et | CN | NHCOMe | NCONH$_2$ | " |
| Et | CN | NHCOMe | NCONHMe | " |
| Et | CN | NHCOMe | NCN | " |
| Et | CN | NHCOMe | NCOSMe | " |
| Et | CN | NHCOMe | NCOSEt | " |
| Et | CN | NHCOMe | NCSOMe | " |
| Et | CN | NHCOMe | NCSOEt | " |
| Et | CN | NHCOMe | NCSOPr | " |
| Et | CN | NHCOMe | NSO$_2$NH$_2$ | " |
| Et | CN | NHCOMe | NSO$_2$NHMe | " |
| Et | CN | NHCOMe | NSO$_2$NMe$_2$ | " |
| Et | CN | NHCOMe | NP(O)(OMe)$_2$ | " |
| Et | CN | NHCOMe | NP(O)(OEt)$_2$ | " |
| Et | CN | NHCOMe | NP(O)Me$_2$ | " |
| Et | CN | NHCOMe | NP(O)Et$_2$ | " |
| Et | CN | NHCOMe | NP(O)Me(OMe) | " |
| Et | CN | NHCOMe | NP(O)(OPr)$_2$ | " |
| Et | CN | NHCOMe | NC(O)C(O)H | " |
| Et | CN | NHCOMe | NC(O)C(O)Me | " |
| Et | CN | NHCOMe | NC(O)C(O)OMe | " |
| Et | CN | NHCOMe | NC(O)C(O)OEt | " |
| Et | CN | NHCOMe | NC(O)C(O)NH$_2$ | " |
| Et | CN | NHCOMe | NC(O)C(O)OH | " |
| Et | CN | NHCOMe | NC(NH)NH$_2$ | " |
| Et | CN | NHCOMe | NC(NOH)NH$_2$ | " |
| Et | CN | NHCOMe | NC(NH)NHMe | " |

TABLE 2-continued

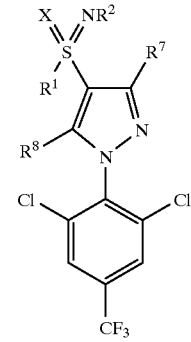

| R¹ | R⁷ | R⁸ | NR² | X |
|---|---|---|---|---|
| Et | CN | NHCOMe | NC(NH)NMe$_2$ | " |
| Et | CN | NHCOMe | NC(NH)OMe | " |
| Et | CN | NHCOMe | NC(NH)OEt | " |
| Me | CN | NHCOOMe | NCOMe | " |
| Me | CN | NHCOOMe | NCOEt | " |
| Me | CN | NHCOOMe | NCOPr | " |
| Me | CN | NHCOOMe | NCHO | " |
| Me | CN | NHCOOMe | NCOiPr | " |
| Me | CN | NHCOOMe | NCOtBu | " |
| Me | CN | NHCOOMe | NCOPh | " |
| Me | CN | NHCOOMe | NSO$_2$Me | " |
| Me | CN | NHCOOMe | NSO$_2$Et | " |
| Me | CN | NHCOOMe | NSO$_2$Pr | " |
| Me | CN | NHCOOMe | NSO$_2$Ph | " |
| Me | CN | NHCOOMe | NSO$_2$iPr | " |
| Me | CN | NHCOOMe | NNO$_2$ | " |
| Me | CN | NHCOOMe | NCOOMe | " |
| Me | CN | NHCOOMe | NCOOEt | " |
| Me | CN | NHCOOMe | NCOOPr | " |
| Me | CN | NHCOOMe | NCOOiPr | " |
| Me | CN | NHCOOMe | NCONHEt | " |
| Me | CN | NHCOOMe | NCONHPr | " |
| Me | CN | NHCOOMe | NCONH$_2$ | " |
| Me | CN | NHCOOMe | NCONHMe | " |
| Me | CN | NHCOOMe | NCN | " |
| Me | CN | NHCOOMe | NCOSMe | " |
| Me | CN | NHCOOMe | NCOSEt | " |
| Me | CN | NHCOOMe | NCSOMe | " |
| Me | CN | NHCOOMe | NCSOEt | " |
| Me | CN | NHCOOMe | NCSOPr | " |
| Me | CN | NHCOOMe | NSO$_2$NH$_2$ | " |
| Me | CN | NHCOOMe | NSO$_2$NHMe | " |
| Me | CN | NHCOOMe | NSO$_2$NMe$_2$ | " |
| Me | CN | NHCOOMe | NP(O)(OMe)$_2$ | " |
| Me | CN | NHCOOMe | NP(O)(OEt)$_2$ | " |
| Me | CN | NHCOOMe | NP(O)Me$_2$ | " |
| Me | CN | NHCOOMe | NP(O)Et$_2$ | " |
| Me | CN | NHCOOMe | NP(O)Me(OMe) | " |
| Me | CN | NHCOOMe | NP(O)(OPr)$_2$ | " |
| Me | CN | NHCOOMe | NC(O)C(O)H | " |
| Me | CN | NHCOOMe | NC(O)C(O)Me | " |
| Me | CN | NHCOOMe | NC(O)C(O)OMe | " |
| Me | CN | NHCOOMe | NC(O)C(O)OEt | " |
| Me | CN | NHCOOMe | NC(O)C(O)NH$_2$ | " |
| Me | CN | NHCOOMe | NC(O)C(O)OH | " |
| Me | CN | NHCOOMe | NC(NH)NH$_2$ | " |
| Me | CN | NHCOOMe | NC(NOH)NH$_2$ | " |
| Me | CN | NHCOOMe | NC(NH)NHMe | " |
| Me | CN | NHCOOMe | NC(NH)NMe$_2$ | " |
| Me | CN | NHCOOMe | NC(NH)OMe | " |
| Me | CN | NHCOOMe | NC(NH)OEt | " |
| Et | CN | NHCOOMe | NCOMe | " |
| Et | CN | NHCOOMe | NCOEt | " |
| Et | CN | NHCOOMe | NCOPr | " |
| Et | CN | NHCOOMe | NCHO | " |
| Et | CN | NHCOOMe | NCOiPr | " |
| Et | CN | NHCOOMe | NCOtBu | " |
| Et | CN | NHCOOMe | NCOPh | " |
| Et | CN | NHCOOMe | NSO$_2$Me | " |

TABLE 2-continued

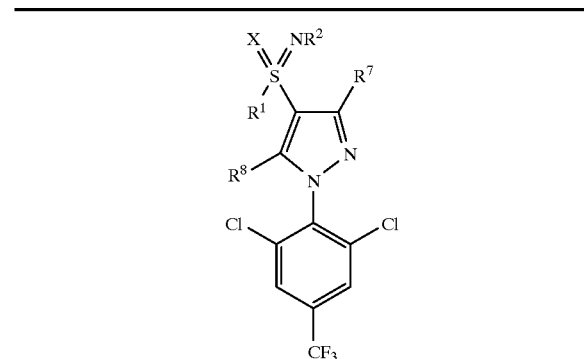

| R¹ | R⁷ | R⁸ | NR² | X |
|---|---|---|---|---|
| Et | CN | NHCOOMe | NSO₂Et | " |
| Et | CN | NHCOOMe | NSO₂Pr | " |
| Et | CN | NHCOOMe | NSO₂Ph | " |
| Et | CN | NHCOOMe | NSO₂iPr | " |
| Et | CN | NHCOOMe | NNO₂ | " |
| Et | CN | NHCOOMe | NCOOMe | " |
| Et | CN | NHCOOMe | NCOOEt | " |
| Et | CN | NHCOOMe | NCOOPr | " |
| Et | CN | NHCOOMe | NCOOiPr | " |
| Et | CN | NHCOOMe | NCONHEt | " |
| Et | CN | NHCOOMe | NCONHPr | " |
| Et | CN | NHCOOMe | NCONH₂ | " |
| Et | CN | NHCOOMe | NCONHMe | " |
| Et | CN | NHCOOMe | NCN | " |
| Et | CN | NHCOOMe | NCOSMe | " |
| Et | CN | NHCOOMe | NCOSEt | " |
| Et | CN | NHCOOMe | NCSOMe | " |
| Et | CN | NHCOOMe | NCSOEt | " |
| Et | CN | NHCOOMe | NCSOPr | " |
| Et | CN | NHCOOMe | NSO₂NH₂ | " |
| Et | CN | NHCOOMe | NSO₂NHMe | " |
| Et | CN | NHCOOMe | NSO₂NMe₂ | " |
| Et | CN | NHCOOMe | NP(O)(OMe)₂ | " |
| Et | CN | NHCOOMe | NP(O)(OEt)₂ | " |
| Et | CN | NHCOOMe | NP(O)Me₂ | " |
| Et | CN | NHCOOMe | NP(O)Et₂ | " |
| Et | CN | NHCOOMe | NP(O)Me(OMe) | " |
| Et | CN | NHCOOMe | NP(O)(OPr)₂ | " |
| Et | CN | NHCOOMe | NC(O)C(O)H | " |
| Et | CN | NHCOOMe | NC(O)C(O)Me | " |
| Et | CN | NHCOOMe | NC(O)C(O)OMe | " |
| Et | CN | NHCOOMe | NC(O)C(O)OEt | " |
| Et | CN | NHCOOMe | NC(O)C(O)NH₂ | " |
| Et | CN | NHCOOMe | NC(O)C(O)OH | " |
| Et | CN | NHCOOMe | NC(NH)NH₂ | " |
| Et | CN | NHCOOMe | NC(NOH)NH₂ | " |
| Et | CN | NHCOOMe | NC(NH)NHMe | " |
| Et | CN | NHCOOMe | NC(NH)NMe₂ | " |
| Et | CN | NHCOOMe | NC(NH)OMe | " |
| Et | CN | NHCOOMe | NC(NH)OEt | " |
| Me | CN | NHCOOEt | NCOMe | " |
| Me | CN | NHCOOEt | NCOEt | " |
| Me | CN | NHCOOEt | NCOPr | " |
| Me | CN | NHCOOEt | NCHO | " |
| Me | CN | NHCOOEt | NCOiPr | " |
| Me | CN | NHCOOEt | NCOtBu | " |
| Me | CN | NHCOOEt | NCOPh | " |
| Me | CN | NHCOOEt | NSO₂Me | " |
| Me | CN | NHCOOEt | NSO₂Et | " |
| Me | CN | NHCOOEt | NSO₂Pr | " |
| Me | CN | NHCOOEt | NSO₂Ph | " |
| Me | CN | NHCOOEt | NSO₂iPr | " |
| Me | CN | NHCOOEt | NNO₂ | " |
| Me | CN | NHCOOEt | NCOOMe | " |
| Me | CN | NHCOOEt | NCOOEt | " |
| Me | CN | NHCOOEt | NCOOPr | " |
| Me | CN | NHCOOEt | NCOOiPr | " |
| Me | CN | NHCOOEt | NCONHEt | " |
| Me | CN | NHCOOEt | NCONHPr | " |
| Me | CN | NHCOOEt | NCONH₂ | " |
| Me | CN | NHCOOEt | NCONHMe | " |
| Me | CN | NHCOOEt | NCN | " |
| Me | CN | NHCOOEt | NCOSMe | " |
| Me | CN | NHCOOEt | NCOSEt | " |
| Me | CN | NHCOOEt | NCSOMe | " |
| Me | CN | NHCOOEt | NCSOEt | " |
| Me | CN | NHCOOEt | NCSOPr | " |
| Me | CN | NHCOOEt | NSO₂NH₂ | " |
| Me | CN | NHCOOEt | NSO₂NHMe | " |
| Me | CN | NHCOOEt | NSO₂NMe₂ | " |
| Me | CN | NHCOOEt | NP(O)(OMe)₂ | " |
| Me | CN | NHCOOEt | NP(O)(OEt)₂ | " |
| Me | CN | NHCOOEt | NP(O)Me₂ | " |
| Me | CN | NHCOOEt | NP(O)Et₂ | " |
| Me | CN | NHCOOEt | NP(O)Me(OMe) | " |
| Me | CN | NHCOOEt | NP(O)(OPr)₂ | " |
| Me | CN | NHCOOEt | NC(O)C(O)H | " |
| Me | CN | NHCOOEt | NC(O)C(O)Me | " |
| Me | CN | NHCOOEt | NC(O)C(O)OMe | " |
| Me | CN | NHCOOEt | NC(O)C(O)OEt | " |
| Me | CN | NHCOOEt | NC(O)C(O)NH₂ | " |
| Me | CN | NHCOOEt | NC(O)C(O)OH | " |
| Me | CN | NHCOOEt | NC(NH)NH₂ | " |
| Me | CN | NHCOOEt | NC(NOH)NH₂ | " |
| Me | CN | NHCOOEt | NC(NH)NHMe | " |
| Me | CN | NHCOOEt | NC(NH)NMe₂ | " |
| Me | CN | NHCOOEt | NC(NH)OMe | " |
| Me | CN | NHCOOEt | NC(NH)OEt | " |
| Et | CN | NHCOOEt | NCOMe | " |
| Et | CN | NHCOOEt | NCOEt | " |
| Et | CN | NHCOOEt | NCOPr | " |
| Et | CN | NHCOOEt | NCHO | " |
| Et | CN | NHCOOEt | NCOiPr | " |
| Et | CN | NHCOOEt | NCOtBu | " |
| Et | CN | NHCOOEt | NCOPh | " |
| Et | CN | NHCOOEt | NSO₂Me | " |
| Et | CN | NHCOOEt | NSO₂Et | " |
| Et | CN | NHCOOEt | NSO₂Pr | " |
| Et | CN | NHCOOEt | NSO₂Ph | " |
| Et | CN | NHCOOEt | NSO₂iPr | " |
| Et | CN | NHCOOEt | NNO₂ | " |
| Et | CN | NHCOOEt | NCOOMe | " |
| Et | CN | NHCOOEt | NCOOEt | " |
| Et | CN | NHCOOEt | NCOOPr | " |
| Et | CN | NHCOOEt | NCOOiPr | " |
| Et | CN | NHCOOEt | NCONHEt | " |
| Et | CN | NHCOOEt | NCONHPr | " |
| Et | CN | NHCOOEt | NCONH₂ | " |
| Et | CN | NHCOOEt | NCONHMe | " |
| Et | CN | NHCOOEt | NCN | " |
| Et | CN | NHCOOEt | NCOSMe | " |
| Et | CN | NHCOOEt | NCOSEt | " |
| Et | CN | NHCOOEt | NCSOMe | " |
| Et | CN | NHCOOEt | NCSOEt | " |
| Et | CN | NHCOOEt | NCSOPr | " |
| Et | CN | NHCOOEt | NSO₂NH₂ | " |
| Et | CN | NHCOOEt | NSO₂NHMe | " |
| Et | CN | NHCOOEt | NSO₂NMe₂ | " |

TABLE 2-continued

[Structure: pyrazole with X=S(=NR²) bearing R¹ at position 4, R⁷ at position 3, R⁸ at position 5, and N-substituted with 2,6-dichloro-4-trifluoromethylphenyl]

| R¹ | R⁷ | R⁸ | NR² | X |
|---|---|---|---|---|
| Et | CN | NHCOOEt | NP(O)(OMe)₂ | " |
| Et | CN | NHCOOEt | NP(O)(OEt)₂ | " |
| Et | CN | NHCOOEt | NP(O)Me₂ | " |
| Et | CN | NHCOOEt | NP(O)Et₂ | " |
| Et | CN | NHCOOEt | NP(O)Me(OMe) | " |
| Et | CN | NHCOOEt | NP(O)(OPr)₂ | " |
| Et | CN | NHCOOEt | NC(O)C(O)H | " |
| Et | CN | NHCOOEt | NC(O)C(O)Me | " |
| Et | CN | NHCOOEt | NC(O)C(O)OMe | " |
| Et | CN | NHCOOEt | NC(O)C(O)OEt | " |
| Et | CN | NHCOOEt | NC(O)C(O)NH₂ | " |
| Et | CN | NHCOOEt | NC(O)C(O)OH | " |
| Et | CN | NHCOOEt | NC(NH)NH₂ | " |
| Et | CN | NHCOOEt | NC(NOH)NH₂ | " |
| Et | CN | NHCOOEt | NC(NH)NHMe | " |
| Et | CN | NHCOOEt | NC(NH)NMe₂ | " |
| Et | CN | NHCOOEt | NC(NH)OMe | " |
| Et | CN | NHCOOEt | NC(NH)OEt | " |
| Me | CN | NHCH₂COOMe | NCOMe | " |
| Me | CN | NHCH₂COOMe | NCOEt | " |
| Me | CN | NHCH₂COOMe | NCOPr | " |
| Me | CN | NHCH₂COOMe | NCHO | " |
| Me | CN | NHCH₂COOMe | NCOiPr | " |
| Me | CN | NHCH₂COOMe | NCOtBu | " |
| Me | CN | NHCH₂COOMe | NCOPh | " |
| Me | CN | NHCH₂COOMe | NSO₂Me | " |
| Me | CN | NHCH₂COOMe | NSO₂Et | " |
| Me | CN | NHCH₂COOMe | NSO₂Pr | " |
| Me | CN | NHCH₂COOMe | NSO₂Ph | " |
| Me | CN | NHCH₂COOMe | NSO₂iPr | " |
| Me | CN | NHCH₂COOMe | NNO₂ | " |
| Me | CN | NHCH₂COOMe | NCOOMe | " |
| Me | CN | NHCH₂COOMe | NCOOEt | " |
| Me | CN | NHCH₂COOMe | NCOOPr | " |
| Me | CN | NHCH₂COOMe | NCOOiPr | " |
| Me | CN | NHCH₂COOMe | NCONHEt | " |
| Me | CN | NHCH₂COOMe | NCONHPr | " |
| Me | CN | NHCH₂COOMe | NCONH₂ | " |
| Me | CN | NHCH₂COOMe | NCONHMe | " |
| Me | CN | NHCH₂COOMe | NCN | " |
| Me | CN | NHCH₂COOMe | NCOSMe | " |
| Me | CN | NHCH₂COOMe | NCOSEt | " |
| Me | CN | NHCH₂COOMe | NCSOMe | " |
| Me | CN | NHCH₂COOMe | NCSOEt | " |
| Me | CN | NHCH₂COOMe | NCSOPr | " |
| Me | CN | NHCH₂COOMe | NSO₂NH₂ | " |
| Me | CN | NHCH₂COOMe | NSO₂NHMe | " |
| Me | CN | NHCH₂COOMe | NSO₂NMe₂ | " |
| Me | CN | NHCH₂COOMe | NP(O)(OMe)₂ | " |
| Me | CN | NHCH₂COOMe | NP(O)(OEt)₂ | " |
| Me | CN | NHCH₂COOMe | NP(O)Me₂ | " |
| Me | CN | NHCH₂COOMe | NP(O)Et₂ | " |
| Me | CN | NHCH₂COOMe | NP(O)Me(OMe) | " |
| Me | CN | NHCH₂COOMe | NP(O)(OPr)₂ | " |
| Me | CN | NHCH₂COOMe | NC(O)C(O)H | " |
| Me | CN | NHCH₂COOMe | NC(O)C(O)Me | " |
| Me | CN | NHCH₂COOMe | NC(O)C(O)OMe | " |
| Me | CN | NHCH₂COOMe | NC(O)C(O)OEt | " |
| Me | CN | NHCH₂COOMe | NC(O)C(O)NH₂ | " |
| Me | CN | NHCH₂COOMe | NC(O)C(O)OH | " |
| Me | CN | NHCH₂COOMe | NC(NH)NH₂ | " |
| Me | CN | NHCH₂COOMe | NC(NOH)NH₂ | " |
| Me | CN | NHCH₂COOMe | NC(NH)NHMe | " |
| Me | CN | NHCH₂COOMe | NC(NH)NMe₂ | " |
| Me | CN | NHCH₂COOMe | NC(NH)OMe | " |
| Me | CN | NHCH₂COOMe | NC(NH)OEt | " |
| Et | CN | NHCH₂COOMe | NCOMe | " |
| Et | CN | NHCH₂COOMe | NCOEt | " |
| Et | CN | NHCH₂COOMe | NCOPr | " |
| Et | CN | NHCH₂COOMe | NCHO | " |
| Et | CN | NHCH₂COOMe | NCOiPr | " |
| Et | CN | NHCH₂COOMe | NCOtBu | " |
| Et | CN | NHCH₂COOMe | NCOPh | " |
| Et | CN | NHCH₂COOMe | NSO₂Me | " |
| Et | CN | NHCH₂COOMe | NSO₂Et | " |
| Et | CN | NHCH₂COOMe | NSO₂Pr | " |
| Et | CN | NHCH₂COOMe | NSO₂Ph | " |
| Et | CN | NHCH₂COOMe | NSO₂iPr | " |
| Et | CN | NHCH₂COOMe | NNO₂ | " |
| Et | CN | NHCH₂COOMe | NCOOMe | " |
| Et | CN | NHCH₂COOMe | NCOOEt | " |
| Et | CN | NHCH₂COOMe | NCOOPr | " |
| Et | CN | NHCH₂COOMe | NCOOiPr | " |
| Et | CN | NHCH₂COOMe | NCONHEt | " |
| Et | CN | NHCH₂COOMe | NCONHPr | " |
| Et | CN | NHCH₂COOMe | NCONH₂ | " |
| Et | CN | NHCH₂COOMe | NCONHMe | " |
| Et | CN | NHCH₂COOMe | NCN | " |
| Et | CN | NHCH₂COOMe | NCOSMe | " |
| Et | CN | NHCH₂COOMe | NCOSEt | " |
| Et | CN | NHCH₂COOMe | NCSOMe | " |
| Et | CN | NHCH₂COOMe | NCSOEt | " |
| Et | CN | NHCH₂COOMe | NCSOPr | " |
| Et | CN | NHCH₂COOMe | NSO₂NH₂ | " |
| Et | CN | NHCH₂COOMe | NSO₂NHMe | " |
| Et | CN | NHCH₂COOMe | NSO₂NMe₂ | " |
| Et | CN | NHCH₂COOMe | NP(O)(OMe)₂ | " |
| Et | CN | NHCH₂COOMe | NP(O)(OEt)₂ | " |
| Et | CN | NHCH₂COOMe | NP(O)Me₂ | " |
| Et | CN | NHCH₂COOMe | NP(O)Et₂ | " |
| Et | CN | NHCH₂COOMe | NP(O)Me(OMe) | " |
| Et | CN | NHCH₂COOMe | NP(O)(OPr)₂ | " |
| Et | CN | NHCH₂COOMe | NC(O)C(O)H | " |
| Et | CN | NHCH₂COOMe | NC(O)C(O)Me | " |
| Et | CN | NHCH₂COOMe | NC(O)C(O)OMe | " |
| Et | CN | NHCH₂COOMe | NC(O)C(O)OEt | " |
| Et | CN | NHCH₂COOMe | NC(O)C(O)NH₂ | " |
| Et | CN | NHCH₂COOMe | NC(O)C(O)OH | " |
| Et | CN | NHCH₂COOMe | NC(NH)NH₂ | " |
| Et | CN | NHCH₂COOMe | NC(NOH)NH₂ | " |
| Et | CN | NHCH₂COOMe | NC(NH)NHMe | " |
| Et | CN | NHCH₂COOMe | NC(NH)NMe₂ | " |
| Et | CN | NHCH₂COOMe | NC(NH)OMe | " |
| Et | CN | NHCH₂COOMe | NC(NH)OEt | " |
| Me | CN | NHCH₂CN | NCOMe | " |
| Me | CN | NHCH₂CN | NCOEt | " |
| Me | CN | NHCH₂CN | NCOPr | " |
| Me | CN | NHCH₂CN | NCHO | " |

TABLE 2-continued

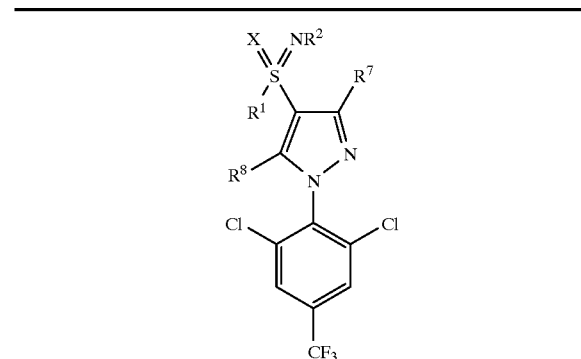

| R¹ | R⁷ | R⁸ | NR² | X |
|---|---|---|---|---|
| Me | CN | NHCH₂CN | NCOiPr | " |
| Me | CN | NHCH₂CN | NCOtBu | " |
| Me | CN | NHCH₂CN | NCOPh | " |
| Me | CN | NHCH₂CN | NSO₂Me | " |
| Me | CN | NHCH₂CN | NSO₂Et | " |
| Me | CN | NHCH₂CN | NSO₂Pr | " |
| Me | CN | NHCH₂CN | NSO₂Ph | " |
| Me | CN | NHCH₂CN | NSO₂iPr | " |
| Me | CN | NHCH₂CN | NNO₂ | " |
| Me | CN | NHCH₂CN | NCOOMe | " |
| Me | CN | NHCH₂CN | NCOOEt | " |
| Me | CN | NHCH₂CN | NCOOPr | " |
| Me | CN | NHCH₂CN | NCOOiPr | " |
| Me | CN | NHCH₂CN | NCONHEt | " |
| Me | CN | NHCH₂CN | NCONHPr | " |
| Me | CN | NHCH₂CN | NCONH₂ | " |
| Me | CN | NHCH₂CN | NCONHMe | " |
| Me | CN | NHCH₂CN | NCN | " |
| Me | CN | NHCH₂CN | NCOSMe | " |
| Me | CN | NHCH₂CN | NCOSEt | " |
| Me | CN | NHCH₂CN | NCSOMe | " |
| Me | CN | NHCH₂CN | NCSOEt | " |
| Me | CN | NHCH₂CN | NCSOPr | " |
| Me | CN | NHCH₂CN | NSO₂NH₂ | " |
| Me | CN | NHCH₂CN | NSO₂NHMe | " |
| Me | CN | NHCH₂CN | NSO₂NMe₂ | " |
| Me | CN | NHCH₂CN | NP(O)(OMe)₂ | " |
| Me | CN | NHCH₂CN | NP(O)(OEt)₂ | " |
| Me | CN | NHCH₂CN | NP(O)Me₂ | " |
| Me | CN | NHCH₂CN | NP(O)Et₂ | " |
| Me | CN | NHCH₂CN | NP(O)Me(OMe) | " |
| Me | CN | NHCH₂CN | NP(O)(OPr)₂ | " |
| Me | CN | NHCH₂CN | NC(O)C(O)H | " |
| Me | CN | NHCH₂CN | NC(O)C(O)Me | " |
| Me | CN | NHCH₂CN | NC(O)C(O)OMe | " |
| Me | CN | NHCH₂CN | NC(O)C(O)OEt | " |
| Me | CN | NHCH₂CN | NC(O)C(O)NH₂ | " |
| Me | CN | NHCH₂CN | NC(O)C(O)OH | " |
| Me | CN | NHCH₂CN | NC(NH)NH₂ | " |
| Me | CN | NHCH₂CN | NC(NOH)NH₂ | " |
| Me | CN | NHCH₂CN | NC(NH)NHMe | " |
| Me | CN | NHCH₂CN | NC(NH)NMe₂ | " |
| Me | CN | NHCH₂CN | NC(NH)OMe | " |
| Me | CN | NHCH₂CN | NC(NH)OEt | " |
| Et | CN | NHCH₂CN | NCOMe | " |
| Et | CN | NHCH₂CN | NCOEt | " |
| Et | CN | NHCH₂CN | NCOPr | " |
| Et | CN | NHCH₂CN | NCHO | " |
| Et | CN | NHCH₂CN | NCOiPr | " |
| Et | CN | NHCH₂CN | NCOtBu | " |
| Et | CN | NHCH₂CN | NCOPh | " |
| Et | CN | NHCH₂CN | NSO₂Me | " |
| Et | CN | NHCH₂CN | NSO₂Et | " |
| Et | CN | NHCH₂CN | NSO₂Pr | " |
| Et | CN | NHCH₂CN | NSO₂Ph | " |
| Et | CN | NHCH₂CN | NSO₂iPr | " |
| Et | CN | NHCH₂CN | NNO₂ | " |
| Et | CN | NHCH₂CN | NCOOMe | " |
| Et | CN | NHCH₂CN | NCOOEt | " |
| Et | CN | NHCH₂CN | NCOOPr | " |
| Et | CN | NHCH₂CN | NCOOiPr | " |
| Et | CN | NHCH₂CN | NCONHEt | " |
| Et | CN | NHCH₂CN | NCONHPr | " |
| Et | CN | NHCH₂CN | NCONH₂ | " |
| Et | CN | NHCH₂CN | NCONHMe | " |
| Et | CN | NHCH₂CN | NCN | " |
| Et | CN | NHCH₂CN | NCOSMe | " |
| Et | CN | NHCH₂CN | NCOSEt | " |
| Et | CN | NHCH₂CN | NCSOMe | " |
| Et | CN | NHCH₂CN | NCSOEt | " |
| Et | CN | NHCH₂CN | NCSOPr | " |
| Et | CN | NHCH₂CN | NSO₂NH₂ | " |
| Et | CN | NHCH₂CN | NSO₂NHMe | " |
| Et | CN | NHCH₂CN | NSO₂NMe₂ | " |
| Et | CN | NHCH₂CN | NP(O)(OMe)₂ | " |
| Et | CN | NHCH₂CN | NP(O)(OEt)₂ | " |
| Et | CN | NHCH₂CN | NP(O)Me₂ | " |
| Et | CN | NHCH₂CN | NP(O)Et₂ | " |
| Et | CN | NHCH₂CN | NP(O)Me(OMe) | " |
| Et | CN | NHCH₂CN | NP(O)(OPr)₂ | " |
| Et | CN | NHCH₂CN | NC(O)C(O)H | " |
| Et | CN | NHCH₂CN | NC(O)C(O)Me | " |
| Et | CN | NHCH₂CN | NC(O)C(O)OMe | " |
| Et | CN | NHCH₂CN | NC(O)C(O)OEt | " |
| Et | CN | NHCH₂CN | NC(O)C(O)NH₂ | " |
| Et | CN | NHCH₂CN | NC(O)C(O)OH | " |
| Et | CN | NHCH₂CN | NC(NH)NH₂ | " |
| Et | CN | NHCH₂CN | NC(NOH)NH₂ | " |
| Et | CN | NHCH₂CN | NC(NH)NHMe | " |
| Et | CN | NHCH₂CN | NC(NH)NMe₂ | " |
| Et | CN | NHCH₂CN | NC(NH)OMe | " |
| Et | CN | NHCH₂CN | NC(NH)OEt | " |
| Me | CN | NHCH₂CONH₂ | NCOMe | " |
| Me | CN | NHCH₂CONH₂ | NCOEt | " |
| Me | CN | NHCH₂CONH₂ | NCOPr | " |
| Me | CN | NHCH₂CONH₂ | NCHO | " |
| Me | CN | NHCH₂CONH₂ | NCOiPr | " |
| Me | CN | NHCH₂CONH₂ | NCOtBu | " |
| Me | CN | NHCH₂CONH₂ | NCOPh | " |
| Me | CN | NHCH₂CONH₂ | NSO₂Me | " |
| Me | CN | NHCH₂CONH₂ | NSO₂Et | " |
| Me | CN | NHCH₂CONH₂ | NSO₂Pr | " |
| Me | CN | NHCH₂CONH₂ | NSO₂Ph | " |
| Me | CN | NHCH₂CONH₂ | NSO₂iPr | " |
| Me | CN | NHCH₂CONH₂ | NNO₂ | " |
| Me | CN | NHCH₂CONH₂ | NCOOMe | " |
| Me | CN | NHCH₂CONH₂ | NCOOEt | " |
| Me | CN | NHCH₂CONH₂ | NCOOPr | " |
| Me | CN | NHCH₂CONH₂ | NCOOiPr | " |
| Me | CN | NHCH₂CONH₂ | NCONHEt | " |
| Me | CN | NHCH₂CONH₂ | NCONHPr | " |
| Me | CN | NHCH₂CONH₂ | NCONH₂ | " |
| Me | CN | NHCH₂CONH₂ | NCONHMe | " |
| Me | CN | NHCH₂CONH₂ | NCN | " |
| Me | CN | NHCH₂CONH₂ | NCOSMe | " |
| Me | CN | NHCH₂CONH₂ | NCOSEt | " |
| Me | CN | NHCH₂CONH₂ | NCSOMe | " |
| Me | CN | NHCH₂CONH₂ | NCSOEt | " |

TABLE 2-continued

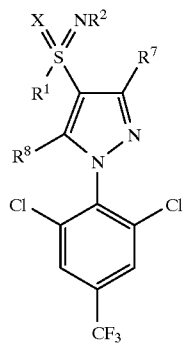

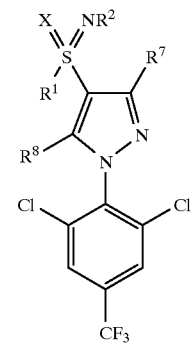

| R¹ | R⁷ | R⁸ | NR² | X | R¹ | R⁷ | R⁸ | NR² | X |
|---|---|---|---|---|---|---|---|---|---|
| Me | CN | NHCH₂CONH₂ | NCSOPr | " | Et | CN | NHCH₂CONH₂ | NC(O)C(O)Me | " |
| Me | CN | NHCH₂CONH₂ | NSO₂NH₂ | " | Et | CN | NHCH₂CONH₂ | NC(O)C(O)OMe | " |
| Me | CN | NHCH₂CONH₂ | NSO₂NHMe | " | Et | CN | NHCH₂CONH₂ | NC(O)C(O)OEt | " |
| Me | CN | NHCH₂CONH₂ | NSO₂NMe₂ | " | Et | CN | NHCH₂CONH₂ | NC(O)C(O)NH₂ | " |
| Me | CN | NHCH₂CONH₂ | NP(O)(OMe)₂ | " | Et | CN | NHCH₂CONH₂ | NC(O)C(O)OH | " |
| Me | CN | NHCH₂CONH₂ | NP(O)(OEt)₂ | " | Et | CN | NHCH₂CONH₂ | NC(NH)NH₂ | " |
| Me | CN | NHCH₂CONH₂ | NP(O)Me₂ | " | Et | CN | NHCH₂CONH₂ | NC(NOH)NH₂ | " |
| Me | CN | NHCH₂CONH₂ | NP(O)Et₂ | " | Et | CN | NHCH₂CONH₂ | NC(NH)NHMe | " |
| Me | CN | NHCH₂CONH₂ | NP(O)Me(OMe) | " | Et | CN | NHCH₂CONH₂ | NC(NH)NMe₂ | " |
| Me | CN | NHCH₂CONH₂ | NP(O)(OPr)₂ | " | Et | CN | NHCH₂CONH₂ | NC(NH)OMe | " |
| Me | CN | NHCH₂CONH₂ | NC(O)C(O)H | " | Et | CN | NHCH₂CONH₂ | NC(NH)OEt | " |
| Me | CN | NHCH₂CONH₂ | NC(O)C(O)Me | " | Me | CN | NHCH₂CH₂SMe | NCOMe | " |
| Me | CN | NHCH₂CONH₂ | NC(O)C(O)OMe | " | Me | CN | NHCH₂CH₂SMe | NCOEt | " |
| Me | CN | NHCH₂CONH₂ | NC(O)C(O)OEt | " | Me | CN | NHCH₂CH₂SMe | NCOPr | " |
| Me | CN | NHCH₂CONH₂ | NC(O)C(O)NH₂ | " | Me | CN | NHCH₂CH₂SMe | NCHO | " |
| Me | CN | NHCH₂CONH₂ | NC(O)C(O)OH | " | Me | CN | NHCH₂CH₂SMe | NCOiPr | " |
| Me | CN | NHCH₂CONH₂ | NC(NH)NH₂ | " | Me | CN | NHCH₂CH₂SMe | NCOtBu | " |
| Me | CN | NHCH₂CONH₂ | NC(NOH)NH₂ | " | Me | CN | NHCH₂CH₂SMe | NCOPh | " |
| Me | CN | NHCH₂CONH₂ | NC(NH)NHMe | " | Me | CN | NHCH₂CH₂SMe | NSO₂Me | " |
| Me | CN | NHCH₂CONH₂ | NC(NH)NMe₂ | " | Me | CN | NHCH₂CH₂SMe | NSO₂Et | " |
| Me | CN | NHCH₂CONH₂ | NC(NH)OMe | " | Me | CN | NHCH₂CH₂SMe | NSO₂Pr | " |
| Me | CN | NHCH₂CONH₂ | NC(NH)OEt | " | Me | CN | NHCH₂CH₂SMe | NSO₂Ph | " |
| Et | CN | NHCH₂CONH₂ | NCOMe | " | Me | CN | NHCH₂CH₂SMe | NSO₂iPr | " |
| Et | CN | NHCH₂CONH₂ | NCOEt | " | Me | CN | NHCH₂CH₂SMe | NNO₂ | " |
| Et | CN | NHCH₂CONH₂ | NCOPr | " | Me | CN | NHCH₂CH₂SMe | NCOOMe | " |
| Et | CN | NHCH₂CONH₂ | NCHO | " | Me | CN | NHCH₂CH₂SMe | NCOOEt | " |
| Et | CN | NHCH₂CONH₂ | NCOiPr | " | Me | CN | NHCH₂CH₂SMe | NCOOPr | " |
| Et | CN | NHCH₂CONH₂ | NCOtBu | " | Me | CN | NHCH₂CH₂SMe | NCOOiPr | " |
| Et | CN | NHCH₂CONH₂ | NCOPh | " | Me | CN | NHCH₂CH₂SMe | NCONHEt | " |
| Et | CN | NHCH₂CONH₂ | NSO₂Me | " | Me | CN | NHCH₂CH₂SMe | NCONHPr | " |
| Et | CN | NHCH₂CONH₂ | NSO₂Et | " | Me | CN | NHCH₂CH₂SMe | NCONH₂ | " |
| Et | CN | NHCH₂CONH₂ | NSO₂Pr | " | Me | CN | NHCH₂CH₂SMe | NCONHMe | " |
| Et | CN | NHCH₂CONH₂ | NSO₂Ph | " | Me | CN | NHCH₂CH₂SMe | NCN | " |
| Et | CN | NHCH₂CONH₂ | NSO₂iPr | " | Me | CN | NHCH₂CH₂SMe | NCOSMe | " |
| Et | CN | NHCH₂CONH₂ | NNO₂ | " | Me | CN | NHCH₂CH₂SMe | NCOSEt | " |
| Et | CN | NHCH₂CONH₂ | NCOOMe | " | Me | CN | NHCH₂CH₂SMe | NCSOMe | " |
| Et | CN | NHCH₂CONH₂ | NCOOEt | " | Me | CN | NHCH₂CH₂SMe | NCSOEt | " |
| Et | CN | NHCH₂CONH₂ | NCOOPr | " | Me | CN | NHCH₂CH₂SMe | NCSOPr | " |
| Et | CN | NHCH₂CONH₂ | NCOOiPr | " | Me | CN | NHCH₂CH₂SMe | NSO₂NH₂ | " |
| Et | CN | NHCH₂CONH₂ | NCONHEt | " | Me | CN | NHCH₂CH₂SMe | NSO₂NHMe | " |
| Et | CN | NHCH₂CONH₂ | NCONHPr | " | Me | CN | NHCH₂CH₂SMe | NSO₂NMe₂ | " |
| Et | CN | NHCH₂CONH₂ | NCONH₂ | " | Me | CN | NHCH₂CH₂SMe | NP(O)(OMe)₂ | " |
| Et | CN | NHCH₂CONH₂ | NCONHMe | " | Me | CN | NHCH₂CH₂SMe | NP(O)(OEt)₂ | " |
| Et | CN | NHCH₂CONH₂ | NCN | " | Me | CN | NHCH₂CH₂SMe | NP(O)Me₂ | " |
| Et | CN | NHCH₂CONH₂ | NCOSMe | " | Me | CN | NHCH₂CH₂SMe | NP(O)Et₂ | " |
| Et | CN | NHCH₂CONH₂ | NCOSEt | " | Me | CN | NHCH₂CH₂SMe | NP(O)Me(OMe) | " |
| Et | CN | NHCH₂CONH₂ | NCSOMe | " | Me | CN | NHCH₂CH₂SMe | NP(O)(OPr)₂ | " |
| Et | CN | NHCH₂CONH₂ | NCSOEt | " | Me | CN | NHCH₂CH₂SMe | NC(O)C(O)H | " |
| Et | CN | NHCH₂CONH₂ | NCSOPr | " | Me | CN | NHCH₂CH₂SMe | NC(O)C(O)Me | " |
| Et | CN | NHCH₂CONH₂ | NSO₂NH₂ | " | Me | CN | NHCH₂CH₂SMe | NC(O)C(O)OMe | " |
| Et | CN | NHCH₂CONH₂ | NSO₂NHMe | " | Me | CN | NHCH₂CH₂SMe | NC(O)C(O)OEt | " |
| Et | CN | NHCH₂CONH₂ | NSO₂NMe₂ | " | Me | CN | NHCH₂CH₂SMe | NC(O)C(O)NH₂ | " |
| Et | CN | NHCH₂CONH₂ | NP(O)(OMe)₂ | " | Me | CN | NHCH₂CH₂SMe | NC(O)C(O)OH | " |
| Et | CN | NHCH₂CONH₂ | NP(O)(OEt)₂ | " | Me | CN | NHCH₂CH₂SMe | NC(NH)NH₂ | " |
| Et | CN | NHCH₂CONH₂ | NP(O)Me₂ | " | Me | CN | NHCH₂CH₂SMe | NC(NOH)NH₂ | " |
| Et | CN | NHCH₂CONH₂ | NP(O)Et₂ | " | Me | CN | NHCH₂CH₂SMe | NC(NH)NHMe | " |
| Et | CN | NHCH₂CONH₂ | NP(O)Me(OMe) | " | Me | CN | NHCH₂CH₂SMe | NC(NH)NMe₂ | " |
| Et | CN | NHCH₂CONH₂ | NP(O)(OPr)₂ | " | Me | CN | NHCH₂CH₂SMe | NC(NH)OMe | " |
| Et | CN | NHCH₂CONH₂ | NC(O)C(O)H | " | Me | CN | NHCH₂CH₂SMe | NC(NH)OEt | " |

TABLE 2-continued

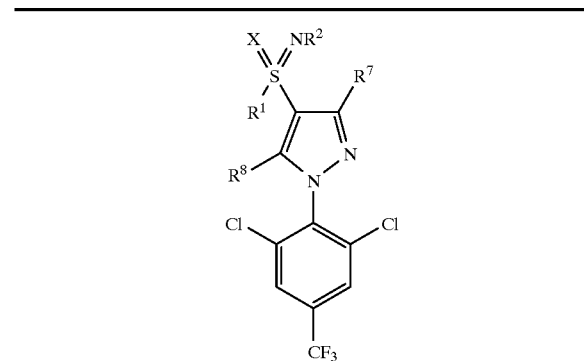

| R¹ | R⁷ | R⁸ | NR² | X |
|---|---|---|---|---|
| Me | CN | NHCH₂CH₂SOMe | NCOMe | " |
| Me | CN | NHCH₂CH₂SOMe | NCOEt | " |
| Me | CN | NHCH₂CH₂SOMe | NCOPr | " |
| Me | CN | NHCH₂CH₂SOMe | NCHO | " |
| Me | CN | NHCH₂CH₂SOMe | NCOiPr | " |
| Me | CN | NHCH₂CH₂SOMe | NCOtBu | " |
| Me | CN | NHCH₂CH₂SOMe | NCOPh | " |
| Me | CN | NHCH₂CH₂SOMe | NSO₂Me | " |
| Me | CN | NHCH₂CH₂SOMe | NSO₂Et | " |
| Me | CN | NHCH₂CH₂SOMe | NSO₂Pr | " |
| Me | CN | NHCH₂CH₂SOMe | NSO₂Ph | " |
| Me | CN | NHCH₂CH₂SOMe | NSO₂iPr | " |
| Me | CN | NHCH₂CH₂SOMe | NNO₂ | " |
| Me | CN | NHCH₂CH₂SOMe | NCOOMe | " |
| Me | CN | NHCH₂CH₂SOMe | NCOOEt | " |
| Me | CN | NHCH₂CH₂SOMe | NCOOPr | " |
| Me | CN | NHCH₂CH₂SOMe | NCOOiPr | " |
| Me | CN | NHCH₂CH₂SOMe | NCONHEt | " |
| Me | CN | NHCH₂CH₂SOMe | NCONHPr | " |
| Me | CN | NHCH₂CH₂SOMe | NCONH₂ | " |
| Me | CN | NHCH₂CH₂SOMe | NCONHMe | " |
| Me | CN | NHCH₂CH₂SOMe | NCN | " |
| Me | CN | NHCH₂CH₂SOMe | NCOSMe | " |
| Me | CN | NHCH₂CH₂SOMe | NCOSEt | " |
| Me | CN | NHCH₂CH₂SOMe | NCSOMe | " |
| Me | CN | NHCH₂CH₂SOMe | NCSOEt | " |
| Me | CN | NHCH₂CH₂SOMe | NCSOPr | " |
| Me | CN | NHCH₂CH₂SOMe | NSO₂NH₂ | " |
| Me | CN | NHCH₂CH₂SOMe | NSO₂NHMe | " |
| Me | CN | NHCH₂CH₂SOMe | NSO₂NMe₂ | " |
| Me | CN | NHCH₂CH₂SOMe | NP(O)(OMe)₂ | " |
| Me | CN | NHCH₂CH₂SOMe | NP(O)(OEt)₂ | " |
| Me | CN | NHCH₂CH₂SOMe | NP(O)Me₂ | " |
| Me | CN | NHCH₂CH₂SOMe | NP(O)Et₂ | " |
| Me | CN | NHCH₂CH₂SOMe | NP(O)Me(OMe) | " |
| Me | CN | NHCH₂CH₂SOMe | NP(O)(OPr)₂ | " |
| Me | CN | NHCH₂CH₂SOMe | NC(O)C(O)H | " |
| Me | CN | NHCH₂CH₂SOMe | NC(O)C(O)Me | " |
| Me | CN | NHCH₂CH₂SOMe | NC(O)C(O)OMe | " |
| Me | CN | NHCH₂CH₂SOMe | NC(O)C(O)OEt | " |
| Me | CN | NHCH₂CH₂SOMe | NC(O)C(O)NH₂ | " |
| Me | CN | NHCH₂CH₂SOMe | NC(O)C(O)OH | " |
| Me | CN | NHCH₂CH₂SOMe | NC(NH)NH₂ | " |
| Me | CN | NHCH₂CH₂SOMe | NC(NOH)NH₂ | " |
| Me | CN | NHCH₂CH₂SOMe | NC(NH)NHMe | " |
| Me | CN | NHCH₂CH₂SOMe | NC(NH)NMe₂ | " |
| Me | CN | NHCH₂CH₂SOMe | NC(NH)OMe | " |
| Me | CN | NHCH₂CH₂SOMe | NC(NH)OEt | " |
| Et | CN | NHCH₂CH₂SMe | NCOMe | " |
| Et | CN | NHCH₂CH₂SMe | NCOEt | " |
| Et | CN | NHCH₂CH₂SMe | NCOPr | " |
| Et | CN | NHCH₂CH₂SMe | NCHO | " |
| Et | CN | NHCH₂CH₂SMe | NCOiPr | " |
| Et | CN | NHCH₂CH₂SMe | NCOtBu | " |
| Et | CN | NHCH₂CH₂SMe | NCOPh | " |
| Et | CN | NHCH₂CH₂SMe | NSO₂Me | " |
| Et | CN | NHCH₂CH₂SMe | NSO₂Et | " |
| Et | CN | NHCH₂CH₂SMe | NSO₂Pr | " |
| Et | CN | NHCH₂CH₂SMe | NSO₂Ph | " |

TABLE 2-continued

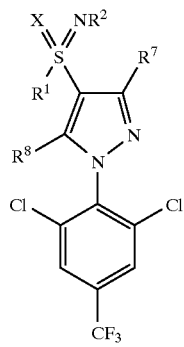

| R¹ | R⁷ | R⁸ | NR² | X |
|---|---|---|---|---|
| Et | CN | NHCH₂CH₂SMe | NSO₂iPr | " |
| Et | CN | NHCH₂CH₂SMe | NNO₂ | " |
| Et | CN | NHCH₂CH₂SMe | NCOOMe | " |
| Et | CN | NHCH₂CH₂SMe | NCOOEt | " |
| Et | CN | NHCH₂CH₂SMe | NCOOPr | " |
| Et | CN | NHCH₂CH₂SMe | NCOOiPr | " |
| Et | CN | NHCH₂CH₂SMe | NCONHEt | " |
| Et | CN | NHCH₂CH₂SMe | NCONHPr | " |
| Et | CN | NHCH₂CH₂SMe | NCONH₂ | " |
| Et | CN | NHCH₂CH₂SMe | NCONHMe | " |
| Et | CN | NHCH₂CH₂SMe | NCN | " |
| Et | CN | NHCH₂CH₂SMe | NCOSMe | " |
| Et | CN | NHCH₂CH₂SMe | NCOSEt | " |
| Et | CN | NHCH₂CH₂SMe | NCSOMe | " |
| Et | CN | NHCH₂CH₂SMe | NCSOEt | " |
| Et | CN | NHCH₂CH₂SMe | NCSOPr | " |
| Et | CN | NHCH₂CH₂SMe | NSO₂NH₂ | " |
| Et | CN | NHCH₂CH₂SMe | NSO₂NHMe | " |
| Et | CN | NHCH₂CH₂SMe | NSO₂NMe₂ | " |
| Et | CN | NHCH₂CH₂SMe | NP(O)(OMe)₂ | " |
| Et | CN | NHCH₂CH₂SMe | NP(O)(OEt)₂ | " |
| Et | CN | NHCH₂CH₂SMe | NP(O)Me₂ | " |
| Et | CN | NHCH₂CH₂SMe | NP(O)Et₂ | " |
| Et | CN | NHCH₂CH₂SMe | NP(O)Me(OMe) | " |
| Et | CN | NHCH₂CH₂SMe | NP(O)(OPr)₂ | " |
| Et | CN | NHCH₂CH₂SMe | NC(O)C(O)H | " |
| Et | CN | NHCH₂CH₂SMe | NC(O)C(O)Me | " |
| Et | CN | NHCH₂CH₂SMe | NC(O)C(O)OMe | " |
| Et | CN | NHCH₂CH₂SMe | NC(O)C(O)OEt | " |
| Et | CN | NHCH₂CH₂SMe | NC(O)C(O)NH₂ | " |
| Et | CN | NHCH₂CH₂SMe | NC(O)C(O)OH | " |
| Et | CN | NHCH₂CH₂SMe | NC(NH)NH₂ | " |
| Et | CN | NHCH₂CH₂SMe | NC(NOH)NH₂ | " |
| Et | CN | NHCH₂CH₂SMe | NC(NH)NHMe | " |
| Et | CN | NHCH₂CH₂SMe | NC(NH)NMe₂ | " |
| Et | CN | NHCH₂CH₂SMe | NC(NH)OMe | " |
| Et | CN | NHCH₂CH₂SMe | NC(NH)OEt | " |
| Et | CN | NHCH₂CH₂SOMe | NCOMe | " |
| Et | CN | NHCH₂CH₂SOMe | NCOEt | " |
| Et | CN | NHCH₂CH₂SOMe | NCOPr | " |
| Et | CN | NHCH₂CH₂SOMe | NCHO | " |
| Et | CN | NHCH₂CH₂SOMe | NCOiPr | " |
| Et | CN | NHCH₂CH₂SOMe | NCOtBu | " |
| Et | CN | NHCH₂CH₂SOMe | NCOPh | " |
| Et | CN | NHCH₂CH₂SOMe | NSO₂Me | " |
| Et | CN | NHCH₂CH₂SOMe | NSO₂Et | " |
| Et | CN | NHCH₂CH₂SOMe | NSO₂Pr | " |
| Et | CN | NHCH₂CH₂SOMe | NSO₂Ph | " |
| Et | CN | NHCH₂CH₂SOMe | NSO₂iPr | " |
| Et | CN | NHCH₂CH₂SOMe | NNO₂ | " |
| Et | CN | NHCH₂CH₂SOMe | NCOOMe | " |
| Et | CN | NHCH₂CH₂SOMe | NCOOEt | " |
| Et | CN | NHCH₂CH₂SOMe | NCOOPr | " |
| Et | CN | NHCH₂CH₂SOMe | NCOOiPr | " |
| Et | CN | NHCH₂CH₂SOMe | NCONHEt | " |
| Et | CN | NHCH₂CH₂SOMe | NCONHPr | " |
| Et | CN | NHCH₂CH₂SOMe | NCONH₂ | " |
| Et | CN | NHCH₂CH₂SOMe | NCONHMe | " |
| Et | CN | NHCH₂CH₂SOMe | NCN | " |

TABLE 2-continued

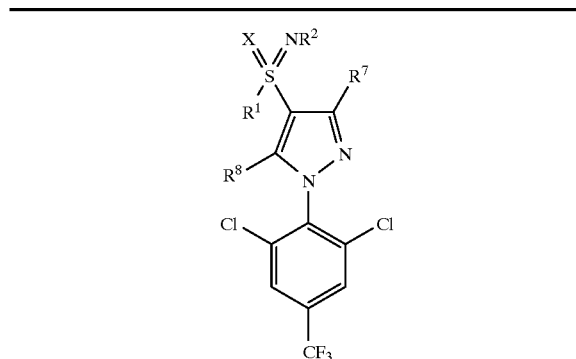

| R¹ | R⁷ | R⁸ | NR² | X |
|---|---|---|---|---|
| Et | CN | NHCH$_2$CH$_2$SOMe | NCOSMe | " |
| Et | CN | NHCH$_2$CH$_2$SOMe | NCOSEt | " |
| Et | CN | NHCH$_2$CH$_2$SOMe | NCSOMe | " |
| Et | CN | NHCH$_2$CH$_2$SOMe | NCSOEt | " |
| Et | CN | NHCH$_2$CH$_2$SOMe | NCSOPr | " |
| Et | CN | NHCH$_2$CH$_2$SOMe | NSO$_2$NH$_2$ | " |
| Et | CN | NHCH$_2$CH$_2$SOMe | NSO$_2$NHMe | " |
| Et | CN | NHCH$_2$CH$_2$SOMe | NSO$_2$NMe$_2$ | " |
| Et | CN | NHCH$_2$CH$_2$SOMe | NP(O)(OMe)$_2$ | " |
| Et | CN | NHCH$_2$CH$_2$SOMe | NP(O)(OEt)$_2$ | " |
| Et | CN | NHCH$_2$CH$_2$SOMe | NP(O)Me$_2$ | " |
| Et | CN | NHCH$_2$CH$_2$SOMe | NP(O)Et$_2$ | " |
| Et | CN | NHCH$_2$CH$_2$SOMe | NP(O)Me(OMe) | " |
| Et | CN | NHCH$_2$CH$_2$SOMe | NP(O)(OPr)$_2$ | " |
| Et | CN | NHCH$_2$CH$_2$SOMe | NC(O)C(O)H | " |
| Et | CN | NHCH$_2$CH$_2$SOMe | NC(O)C(O)Me | " |
| Et | CN | NHCH$_2$CH$_2$SOMe | NC(O)C(O)OMe | " |
| Et | CN | NHCH$_2$CH$_2$SOMe | NC(O)C(O)OEt | " |
| Et | CN | NHCH$_2$CH$_2$SOMe | NC(O)C(O)NH$_2$ | " |
| Et | CN | NHCH$_2$CH$_2$SOMe | NC(O)C(O)OH | " |
| Et | CN | NHCH$_2$CH$_2$SOMe | NC(NH)NH$_2$ | " |
| Et | CN | NHCH$_2$CH$_2$SOMe | NC(NOH)NH$_2$ | " |
| Et | CN | NHCH$_2$CH$_2$SOMe | NC(NH)NHMe | " |
| Et | CN | NHCH$_2$CH$_2$SOMe | NC(NH)NMe$_2$ | " |
| Et | CN | NHCH$_2$CH$_2$SOMe | NC(NH)OMe | " |
| Et | CN | NHCH$_2$CH$_2$SOMe | NC(NH)OEt | " |
| Me | CN | NHCOMe | NCOMe | O |
| Me | CN | NHCOMe | NCOEt | O |
| Me | CN | NHCOMe | NCOPr | O |
| Me | CN | NHCOMe | NCHO | O |
| Me | CN | NHCOMe | NCOiPr | O |
| Me | CN | NHCOMe | NCOtBu | O |
| Me | CN | NHCOMe | NCOPh | O |
| Me | CN | NHCOMe | NSO$_2$Me | O |
| Me | CN | NHCOMe | NSO$_2$Et | O |
| Me | CN | NHCOMe | NSO$_2$Pr | O |
| Me | CN | NHCOMe | NSO$_2$Ph | O |
| Me | CN | NHCOMe | NSO$_2$iPr | O |
| Me | CN | NHCOMe | NNO$_2$ | O |
| Me | CN | NHCOMe | NCOOMe | O |
| Me | CN | NHCOMe | NCOOEt | O |
| Me | CN | NHCOMe | NCOOPr | O |
| Me | CN | NHCOMe | NCOOiPr | O |
| Me | CN | NHCOMe | NCONHEt | O |
| Me | CN | NHCOMe | NCONHPr | O |
| Me | CN | NHCOMe | NCONH$_2$ | O |
| Me | CN | NHCOMe | NCONHMe | O |
| Me | CN | NHCOMe | NCN | O |
| Me | CN | NHCOMe | NCOSMe | O |
| Me | CN | NHCOMe | NCOSEt | O |
| Me | CN | NHCOMe | NCSOMe | O |
| Me | CN | NHCOMe | NCSOEt | O |
| Me | CN | NHCOMe | NCSOPr | O |
| Me | CN | NHCOMe | NSO$_2$NH$_2$ | O |
| Me | CN | NHCOMe | NSO$_2$NHMe | O |
| Me | CN | NHCOMe | NSO$_2$NMe$_2$ | O |
| Me | CN | NHCOMe | NP(O)(OMe)$_2$ | O |
| Me | CN | NHCOMe | NP(O)(OEt)$_2$ | O |
| Me | CN | NHCOMe | NP(O)Me$_2$ | O |
| Me | CN | NHCOMe | NP(O)Et$_2$ | O |
| Me | CN | NHCOMe | NP(O)Me(OMe) | O |
| Me | CN | NHCOMe | NP(O)(OPr)$_2$ | O |
| Me | CN | NHCOMe | NC(O)C(O)H | O |
| Me | CN | NHCOMe | NC(O)C(O)Me | O |
| Me | CN | NHCOMe | NC(O)C(O)OMe | O |
| Me | CN | NHCOMe | NC(O)C(O)OEt | O |
| Me | CN | NHCOMe | NC(O)C(O)NH$_2$ | O |
| Me | CN | NHCOMe | NC(O)C(O)OH | O |
| Me | CN | NHCOMe | NC(NH)NH$_2$ | O |
| Me | CN | NHCOMe | NC(NOH)NH$_2$ | O |
| Me | CN | NHCOMe | NC(NH)NHMe | O |
| Me | CN | NHCOMe | NC(NH)NMe$_2$ | O |
| Me | CN | NHCOMe | NC(NH)OMe | O |
| Me | CN | NHCOMe | NC(NH)OEt | O |
| Et | CN | NHCOMe | NCOMe | O |
| Et | CN | NHCOMe | NCOEt | O |
| Et | CN | NHCOMe | NCOPr | O |
| Et | CN | NHCOMe | NCHO | O |
| Et | CN | NHCOMe | NCOiPr | O |
| Et | CN | NHCOMe | NCOtBu | O |
| Et | CN | NHCOMe | NCOPh | O |
| Et | CN | NHCOMe | NSO$_2$Me | O |
| Et | CN | NHCOMe | NSO$_2$Et | O |
| Et | CN | NHCOMe | NSO$_2$Pr | O |
| Et | CN | NHCOMe | NSO$_2$Ph | O |
| Et | CN | NHCOMe | NSO$_2$iPr | O |
| Et | CN | NHCOMe | NNO$_2$ | O |
| Et | CN | NHCOMe | NCOOMe | O |
| Et | CN | NHCOMe | NCOOEt | O |
| Et | CN | NHCOMe | NCOOPr | O |
| Et | CN | NHCOMe | NCOOiPr | O |
| Et | CN | NHCOMe | NCONHEt | O |
| Et | CN | NHCOMe | NCONHPr | O |
| Et | CN | NHCOMe | NCONH$_2$ | O |
| Et | CN | NHCOMe | NCONHMe | O |
| Et | CN | NHCOMe | NCN | O |
| Et | CN | NHCOMe | NCOSMe | O |
| Et | CN | NHCOMe | NCOSEt | O |
| Et | CN | NHCOMe | NCSOMe | O |
| Et | CN | NHCOMe | NCSOEt | O |
| Et | CN | NHCOMe | NCSOPr | O |
| Et | CN | NHCOMe | NSO$_2$NH$_2$ | O |
| Et | CN | NHCOMe | NSO$_2$NHMe | O |
| Et | CN | NHCOMe | NSO$_2$NMe$_2$ | O |
| Et | CN | NHCOMe | NP(O)(OMe)$_2$ | O |
| Et | CN | NHCOMe | NP(O)(OEt)$_2$ | O |
| Et | CN | NHCOMe | NP(O)Me$_2$ | O |
| Et | CN | NHCOMe | NP(O)Et$_2$ | O |
| Et | CN | NHCOMe | NP(O)Me(OMe) | O |
| Et | CN | NHCOMe | NP(O)(OPr)$_2$ | O |
| Et | CN | NHCOMe | NC(O)C(O)H | O |
| Et | CN | NHCOMe | NC(O)C(O)Me | O |
| Et | CN | NHCOMe | NC(O)C(O)OMe | O |
| Et | CN | NHCOMe | NC(O)C(O)OEt | O |
| Et | CN | NHCOMe | NC(O)C(O)NH$_2$ | O |
| Et | CN | NHCOMe | NC(O)C(O)OH | O |
| Et | CN | NHCOMe | NC(NH)NH$_2$ | O |
| Et | CN | NHCOMe | NC(NOH)NH$_2$ | O |

TABLE 2-continued

| R¹ | R⁷ | R⁸ | NR² | X |
|---|---|---|---|---|
| Et | CN | NHCOMe | NC(NH)NHMe | O |
| Et | CN | NHCOMe | NC(NH)NMe₂ | O |
| Et | CN | NHCOMe | NC(NH)OMe | O |
| Et | CN | NHCOMe | NC(NH)OEt | O |
| Me | CN | NHCOOMe | NCOMe | O |
| Me | CN | NHCOOMe | NCOEt | O |
| Me | CN | NHCOOMe | NCOPr | O |
| Me | CN | NHCOOMe | NCHO | O |
| Me | CN | NHCOOMe | NCOiPr | O |
| Me | CN | NHCOOMe | NCOtBu | O |
| Me | CN | NHCOOMe | NCOPh | O |
| Me | CN | NHCOOMe | NSO₂Me | O |
| Me | CN | NHCOOMe | NSO₂Et | O |
| Me | CN | NHCOOMe | NSO₂Pr | O |
| Me | CN | NHCOOMe | NSO₂Ph | O |
| Me | CN | NHCOOMe | NSO₂iPr | O |
| Me | CN | NHCOOMe | NNO₂ | O |
| Me | CN | NHCOOMe | NCOOMe | O |
| Me | CN | NHCOOMe | NCOOEt | O |
| Me | CN | NHCOOMe | NCOOPr | O |
| Me | CN | NHCOOMe | NCOOiPr | O |
| Me | CN | NHCOOMe | NCONHEt | O |
| Me | CN | NHCOOMe | NCONHPr | O |
| Me | CN | NHCOOMe | NCONH₂ | O |
| Me | CN | NHCOOMe | NCONHMe | O |
| Me | CN | NHCOOMe | NCN | O |
| Me | CN | NHCOOMe | NCOSMe | O |
| Me | CN | NHCOOMe | NCOSEt | O |
| Me | CN | NHCOOMe | NCSOMe | O |
| Me | CN | NHCOOMe | NCSOEt | O |
| Me | CN | NHCOOMe | NCSOPr | O |
| Me | CN | NHCOOMe | NSO₂NH₂ | O |
| Me | CN | NHCOOMe | NSO₂NHMe | O |
| Me | CN | NHCOOMe | NSO₂NMe₂ | O |
| Me | CN | NHCOOMe | NP(O)(OMe)₂ | O |
| Me | CN | NHCOOMe | NP(O)(OEt)₂ | O |
| Me | CN | NHCOOMe | NP(O)Me₂ | O |
| Me | CN | NHCOOMe | NP(O)Et₂ | O |
| Me | CN | NHCOOMe | NP(O)Me(OMe) | O |
| Me | CN | NHCOOMe | NP(O)(OPr)₂ | O |
| Me | CN | NHCOOMe | NC(O)C(O)H | O |
| Me | CN | NHCOOMe | NC(O)C(O)Me | O |
| Me | CN | NHCOOMe | NC(O)C(O)OMe | O |
| Me | CN | NHCOOMe | NC(O)C(O)OEt | O |
| Me | CN | NHCOOMe | NC(O)C(O)NH₂ | O |
| Me | CN | NHCOOMe | NC(O)C(O)OH | O |
| Me | CN | NHCOOMe | NC(NH)NH₂ | O |
| Me | CN | NHCOOMe | NC(NOH)NH₂ | O |
| Me | CN | NHCOOMe | NC(NH)NHMe | O |
| Me | CN | NHCOOMe | NC(NH)NMe₂ | O |
| Me | CN | NHCOOMe | NC(NH)OMe | O |
| Me | CN | NHCOOMe | NC(NH)OEt | O |
| Et | CN | NHCOOMe | NCOMe | O |
| Et | CN | NHCOOMe | NCOEt | O |
| Et | CN | NHCOOMe | NCOPr | O |
| Et | CN | NHCOOMe | NCHO | O |
| Et | CN | NHCOOMe | NCOiPr | O |
| Et | CN | NHCOOMe | NCOtBu | O |
| Et | CN | NHCOOMe | NCOPh | O |
| Et | CN | NHCOOMe | NSO₂Me | O |
| Et | CN | NHCOOMe | NSO₂Et | O |
| Et | CN | NHCOOMe | NSO₂Pr | O |
| Et | CN | NHCOOMe | NSO₂Ph | O |
| Et | CN | NHCOOMe | NSO₂iPr | O |
| Et | CN | NHCOOMe | NNO₂ | O |
| Et | CN | NHCOOMe | NCOOMe | O |
| Et | CN | NHCOOMe | NCOOEt | O |
| Et | CN | NHCOOMe | NCOOPr | O |
| Et | CN | NHCOOMe | NCOOiPr | O |
| Et | CN | NHCOOMe | NCONHEt | O |
| Et | CN | NHCOOMe | NCONHPr | O |
| Et | CN | NHCOOMe | NCONH₂ | O |
| Et | CN | NHCOOMe | NCONHMe | O |
| Et | CN | NHCOOMe | NCN | O |
| Et | CN | NHCOOMe | NCOSMe | O |
| Et | CN | NHCOOMe | NCOSEt | O |
| Et | CN | NHCOOMe | NCSOMe | O |
| Et | CN | NHCOOMe | NCSOEt | O |
| Et | CN | NHCOOMe | NCSOPr | O |
| Et | CN | NHCOOMe | NSO₂NH₂ | O |
| Et | CN | NHCOOMe | NSO₂NHMe | O |
| Et | CN | NHCOOMe | NSO₂NMe₂ | O |
| Et | CN | NHCOOMe | NP(O)(OMe)₂ | O |
| Et | CN | NHCOOMe | NP(O)(OEt)₂ | O |
| Et | CN | NHCOOMe | NP(O)Me₂ | O |
| Et | CN | NHCOOMe | NP(O)Et₂ | O |
| Et | CN | NHCOOMe | NP(O)Me(OMe) | O |
| Et | CN | NHCOOMe | NP(O)(OPr)₂ | O |
| Et | CN | NHCOOMe | NC(O)C(O)H | O |
| Et | CN | NHCOOMe | NC(O)C(O)Me | O |
| Et | CN | NHCOOMe | NC(O)C(O)OMe | O |
| Et | CN | NHCOOMe | NC(O)C(O)OEt | O |
| Et | CN | NHCOOMe | NC(O)C(O)NH₂ | O |
| Et | CN | NHCOOMe | NC(O)C(O)OH | O |
| Et | CN | NHCOOMe | NC(NH)NH₂ | O |
| Et | CN | NHCOOMe | NC(NOH)NH₂ | O |
| Et | CN | NHCOOMe | NC(NH)NHMe | O |
| Et | CN | NHCOOMe | NC(NH)NMe₂ | O |
| Et | CN | NHCOOMe | NC(NH)OMe | O |
| Et | CN | NHCOOMe | NC(NH)OEt | O |
| CF₃ | CN | NH₂ | NCOMe | " |
| CF₃ | CN | NH₂ | NCOEt | " |
| CF₃ | CN | NH₂ | NCOPr | " |
| CF₃ | CN | NH₂ | NCHO | " |
| CF₃ | CN | NH₂ | NCOiPr | " |
| CF₃ | CN | NH₂ | NCOtBu | " |
| CF₃ | CN | NH₂ | NCOPh | " |
| CF₃ | CN | NH₂ | NSO₂Me | " |
| CF₃ | CN | NH₂ | NSO₂Et | " |
| CF₃ | CN | NH₂ | NSO₂Pr | " |
| CF₃ | CN | NH₂ | NSO₂Ph | " |
| CF₃ | CN | NH₂ | NSO₂iPr | " |
| CF₃ | CN | NH₂ | NNO₂ | " |
| CF₃ | CN | NH₂ | NCOOMe | " |
| CF₃ | CN | NH₂ | NCOOEt | " |
| CF₃ | CN | NH₂ | NCOOPr | " |
| CF₃ | CN | NH₂ | NCOOiPr | " |
| CF₃ | CN | NH₂ | NCONHEt | " |

TABLE 2-continued

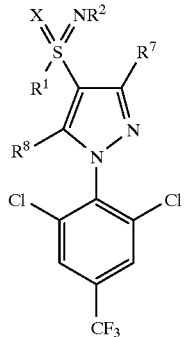

| R¹ | R⁷ | R⁸ | NR² | X |
|---|---|---|---|---|
| CF₃ | CN | NH₂ | NCONHPr | " |
| CF₃ | CN | NH₂ | NCONH₂ | " |
| CF₃ | CN | NH₂ | NCONHMe | " |
| CF₃ | CN | NH₂ | NCN | " |
| CF₃ | CN | NH₂ | NCOSMe | " |
| CF₃ | CN | NH₂ | NCOSEt | " |
| CF₃ | CN | NH₂ | NCSOMe | " |
| CF₃ | CN | NH₂ | NCSOEt | " |
| CF₃ | CN | NH₂ | NCSOPr | " |
| CF₃ | CN | NH₂ | NSO₂NH₂ | " |
| CF₃ | CN | NH₂ | NSO₂NHMe | " |
| CF₃ | CN | NH₂ | NSO₂NMe₂ | " |
| CF₃ | CN | NH₂ | NP(O)(OMe)₂ | " |
| CF₃ | CN | NH₂ | NP(O)(OEt)₂ | " |
| CF₃ | CN | NH₂ | NP(O)Me₂ | " |
| CF₃ | CN | NH₂ | NP(O)Et₂ | " |
| CF₃ | CN | NH₂ | NP(O)Me(OMe) | " |
| CF₃ | CN | NH₂ | NP(O)(OPr)₂ | " |
| CF₃ | CN | NH₂ | NC(O)C(O)H | " |
| CF₃ | CN | NH₂ | NC(O)C(O)Me | " |
| CF₃ | CN | NH₂ | NC(O)C(O)OMe | " |
| CF₃ | CN | NH₂ | NC(O)C(O)OEt | " |
| CF₃ | CN | NH₂ | NC(O)C(O)NH₂ | " |
| CF₃ | CN | NH₂ | NC(O)C(O)OH | " |
| CF₃ | CN | NH₂ | NC(NH)NH₂ | " |
| CF₃ | CN | NH₂ | NC(NOH)NH₂ | " |
| CF₃ | CN | NH₂ | NC(NH)NHMe | " |
| CF₃ | CN | NH₂ | NC(NH)NMe₂ | " |
| CF₃ | CN | NH₂ | NC(NH)OMe | " |
| CF₃ | CN | NH₂ | NC(NH)OEt | " |
| CF₃ | CN | NHMe | NCOMe | " |
| CF₃ | CN | NHMe | NCOEt | " |
| CF₃ | CN | NHMe | NCOPr | " |
| CF₃ | CN | NHMe | NCHO | " |
| CF₃ | CN | NHMe | NCOiPr | " |
| CF₃ | CN | NHMe | NCOtBu | " |
| CF₃ | CN | NHMe | NCOPh | " |
| CF₃ | CN | NHMe | NSO₂Me | " |
| CF₃ | CN | NHMe | NSO₂Et | " |
| CF₃ | CN | NHMe | NSO₂Pr | " |
| CF₃ | CN | NHMe | NSO₂Ph | " |
| CF₃ | CN | NHMe | NSO₂iPr | " |
| CF₃ | CN | NHMe | NNO₂ | " |
| CF₃ | CN | NHMe | NCOOMe | " |
| CF₃ | CN | NHMe | NCOOEt | " |
| CF₃ | CN | NHMe | NCOOPr | " |
| CF₃ | CN | NHMe | NCOOiPr | " |
| CF₃ | CN | NHMe | NCONHEt | " |
| CF₃ | CN | NHMe | NCONHPr | " |
| CF₃ | CN | NHMe | NCONH₂ | " |
| CF₃ | CN | NHMe | NCONHMe | " |
| CF₃ | CN | NHMe | NCN | " |
| CF₃ | CN | NHMe | NCOSMe | " |
| CF₃ | CN | NHMe | NCOSEt | " |
| CF₃ | CN | NHMe | NCSOMe | " |
| CF₃ | CN | NHMe | NCSOEt | " |
| CF₃ | CN | NHMe | NCSOPr | " |
| CF₃ | CN | NHMe | NSO₂NH₂ | " |
| CF₃ | CN | NHMe | NSO₂NHMe | " |

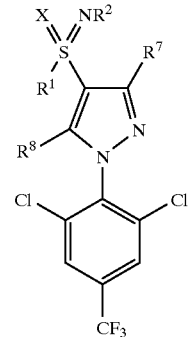

| R¹ | R⁷ | R⁸ | NR² | X |
|---|---|---|---|---|
| CF₃ | CN | NHMe | NSO₂NMe₂ | " |
| CF₃ | CN | NHMe | NP(O)(OMe)₂ | " |
| CF₃ | CN | NHMe | NP(O)(OEt)₂ | " |
| CF₃ | CN | NHMe | NP(O)Me₂ | " |
| CF₃ | CN | NHMe | NP(O)Et₂ | " |
| CF₃ | CN | NHMe | NP(O)Me(OMe) | " |
| CF₃ | CN | NHMe | NP(O)(OPr)₂ | " |
| CF₃ | CN | NHMe | NC(O)C(O)H | " |
| CF₃ | CN | NHMe | NC(O)C(O)Me | " |
| CF₃ | CN | NHMe | NC(O)C(O)OMe | " |
| CF₃ | CN | NHMe | NC(O)C(O)OEt | " |
| CF₃ | CN | NHMe | NC(O)C(O)NH₂ | " |
| CF₃ | CN | NHMe | NC(O)C(O)OH | " |
| CF₃ | CN | NHMe | NC(NH)NH₂ | " |
| CF₃ | CN | NHMe | NC(NOH)NH₂ | " |
| CF₃ | CN | NHMe | NC(NH)NHMe | " |
| CF₃ | CN | NHMe | NC(NH)NMe₂ | " |
| CF₃ | CN | NHMe | NC(NH)OMe | " |
| CF₃ | CN | NHMe | NC(NH)OEt | " |
| CF₃ | CN | NHEt | NCOMe | " |
| CF₃ | CN | NHEt | NCOEt | " |
| CF₃ | CN | NHEt | NCOPr | " |
| CF₃ | CN | NHEt | NCHO | " |
| CF₃ | CN | NHEt | NCOiPr | " |
| CF₃ | CN | NHEt | NCOtBu | " |
| CF₃ | CN | NHEt | NCOPh | " |
| CF₃ | CN | NHEt | NSO₂Me | " |
| CF₃ | CN | NHEt | NSO₂Et | " |
| CF₃ | CN | NHEt | NSO₂Pr | " |
| CF₃ | CN | NHEt | NSO₂Ph | " |
| CF₃ | CN | NHEt | NSO₂iPr | " |
| CF₃ | CN | NHEt | NNO₂ | " |
| CF₃ | CN | NHEt | NCOOMe | " |
| CF₃ | CN | NHEt | NCOOEt | " |
| CF₃ | CN | NHEt | NCOOPr | " |
| CF₃ | CN | NHEt | NCOOiPr | " |
| CF₃ | CN | NHEt | NCONHEt | " |
| CF₃ | CN | NHEt | NCONHPr | " |
| CF₃ | CN | NHEt | NCONH₂ | " |
| CF₃ | CN | NHEt | NCONHMe | " |
| CF₃ | CN | NHEt | NCN | " |
| CF₃ | CN | NHEt | NCOSMe | " |
| CF₃ | CN | NHEt | NCOSEt | " |
| CF₃ | CN | NHEt | NCSOMe | " |
| CF₃ | CN | NHEt | NCSOEt | " |
| CF₃ | CN | NHEt | NCSOPr | " |
| CF₃ | CN | NHEt | NSO₂NH₂ | " |
| CF₃ | CN | NHEt | NSO₂NHMe | " |
| CF₃ | CN | NHE | NSO₂NMe₂ | " |
| CF₃ | CN | NHEt | NP(O)(OMe)₂ | " |
| CF₃ | CN | NHEt | NP(O)(OEt)₂ | " |
| CF₃ | CN | NHEt | NP(O)Me₂ | " |
| CF₃ | CN | NHEt | NP(O)Et₂ | " |
| CF₃ | CN | NHEt | NP(O)Me(OMe) | " |
| CF₃ | CN | NHEt | NP(O)(OPr)₂ | " |
| CF₃ | CN | NHEt | NC(O)C(O)H | " |
| CF₃ | CN | NHEt | NC(O)C(O)Me | " |
| CF₃ | CN | NHEt | NC(O)C(O)OMe | " |
| CF₃ | CN | NHEt | NC(O)C(O)OEt | " |

TABLE 2-continued

[Structure: pyrazole with S(=X)(=NR²) group bearing R¹, R⁷ at 3-position, R⁸ at 5-position, and N-1 attached to 2,6-dichloro-4-(trifluoromethyl)phenyl]

| R¹ | R⁷ | R⁸ | NR² | X |
|---|---|---|---|---|
| CF₃ | CN | NHEt | NC(O)C(O)NH₂ | " |
| CF₃ | CN | NHEt | NC(O)C(O)OH | " |
| CF₃ | CN | NHEt | NC(NH)NH₂ | " |
| CF₃ | CN | NHEt | NC(NOH)NH₂ | " |
| CF₃ | CN | NHEt | NC(NH)NHMe | " |
| CF₃ | CN | NHEt | NC(NH)NMe₂ | " |
| CF₃ | CN | NHEt | NC(NH)OMe | " |
| CF₃ | CN | NHEt | NC(NH)OEt | " |
| CF₃ | CN | NHCOMe | NCOMe | " |
| CF₃ | CN | NHCOMe | NCOEt | " |
| CF₃ | CN | NHCOMe | NCOPr | " |
| CF₃ | CN | NHCOMe | NCHO | " |
| CF₃ | CN | NHCOMe | NCOiPr | " |
| CF₃ | CN | NHCOMe | NCOtBu | " |
| CF₃ | CN | NHCOMe | NCOPh | " |
| CF₃ | CN | NHCOMe | NSO₂Me | " |
| CF₃ | CN | NHCOMe | NSO₂Et | " |
| CF₃ | CN | NHCOMe | NSO₂Pr | " |
| CF₃ | CN | NHCOMe | NSO₂Ph | " |
| CF₃ | CN | NHCOMe | NSO₂iPr | " |
| CF₃ | CN | NHCOMe | NNO₂ | " |
| CF₃ | CN | NHCOMe | NCOOMe | " |
| CF₃ | CN | NHCOMe | NCOOEt | " |
| CF₃ | CN | NHCOMe | NCOOPr | " |
| CF₃ | CN | NHCOMe | NCOOiPr | " |
| CF₃ | CN | NHCOMe | NCONHEt | " |
| CF₃ | CN | NHCOMe | NCONHPr | " |
| CF₃ | CN | NHCOMe | NCONH₂ | " |
| CF₃ | CN | NHCOMe | NCONHMe | " |
| CF₃ | CN | NHCOMe | NCN | " |
| CF₃ | CN | NHCOMe | NCOSMe | " |
| CF₃ | CN | NHCOMe | NCOSEt | " |
| CF₃ | CN | NHCOMe | NCSOMe | " |
| CF₃ | CN | NHCOMe | NCSOEt | " |
| CF₃ | CN | NHCOMe | NCSOPr | " |
| CF₃ | CN | NHCOMe | NSO₂NH₂ | " |
| CF₃ | CN | NHCOMe | NSO₂NHMe | " |
| CF₃ | CN | NHCOMe | NSO₂NMe₂ | " |
| CF₃ | CN | NHCOMe | NP(O)(OMe)₂ | " |
| CF₃ | CN | NHCOMe | NP(O)(OEt)₂ | " |
| CF₃ | CN | NHCOMe | NP(O)Me₂ | " |
| CF₃ | CN | NHCOMe | NP(O)Et₂ | " |
| CF₃ | CN | NHCOMe | NP(O)Me(OMe) | " |
| CF₃ | CN | NHCOMe | NP(O)(OPr)₂ | " |
| CF₃ | CN | NHCOMe | NC(O)C(O)H | " |
| CF₃ | CN | NHCOMe | NC(O)C(O)Me | " |
| CF₃ | CN | NHCOMe | NC(O)C(O)OMe | " |
| CF₃ | CN | NHCOMe | NC(O)C(O)OEt | " |
| CF₃ | CN | NHCOMe | NC(O)C(O)NH₂ | " |
| CF₃ | CN | NHCOMe | NC(O)C(O)OH | " |
| CF₃ | CN | NHCOMe | NC(NH)NH₂ | " |
| CF₃ | CN | NHCOMe | NC(NOH)NH₂ | " |
| CF₃ | CN | NHCOMe | NC(NH)NHMe | " |
| CF₃ | CN | NHCOMe | NC(NH)NMe₂ | " |
| CF₃ | CN | NHCOMe | NC(NH)OMe | " |
| CF₃ | CN | NHCOMe | NC(NH)OEt | " |
| CF₃ | CN | NH₂ | NCOMe | O |
| CF₃ | CN | NH₂ | NH | O |
| CF₃ | CN | NH₂ | NCOEt | O |
| CF₃ | CN | NH₂ | NCOPr | O |
| CF₃ | CN | NH₂ | NCHO | O |
| CF₃ | CN | NH₂ | NCOiPr | O |
| CF₃ | CN | NH₂ | NCOtBu | O |
| CF₃ | CN | NH₂ | NCOPh | O |
| CF₃ | CN | NH₂ | NSO₂Me | O |
| CF₃ | CN | NH₂ | NSO₂Et | O |
| CF₃ | CN | NH₂ | NSO₂Pr | O |
| CF₃ | CN | NH₂ | NSO₂Ph | O |
| CF₃ | CN | NH₂ | NSO₂iPr | O |
| CF₃ | CN | NH₂ | NNO₂ | O |
| CF₃ | CN | NH₂ | NCOOMe | O |
| CF₃ | CN | NH₂ | NCOOEt | O |
| CF₃ | CN | NH₂ | NCOOPr | O |
| CF₃ | CN | NH₂ | NCOOiPr | O |
| CF₃ | CN | NH₂ | NCONHEt | O |
| CF₃ | CN | NH₂ | NCONHPr | O |
| CF₃ | CN | NH₂ | NCONH₂ | O |
| CF₃ | CN | NH₂ | NCONHMe | O |
| CF₃ | CN | NH₂ | NCN | O |
| CF₃ | CN | NH₂ | NCOSMe | O |
| CF₃ | CN | NH₂ | NCOSEt | O |
| CF₃ | CN | NH₂ | NCSOMe | O |
| CF₃ | CN | NH₂ | NCSOEt | O |
| CF₃ | CN | NH₂ | NCSOPr | O |
| CF₃ | CN | NH₂ | NSO₂NH₂ | O |
| CF₃ | CN | NH₂ | NSO₂NHMe | O |
| CF₃ | CN | NH₂ | NSO₂NMe₂ | O |
| CF₃ | CN | NH₂ | NP(O)(OMe)₂ | O |
| CF₃ | CN | NH₂ | NP(O)(OEt)₂ | O |
| CF₃ | CN | NH₂ | NP(O)Me₂ | O |
| CF₃ | CN | NH₂ | NP(O)Et₂ | O |
| CF₃ | CN | NH₂ | NP(O)Me(OMe) | O |
| CF₃ | CN | NH₂ | NP(O)(OPr)₂ | O |
| CF₃ | CN | NH₂ | NC(O)C(O)H | O |
| CF₃ | CN | NH₂ | NC(O)C(O)Me | O |
| CF₃ | CN | NH₂ | NC(O)C(O)OMe | O |
| CF₃ | CN | NH₂ | NC(O)C(O)OEt | O |
| CF₃ | CN | NH₂ | NC(O)C(O)NH₂ | O |
| CF₃ | CN | NH₂ | NC(O)C(O)OH | O |
| CF₃ | CN | NH₂ | NC(NH)NH₂ | O |
| CF₃ | CN | NH₂ | NC(NOH)NH₂ | O |
| CF₃ | CN | NH₂ | NC(NH)NHMe | O |
| CF₃ | CN | NH₂ | NC(NH)NMe₂ | O |
| CF₃ | CN | NH₂ | NC(NH)OMe | O |
| CF₃ | CN | NH₂ | NC(NH)OEt | O |
| CF₃ | CN | NHMe | NCOMe | O |
| CF₃ | CN | NHMe | NCOEt | O |
| CF₃ | CN | NHMe | NCOPr | O |
| CF₃ | CN | NHMe | NCHO | O |
| CF₃ | CN | NHMe | NCOiPr | O |
| CF₃ | CN | NHMe | NCOtBu | O |
| CF₃ | CN | NHMe | NCOPh | O |
| CF₃ | CN | NHMe | NSO₂Me | O |
| CF₃ | CN | NHMe | NSO₂Et | O |
| CF₃ | CN | NHMe | NSO₂Pr | O |
| CF₃ | CN | NHMe | NSO₂Ph | O |
| CF₃ | CN | NHMe | NSO₂iPr | O |
| CF₃ | CN | NHMe | NNO₂ | O |

TABLE 2-continued

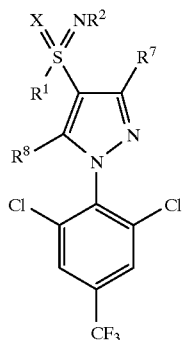

| R¹ | R⁷ | R⁸ | NR² | X |
|---|---|---|---|---|
| CF₃ | CN | NHMe | NCOOMe | O |
| CF₃ | CN | NHMe | NCOOEt | O |
| CF₃ | CN | NHMe | NCOOPr | O |
| CF₃ | CN | NHMe | NCOOiPr | O |
| CF₃ | CN | NHMe | NCONHEt | O |
| CF₃ | CN | NHMe | NCONHPr | O |
| CF₃ | CN | NHMe | NCONH₂ | O |
| CF₃ | CN | NHMe | NCONHMe | O |
| CF₃ | CN | NHMe | NCN | O |
| CF₃ | CN | NHMe | NCOSMe | O |
| CF₃ | CN | NHMe | NCOSEt | O |
| CF₃ | CN | NHMe | NCSOMe | O |
| CF₃ | CN | NHMe | NCSOEt | O |
| CF₃ | CN | NHMe | NCSOPr | O |
| CF₃ | CN | NHMe | NSO₂NH₂ | O |
| CF₃ | CN | NHMe | NSO₂NHMe | O |
| CF₃ | CN | NHMe | NSO₂NMe₂ | O |
| CF₃ | CN | NHMe | NP(O)(OMe)₂ | O |
| CF₃ | CN | NHMe | NP(O)(OEt)₂ | O |
| CF₃ | CN | NHMe | NP(O)Me₂ | O |
| CF₃ | CN | NHMe | NP(O)Et₂ | O |
| CF₃ | CN | NHMe | NP(O)Me(OMe) | O |
| CF₃ | CN | NHMe | NP(O)(OPr)₂ | O |
| CF₃ | CN | NHMe | NC(O)C(O)H | O |
| CF₃ | CN | NHMe | NC(O)C(O)Me | O |
| CF₃ | CN | NHMe | NC(O)C(O)OMe | O |
| CF₃ | CN | NHMe | NC(O)C(O)OEt | O |
| CF₃ | CN | NHMe | NC(O)C(O)NH₂ | O |
| CF₃ | CN | NHMe | NC(O)C(O)OH | O |
| CF₃ | CN | NHMe | NC(NH)NH₂ | O |
| CF₃ | CN | NHMe | NC(NOH)NH₂ | O |
| CF₃ | CN | NHMe | NC(NH)NHMe | O |
| CF₃ | CN | NHMe | NC(NH)NMe₂ | O |
| CF₃ | CN | NHMe | NC(NH)OMe | O |
| CF₃ | CN | NHMe | NC(NH)OEt | O |
| CF₃ | CN | NHEt | NCOMe | O |
| CF₃ | CN | NHEt | NCOEt | O |
| CF₃ | CN | NHEt | NCOPr | O |
| CF₃ | CN | NHEt | NCHO | O |
| CF₃ | CN | NHEt | NCOiPr | O |
| CF₃ | CN | NHEt | NCOtBu | O |
| CF₃ | CN | NHEt | NCOPh | O |
| CF₃ | CN | NHEt | NSO₂Me | O |
| CF₃ | CN | NHEt | NSO₂Et | O |
| CF₃ | CN | NHEt | NSO₂Pr | O |
| CF₃ | CN | NHEt | NSO₂Ph | O |
| CF₃ | CN | NHEt | NSO₂iPr | O |
| CF₃ | CN | NHEt | NNO₂ | O |
| CF₃ | CN | NHEt | NCOOMe | O |
| CF₃ | CN | NHEt | NCOOEt | O |
| CF₃ | CN | NHEt | NCOOPr | O |
| CF₃ | CN | NHEt | NCOOiPr | O |
| CF₃ | CN | NHEt | NCONHEt | O |
| CF₃ | CN | NHEt | NCONHPr | O |
| CF₃ | CN | NHEt | NCONH₂ | O |
| CF₃ | CN | NHEt | NCONHMe | O |
| CF₃ | CN | NHEt | NCN | O |
| CF₃ | CN | NHEt | NCOSMe | O |
| CF₃ | CN | NHEt | NCOSEt | O |

TABLE 2-continued

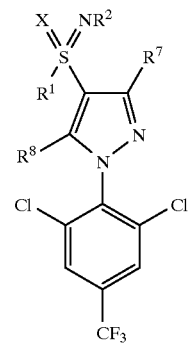

| R¹ | R⁷ | R⁸ | NR² | X |
|---|---|---|---|---|
| CF₃ | CN | NHEt | NCSOMe | O |
| CF₃ | CN | NHEt | NCSOEt | O |
| CF₃ | CN | NHEt | NCSOPr | O |
| CF₃ | CN | NHEt | NSO₂NH₂ | O |
| CF₃ | CN | NHEt | NSO₂NHMe | O |
| CF₃ | CN | NHEt | NSO₂NMe₂ | O |
| CF₃ | CN | NHEt | NP(O)(OMe)₂ | O |
| CF₃ | CN | NHEt | NP(O)(OEt)₂ | O |
| CF₃ | CN | NHEt | NP(O)Me₂ | O |
| CF₃ | CN | NHEt | NP(O)Et₂ | O |
| CF₃ | CN | NHEt | NP(O)Me(OMe) | O |
| CF₃ | CN | NHEt | NP(O)(OPr)₂ | O |
| CF₃ | CN | NHEt | NC(O)C(O)H | O |
| CF₃ | CN | NHEt | NC(O)C(O)Me | O |
| CF₃ | CN | NHEt | NC(O)C(O)OMe | O |
| CF₃ | CN | NHEt | NC(O)C(O)OEt | O |
| CF₃ | CN | NHEt | NC(O)C(O)NH₂ | O |
| CF₃ | CN | NHEt | NC(O)C(O)OH | O |
| CF₃ | CN | NHEt | NC(NH)NH₂ | O |
| CF₃ | CN | NHEt | NC(NOH)NH₂ | O |
| CF₃ | CN | NHEt | NC(NH)NHMe | O |
| CF₃ | CN | NHEt | NC(NH)NMe₂ | O |
| CF₃ | CN | NHEt | NC(NH)OMe | O |
| CF₃ | CN | NHEt | NC(NH)OEt | O |
| CCl₂F | CN | NH₂ | NCOMe | " |
| CCl₂F | CN | NH₂ | NCOEt | " |
| CCl₂F | CN | NH₂ | NCOPr | " |
| CCl₂F | CN | NH₂ | NCHO | " |
| CCl₂F | CN | NH₂ | NCOiPr | " |
| CCl₂F | CN | NH₂ | NCOtBu | " |
| CCl₂F | CN | NH₂ | NCOPh | " |
| CCl₂F | CN | NH₂ | NSO₂Me | " |
| CCl₂F | CN | NH₂ | NSO₂Et | " |
| CCl₂F | CN | NH₂ | NSO₂Pr | " |
| CCl₂F | CN | NH₂ | NSO₂Ph | " |
| CCl₂F | CN | NH₂ | NSO₂iPr | " |
| CCl₂F | CN | NH₂ | NNO₂ | " |
| CCl₂F | CN | NH₂ | NCOOMe | " |
| CCl₂F | CN | NH | NCOOEt | " |
| CCl2F | CN | NH₂ | NCOOPr | " |
| CCl₂F | CN | NH₂ | NCOOiPr | " |
| CCl₂F | CN | NH₂ | NCONHEt | " |
| CCl₂F | CN | NH₂ | NCONHPr | " |
| CCl₂F | CN | NH₂ | NCONH₂ | " |
| CCl₂F | CN | NH₂ | NCONHMe | " |
| CCl₂F | CN | NH₂ | NCN | " |
| CCl₂F | CN | NH₂ | NCOSMe | " |
| CCl₂F | CN | NH₂ | NCOSEt | " |
| CCl₂F | CN | NH₂ | NCSOMe | " |
| CCl₂F | CN | NH₂ | NCSOEt | " |
| CCl₂F | CN | NH₂ | NCSOPr | " |
| CCl₂F | CN | NH₂ | NSO₂NH₂ | " |
| CCl₂F | CN | NH₂ | NSO₂NHMe | " |
| CCl₂F | CN | NH₂ | NSO₂NMe₂ | " |
| CCl₂F | CN | NH₂ | NP(O)(OMe)₂ | " |
| CCl₂F | CN | NH₂ | NP(O)(OEt)₂ | " |
| CCl₂F | CN | NH₂ | NP(O)Me₂ | " |
| CCl₂F | CN | NH₂ | NP(O)Et₂ | " |
| CCl₂F | CN | NH₂ | NP(O)Me(OMe) | " |

TABLE 2-continued

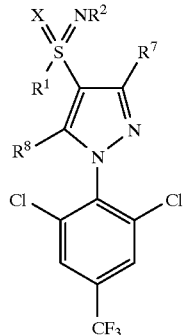

| R¹ | R⁷ | R⁸ | NR² | X |
|---|---|---|---|---|
| CCl₂F | CN | NH₂ | NP(O)(OPr)₂ | " |
| CCl₂F | CN | NH₂ | NC(O)C(O)H | " |
| CCl₂F | CN | NH₂ | NC(O)C(O)Me | " |
| CCl₂F | CN | NH₂ | NC(O)C(O)OMe | " |
| CCl₂F | CN | NH₂ | NC(O)C(O)OEt | " |
| CCl₂F | CN | NH₂ | NC(O)C(O)NH₂ | " |
| CCl₂F | CN | NH₂ | NC(O)C(O)OH | " |
| CCl₂F | CN | NH₂ | NC(NH)NH₂ | " |
| CCl₂F | CN | NH₂ | NC(NOH)NH₂ | " |
| CCl₂F | CN | NH₂ | NC(NH)NHMe | " |
| CCl₂F | CN | NH₂ | NC(NH)NMe₂ | " |
| CCl₂F | CN | NH₂ | NC(NH)OMe | " |
| CCl₂F | CN | NH₂ | NC(NH)OEt | " |
| CCl₂F | CN | NHMe | NCOMe | " |
| CCl₂F | CN | NHMe | NCOEt | " |
| CCl₂F | CN | NHMe | NCOPr | " |
| CCl₂F | CN | NHMe | NCHO | " |
| CCl₂F | CN | NHMe | NCOiPr | " |
| CCl₂F | CN | NHMe | NCOtBu | " |
| CCl₂F | CN | NHMe | NCOPh | " |
| CCl₂F | CN | NHMe | NSO₂Me | " |
| CCl₂F | CN | NHMe | NSO₂Et | " |
| CCl₂F | CN | NHMe | NSO₂Pr | " |
| CCl₂F | CN | NHMe | NSO₂Ph | " |
| CCl₂F | CN | NHMe | NSO₂iPr | " |
| CCl₂F | CN | NHMe | NNO₂ | " |
| CCl₂F | CN | NHMe | NCOOMe | " |
| CCl₂F | CN | NHMe | NCOOEt | " |
| CCl₂F | CN | NHMe | NCOOPr | " |
| CCl₂F | CN | NHMe | NCOOiPr | " |
| CCl₂F | CN | NHMe | NCONHEt | " |
| CCl₂F | CN | NHMe | NCONHPr | " |
| CCl₂F | CN | NHMe | NCONH₂ | " |
| CCl₂F | CN | NHMe | NCONHMe | " |
| CCl₂F | CN | NHMe | NCN | " |
| CCl₂F | CN | NHMe | NCOSMe | " |
| CCl₂F | CN | NHMe | NCOSEt | " |
| CCl₂F | CN | NHMe | NCSOMe | " |
| CCl₂F | CN | NHMe | NCSOEt | " |
| CCl₂F | CN | NHMe | NCSOPr | " |
| CCl₂F | CN | NHMe | NSO₂NH₂ | " |
| CCl₂F | CN | NHMe | NSO₂NHMe | " |
| CCl₂F | CN | NHMe | NSO₂NMe₂ | " |
| CCl₂F | CN | NHMe | NP(O)(OMe)₂ | " |
| CCl₂F | CN | NHMe | NP(O)(OEt)₂ | " |
| CCl₂F | CN | NHMe | NP(O)Me₂ | " |
| CCl₂F | CN | NHMe | NP(O)Et₂ | " |
| CCl₂F | CN | NHMe | NP(O)Me(OMe) | " |
| CCl₂F | CN | NHMe | NP(O)(OPr)₂ | " |
| CCl₂F | CN | NHMe | NC(O)C(O)H | " |
| CCl₂F | CN | NHMe | NC(O)C(O)Me | " |
| CCl₂F | CN | NHMe | NC(O)C(O)OMe | " |
| CCl₂F | CN | NHMe | NC(O)C(O)OEt | " |
| CCl₂F | CN | NHMe | NC(O)C(O)NH₂ | " |
| CCl₂F | CN | NHMe | NC(O)C(O)OH | " |
| CCl₂F | CN | NHMe | NC(NH)NH₂ | " |
| CCl₂F | CN | NHMe | NC(NOH)NH₂ | " |
| CCl₂F | CN | NHMe | NC(NH)NHMe | " |
| CCl₂F | CN | NHMe | NC(NH)NMe₂ | " |

TABLE 2-continued

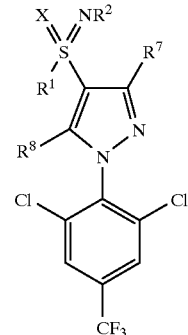

| R¹ | R⁷ | R⁸ | NR² | X |
|---|---|---|---|---|
| CCl₂F | CN | NHMe | NC(NH)OMe | " |
| CCl₂F | CN | NHMe | NC(NH)OEt | " |
| CCl₂F | CN | NHEt | NCOMe | " |
| CCl₂F | CN | NHEt | NCOEt | " |
| CCl₂F | CN | NHEt | NCOPr | " |
| CCl₂F | CN | NHEt | NCHO | " |
| CCl₂F | CN | NHEt | NCOiPr | " |
| CCl₂F | CN | NHEt | NCOtBu | " |
| CCl₂F | CN | NHEt | NCOPh | " |
| CCl₂F | CN | NHEt | NSO₂Me | " |
| CCl₂F | CN | NHEt | NSO₂Et | " |
| CCl₂F | CN | NHEt | NSO₂Pr | " |
| CCl₂F | CN | NHEt | NSO₂Ph | " |
| CCl₂F | CN | NHEt | NSO₂iPr | " |
| CCl₂F | CN | NHEt | NNO₂ | " |
| CCl₂F | CN | NHEt | NCOOMe | " |
| CCl₂F | CN | NHEt | NCOOEt | " |
| CCl₂F | CN | NHEt | NCOOPr | " |
| CCl₂F | CN | NHEt | NCOOiPr | " |
| CCl₂F | CN | NHEt | NCONHEt | " |
| CCl₂F | CN | NHEt | NCONHPr | " |
| CCl₂F | CN | NHEt | NCONH₂ | " |
| CCl₂F | CN | NHEt | NCONHMe | " |
| CCl₂F | CN | NHEt | NCN | " |
| CCl₂F | CN | NHEt | NCOSMe | " |
| CCl₂F | CN | NHEt | NCOSEt | " |
| CCl₂F | CN | NHEt | NCSOMe | " |
| CCl₂F | CN | NHEt | NCSOEt | " |
| CCl₂F | CN | NHEt | NCSOPr | " |
| CCl₂F | CN | NHEt | NSO₂NH₂ | " |
| CCl₂F | CN | NHEt | NSO₂NHMe | " |
| CCl₂F | CN | NHEt | NSO₂NMe₂ | " |
| CCl₂F | CN | NHEt | NP(O)(OMe)₂ | " |
| CCl₂F | CN | NHEt | NP(O)(OEt)₂ | " |
| CCl₂F | CN | NHEt | NP(O)Me₂ | " |
| CCl₂F | CN | NHEt | NP(O)Et₂ | " |
| CCl₂F | CN | NHEt | NP(O)Me(OMe) | " |
| CCl₂F | CN | NHEt | NP(O)(OPr)₂ | " |
| CCl₂F | CN | NHEt | NC(O)C(O)H | " |
| CCl₂F | CN | NHEt | NC(O)C(O)Me | " |
| CCl₂F | CN | NHEt | NC(O)C(O)OMe | " |
| CCl₂F | CN | NHEt | NC(O)C(O)OEt | " |
| CCl₂F | CN | NHEt | NC(O)C(O)NH₂ | " |
| CCl₂F | CN | NHEt | NC(O)C(O)OH | " |
| CCl₂F | CN | NHEt | NC(NH)NH₂ | " |
| CCl₂F | CN | NHEt | NC(NOH)NH₂ | " |
| CCl₂F | CN | NHEt | NC(NH)NHMe | " |
| CCl₂F | CN | NHEt | NC(NH)NMe₂ | " |
| CCl₂F | CN | NHEt | NC(NH)OMe | " |
| CCl₂F | CN | NHEt | NC(NH)OEt | " |
| CCl₂F | CN | NH₂ | NH | O |
| CCl₂F | CN | NH₂ | NCOMe | O |
| CCl₂F | CN | NH₂ | NCOEt | O |
| CCl₂F | CN | NH₂ | NCOPr | O |
| CCl₂F | CN | NH₂ | NCHO | O |
| CCl₂F | CN | NH₂ | NCOiPr | O |
| CCl₂F | CN | NH₂ | NCOtBu | O |
| CCl₂F | CN | NH₂ | NCOPh | O |
| CCl₂F | CN | NH₂ | NSO₂Me | O |

TABLE 2-continued

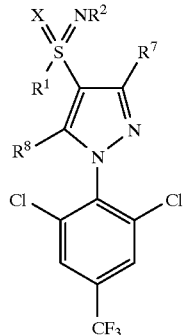

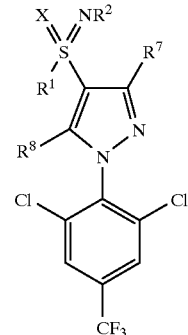

| R¹ | R⁷ | R⁸ | NR² | X |
|---|---|---|---|---|
| CCl₂F | CN | NH₂ | NSO₂Et | O |
| CCl₂F | CN | NH₂ | NSO₂Pr | O |
| CCl₂F | CN | NH₂ | NSO₂Ph | O |
| CCl₂F | CN | NH₂ | NSO₂iPr | O |
| CCl₂F | CN | NH₂ | NNO₂ | O |
| CCl₂F | CN | NH₂ | NCOOMe | O |
| CCl₂F | CN | NH₂ | NCOOEt | O |
| CCl₂F | CN | NH₂ | NCOOPr | O |
| CCl₂F | CN | NH₂ | NCOOiPr | O |
| CCl₂F | CN | NH₂ | NCONHEt | O |
| CCl₂F | CN | NH₂ | NCONHPr | O |
| CCl₂F | CN | NH₂ | NCONH₂ | O |
| CCl₂F | CN | NH₂ | NCONHMe | O |
| CCl₂F | CN | NH₂ | NCN | O |
| CCl₂F | CN | NH₂ | NCOSMe | O |
| CCl₂F | CN | NH₂ | NCOSEt | O |
| CCl₂F | CN | NH₂ | NCSOMe | O |
| CCl₂F | CN | NH₂ | NCSOEt | O |
| CCl₂F | CN | NH₂ | NCSOPr | O |
| CCl₂F | CN | NH₂ | NSO₂NH₂ | O |
| CCl₂F | CN | NH₂ | NSO₂NHMe | O |
| CCl₂F | CN | NH₂ | NSO₂NMe₂ | O |
| CCl₂F | CN | NH₂ | NP(O)(OMe)₂ | O |
| CCl₂F | CN | NH₂ | NP(O)(OEt)₂ | O |
| CCl₂F | CN | NH₂ | NP(O)Me₂ | O |
| CCl₂F | CN | NH₂ | NP(O)Et₂ | O |
| CCl₂F | CN | NH₂ | NP(O)Me(OMe) | O |
| CCl₂F | CN | NH | NP(O)(OPr)₂ | O |
| CCl₂F | CN | NH₂ | NC(O)C(O)H | O |
| CCl₂F | CN | NH₂ | NC(O)C(O)Me | O |
| CCl₂F | CN | NH₂ | NC(O)C(O)OMe | O |
| CCl₂F | CN | NH₂ | NC(O)C(O)OEt | O |
| CCl₂F | CN | NH₂ | NC(O)C(O)NH₂ | O |
| CCl₂F | CN | NH₂ | NC(O)C(O)OH | O |
| CCl₂F | CN | NH₂ | NC(NH)NH₂ | O |
| CCl₂F | CN | NH₂ | NC(NOH)NH₂ | O |
| CCl₂F | CN | NH₂ | NC(NH)NHMe | O |
| CCl₂F | CN | NH₂ | NC(NH)NMe₂ | O |
| CCl₂F | CN | NH₂ | NC(NH)OMe | O |
| CCl₂F | CN | NH₂ | NC(NH)OEt | O |
| CCl₂F | CN | NHMe | NCOMe | O |
| CCl₂F | CN | NHMe | NCOEt | O |
| CCl₂F | CN | NHMe | NCOPr | O |
| CCl₂F | CN | NHMe | NCHO | O |
| CCl₂F | CN | NHMe | NCOiPr | O |
| CCl₂F | CN | NHMe | NCOtBu | O |
| CCl₂F | CN | NHMe | NCOPh | O |
| CCl₂F | CN | NHMe | NSO₂Me | O |
| CCl₂F | CN | NHMe | NSO₂Et | O |
| CCl₂F | CN | NHMe | NSO₂Pr | O |
| CCl₂F | CN | NHMe | NSO₂Ph | O |
| CCl₂F | CN | NHMe | NSO₂iPr | O |
| CCl₂F | CN | NHMe | NNO₂ | O |
| CCl₂F | CN | NHMe | NCOOMe | O |
| CCl₂F | CN | NHMe | NCOOEt | O |
| CCl₂F | CN | NHMe | NCOOPr | O |
| CCl₂F | CN | NHMe | NCOOiPr | O |
| CCl₂F | CN | NHMe | NCONHEt | O |
| CCl₂F | CN | NHMe | NCONHPr | O |
| CCl₂F | CN | NHMe | NCONH₂ | O |
| CCl₂F | CN | NHMe | NCONHMe | O |
| CCl₂F | CN | NHMe | NCN | O |
| CCl₂F | CN | NHMe | NCOSMe | O |
| CCl₂F | CN | NHMe | NCOSEt | O |
| CCl₂F | CN | NHMe | NCSOMe | O |
| CCl₂F | CN | NHMe | NCSOEt | O |
| CCl₂F | CN | NHMe | NCSOPr | O |
| CCl₂F | CN | NHMe | NSO₂NH₂ | O |
| CCl₂F | CN | NHMe | NSO₂NHMe | O |
| CCl₂F | CN | NHMe | NSO₂NMe₂ | O |
| CCl₂F | CN | NHMe | NP(O)(OMe)₂ | O |
| CCl₂F | CN | NHMe | NP(O)(OEt)₂ | O |
| CCl₂F | CN | NHMe | NP(O)Me₂ | O |
| CCl₂F | CN | NHMe | NP(O)Et₂ | O |
| CCl₂F | CN | NHMe | NP(O)Me(OMe) | O |
| CCl₂F | CN | NHMe | NP(O)(OPr)₂ | O |
| CCl₂F | CN | NHMe | NC(O)C(O)H | O |
| CCl₂F | CN | NHMe | NC(O)C(O)Me | O |
| CCl₂F | CN | NHMe | NC(O)C(O)OMe | O |
| CCl₂F | CN | NHMe | NC(O)C(O)OEt | O |
| CCl₂F | CN | NHMe | NC(O)C(O)NH₂ | O |
| CCl₂F | CN | NHMe | NC(O)C(O)OH | O |
| CCl₂F | CN | NHMe | NC(NH)NH₂ | O |
| CCl₂F | CN | NHMe | NC(NOH)NH₂ | O |
| CCl₂F | CN | NHMe | NC(NH)NHMe | O |
| CCl₂F | CN | NHMe | NC(NH)NMe₂ | O |
| CCl₂F | CN | NHMe | NC(NH)OMe | O |
| CCl₂F | CN | NHMe | NC(NH)OEt | O |
| CCl₂F | CN | NHEt | NCOMe | O |
| CCl₂F | CN | NHEt | NCOEt | O |
| CCl₂F | CN | NHEt | NCOPr | O |
| CCl₂F | CN | NHEt | NCHO | O |
| CCl₂F | CN | NHEt | NCOiPr | O |
| CCl₂F | CN | NHEt | NCOtBu | O |
| CCl₂F | CN | NHEt | NCOPh | O |
| CCl₂F | CN | NHEt | NSO₂Me | O |
| CCl₂F | CN | NHEt | NSO₂Et | O |
| CCl₂F | CN | NHEt | NSO₂Pr | O |
| CCl₂F | CN | NHEt | NSO₂Ph | O |
| CCl₂F | CN | NHEt | NSO₂iPr | O |
| CCl₂F | CN | NHEt | NNO₂ | O |
| CCl₂F | CN | NHEt | NCOOMe | O |
| CCl₂F | CN | NHEt | NCOOEt | O |
| CCl₂F | CN | NHEt | NCOOPr | O |
| CCl₂F | CN | NHEt | NCOOiPr | O |
| CCl₂F | CN | NHEt | NCONHEt | O |
| CCl₂F | CN | NHEt | NCONHPr | O |
| CCl₂F | CN | NHEt | NCONH₂ | O |
| CCl₂F | CN | NHEt | NCONHMe | O |
| CCl₂F | CN | NHEt | NCN | O |
| CCl₂F | CN | NHEt | NCOSMe | O |
| CCl₂F | CN | NHEt | NCOSEt | O |
| CCl₂F | CN | NHEt | NCSOMe | O |
| CCl₂F | CN | NHEt | NCSOEt | O |
| CCl₂F | CN | NHEt | NCSOPr | O |
| CCl₂F | CN | NHEt | NSO₂NH₂ | O |
| CCl₂F | CN | NHEt | NSO₂NHMe | O |
| CCl₂F | CN | NHEt | NSO₂NMe₂ | O |

TABLE 2-continued

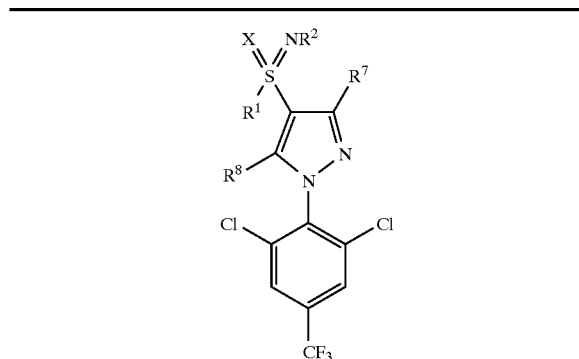

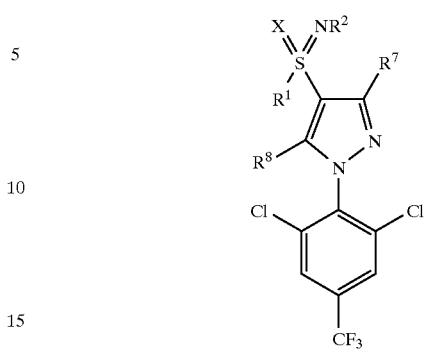

| R¹ | R⁷ | R⁸ | NR² | X |
|---|---|---|---|---|
| CCl₂F | CN | NHEt | NP(O)(OMe)₂ | O |
| CCl₂F | CN | NHEt | NP(O)(OEt)₂ | O |
| CCl₂F | CN | NHEt | NP(O)Me₂ | O |
| CCl₂F | CN | NHEt | NP(O)Et₂ | O |
| CCl₂F | CN | NHEt | NP(O)Me(OMe) | O |
| CCl₂F | CN | NHEt | NP(O)(OPr)₂ | O |
| CCl₂F | CN | NHEt | NC(O)C(O)H | O |
| CCl₂F | CN | NHEt | NC(O)C(O)Me | O |
| CCl₂F | CN | NHEt | NC(O)C(O)OMe | O |
| CCl₂F | CN | NHEt | NC(O)C(O)OEt | O |
| CCl₂F | CN | NHEt | NC(O)C(O)NH₂ | O |
| CCl₂F | CN | NHEt | NC(O)C(O)OH | O |
| CCl₂F | CN | NHEt | NC(NH)NH₂ | O |
| CCl₂F | CN | NHEt | NC(NOH)NH₂ | O |
| CCl₂F | CN | NHEt | NC(NH)NHMe | O |
| CCl₂F | CN | NHEt | NC(NH)NMe₂ | O |
| CCl₂F | CN | NHEt | NC(NH)OMe | O |
| CCl₂F | CN | NHEt | NC(NH)OEt | O |
| CCl₂F | CN | NH₂ | NCOMe | O |
| CCl₂F | CN | NH₂ | NCOEt | O |
| CCl₂F | CN | NH₂ | NCOPr | O |
| CF₂Cl | CN | NH₂ | NCHO | " |
| CF₂Cl | CN | NH₂ | NCOiPr | " |
| CF₂Cl | CN | NH₂ | NCOtBu | " |
| CF₂Cl | CN | NH₂ | NCOPh | " |
| CF₂Cl | CN | NH₂ | NSO₂Me | " |
| CF₂Cl | CN | NH₂ | NSO₂Et | " |
| CF₂Cl | CN | NH₂ | NSO₂Pr | " |
| CF₂Cl | CN | NH₂ | NSO₂Ph | " |
| CF₂Cl | CN | NH₂ | NSO₂iPr | " |
| CF₂Cl | CN | NH₂ | NNO₂ | " |
| CF₂Cl | CN | NH₂ | NCOOMe | " |
| CF₂Cl | CN | NH₂ | NCOOEt | " |
| CF₂Cl | CN | NH₂ | NCOOPr | " |
| CF₂Cl | CN | NH₂ | NCOOiPr | " |
| CF₂Cl | CN | NH₂ | NCONHEt | " |
| CF₂Cl | CN | NH₂ | NCONHPr | " |
| CF₂Cl | CN | NH₂ | NCONH₂ | " |
| CF₂Cl | CN | NH₂ | NCONHMe | " |
| CF₂Cl | CN | NH₂ | NCN | " |
| CF₂Cl | CN | NH₂ | NCOSMe | " |
| CF₂Cl | CN | NH₂ | NCOSEt | " |
| CF₂Cl | CN | NH₂ | NCSOMe | " |
| CF₂Cl | CN | NH₂ | NCSOEt | " |
| CF₂Cl | CN | NH₂ | NCSOPr | " |
| CF₂Cl | CN | NH₂ | NSO₂NH₂ | " |
| CF₂Cl | CN | NH₂ | NSO₂NHMe | " |
| CF₂Cl | CN | NH₂ | NSO₂NMe₂ | " |
| CF₂Cl | CN | NH₂ | NP(O)(OMe)₂ | " |
| CF₂Cl | CN | NH₂ | NP(O)(OEt)2 | " |
| CF₂Cl | CN | NH₂ | NP(O)Me₂ | " |
| CF₂Cl | CN | NH₂ | NP(O)Et₂ | " |
| CF₂Cl | CN | NH₂ | NP(O)Me(OMe) | " |
| CF₂Cl | CN | NH₂ | NP(O)(OPr)₂ | " |
| CF₂Cl | CN | NH₂ | NC(O)C(O)H | " |
| CF₂Cl | CN | NH₂ | NC(O)C(O)Me | " |
| CF₂Cl | CN | NH₂ | NC(O)C(O)OMe | " |
| CF₂Cl | CN | NH₂ | NC(O)C(O)OEt | " |
| CF₂Cl | CN | NH₂ | NC(O)C(O)NH₂ | " |
| CF₂Cl | CN | NH₂ | NC(O)C(O)OH | " |
| CF₂Cl | CN | NH₂ | NC(NH)NH₂ | " |
| CF₂Cl | CN | NH₂ | NC(NOH)NH₂ | " |
| CF₂Cl | CN | NH₂ | NC(NH)NHMe | " |
| CF₂Cl | CN | NH₂ | NC(NH)NMe₂ | " |
| CF₂Cl | CN | NH₂ | NC(NH)OMe | " |
| CF₂Cl | CN | NH₂ | NC(NH)OEt | " |
| CF₂Cl | CN | NHMe | NCOMe | " |
| CF₂Cl | CN | NHMe | NCOEt | " |
| CF₂Cl | CN | NHMe | NCOPr | " |
| CF₂Cl | CN | NHMe | NCHO | " |
| CF₂Cl | CN | NHMe | NCOiPr | " |
| CF₂Cl | CN | NHMe | NCOtBu | " |
| CF₂Cl | CN | NHMe | NCOPh | " |
| CF₂Cl | CN | NHMe | NSO₂Me | " |
| CF₂Cl | CN | NHMe | NSO₂Et | " |
| CF₂Cl | CN | NHMe | NSO₂Pr | " |
| CF₂Cl | CN | NHMe | NSO₂Ph | " |
| CF₂Cl | CN | NHMe | NSO₂iPr | " |
| CF₂Cl | CN | NHMe | NNO₂ | " |
| CF₂Cl | CN | NHMe | NCOOMe | " |
| CF₂Cl | CN | NHMe | NCOOEt | " |
| CF₂Cl | CN | NHMe | NCOOPr | " |
| CF₂Cl | CN | NHMe | NCOOiPr | " |
| CF₂Cl | CN | NHMe | NCONHEt | " |
| CF₂Cl | CN | NHMe | NCONHPr | " |
| CF₂Cl | CN | NHMe | NCONH₂ | " |
| CF₂Cl | CN | NHMe | NCONHMe | " |
| CF₂Cl | CN | NHMe | NCN | " |
| CF₂Cl | CN | NHMe | NCOSMe | " |
| CF₂Cl | CN | NHMe | NCOSEt | " |
| CF₂Cl | CN | NHMe | NCSOMe | " |
| CF₂Cl | CN | NHMe | NCSOEt | " |
| CF₂Cl | CN | NHMe | NCSOPr | " |
| CF₂Cl | CN | NHMe | NSO₂NH₂ | " |
| CF₂Cl | CN | NHMe | NSO₂NHMe | " |
| CF₂Cl | CN | NHMe | NSO₂NMe₂ | " |
| CF₂Cl | CN | NHMe | NP(O)(OMe)₂ | " |
| CF₂Cl | CN | NHMe | NP(O)(OEt)₂ | " |
| CF₂Cl | CN | NHMe | NP(O)Me₂ | " |
| CF₂Cl | CN | NHMe | NP(O)Et₂ | " |
| CF₂Cl | CN | NHMe | NP(O)Me(OMe) | " |
| CF₂Cl | CN | NHMe | NP(O)(OPr)₂ | " |
| CF₂Cl | CN | NHMe | NC(O)C(O)H | " |
| CF₂Cl | CN | NHMe | NC(O)C(O)Me | " |
| CF₂Cl | CN | NHMe | NC(O)C(O)OMe | " |
| CF₂Cl | CN | NHMe | NC(O)C(O)OEt | " |
| CF₂Cl | CN | NHMe | NC(O)C(O)NH₂ | " |
| CF₂Cl | CN | NHMe | NC(O)C(O)OH | " |
| CF₂Cl | CN | NHMe | NC(NH)NH₂ | " |
| CF₂Cl | CN | NHMe | NC(NOH)NH₂ | " |
| CF₂Cl | CN | NHMe | NC(NH)NHMe | " |
| CF₂Cl | CN | NHMe | NC(NH)NMe₂ | " |
| CF₂Cl | CN | NHMe | NC(NH)OMe | " |
| CF₂Cl | CN | NHMe | NC(NH)OEt | " |
| CF₂Cl | CN | NHEt | NCOMe | " |
| CF₂Cl | CN | NHEt | NCOEt | " |
| CF₂Cl | CN | NHEt | NCOPr | " |
| CF₂Cl | CN | NHEt | NCHO | " |

TABLE 2-continued

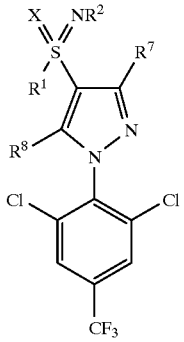

| R¹ | R⁷ | R⁸ | NR² | X |
|---|---|---|---|---|
| CF₂Cl | CN | NHEt | NCOiPr | " |
| CF₂Cl | CN | NHEt | NCOtBu | " |
| CF₂Cl | CN | NHEt | NCOPh | " |
| CF₂Cl | CN | NHEt | NSO₂Me | " |
| CF₂Cl | CN | NHEt | NSO₂Et | " |
| CF₂Cl | CN | NHEt | NSO₂Pr | " |
| CF₂Cl | CN | NHEt | NSO₂Ph | " |
| CF₂Cl | CN | NHEt | NSO₂iPr | " |
| CF₂Cl | CN | NHEt | NNO₂ | " |
| CF₂Cl | CN | NHEt | NCOOMe | " |
| CF₂Cl | CN | NHEt | NCOOEt | " |
| CF₂Cl | CN | NHEt | NCOOPr | " |
| CF₂Cl | CN | NHEt | NCOOiPr | " |
| CF₂Cl | CN | NHEt | NCONHEt | " |
| CF₂Cl | CN | NHEt | NCONHPr | " |
| CF₂Cl | CN | NHEt | NCONH₂ | " |
| CF₂Cl | CN | NHEt | NCONHMe | " |
| CF₂Cl | CN | NHEt | NCN | " |
| CF₂Cl | CN | NHEt | NCOSMe | " |
| CF₂Cl | CN | NHEt | NCOSEt | " |
| CF₂Cl | CN | NHEt | NCSOMe | " |
| CF₂Cl | CN | NHEt | NCSOEt | " |
| CF₂Cl | CN | NHEt | NCSOPr | " |
| CF₂Cl | CN | NHEt | NSO₂NH₂ | " |
| CF₂Cl | CN | NHEt | NSO₂NHMe | " |
| CF₂Cl | CN | NHEt | NSO₂NMe₂ | " |
| CF₂Cl | CN | NHEt | NP(O)(OMe)₂ | " |
| CF₂Cl | CN | NHEt | NP(O)(OEt)₂ | " |
| CF₂Cl | CN | NHEt | NP(O)Me₂ | " |
| CF₂Cl | CN | NHEt | NP(O)Et₂ | " |
| CF₂Cl | CN | NHEt | NP(O)Me(OMe) | " |
| CF₂Cl | CN | NHEt | NP(O)(OPr)₂ | " |
| CF₂Cl | CN | NHEt | NC(O)C(O)H | " |
| CF₂Cl | CN | NHEt | NC(O)C(O)Me | " |
| CF₂Cl | CN | NHEt | NC(O)C(O)OMe | " |
| CF₂Cl | CN | NHEt | NC(O)C(O)OEt | " |
| CF₂Cl | CN | NHEt | NC(O)C(O)NH₂ | " |
| CF₂Cl | CN | NHEt | NC(O)C(O)OH | " |
| CF₂Cl | CN | NHEt | NC(NH)NH₂ | " |
| CF₂Cl | CN | NHEt | NC(NOH)NH₂ | " |
| CF₂Cl | CN | NHEt | NC(NH)NHMe | " |
| CF₂Cl | CN | NHEt | NC(NH)NMe₂ | " |
| CF₂Cl | CN | NHEt | NC(NH)OMe | " |
| CF₂Cl | CN | NHEt | NC(NH)OEt | " |
| CF₂Cl | CN | NH₂ | NH | O |
| CF₂Cl | CN | NH₂ | NCOMe | O |
| CF₂Cl | CN | NH₂ | NCOEt | O |
| CF₂Cl | CN | NH₂ | NCOPr | O |
| CF₂Cl | CN | NH₂ | NCHO | O |
| CF₂Cl | CN | NH₂ | NCOiPr | O |
| CF₂Cl | CN | NH₂ | NCOtBu | O |
| CF₂Cl | CN | NH₂ | NCOPh | O |
| CF₂Cl | CN | NH₂ | NSO₂Me | O |
| CF₂Cl | CN | NH₂ | NSO₂Et | O |
| CF₂Cl | CN | NH₂ | NSO₂Pr | O |
| CF₂Cl | CN | NH₂ | NSO₂Ph | O |
| CF₂Cl | CN | NH₂ | NSO₂iPr | O |
| CF₂Cl | CN | NH₂ | NNO₂ | O |
| CF₂Cl | CN | NH₂ | NCOOMe | O |
| CF₂Cl | CN | NH₂ | NCOOEt | O |
| CF₂Cl | CN | NH₂ | NCOOPr | O |
| CF₂Cl | CN | NH₂ | NCOOiPr | O |
| CF₂Cl | CN | NH₂ | NCONHEt | O |
| CF₂Cl | CN | NH₂ | NCONHPr | O |
| CF₂Cl | CN | NH₂ | NCONH₂ | O |
| CF₂Cl | CN | NH₂ | NCONHMe | O |
| CF₂Cl | CN | NH₂ | NCN | O |
| CF₂Cl | CN | NH₂ | NCOSMe | O |
| CF₂Cl | CN | NH₂ | NCOSEt | O |
| CF₂Cl | CN | NH₂ | NCSOMe | O |
| CF₂Cl | CN | NH₂ | NCSOEt | O |
| CF₂Cl | CN | NH₂ | NCSOPr | O |
| CF₂Cl | CN | NH₂ | NSO₂NH₂ | O |
| CF₂Cl | CN | NH₂ | NSO₂NHMe | O |
| CF₂Cl | CN | NH₂ | NSO₂NMe₂ | O |
| CF₂Cl | CN | NH₂ | NP(O)(OMe)₂ | O |
| CF₂Cl | CN | NH₂ | NP(O)(OEt)₂ | O |
| CF₂Cl | CN | NH₂ | NP(O)Me₂ | O |
| CF₂Cl | CN | NH₂ | NP(O)Et₂ | O |
| CF₂Cl | CN | NH₂ | NP(O)Me(OMe) | O |
| CF₂Cl | CN | NH₂ | NP(O)(OPr)₂ | O |
| CF₂Cl | CN | NH₂ | NC(O)C(O)H | O |
| CF₂Cl | CN | NH₂ | NC(O)C(O)Me | O |
| CF₂Cl | CN | NH₂ | NC(O)C(O)OMe | O |
| CF₂Cl | CN | NH₂ | NC(O)C(O)OEt | O |
| CF₂Cl | CN | NH₂ | NC(O)C(O)NH₂ | O |
| CF₂Cl | CN | NH₂ | NC(O)C(O)OH | O |
| CF₂Cl | CN | NH₂ | NC(NH)NH₂ | O |
| CF₂Cl | CN | NH₂ | NC(NOH)NH₂ | O |
| CF₂Cl | CN | NH₂ | NC(NH)NHMe | O |
| CF₂Cl | CN | NH₂ | NC(NH)NMe₂ | O |
| CF₂Cl | CN | NH₂ | NC(NH)OMe | O |
| CF₂Cl | CN | NH₂ | NC(NH)OEt | O |
| CF₂Cl | CN | NHMe | NCOMe | O |
| CF₂Cl | CN | NHMe | NCOEt | O |
| CF₂Cl | CN | NHMe | NCOPr | O |
| CF₂Cl | CN | NHMe | NCHO | O |
| CF₂Cl | CN | NHMe | NCOiPr | O |
| CF₂Cl | CN | NHMe | NCOtBu | O |
| CF₂Cl | CN | NHMe | NCOPh | O |
| CF₂Cl | CN | NHMe | NSO₂Me | O |
| CF₂Cl | CN | NHMe | NSO₂Et | O |
| CF₂Cl | CN | NHMe | NSO₂Pr | O |
| CF₂Cl | CN | NHMe | NSO₂Ph | O |
| CF₂Cl | CN | NHMe | NSO₂iPr | O |
| CF₂Cl | CN | NHMe | NNO₂ | O |
| CF₂Cl | CN | NHMe | NCOOMe | O |
| CF₂Cl | CN | NHMe | NCOOEt | O |
| CF₂Cl | CN | NHMe | NCOOPr | O |
| CF₂Cl | CN | NHMe | NCOOiPr | O |
| CF₂Cl | CN | NHMe | NCONHEt | O |
| CF₂Cl | CN | NHMe | NCONHPr | O |
| CF₂Cl | CN | NHMe | NCONH₂ | O |
| CF₂Cl | CN | NHMe | NCONHMe | O |
| CF₂Cl | CN | NHMe | NCN | O |
| CF₂Cl | CN | NHMe | NCOSMe | O |
| CF₂Cl | CN | NHMe | NCOSEt | O |
| CF₂Cl | CN | NHMe | NCSOMe | O |

TABLE 2-continued

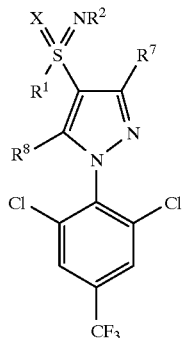

| R¹ | R⁷ | R⁸ | NR² | X |
|---|---|---|---|---|
| CF₂Cl | CN | NHMe | NCSOEt | O |
| CF₂Cl | CN | NHMe | NCSOPr | O |
| CF₂Cl | CN | NHMe | NSO₂NH₂ | O |
| CF₂Cl | CN | NHMe | NSO₂NHMe | O |
| CF₂Cl | CN | NHMe | NSO₂NMe₂ | O |
| CF₂Cl | CN | NHMe | NP(O)(OMe)₂ | O |
| CF₂Cl | CN | NHMe | NP(O)(OEt)₂ | O |
| CF₂Cl | CN | NHMe | NP(O)Me₂ | O |
| CF₂Cl | CN | NHMe | NP(O)Et₂ | O |
| CF₂Cl | CN | NHMe | NP(O)Me(OMe) | O |
| CF₂Cl | CN | NHMe | NP(O)(OPr)₂ | O |
| CF₂Cl | CN | NHMe | NC(O)C(O)H | O |
| CF₂Cl | CN | NHMe | NC(O)C(O)Me | O |
| CF₂Cl | CN | NHMe | NC(O)C(O)OMe | O |
| CF₂Cl | CN | NHMe | NC(O)C(O)OEt | O |
| CF₂Cl | CN | NHMe | NC(O)C(O)NH₂ | O |
| CF₂Cl | CN | NHMe | NC(O)C(O)OH | O |
| CF₂Cl | CN | NHMe | NC(NH)NH₂ | O |
| CF₂Cl | CN | NHMe | NC(NOH)NH₂ | O |
| CF₂Cl | CN | NHMe | NC(NH)NHMe | O |
| CF₂Cl | CN | NHMe | NC(NH)NMe₂ | O |
| CF₂Cl | CN | NHMe | NC(NH)OMe | O |
| CF₂Cl | CN | NHMe | NC(NH)OEt | O |
| CF₂Cl | CN | NHEt | NCOMe | O |
| CF₂Cl | CN | NHEt | NCOEt | O |
| CF₂Cl | CN | NHEt | NCOPr | O |
| CF₂Cl | CN | NHEt | NCHO | O |
| CF₂Cl | CN | NHEt | NCOiPr | O |
| CF₂Cl | CN | NHEt | NCOtBu | O |
| CF₂Cl | CN | NHEt | NCOPh | O |
| CF₂Cl | CN | NHEt | NSO₂Me | O |
| CF₂Cl | CN | NHEt | NSO₂Et | O |
| CF₂Cl | CN | NHEt | NSO₂Pr | O |
| CF₂Cl | CN | NHEt | NSO₂Ph | O |
| CF₂Cl | CN | NHEt | NSO₂iPr | O |
| CF₂Cl | CN | NHEt | NNO₂ | O |
| CF₂Cl | CN | NHEt | NCOOMe | O |
| CF₂Cl | CN | NHEt | NCOOEt | O |
| CF₂Cl | CN | NHEt | NCOOPr | O |
| CF₂Cl | CN | NHEt | NCOOiPr | O |
| CF₂Cl | CN | NHEt | NCONHEt | O |
| CF₂Cl | CN | NHEt | NCONHPr | O |
| CF₂Cl | CN | NHEt | NCONH₂ | O |
| CF₂Cl | CN | NHEt | NCONHMe | O |
| CF₂Cl | CN | NHEt | NCN | O |
| CF₂Cl | CN | NHEt | NCOSMe | O |
| CF₂Cl | CN | NHEt | NCOSEt | O |
| CF₂Cl | CN | NHEt | NCSOMe | O |
| CF₂Cl | CN | NHEt | NCSOEt | O |
| CF₂Cl | CN | NHEt | NCSOPr | O |
| CF₂Cl | CN | NHEt | NSO₂NH₂ | O |
| CF₂Cl | CN | NHEt | NSO₂NHMe | O |
| CF₂Cl | CN | NHEt | NSO₂NMe₂ | O |
| CF₂Cl | CN | NHEt | NP(O)(OMe)₂ | O |
| CF₂Cl | CN | NHEt | NP(O)(OEt)₂ | O |
| CF₂Cl | CN | NHEt | NP(O)Me₂ | O |
| CF₂Cl | CN | NHEt | NP(O)Et₂ | O |
| CF₂Cl | CN | NHEt | NP(O)Me(OMe) | O |
| CF₂Cl | CN | NHEt | NP(O)(OPr)₂ | O |

TABLE 2-continued

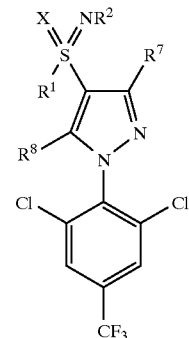

| R¹ | R⁷ | R⁸ | NR² | X |
|---|---|---|---|---|
| CF₂Cl | CN | NHEt | NC(O)C(O)H | O |
| CF₂Cl | CN | NHEt | NC(O)C(O)Me | O |
| CF₂Cl | CN | NHEt | NC(O)C(O)OMe | O |
| CF₂Cl | CN | NHEt | NC(O)C(O)OEt | O |
| CF₂Cl | CN | NHEt | NC(O)C(O)NH₂ | O |
| CF₂Cl | CN | NHEt | NC(O)C(O)OH | O |
| CF₂Cl | CN | NHEt | NC(NH)NH₂ | O |
| CF₂Cl | CN | NHEt | NC(NOH)NH₂ | O |
| CF₂Cl | CN | NHEt | NC(NH)NHMe | O |
| CF₂Cl | CN | NHEt | NC(NH)NMe₂ | O |
| CF₂Cl | CN | NHEt | NC(NH)OMe | O |
| CF₂Cl | CN | NHEt | NC(NH)OEt | O |
| CF₃ | CN | H | NCOMe | " |
| CF₃ | CN | H | NCOEt | " |
| CF₃ | CN | H | NCOPr | " |
| CF₃ | CN | H | NCHO | " |
| CF₃ | CN | H | NCOiPr | " |
| CF₃ | CN | H | NCOtBu | " |
| CF₃ | CN | H | NCOPh | " |
| CF₃ | CN | H | NSO₂Me | " |
| CF₃ | CN | H | NSO₂Et | " |
| CF₃ | CN | H | NSO₂Pr | " |
| CF₃ | CN | H | NSO₂Ph | " |
| CF₃ | CN | H | NSO₂iPr | " |
| CF₃ | CN | H | NNO₂ | " |
| CF₃ | CN | H | NCOOMe | " |
| CF₃ | CN | H | NCOOEt | " |
| CF₃ | CN | H | NCOOPr | " |
| CF₃ | CN | H | NCOOiPr | " |
| CF₃ | CN | H | NCONHEt | " |
| CF₃ | CN | H | NCONHPr | " |
| CF₃ | CN | H | NCONH₂ | " |
| CF₃ | CN | H | NCONHMe | " |
| CF₃ | CN | H | NCN | " |
| CF₃ | CN | H | NCOSMe | " |
| CF₃ | CN | H | NCOSEt | " |
| CF₃ | CN | H | NCSOMe | " |
| CF₃ | CN | H | NCSOEt | " |
| CF₃ | CN | H | NCSOPr | " |
| CF₃ | CN | H | NSO₂NH₂ | " |
| CF₃ | CN | H | NSO₂NHMe | " |
| CF₃ | CN | H | NSO₂NMe₂ | " |
| CF₃ | CN | H | NP(O)(OMe)₂ | " |
| CF₃ | CN | H | NP(O)(OEt)₂ | " |
| CF₃ | CN | H | NP(O)Me₂ | " |
| CF₃ | CN | H | NP(O)Et₂ | " |
| CF₃ | CN | H | NP(O)Me(OMe) | " |
| CF₃ | CN | H | NP(O)(OPr)₂ | " |
| CF₃ | CN | H | NC(O)C(O)H | " |
| CF₃ | CN | H | NC(O)C(O)Me | " |
| CF₃ | CN | H | NC(O)C(O)OMe | " |
| CF₃ | CN | H | NC(O)C(O)OEt | " |
| CF₃ | CN | H | NC(O)C(O)NH₂ | " |
| CF₃ | CN | H | NC(O)C(O)OH | " |
| CF₃ | CN | H | NC(NH)NH₂ | " |
| CF₃ | CN | H | NC(NOH)NH₂ | " |
| CF₃ | CN | H | NC(NH)NHMe | " |
| CF₃ | CN | H | NC(NH)NMe₂ | " |
| CF₃ | CN | H | NC(NH)OMe | " |

TABLE 2-continued

[Structure: pyrazole with S(=X)(=NR²)R¹ at position 4, R⁷ at position 3, R⁸ at position 5, N1 attached to 2,6-dichloro-4-trifluoromethylphenyl]

| R¹ | R⁷ | R⁸ | NR² | X |
|---|---|---|---|---|
| CF₃ | CN | H | NC(NH)OEt | " |
| CF₃ | CN | H | NH | O |
| CF₃ | CN | H | NCOMe | O |
| CF₃ | CN | H | NCOEt | O |
| CF₃ | CN | H | NCOPr | O |
| CF₃ | CN | H | NCHO | O |
| CF₃ | CN | H | NCOiPr | O |
| CF₃ | CN | H | NCOtBu | O |
| CF₃ | CN | H | NCOPh | O |
| CF₃ | CN | H | NSO₂Me | O |
| CF₃ | CN | H | NSO₂Et | O |
| CF₃ | CN | H | NSO₂Pr | O |
| CF₃ | CN | H | NSO₂Ph | O |
| CF₃ | CN | H | NSO₂iPr | O |
| CF₃ | CN | H | NNO₂ | O |
| CF₃ | CN | H | NCOOMe | O |
| CF₃ | CN | H | NCOOEt | O |
| CF₃ | CN | H | NCOOPr | O |
| CF₃ | CN | H | NCOOiPr | O |
| CF₃ | CN | H | NCONHEt | O |
| CF₃ | CN | H | NCONHPr | O |
| CF₃ | CN | H | NCONH₂ | O |
| CF₃ | CN | H | NCONHMe | O |
| CF₃ | CN | H | NCN | O |
| CF₃ | CN | H | NCOSMe | O |
| CF₃ | CN | H | NCOSEt | O |
| CF₃ | CN | H | NCSOMe | O |
| CF₃ | CN | H | NCSOEt | O |
| CF₃ | CN | H | NCSOPr | O |
| CF₃ | CN | H | NSO₂NH₂ | O |
| CF₃ | CN | H | NSO₂NHMe | O |
| CF₃ | CN | H | NSO₂NMe₂ | O |
| CF₃ | CN | H | NP(O)(OMe)₂ | O |
| CF₃ | CN | H | NP(O)(OEt)₂ | O |
| CF₃ | CN | H | NP(O)Me₂ | O |
| CF₃ | CN | H | NP(O)Et₂ | O |
| CF₃ | CN | H | NP(O)Me(OMe) | O |
| CF₃ | CN | H | NP(O)(OPr)₂ | O |
| CF₃ | CN | H | NC(O)C(O)H | O |
| CF₃ | CN | H | NC(O)C(O)Me | O |
| CF₃ | CN | H | NC(O)C(O)OMe | O |
| CF₃ | CN | H | NC(O)C(O)OEt | O |
| CF₃ | CN | H | NC(O)C(O)NH₂ | O |
| CF₃ | CN | H | NC(O)C(O)OH | O |
| CF₃ | CN | H | NC(NH)NH₂ | O |
| CF₃ | CN | H | NC(NOH)NH₂ | O |
| CF₃ | CN | H | NC(NH)NHMe | O |
| CF₃ | CN | H | NC(NH)NMe₂ | O |
| CF₃ | CN | H | NC(NH)OMe | O |
| CF₃ | CN | H | NC(NH)OEt | O |
| CF₃ | CN | Me | NCOMe | " |
| CF₃ | CN | Me | NCOEt | " |
| CF₃ | CN | Me | NCOPr | " |
| CF₃ | CN | Me | NCHO | " |
| CF₃ | CN | Me | NCOiPr | " |
| CF₃ | CN | Me | NCOtBu | " |
| CF₃ | CN | Me | NCOPh | " |
| CF₃ | CN | Me | NSO₂Me | " |
| CF₃ | CN | Me | NSO₂Et | " |
| CF₃ | CN | Me | NSO₂Pr | " |
| CF₃ | CN | Me | NSO₂Ph | " |
| CF₃ | CN | Me | NSO₂iPr | " |
| CF₃ | CN | Me | NNO₂ | " |
| CF₃ | CN | Me | NCOOMe | " |
| CF₃ | CN | Me | NCOOEt | " |
| CF₃ | CN | Me | NCOOPr | " |
| CF₃ | CN | Me | NCOOiPr | " |
| CF₃ | CN | Me | NCONHEt | " |
| CF₃ | CN | Me | NCONHPr | " |
| CF₃ | CN | Me | NCOH | " |
| CF₃ | CN | Me | NCONHMe | " |
| CF₃ | CN | Me | NCN | " |
| CF₃ | CN | Me | NCOSMe | " |
| CF₃ | CN | Me | NCOSEt | " |
| CF₃ | CN | Me | NCSOMe | " |
| CF₃ | CN | Me | NCSOEt | " |
| CF₃ | CN | Me | NCSOPr | " |
| CF₃ | CN | Me | NSO₂H | " |
| CF₃ | CN | Me | NSO₂NHMe | " |
| CF₃ | CN | Me | NSO₂NMe₂ | " |
| CF₃ | CN | Me | NP(O)(OMe)₂ | " |
| CF₃ | CN | Me | NP(O)(OEt)₂ | " |
| CF₃ | CN | Me | NP(O)Me₂ | " |
| CF₃ | CN | Me | NP(O)Et₂ | " |
| CF₃ | CN | Me | NP(O)Me(OMe) | " |
| CF₃ | CN | Me | NP(O)(OPr)₂ | " |
| CF₃ | CN | Me | NC(O)C(O)H | " |
| CF₃ | CN | Me | NC(O)C(O)Me | " |
| CF₃ | CN | Me | NC(O)C(O)OMe | " |
| CF₃ | CN | Me | NC(O)C(O)OEt | " |
| CF₃ | CN | Me | NC(O)C(O)NH₂ | " |
| CF₃ | CN | Me | NC(O)C(O)OH | " |
| CF₃ | CN | Me | NC(NH)H | " |
| CF₃ | CN | Me | NC(NOH)H | " |
| CF₃ | CN | Me | NC(NH)NHMe | " |
| CF₃ | CN | Me | NC(NH)NMe₂ | " |
| CF₃ | CN | Me | NC(NH)OMe | " |
| CF₃ | CN | Me | NC(NH)OEt | " |
| CF₃ | CN | Me | NH | O |
| CF₃ | CN | Me | NCOMe | O |
| CF₃ | CN | Me | NCOEt | O |
| CF₃ | CN | Me | NCOPr | O |
| CF₃ | CN | Me | NCHO | O |
| CF₃ | CN | Me | NCOiPr | O |
| CF₃ | CN | Me | NCOtBu | O |
| CF₃ | CN | Me | NCOPh | O |
| CF₃ | CN | Me | NSO₂Me | O |
| CF₃ | CN | Me | NSO₂Et | O |
| CF₃ | CN | Me | NSO₂Pr | O |
| CF₃ | CN | Me | NSO₂Ph | O |
| CF₃ | CN | Me | NSO₂iPr | O |
| CF₃ | CN | Me | NNO₂ | O |
| CF₃ | CN | Me | NCOOMe | O |
| CF₃ | CN | Me | NCOOEt | O |
| CF₃ | CN | Me | NCOOPr | O |
| CF₃ | CN | Me | NCOOiPr | O |
| CF₃ | CN | Me | NCONHEt | O |
| CF₃ | CN | Me | NCONHPr | O |

TABLE 2-continued

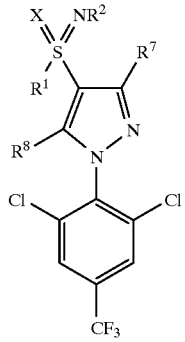

| R¹ | R⁷ | R⁸ | NR² | X |
|---|---|---|---|---|
| CF₃ | CN | Me | NCONH₂ | O |
| CF₃ | CN | Me | NCONHMe | O |
| CF₃ | CN | Me | NCN | O |
| CF₃ | CN | Me | NCOSMe | O |
| CF₃ | CN | Me | NCOSEt | O |
| CF₃ | CN | Me | NCSOMe | O |
| CF₃ | CN | Me | NCSOEt | O |
| CF₃ | CN | Me | NCSOPr | O |
| CF₃ | CN | Me | NSO₂NH₂ | O |
| CF₃ | CN | Me | NSO₂NHMe | O |
| CF₃ | CN | Me | NSO₂NMe₂ | O |
| CF₃ | CN | Me | NP(O)(OMe)₂ | O |
| CF₃ | CN | Me | NP(O)(OEt)₂ | O |
| CF₃ | CN | Me | NP(O)Me₂ | O |
| CF₃ | CN | Me | NP(O)Et₂ | O |
| CF₃ | CN | Me | NP(O)Me(OMe) | O |
| CF₃ | CN | Me | NP(O)(OPr)₂ | O |
| CF₃ | CN | Me | NC(O)C(O)H | O |
| CF₃ | CN | Me | NC(O)C(O)Me | O |
| CF₃ | CN | Me | NC(O)C(O)OMe | O |
| CF₃ | CN | Me | NC(O)C(O)OEt | O |
| CF₃ | CN | Me | NC(O)C(O)NH₂ | O |
| CF₃ | CN | Me | NC(O)C(O)OH | O |
| CF₃ | CN | Me | NC(NH)NH₂ | O |
| CF₃ | CN | Me | NC(NOH)NH₂ | O |
| CF₃ | CN | Me | NC(NH)NHMe | O |
| CF₃ | CN | Me | NC(NH)NMe₂ | O |
| CF₃ | CN | Me | NC(NH)OMe | O |
| CF₃ | CN | Me | NC(NH)OEt | O |
| CF₃ | CN | Cl | NCOMe | " |
| CF₃ | CN | Cl | NCOEt | " |
| CF₃ | CN | Cl | NCOPr | " |
| CF₃ | CN | Cl | NCHO | " |
| CF₃ | CN | Cl | NCOiPr | " |
| CF₃ | CN | Cl | NCOtBu | " |
| CF₃ | CN | Cl | NCOPh | " |
| CF₃ | CN | Cl | NSO₂Me | " |
| CF₃ | CN | Cl | NSO₂Et | " |
| CF₃ | CN | Cl | NSO₂Pr | " |
| CF₃ | CN | Cl | NSO₂Ph | " |
| CF₃ | CN | Cl | NSO₂iPr | " |
| CF₃ | CN | Cl | NNO₂ | " |
| CF₃ | CN | Cl | NCOOMe | " |
| CF₃ | CN | Cl | NCOOEt | " |
| CF₃ | CN | Cl | NCOOPr | " |
| CF₃ | CN | Cl | NCOOiPr | " |
| CF₃ | CN | Cl | NCONHEt | " |
| CF₃ | CN | Cl | NCONHPr | " |
| CF₃ | CN | Cl | NCOH | " |
| CF₃ | CN | Cl | NCONHMe | " |
| CF₃ | CN | Cl | NCN | " |
| CF₃ | CN | Cl | NCOSMe | " |
| CF₃ | CN | Cl | NCOSEt | " |
| CF₃ | CN | Cl | NCSOMe | " |
| CF₃ | CN | Cl | NCSOEt | " |
| CF₃ | CN | Cl | NCSOPr | " |
| CF₃ | CN | Cl | NSO₂H | " |
| CF₃ | CN | Cl | NSO₂NHMe | " |
| CF₃ | CN | Cl | NSO₂NMe₂ | " |

TABLE 2-continued

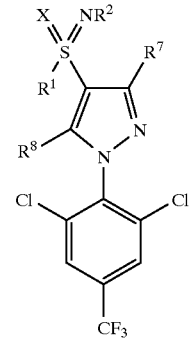

| R¹ | R⁷ | R⁸ | NR² | X |
|---|---|---|---|---|
| CF₃ | CN | Cl | NP(O)(OMe)₂ | " |
| CF₃ | CN | Cl | NP(O)(OEt)₂ | " |
| CF₃ | CN | Cl | NP(O)Me₂ | " |
| CF₃ | CN | Cl | NP(O)Et₂ | " |
| CF₃ | CN | Cl | NP(O)Me(OMe) | " |
| CF₃ | CN | Cl | NP(O)(OPr)₂ | " |
| CF₃ | CN | Cl | NC(O)C(O)H | " |
| CF₃ | CN | Cl | NC(O)C(O)Me | " |
| CF₃ | CN | Cl | NC(O)C(O)OMe | " |
| CF₃ | CN | Cl | NC(O)C(O)OEt | " |
| CF₃ | CN | Cl | NC(O)C(O)NH₂ | " |
| CF₃ | CN | Cl | NC(O)C(O)OH | " |
| CF₃ | CN | Cl | NC(NH)H | " |
| CF₃ | CN | Cl | NC(NOH)H | " |
| CF₃ | CN | Cl | NC(NH)NHMe | " |
| CF₃ | CN | Cl | NC(NH)NMe₂ | " |
| CF₃ | CN | Cl | NC(NH)OMe | " |
| CF₃ | CN | Cl | NC(NH)OEt | " |
| CF₃ | CN | Cl | NCOMe | O |
| CF₃ | CN | Cl | NCOEt | O |
| CF₃ | CN | Cl | NCOPr | O |
| CF₃ | CN | Cl | NCHO | O |
| CF₃ | CN | Cl | NCOiPr | O |
| CF₃ | CN | Cl | NCOtBu | O |
| CF₃ | CN | Cl | NCOPh | O |
| CF₃ | CN | Cl | NSO₂Me | O |
| CF₃ | CN | Cl | NSO₂Et | O |
| CF₃ | CN | Cl | NSO₂Pr | O |
| CF₃ | CN | Cl | NSO₂Ph | O |
| CF₃ | CN | Cl | NSO₂iPr | O |
| CF₃ | CN | Cl | NNO₂ | O |
| CF₃ | CN | Cl | NCOOMe | O |
| CF₃ | CN | Cl | NCOOEt | O |
| CF₃ | CN | Cl | NCOOPr | O |
| CF₃ | CN | Cl | NCOOiPr | O |
| CF₃ | CN | Cl | NCONHEt | O |
| CF₃ | CN | Cl | NCONHPr | O |
| CF₃ | CN | Cl | NCONH₂ | O |
| CF₃ | CN | Cl | NCONHMe | O |
| CF₃ | CN | Cl | NCN | O |
| CF₃ | CN | Cl | NCOSMe | O |
| CF₃ | CN | Cl | NCOSEt | O |
| CF₃ | CN | Cl | NCSOMe | O |
| CF₃ | CN | Cl | NCSOEt | O |
| CF₃ | CN | Cl | NCSOPr | O |
| CF₃ | CN | Cl | NSO₂NH₂ | O |
| CF₃ | CN | Cl | NSO₂NHMe | O |
| CF₃ | CN | Cl | NSO₂NMe₂ | O |
| CF₃ | CN | Cl | NP(O)(OMe)₂ | O |
| CF₃ | CN | Cl | NP(O)(OEt)₂ | O |
| CF₃ | CN | Cl | NP(O)Me₂ | O |
| CF₃ | CN | Cl | NP(O)Et₂ | O |
| CF₃ | CN | Cl | NP(O)Me(OMe) | O |
| CF₃ | CN | Cl | NP(O)(OPr)₂ | O |
| CF₃ | CN | Cl | NC(O)C(O)H | O |
| CF₃ | CN | Cl | NC(O)C(O)Me | O |
| CF₃ | CN | Cl | NC(O)C(O)OMe | O |
| CF₃ | CN | Cl | NC(O)C(O)OEt | O |
| CF₃ | CN | Cl | NC(O)C(O)NH₂ | O |

TABLE 2-continued

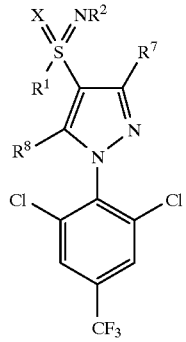

| R[1] | R[7] | R[8] | NR[2] | X |
|---|---|---|---|---|
| CF$_3$ | CN | Cl | NC(O)C(O)OH | O |
| CF$_3$ | CN | Cl | NC(NH)NH$_2$ | O |
| CF$_3$ | CN | Cl | NC(NOH)NH$_2$ | O |
| CF$_3$ | CN | Cl | NC(NH)NHMe | O |
| CF$_3$ | CN | Cl | NC(NH)NMe$_2$ | O |
| CF$_3$ | CN | Cl | NC(NH)OMe | O |
| CF$_3$ | CN | Cl | NC(NH)OEt | O |
| CF$_3$ | CN | SMe | NCOMe | " |
| CF$_3$ | CN | SMe | NCOEt | " |
| CF$_3$ | CN | SMe | NCOPr | " |
| CF$_3$ | CN | SMe | NCHO | " |
| CF$_3$ | CN | SMe | NCOiPr | " |
| CF$_3$ | CN | SMe | NCOtBu | " |
| CF$_3$ | CN | SMe | NCOPh | " |
| CF$_3$ | CN | SMe | NSO$_2$Me | " |
| CF$_3$ | CN | SMe | NSO$_2$Et | " |
| CF$_3$ | CN | SMe | NSO$_2$Pr | " |
| CF$_3$ | CN | SMe | NSO$_2$Ph | " |
| CF$_3$ | CN | SMe | NSO$_2$iPr | " |
| CF$_3$ | CN | SMe | NNO$_2$ | " |
| CF$_3$ | CN | SMe | NCOOMe | " |
| CF$_3$ | CN | SMe | NCOOEt | " |
| CF$_3$ | CN | SMe | NCOOPr | " |
| CF$_3$ | CN | SMe | NCOOiPr | " |
| CF$_3$ | CN | SMe | NCONHEt | " |
| CF$_3$ | CN | SMe | NCONHPr | " |
| CF$_3$ | CN | SMe | NCOH | " |
| CF$_3$ | CN | SMe | NCONHMe | " |
| CF$_3$ | CN | SMe | NCN | " |
| CF$_3$ | CN | SMe | NCOSMe | " |
| CF$_3$ | CN | SMe | NCOSEt | " |
| CF$_3$ | CN | SMe | NCSOMe | " |
| CF$_3$ | CN | SMe | NCSOEt | " |
| CF$_3$ | CN | SMe | NCSOPr | " |
| CF$_3$ | CN | SMe | NSO$_2$H | " |
| CF$_3$ | CN | SMe | NSO$_2$NHMe | " |
| CF$_3$ | CN | SMe | NSO$_2$NMe$_2$ | " |
| CF$_3$ | CN | SMe | NP(O)(OMe)$_2$ | " |
| CF$_3$ | CN | SMe | NP(O)(OEt)$_2$ | " |
| CF$_3$ | CN | SMe | NP(O)Me$_2$ | " |
| CF$_3$ | CN | SMe | NP(O)Et$_2$ | " |
| CF$_3$ | CN | SMe | NP(O)Me(OMe) | " |
| CF$_3$ | CN | SMe | NP(O)(OPr)$_2$ | " |
| CF$_3$ | CN | SMe | NC(O)C(O)H | " |
| CF$_3$ | CN | SMe | NC(O)C(O)Me | " |
| CF$_3$ | CN | SMe | NC(O)C(O)OMe | " |
| CF$_3$ | CN | SMe | NC(O)C(O)OEt | " |
| CF$_3$ | CN | SMe | NC(O)C(O)NH$_2$ | " |
| CF$_3$ | CN | SMe | NC(O)C(O)OH | " |
| CF$_3$ | CN | SMe | NC(NH)H | " |
| CF$_3$ | CN | SMe | NC(NOH)H | " |
| CF$_3$ | CN | SMe | NC(NH)NHMe | " |
| CF$_3$ | CN | SMe | NC(NH)NMe$_2$ | " |
| CF$_3$ | CN | SMe | NC(NH)OMe | " |
| CF$_3$ | CN | SMe | NC(NH)OEt | " |
| CF$_3$ | H | NH$_2$ | NCOMe | " |
| CF$_3$ | H | NH$_2$ | NCOEt | " |
| CF$_3$ | H | NH$_2$ | NCOPr | " |
| CF$_3$ | H | NH$_2$ | NCHO | " |

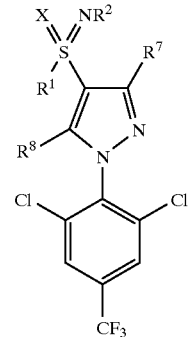

| R[1] | R[7] | R[8] | NR[2] | X |
|---|---|---|---|---|
| CF$_3$ | H | NH$_2$ | NCOiPr | " |
| CF$_3$ | H | NH$_2$ | NCOtBu | " |
| CF$_3$ | H | NH$_2$ | NCOPh | " |
| CF$_3$ | H | NH$_2$ | NSO$_2$Me | " |
| CF$_3$ | H | NH$_2$ | NSO$_2$Et | " |
| CF$_3$ | H | NH$_2$ | NSO$_2$Pr | " |
| CF$_3$ | H | NH$_2$ | NSO$_2$Ph | " |
| CF$_3$ | H | NH$_2$ | NSO$_2$iPr | " |
| CF$_3$ | H | NH$_2$ | NNO$_2$ | " |
| CF$_3$ | H | NH$_2$ | NCOOMe | " |
| CF$_3$ | H | NH$_2$ | NCOOEt | " |
| CF$_3$ | H | NH$_2$ | NCOOPr | " |
| CF$_3$ | H | NH$_2$ | NCOOiPr | " |
| CF$_3$ | H | NH$_2$ | NCONHEt | " |
| CF$_3$ | H | NH$_2$ | NCONHPr | " |
| CF$_3$ | H | NH$_2$ | NCOH | " |
| CF$_3$ | H | NH$_2$ | NCONHMe | " |
| CF$_3$ | H | NH$_2$ | NCN | " |
| CF$_3$ | H | NH$_2$ | NCOSMe | " |
| CF$_3$ | H | NH$_2$ | NCOSEt | " |
| CF$_3$ | H | NH$_2$ | NCSOMe | " |
| CF$_3$ | H | NH$_2$ | NCSOEt | " |
| CF$_3$ | H | NH$_2$ | NCSOPr | " |
| CF$_3$ | H | NH$_2$ | NSO$_2$H | " |
| CF$_3$ | H | NH$_2$ | NSO$_2$NHMe | " |
| CF$_3$ | H | NH$_2$ | NSO$_2$NMe$_2$ | " |
| CF$_3$ | H | NH$_2$ | NP(O)(OMe)$_2$ | " |
| CF$_3$ | H | NH$_2$ | NP(O)(OEt)$_2$ | " |
| CF$_3$ | H | NH$_2$ | NP(O)Me$_2$ | " |
| CF$_3$ | H | NH$_2$ | NP(O)Et$_2$ | " |
| CF$_3$ | H | NH$_2$ | NP(O)Me(OMe) | " |
| CF$_3$ | H | NH$_2$ | NP(O)(OPr)$_2$ | " |
| CF$_3$ | H | NH$_2$ | NC(O)C(O)H | " |
| CF$_3$ | H | NH$_2$ | NC(O)C(O)Me | " |
| CF$_3$ | H | NH$_2$ | NC(O)C(O)OMe | " |
| CF$_3$ | H | NH$_2$ | NC(O)C(O)OEt | " |
| CF$_3$ | H | NH$_2$ | NC(O)C(O)NH$_2$ | " |
| CF$_3$ | H | NH$_2$ | NC(O)C(O)OH | " |
| CF$_3$ | H | NH$_2$ | NC(NH)H | " |
| CF$_3$ | H | NH$_2$ | NC(NOH)H | " |
| CF$_3$ | H | NH$_2$ | NC(NH)NHMe | " |
| CF$_3$ | H | NH$_2$ | NC(NH)NMe$_2$ | " |
| CF$_3$ | H | NH$_2$ | NC(NH)OMe | " |
| CF$_3$ | H | NH$_2$ | NC(NH)OEt | " |
| CF$_3$ | Me | NH$_2$ | NCOMe | " |
| CF$_3$ | Me | NH$_2$ | NCOEt | " |
| CF$_3$ | Me | NH$_2$ | NCOPr | " |
| CF$_3$ | Me | NH$_2$ | NCHO | " |
| CF$_3$ | Me | NH$_2$ | NCOiPr | " |
| CF$_3$ | Me | NH$_2$ | NCOtBu | " |
| CF$_3$ | Me | NH$_2$ | NCOPh | " |
| CF$_3$ | Me | NH$_2$ | NSO$_2$Me | " |
| CF$_3$ | Me | NH$_2$ | NSO$_2$Et | " |
| CF$_3$ | Me | NH$_2$ | NSO$_2$Pr | " |
| CF$_3$ | Me | NH$_2$ | NSO$_2$Ph | " |
| CF$_3$ | Me | NH$_2$ | NSO$_2$iPr | " |
| CF$_3$ | Me | NH$_2$ | NNO$_2$ | " |
| CF$_3$ | Me | NH$_2$ | NCOOMe | " |
| CF$_3$ | Me | NH$_2$ | NCOOEt | " |

TABLE 2-continued

Structure: pyrazole with S(=X)(=NR²)R¹ at 4-position, R⁷ at 3-position, R⁸ at 5-position, N1 substituted with 2,6-dichloro-4-(trifluoromethyl)phenyl.

| R¹ | R⁷ | R⁸ | NR² | X |
|---|---|---|---|---|
| CF₃ | Me | NH₂ | NCOOPr | " |
| CF₃ | Me | NH₂ | NCOOiPr | " |
| CF₃ | Me | NH₂ | NCONHEt | " |
| CF₃ | Me | NH₂ | NCONHPr | " |
| CF₃ | Me | NH₂ | NCOH | " |
| CF₃ | Me | NH₂ | NCONHMe | " |
| CF₃ | Me | NH₂ | NCN | " |
| CF₃ | Me | NH₂ | NCOSMe | " |
| CF₃ | Me | NH₂ | NCOSEt | " |
| CF₃ | Me | NH₂ | NCSOMe | " |
| CF₃ | Me | NH₂ | NCSOEt | " |
| CF₃ | Me | NH₂ | NCSOPr | " |
| CF₃ | Me | NH₂ | NSO₂H | " |
| CF₃ | Me | NH₂ | NSO₂NHMe | " |
| CF₃ | Me | NH₂ | NSO₂NMe₂ | " |
| CF₃ | Me | NH₂ | NP(O)(OMe)₂ | " |
| CF₃ | Me | NH₂ | NP(O)(OEt)₂ | " |
| CF₃ | Me | NH₂ | NP(O)Me₂ | " |
| CF₃ | Me | NH₂ | NP(O)Et₂ | " |
| CF₃ | Me | NH₂ | NP(O)Me(OMe) | " |
| CF₃ | Me | NH₂ | NP(O)(OPr)₂ | " |
| CF₃ | Me | NH₂ | NC(O)C(O)H | " |
| CF₃ | Me | NH₂ | NC(O)C(O)Me | " |
| CF₃ | Me | NH₂ | NC(O)C(O)OMe | " |
| CF₃ | Me | NH₂ | NC(O)C(O)OEt | " |
| CF₃ | Me | NH₂ | NC(O)C(O)NH₂ | " |
| CF₃ | Me | NH₂ | NC(O)C(O)OH | " |
| CF₃ | Me | NH₂ | NC(NH)H | " |
| CF₃ | Me | NH₂ | NC(NOH)H | " |
| CF₃ | Me | NH₂ | NC(NH)NHMe | " |
| CF₃ | Me | NH₂ | NC(NH)NMe₂ | " |
| CF₃ | Me | NH₂ | NC(NH)OMe | " |
| CF₃ | Me | NH₂ | NC(NH)OEt | " |
| CF₃ | H | H | NCOMe | " |
| CF₃ | H | H | NCOEt | " |
| CF₃ | H | H | NCOPr | " |
| CF₃ | H | H | NCHO | " |
| CF₃ | H | H | NCOiPr | " |
| CF₃ | H | H | NCOtBu | " |
| CF₃ | H | H | NCOPh | " |
| CF₃ | H | H | NSO₂Me | " |
| CF₃ | H | H | NSO₂Et | " |
| CF₃ | H | H | NSO₂Pr | " |
| CF₃ | H | H | NSO₂Ph | " |
| CF₃ | H | H | NSO₂iPr | " |
| CF₃ | H | H | NNO₂ | " |
| CF₃ | H | H | NCOOMe | " |
| CF₃ | H | H | NCOOEt | " |
| CF₃ | H | H | NCOOPr | " |
| CF₃ | H | H | NCOOiPr | " |
| CF₃ | H | H | NCONHEt | " |
| CF₃ | H | H | NCONHPr | " |
| CF₃ | H | H | NCOH | " |
| CF₃ | H | H | NCONHMe | " |
| CF₃ | H | H | NCN | " |
| CF₃ | H | H | NCOSMe | " |
| CF₃ | H | H | NCOSEt | " |
| CF₃ | H | H | NCSOMe | " |
| CF₃ | H | H | NCSOEt | " |
| CF₃ | H | H | NCSOPr | " |
| CF₃ | H | H | NSO₂H | " |
| CF₃ | H | H | NSO₂NHMe | " |
| CF₃ | H | H | NSO₂NMe₂ | " |
| CF₃ | H | H | NP(O)(OMe)₂ | " |
| CF₃ | H | H | NP(O)(OEt)₂ | " |
| CF₃ | H | H | NP(O)Me₂ | " |
| CF₃ | H | H | NP(O)Et₂ | " |
| CF₃ | H | H | NP(O)Me(OMe) | " |
| CF₃ | H | H | NP(O)(OPr)₂ | " |
| CF₃ | H | H | NC(O)C(O)H | " |
| CF₃ | H | H | NC(O)C(O)Me | " |
| CF₃ | H | H | NC(O)C(O)OMe | " |
| CF₃ | H | H | NC(O)C(O)OEt | " |
| CF₃ | H | H | NC(O)C(O)NH₂ | " |
| CF₃ | H | H | NC(O)C(O)OH | " |
| CF₃ | H | H | NC(NH)H | " |
| CF₃ | H | H | NC(NOH)H | " |
| CF₃ | H | H | NC(NH)NHMe | " |
| CF₃ | H | H | NC(NH)NMe₂ | " |
| CF₃ | H | H | NC(NH)OMe | " |
| CF₃ | H | H | NC(NH)OEt | " |
| CF₃ | Me | H | NCOMe | " |
| CF₃ | Me | H | NCOEt | " |
| CF₃ | Me | H | NCOPr | " |
| CF₃ | Me | H | NCHO | " |
| CF₃ | Me | H | NCOiPr | " |
| CF₃ | Me | H | NCOtBu | " |
| CF₃ | Me | H | NCOPh | " |
| CF₃ | Me | H | NSO₂Me | " |
| CF₃ | Me | H | NSO₂Et | " |
| CF₃ | Me | H | NSO₂Pr | " |
| CF₃ | Me | H | NSO₂Ph | " |
| CF₃ | Me | H | NSO₂iPr | " |
| CF₃ | Me | H | NNO₂ | " |
| CF₃ | Me | H | NCOOMe | " |
| CF₃ | Me | H | NCOOEt | " |
| CF₃ | Me | H | NCOOPr | " |
| CF₃ | Me | H | NCOOiPr | " |
| CF₃ | Me | H | NCONHEt | " |
| CF₃ | Me | H | NCONHPr | " |
| CF₃ | Me | H | NCOH | " |
| CF₃ | Me | H | NCONHMe | " |
| CF₃ | Me | H | NCN | " |
| CF₃ | Me | H | NCOSMe | " |
| CF₃ | Me | H | NCOSEt | " |
| CF₃ | Me | H | NCSOMe | " |
| CF₃ | Me | H | NCSOEt | " |
| CF₃ | Me | H | NCSOPr | " |
| CF₃ | Me | H | NSO₂H | " |
| CF₃ | Me | H | NSO₂NHMe | " |
| CF₃ | Me | H | NSO₂NMe₂ | " |
| CF₃ | Me | H | NP(O)(OMe)₂ | " |
| CF₃ | Me | H | NP(O)(OEt)₂ | " |
| CF₃ | Me | H | NP(O)Me₂ | " |
| CF₃ | Me | H | NP(O)Et₂ | " |
| CF₃ | Me | H | NP(O)Me(OMe) | " |
| CF₃ | Me | H | NP(O)(OPr)₂ | " |
| CF₃ | Me | H | NC(O)C(O)H | " |

TABLE 2-continued

Structure: Pyrazole with S(=X)(=NR²) substituent at 4-position, R⁷ at 3-position, R⁸ at 5-position, R¹ at 4-position adjacent to S, N1 attached to 2,6-dichloro-4-(trifluoromethyl)phenyl.

| R¹ | R⁷ | R⁸ | NR² | X |
|---|---|---|---|---|
| CF₃ | Me | H | NC(O)C(O)Me | " |
| CF₃ | Me | H | NC(O)C(O)OMe | " |
| CF₃ | Me | H | NC(O)C(O)OEt | " |
| CF₃ | Me | H | NC(O)C(O)NH₂ | " |
| CF₃ | Me | H | NC(O)C(O)OH | " |
| CF₃ | Me | H | NC(NH)H | " |
| CF₃ | Me | H | NC(NOH)H | " |
| CF₃ | Me | H | NC(NH)NHMe | " |
| CF₃ | Me | H | NC(NH)NMe₂ | " |
| CF₃ | Me | H | NC(NH)OMe | " |
| CF₃ | Me | H | NC(NH)OEt | " |
| CF₃ | H | Cl | NCOMe | " |
| CF₃ | H | Cl | NCOEt | " |
| CF₃ | H | Cl | NCOPr | " |
| CF₃ | H | Cl | NCHO | " |
| CF₃ | H | Cl | NCOiPr | " |
| CF₃ | H | Cl | NCOtBu | " |
| CF₃ | H | Cl | NCOPh | " |
| CF₃ | H | Cl | NSO₂Me | " |
| CF₃ | H | Cl | NSO₂Et | " |
| CF₃ | H | Cl | NSO₂Pr | " |
| CF₃ | H | Cl | NSO₂Ph | " |
| CF₃ | H | Cl | NSO₂iPr | " |
| CF₃ | H | Cl | NNO₂ | " |
| CF₃ | H | Cl | NCOOMe | " |
| CF₃ | H | Cl | NCOOEt | " |
| CF₃ | H | Cl | NCOOPr | " |
| CF₃ | H | Cl | NCOOiPr | " |
| CF₃ | H | Cl | NCONHEt | " |
| CF₃ | H | Cl | NCONHPr | " |
| CF₃ | H | Cl | NCOH | " |
| CF₃ | H | Cl | NCONHMe | " |
| CF₃ | H | Cl | NCN | " |
| CF₃ | H | Cl | NCOSMe | " |
| CF₃ | H | Cl | NCOSEt | " |
| CF₃ | H | Cl | NCSOMe | " |
| CF₃ | H | Cl | NCSOEt | " |
| CF₃ | H | Cl | NCSOPr | " |
| CF₃ | H | Cl | NSO₂H | " |
| CF₃ | H | Cl | NSO₂NHMe | " |
| CF₃ | H | Cl | NSO₂NMe₂ | " |
| CF₃ | H | Cl | NP(O)(OMe)₂ | " |
| CF₃ | H | Cl | NP(O)(OEt)₂ | " |
| CF₃ | H | Cl | NP(O)Me₂ | " |
| CF₃ | H | Cl | NP(O)Et₂ | " |
| CF₃ | H | Cl | NP(O)Me(OMe) | " |
| CF₃ | H | Cl | NP(O)(OPr)₂ | " |
| CF₃ | H | Cl | NC(O)C(O)H | " |
| CF₃ | H | Cl | NC(O)C(O)Me | " |
| CF₃ | H | Cl | NC(O)C(O)OMe | " |
| CF₃ | H | Cl | NC(O)C(O)OEt | " |
| CF₃ | H | Cl | NC(O)C(O)NH₂ | " |
| CF₃ | H | Cl | NC(O)C(O)OH | " |
| CF₃ | H | Cl | NC(NH)H | " |
| CF₃ | H | Cl | NC(NOH)H | " |
| CF₃ | H | Cl | NC(NH)NHMe | " |
| CF₃ | H | Cl | NC(NH)NMe₂ | " |
| CF₃ | H | Cl | NC(NH)OMe | " |
| CF₃ | H | Cl | NC(NH)OEt | " |

| R¹ | R⁷ | R⁸ | NR² | X |
|---|---|---|---|---|
| CF₃ | Me | Cl | NCOMe | " |
| CF₃ | Me | Cl | NCOEt | " |
| CF₃ | Me | Cl | NCOPr | " |
| CF₃ | Me | Cl | NCHO | " |
| CF₃ | Me | Cl | NCOiPr | " |
| CF₃ | Me | Cl | NCOtBu | " |
| CF₃ | Me | Cl | NCOPh | " |
| CF₃ | Me | Cl | NSO₂Me | " |
| CF₃ | Me | Cl | NSO₂Et | " |
| CF₃ | Me | Cl | NSO₂Pr | " |
| CF₃ | Me | Cl | NSO₂Ph | " |
| CF₃ | Me | Cl | NSO₂iPr | " |
| CF₃ | Me | Cl | NNO₂ | " |
| CF₃ | Me | Cl | NCOOMe | " |
| CF₃ | Me | Cl | NCOOEt | " |
| CF₃ | Me | Cl | NCOOPr | " |
| CF₃ | Me | Cl | NCOOiPr | " |
| CF₃ | Me | Cl | NCONHEt | " |
| CF₃ | Me | Cl | NCONHPr | " |
| CF₃ | Me | Cl | NCOH | " |
| CF₃ | Me | Cl | NCONHMe | " |
| CF₃ | Me | Cl | NCN | " |
| CF₃ | Me | Cl | NCOSMe | " |
| CF₃ | Me | Cl | NCOSEt | " |
| CF₃ | Me | Cl | NCSOMe | " |
| CF₃ | Me | Cl | NCSOEt | " |
| CF₃ | Me | Cl | NCSOPr | " |
| CF₃ | Me | Cl | NSO₂H | " |
| CF₃ | Me | Cl | NSO₂NHMe | " |
| CF₃ | Me | Cl | NSO₂NMe₂ | " |
| CF₃ | Me | Cl | NP(O)(OMe)₂ | " |
| CF₃ | Me | Cl | NP(O)(OEt)₂ | " |
| CF₃ | Me | Cl | NP(O)Me₂ | " |
| CF₃ | Me | Cl | NP(O)Et₂ | " |
| CF₃ | Me | Cl | NP(O)Me(OMe) | " |
| CF₃ | Me | Cl | NP(O)(OPr)₂ | " |
| CF₃ | Me | Cl | NC(O)C(O)H | " |
| CF₃ | Me | Cl | NC(O)C(O)Me | " |
| CF₃ | Me | Cl | NC(O)C(O)OMe | " |
| CF₃ | Me | Cl | NC(O)C(O)OEt | " |
| CF₃ | Me | Cl | NC(O)C(O)NH₂ | " |
| CF₃ | Me | Cl | NC(O)C(O)OH | " |
| CF₃ | Me | Cl | NC(NH)H | " |
| CF₃ | Me | Cl | NC(NOH)H | " |
| CF₃ | Me | Cl | NC(NH)NHMe | " |
| CF₃ | Me | Cl | NC(NH)NMe₂ | " |
| CF₃ | Me | Cl | NC(NH)OMe | " |
| CF₃ | Me | Cl | NC(NH)OEt | " |
| Me | H | NH₂ | NCOMe | " |
| Me | H | NH₂ | NCOEt | " |
| Me | H | NH₂ | NCOPr | " |
| Me | H | NH₂ | NCHO | " |
| Me | H | NH₂ | NCOiPr | " |
| Me | H | NH₂ | NCOtBu | " |
| Me | H | NH₂ | NCOPh | " |
| Me | H | NH₂ | NSO₂Me | " |
| Me | H | NH₂ | NSO₂Et | " |
| Me | H | NH₂ | NSO₂Pr | " |
| Me | H | NH₂ | NSO₂Ph | " |

TABLE 2-continued

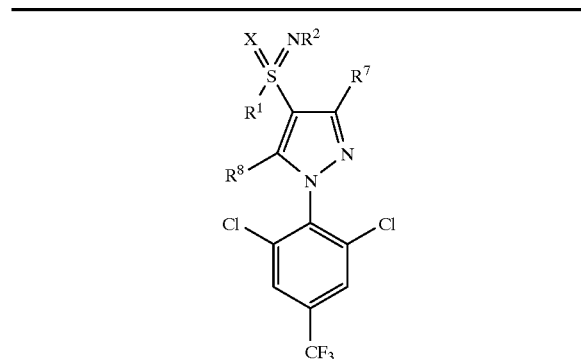

| R¹ | R⁷ | R⁸ | NR² | X |
|---|---|---|---|---|
| Me | H | NH₂ | NSO₂iPr | " |
| Me | H | NH₂ | NNO₂ | " |
| Me | H | NH₂ | NCOOMe | " |
| Me | H | NH₂ | NCOOEt | " |
| Me | H | NH₂ | NCOOPr | " |
| Me | H | NH₂ | NCOOiPr | " |
| Me | H | NH₂ | NCONHEt | " |
| Me | H | NH₂ | NCONHPr | " |
| Me | H | NH₂ | NCOH | " |
| Me | H | NH₂ | NCONHMe | " |
| Me | H | NH₂ | NCN | " |
| Me | H | NH₂ | NCOSMe | " |
| Me | H | NH₂ | NCOSEt | " |
| Me | H | NH₂ | NCSOMe | " |
| Me | H | NH₂ | NCSOEt | " |
| Me | H | NH₂ | NCSOPr | " |
| Me | H | NH₂ | NSO₂H | " |
| Me | H | NH₂ | NSO₂NHMe | " |
| Me | H | NH₂ | NSO₂NMe₂ | " |
| Me | H | NH₂ | NP(O)(OMe)₂ | " |
| Me | H | NH₂ | NP(O)(OEt)₂ | " |
| Me | H | NH₂ | NP(O)Me₂ | " |
| Me | H | NH₂ | NP(O)Et₂ | " |
| Me | H | NH₂ | NP(O)Me(OMe) | " |
| Me | H | NH₂ | NP(O)(OPr)₂ | " |
| Me | H | NH₂ | NC(O)C(O)H | " |
| Me | H | NH₂ | NC(O)C(O)Me | " |
| Me | H | NH₂ | NC(O)C(O)OMe | " |
| Me | H | NH₂ | NC(O)C(O)OEt | " |
| Me | H | NH₂ | NC(O)C(O)NH₂ | " |
| Me | H | NH₂ | NC(O)C(O)OH | " |
| Me | H | NH₂ | NC(NH)H | " |
| Me | H | NH₂ | NC(NOH)H | " |
| Me | H | NH₂ | NC(NH)NHMe | " |
| Me | H | NH₂ | NC(NH)NMe₂ | " |
| Me | H | NH₂ | NC(NH)OMe | " |
| Me | H | NH₂ | NC(NH)OEt | " |
| Me | H | NH₂ | NH | O |
| Me | H | NH₂ | NCOMe | O |
| Me | H | NH₂ | NCOEt | O |
| Me | H | NH₂ | NCOPr | O |
| Me | H | NH₂ | NCHO | O |
| Me | H | NH₂ | NCOiPr | O |
| Me | H | NH₂ | NCOtBu | O |
| Me | H | NH₂ | NCOPh | O |
| Me | H | NH₂ | NSO₂Me | O |
| Me | H | NH₂ | NSO₂Et | O |
| Me | H | NH₂ | NSO₂Pr | O |
| Me | H | NH₂ | NSO₂Ph | O |
| Me | H | NH₂ | NSO₂iPr | O |
| Me | H | NH₂ | NNO₂ | O |
| Me | H | NH₂ | NCOOMe | O |
| Me | H | NH₂ | NCOOEt | O |
| Me | H | NH₂ | NCOOPr | O |
| Me | H | NH₂ | NCOOiPr | O |
| Me | H | NH₂ | NCONHEt | O |
| Me | H | NH₂ | NCONHPr | O |
| Me | H | NH₂ | NCOH | O |
| Me | H | NH₂ | NCONHMe | O |

TABLE 2-continued

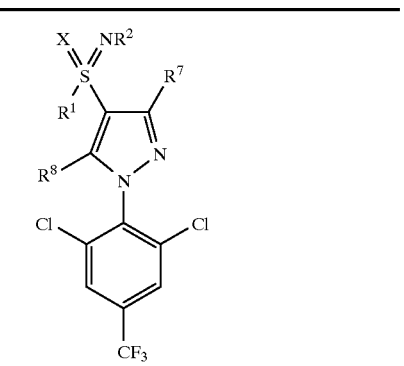

| R¹ | R⁷ | R⁸ | NR² | X |
|---|---|---|---|---|
| Me | H | NH₂ | NCN | O |
| Me | H | NH₂ | NCOSMe | O |
| Me | H | NH₂ | NCOSEt | O |
| Me | H | NH₂ | NCSOMe | O |
| Me | H | NH₂ | NCSOEt | O |
| Me | H | NH₂ | NCSOPr | O |
| Me | H | NH₂ | NSO₂H | O |
| Me | H | NH₂ | NSO₂NHMe | O |
| Me | H | NH₂ | NSO₂NMe₂ | O |
| Me | H | NH₂ | NP(O)(OMe)₂ | O |
| Me | H | NH₂ | NP(O)(OEt)₂ | O |
| Me | H | NH₂ | NP(O)Me₂ | O |
| Me | H | NH₂ | NP(O)Et₂ | O |
| Me | H | NH₂ | NP(O)Me(OMe) | O |
| Me | H | NH₂ | NP(O)(OPr)₂ | O |
| Me | H | NH₂ | NC(O)C(O)H | O |
| Me | H | NH₂ | NC(O)C(O)Me | O |
| Me | H | NH₂ | NC(O)C(O)OMe | O |
| Me | H | NH₂ | NC(O)C(O)OEt | O |
| Me | H | NH₂ | NC(O)C(O)NH₂ | O |
| Me | H | NH₂ | NC(O)C(O)OH | O |
| Me | H | NH₂ | NC(NH)H | O |
| Me | H | NH₂ | NC(NOH)H | O |
| Me | H | NH₂ | NC(NH)NHMe | O |
| Me | H | NH₂ | NC(NH)NMe₂ | O |
| Me | H | NH₂ | NC(NH)OMe | O |
| Me | H | NH₂ | NC(NH)OEt | O |
| Me | Me | NH₂ | NCOMe | " |
| Me | Me | NH₂ | NCOEt | " |
| Me | Me | NH₂ | NCOPr | " |
| Me | Me | NH₂ | NCHO | " |
| Me | Me | NH₂ | NCOiPr | " |
| Me | Me | NH₂ | NCOtBu | " |
| Me | Me | NH₂ | NCOPh | " |
| Me | Me | NH₂ | NSO₂Me | " |
| Me | Me | NH₂ | NSO₂Et | " |
| Me | Me | NH₂ | NSO₂Pr | " |
| Me | Me | NH₂ | NSO₂Ph | " |
| Me | Me | NH₂ | NSO₂iPr | " |
| Me | Me | NH₂ | NNO₂ | " |
| Me | Me | NH₂ | NCOOMe | " |
| Me | Me | NH₂ | NCOOEt | " |
| Me | Me | NH₂ | NCOOPr | " |
| Me | Me | NH₂ | NCOOiPr | " |
| Me | Me | NH₂ | NCONHEt | " |
| Me | Me | NH₂ | NCONHPr | " |
| Me | Me | NH₂ | NCOH | " |
| Me | Me | NH₂ | NCONHMe | " |
| Me | Me | NH₂ | NCN | " |
| Me | Me | NH₂ | NCOSMe | " |
| Me | Me | NH₂ | NCOSEt | " |
| Me | Me | NH₂ | NCSOMe | " |
| Me | Me | NH₂ | NCSOEt | " |
| Me | Me | NH₂ | NCSOPr | " |
| Me | Me | NH₂ | NSO₂H | " |
| Me | Me | NH₂ | NSO₂NHMe | " |
| Me | Me | NH₂ | NSO₂NMe₂ | " |
| Me | Me | NH₂ | NP(O)(OMe)₂ | " |
| Me | Me | NH₂ | NP(O)(OEt)₂ | " |

TABLE 2-continued

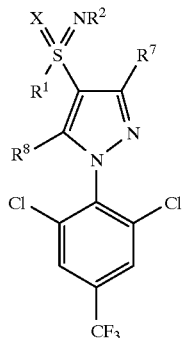

| R¹ | R⁷ | R⁸ | NR² | X |
|---|---|---|---|---|
| Me | Me | NH₂ | NP(O)Me₂ | " |
| Me | Me | NH₂ | NP(O)Et₂ | " |
| Me | Me | NH₂ | NP(O)Me(OMe) | " |
| Me | Me | NH₂ | NP(O)(OPr)₂ | " |
| Me | Me | NH₂ | NC(O)C(O)H | " |
| Me | Me | NH₂ | NC(O)C(O)Me | " |
| Me | Me | NH₂ | NC(O)C(O)OMe | " |
| Me | Me | NH₂ | NC(O)C(O)OEt | " |
| Me | Me | NH₂ | NC(O)C(O)NH₂ | " |
| Me | Me | NH₂ | NC(O)C(O)OH | " |
| Me | Me | NH₂ | NC(NH)H | " |
| Me | Me | NH₂ | NC(NOH)H | " |
| Me | Me | NH₂ | NC(NH)NHMe | " |
| Me | Me | NH₂ | NC(NH)NMe₂ | " |
| Me | Me | NH₂ | NC(NH)OMe) | " |
| Me | Me | NH₂ | NC(NH)OEt | " |
| Me | Me | NH₂ | NH | O |
| Me | Me | NH₂ | NCOMe | O |
| Me | Me | NH₂ | NCOEt | O |
| Me | Me | NH₂ | NCOPr | O |
| Me | Me | NH₂ | NCHO | O |
| Me | Me | NH₂ | NCOiPr | O |
| Me | Me | NH₂ | NCOtBu | O |
| Me | Me | NH₂ | NCOPh | O |
| Me | Me | NH₂ | NSO₂Me | O |
| Me | Me | NH₂ | NSO₂Et | O |
| Me | Me | NH₂ | NSO₂Pr | O |
| Me | Me | NH₂ | NSO₂Ph | O |
| Me | Me | NH₂ | NSO₂iPr | O |
| Me | Me | NH₂ | NNO₂ | O |
| Me | Me | NH₂ | NCOOMe | O |
| Me | Me | NH₂ | NCOOEt | O |
| Me | Me | NH₂ | NCOOPr | O |
| Me | Me | NH₂ | NCOOiPr | O |
| Me | Me | NH₂ | NCONHEt | O |
| Me | Me | NH₂ | NCONHPr | O |
| Me | Me | NH₂ | NCOH | O |
| Me | Me | NH₂ | NCONHMe | O |
| Me | Me | NH₂ | NCN | O |
| Me | Me | NH₂ | NCOSMe | O |
| Me | Me | NH₂ | NCOSEt | O |
| Me | Me | NH₂ | NCSOMe | O |
| Me | Me | NH₂ | NCSOEt | O |
| Me | Me | NH₂ | NCSOPr | O |
| Me | Me | NH₂ | NSO₂H | O |
| Me | Me | NH₂ | NSO₂NHMe | O |
| Me | Me | NH₂ | NSO₂NMe₂ | O |
| Me | Me | NH₂ | NP(O)(OMe)₂ | O |
| Me | Me | NH₂ | NP(O)(OEt)₂ | O |
| Me | Me | NH₂ | NP(O)Me₂ | O |
| Me | Me | NH₂ | NP(O)Et₂ | O |
| Me | Me | NH₂ | NP(O)Me(OMe) | O |
| Me | Me | NH₂ | NP(O)(OPr)₂ | O |
| Me | Me | NH₂ | NC(O)C(O)H | O |
| Me | Me | NH₂ | NC(O)C(O)Me | O |
| Me | Me | NH₂ | NC(O)C(O)OMe | O |
| Me | Me | NH₂ | NC(O)C(O)OEt | O |
| Me | Me | NH₂ | NC(O)C(O)NH₂ | O |
| Me | Me | NH₂ | NC(O)C(O)OH | O |

TABLE 2-continued

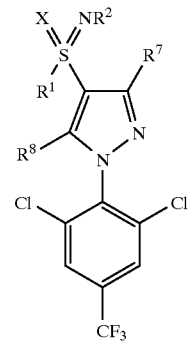

| R¹ | R⁷ | R⁸ | NR² | X |
|---|---|---|---|---|
| Me | Me | NH₂ | NC(NH)H | O |
| Me | Me | NH₂ | NC(NOH)H | O |
| Me | Me | NH₂ | NC(NH)NHMe | O |
| Me | Me | NH₂ | NC(NH)NMe₂ | O |
| Me | Me | NH₂ | NC(NH)OMe | O |
| Me | Me | NH₂ | NC(NH)OEt | O |
| Me | H | H | NCOMe | " |
| Me | H | H | NCOEt | " |
| Me | H | H | NCOPr | " |
| Me | H | H | NCHO | " |
| Me | H | H | NCOiPr | " |
| Me | H | H | NCOtBu | " |
| Me | H | H | NCOPh | " |
| Me | H | H | NSO₂Me | " |
| Me | H | H | NSO₂Et | " |
| Me | H | H | NSO₂Pr | " |
| Me | H | H | NSO₂Ph | " |
| Me | H | H | NSO₂iPr | " |
| Me | H | H | NNO₂ | " |
| Me | H | H | NCOOMe | " |
| Me | H | H | NCOOEt | " |
| Me | H | H | NCOOPr | " |
| Me | H | H | NCOOiPr | " |
| Me | H | H | NCONHEt | " |
| Me | H | H | NCONHPr | " |
| Me | H | H | NCOH | " |
| Me | H | H | NCONHMe | " |
| Me | H | H | NCN | " |
| Me | H | H | NCOSMe | " |
| Me | H | H | NCOSEt | " |
| Me | H | H | NCSOMe | " |
| Me | H | H | NCSOEt | " |
| Me | H | H | NCSOPr | " |
| Me | H | H | NSO₂H | " |
| Me | H | H | NSO₂NHMe | " |
| Me | H | H | NSO₂NMe₂ | " |
| Me | H | H | NP(O)(OMe)₂ | " |
| Me | H | H | NP(O)(OEt)₂ | " |
| Me | H | H | NP(O)Me₂ | " |
| Me | H | H | NP(O)Et₂ | " |
| Me | H | H | NP(O)Me(OMe) | " |
| Me | H | H | NP(O)(OPr)₂ | " |
| Me | H | H | NC(O)C(O)H | " |
| Me | H | H | NC(O)C(O)Me | " |
| Me | H | H | NC(O)C(O)OMe | " |
| Me | H | H | NC(O)C(O)OEt | " |
| Me | H | H | NC(O)C(O)NH₂ | " |
| Me | H | H | NC(O)C(O)OH | " |
| Me | H | H | NC(NH)H | " |
| Me | H | H | NC(NOH)H | " |
| Me | H | H | NC(NH)NHMe | " |
| Me | H | H | NC(NH)NMe₂ | " |
| Me | H | H | NC(NH)OMe | " |
| Me | H | H | NC(NH)OEt | " |
| Me | H | Me | NCOMe | " |
| Me | H | Me | NCOEt | " |
| Me | H | Me | NCOPr | " |
| Me | H | Me | NCHO | " |
| Me | H | Me | NCOiPr | " |

TABLE 2-continued

| R¹ | R⁷ | R⁸ | NR² | X |
|---|---|---|---|---|
| Me | H | Me | NCOtBu | " |
| Me | H | Me | NCOPh | " |
| Me | H | Me | NSO₂Me | " |
| Me | H | Me | NSO₂Et | " |
| Me | H | Me | NSO₂Pr | " |
| Me | H | Me | NSO₂Ph | " |
| Me | H | Me | NSO₂iPr | " |
| Me | H | Me | NNO₂ | " |
| Me | H | Me | NCOOMe | " |
| Me | H | Me | NCOOEt | " |
| Me | H | Me | NCOOPr | " |
| Me | H | Me | NCOOiPr | " |
| Me | H | Me | NCONHEt | " |
| Me | H | Me | NCONHPr | " |
| Me | H | Me | NCOH | " |
| Me | H | Me | NCONHMe | " |
| Me | H | Me | NCN | " |
| Me | H | Me | NCOSMe | " |
| Me | H | Me | NCOSEt | " |
| Me | H | Me | NCSOMe | " |
| Me | H | Me | NCSOEt | " |
| Me | H | Me | NCSOPr | " |
| Me | H | Me | NSO₂H | " |
| Me | H | Me | NSO₂NHMe | " |
| Me | H | Me | NSO₂NMe₂ | " |
| Me | H | Me | NP(O)(OMe)₂ | " |
| Me | H | Me | NP(O)(OEt)₂ | " |
| Me | H | Me | NP(O)Me₂ | " |
| Me | H | Me | NP(O)Et₂ | " |
| Me | H | Me | NP(O)Me(OMe) | " |
| Me | H | Me | NP(O)(OPr)₂ | " |
| Me | H | Me | NC(O)C(O)H | " |
| Me | H | Me | NC(O)C(O)Me | " |
| Me | H | Me | NC(O)C(O)OMe | " |
| Me | H | Me | NC(O)C(O)OEt | " |
| Me | H | Me | NC(O)C(O)NH₂ | " |
| Me | H | Me | NC(O)C(O)OH | " |
| Me | H | Me | NC(NH)H | " |
| Me | H | Me | NC(NOH)H | " |
| Me | H | Me | NC(NH)NHMe | " |
| Me | H | Me | NC(NH)NMe₂ | " |
| Me | H | Me | NC(NH)OMe | " |
| Me | H | Me | NC(NH)OEt | " |
| Me | Me | Me | NCOMe | " |
| Me | Me | Me | NCOEt | " |
| Me | Me | Me | NCOPr | " |
| Me | Me | Me | NCHO | " |
| Me | Me | Me | NCOiPr | " |
| Me | Me | Me | NCOtBu | " |
| Me | Me | Me | NCOPh | " |
| Me | Me | Me | NSO₂Me | " |
| Me | Me | Me | NSO₂Et | " |
| Me | Me | Me | NSO₂Pr | " |
| Me | Me | Me | NSO₂Ph | " |
| Me | Me | Me | NSO₂iPr | " |
| Me | Me | Me | NNO₂ | " |
| Me | Me | Me | NCOOMe | " |
| Me | Me | Me | NCOOEt | " |
| Me | Me | Me | NCOOPr | " |
| Me | Me | Me | NCOOiPr | " |
| Me | Me | Me | NCONHEt | " |
| Me | Me | Me | NCONHPr | " |
| Me | Me | Me | NCOH | " |
| Me | Me | Me | NCONHMe | " |
| Me | Me | Me | NCN | " |
| Me | Me | Me | NCOSMe | " |
| Me | Me | Me | NCOSEt | " |
| Me | Me | Me | NCSOMe | " |
| Me | Me | Me | NCSOEt | " |
| Me | Me | Me | NCSOPr | " |
| Me | Me | Me | NSO₂H | " |
| Me | Me | Me | NSO₂NHMe | " |
| Me | Me | Me | NSO₂NMe₂ | " |
| Me | Me | Me | NP(O)(OMe)₂ | " |
| Me | Me | Me | NP(O)(OEt)₂ | " |
| Me | Me | Me | NP(O)Me₂ | " |
| Me | Me | Me | NP(O)Et₂ | " |
| Me | Me | Me | NP(O)Me(OMe) | " |
| Me | Me | Me | NP(O)(OPr)₂ | " |
| Me | Me | Me | NC(O)C(O)H | " |
| Me | Me | Me | NC(O)C(O)Me | " |
| Me | Me | Me | NC(O)C(O)OMe | " |
| Me | Me | Me | NC(O)C(O)OEt | " |
| Me | Me | Me | NC(O)C(O)NH₂ | " |
| Me | Me | Me | NC(O)C(O)OH | " |
| Me | Me | Me | NC(NH)H | " |
| Me | Me | Me | NC(NOH)H | " |
| Me | Me | Me | NC(NH)NHMe | " |
| Me | Me | Me | NC(NH)NMe₂ | " |
| Me | Me | Me | NC(NH)OMe | " |
| Me | Me | Me | NC(NH)OEt | " |
| Me | Me | H | NCOMe | " |
| Me | Me | H | NCOEt | " |
| Me | Me | H | NCOPr | " |
| Me | Me | H | NCHO | " |
| Me | Me | H | NCOiPr | " |
| Me | Me | H | NCOtBu | " |
| Me | Me | H | NCOPh | " |
| Me | Me | H | NSO₂Me | " |
| Me | Me | H | NSO₂Et | " |
| Me | Me | H | NSO₂Pr | " |
| Me | Me | H | NSO₂Ph | " |
| Me | Me | H | NSO₂iPr | " |
| Me | Me | H | NNO₂ | " |
| Me | Me | H | NCOOMe | " |
| Me | Me | H | NCOOEt | " |
| Me | Me | H | NCOOPr | " |
| Me | Me | H | NCOOiPr | " |
| Me | Me | H | NCONHEt | " |
| Me | Me | H | NCONHPr | " |
| Me | Me | H | NCOH | " |
| Me | Me | H | NCONHMe | " |
| Me | Me | H | NCN | " |
| Me | Me | H | NCOSMe | " |
| Me | Me | H | NCOSEt | " |
| Me | Me | H | NCSOMe | " |
| Me | Me | H | NCSOEt | " |
| Me | Me | H | NCSOPr | " |

TABLE 2-continued

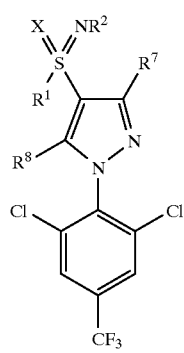

| R¹ | R⁷ | R⁸ | NR² | X |
|---|---|---|---|---|
| Me | Me | H | NSO₂H | " |
| Me | Me | H | NSO₂NHMe | " |
| Me | Me | H | NSO₂NMe₂ | " |
| Me | Me | H | NP(O)(OMe)₂ | " |
| Me | Me | H | NP(O)(OEt)₂ | " |
| Me | Me | H | NP(O)Me₂ | " |
| Me | Me | H | NP(O)Et₂ | " |
| Me | Me | H | NP(O)Me(OMe) | " |
| Me | Me | H | NP(O)(OPr)₂ | " |
| Me | Me | H | NC(O)C(O)H | " |
| Me | Me | H | NC(O)C(O)Me | " |
| Me | Me | H | NC(O)C(O)OMe | " |
| Me | Me | H | NC(O)C(O)OEt | " |
| Me | Me | H | NC(O)C(O)NH₂ | " |
| Me | Me | H | NC(O)C(O)OH | " |
| Me | Me | H | NC(NH)H | " |
| Me | Me | H | NC(NOH)H | " |
| Me | Me | H | NC(NH)NHMe | " |
| Me | Me | H | NC(NH)NMe₂ | " |
| Me | Me | H | NC(NH)OMe | " |
| Me | Me | H | NC(NH)OEt | " |
| Me | CN | NH₂ | NH | NH |
| Me | CN | NHMe | NH | NH |
| Me | CN | NMe₂ | NH | NH |
| Me | CN | NHEt | NH | NH |
| Et | CN | NH₂ | NH | NH |
| Et | CN | NHMe | NH | NH |
| Et | CN | NMe₂ | NH | NH |
| Et | CN | NHEt | NH | NH |
| CF₃ | CN | NH₂ | NH | NH |
| CF₃ | CN | NHMe | NH | NH |
| CF₃ | CN | NMe₂ | NH | NH |
| CF₃ | CN | NHEt | NH | NH |

TABLE 3

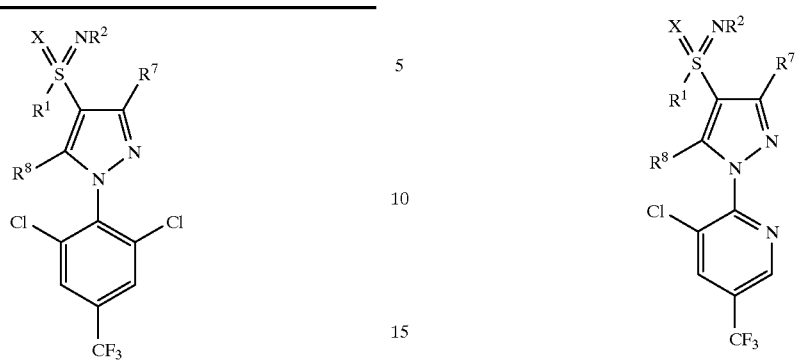

| R¹ | R⁷ | R⁸ | NR² | X |
|---|---|---|---|---|
| CF₃ | CN | NH₂ | NCOMe | " |
| CF₃ | CN | NH₂ | NCOEt | " |

TABLE 3-continued

| R¹ | R⁷ | R⁸ | NR² | X |
|---|---|---|---|---|
| CF₃ | CN | NH₂ | NCOPr | " |
| CF₃ | CN | NH₂ | NCHO | " |
| CF₃ | CN | NH₂ | NCOiPr | " |
| CF₃ | CN | NH₂ | NCOtBu | " |
| CF₃ | CN | NH₂ | NCOPh | " |
| CF₃ | CN | NH₂ | NSO₂Me | " |
| CF₃ | CN | NH₂ | NSO₂Et | " |
| CF₃ | CN | NH₂ | NSO₂Pr | " |
| CF₃ | CN | NH₂ | NSO₂Ph | " |
| CF₃ | CN | NH₂ | NSO₂iPr | " |
| CF₃ | CN | NH₂ | NNO₂ | " |
| CF₃ | CN | NH₂ | NCOOMe | " |
| CF₃ | CN | NH₂ | NCOOEt | " |
| CF₃ | CN | NH₂ | NCOOPr | " |
| CF₃ | CN | NH₂ | NCOOiPr | " |
| CF₃ | CN | NH₂ | NCONHEt | " |
| CF₃ | CN | NH₂ | NCONHPr | " |
| CF₃ | CN | NH₂ | NCONH₂ | " |
| CF₃ | CN | NH₂ | NCONHMe | " |
| CF₃ | CN | NH₂ | NCN | " |
| CF₃ | CN | NH₂ | NCOSMe | " |
| CF₃ | CN | NH₂ | NCOSEt | " |
| CF₃ | CN | NH₂ | NCSOMe | " |
| CF₃ | CN | NH₂ | NCSOEt | " |
| CF₃ | CN | NH₂ | NCSOPr | " |
| CF₃ | CN | NH₂ | NSO₂NH₂ | " |
| CF₃ | CN | NH₂ | NSO₂NHMe | " |
| CF₃ | CN | NH₂ | NSO₂NMe₂ | " |
| CF₃ | CN | NH₂ | NP(O)(OMe)₂ | " |
| CF₃ | CN | NH₂ | NP(O)(OEt)₂ | " |
| CF₃ | CN | NH₂ | NP(O)Me₂ | " |
| CF₃ | CN | NH₂ | NP(O)Et₂ | " |
| CF₃ | CN | NH₂ | NP(O)Me(OMe) | " |
| CF₃ | CN | NH₂ | NP(O)(OPr)₂ | " |
| CF₃ | CN | NH₂ | NC(O)C(O)H | " |
| CF₃ | CN | NH₂ | NC(O)C(O)Me | " |
| CF₃ | CN | NH₂ | NC(O)C(O)OMe | " |
| CF₃ | CN | NH₂ | NC(O)C(O)OEt | " |
| CF₃ | CN | NH₂ | NC(O)C(O)NH₂ | " |
| CF₃ | CN | NH₂ | NC(O)C(O)OH | " |
| CF₃ | CN | NH₂ | NC(NH)NH₂ | " |
| CF₃ | CN | NH₂ | NC(NOH)NH₂ | " |
| CF₃ | CN | NH₂ | NC(NH)NHMe | " |
| CF₃ | CN | NH₂ | NC(NH)NMe₂ | " |
| CF₃ | CN | NH₂ | NC(NH)OMe | " |
| CF₃ | CN | NH₂ | NC(NH)OEt | " |
| CF₃ | CN | NH₂ | NH | O |
| CF₃ | CN | NH₂ | NCOMe | O |
| CF₃ | CN | NH₂ | NCOEt | O |
| CF₃ | CN | NH₂ | NCOPr | O |
| CF₃ | CN | NH₂ | NCHO | O |
| CF₃ | CN | NH₂ | NCOiPr | O |
| CF₃ | CN | NH₂ | NCOtBu | O |
| CF₃ | CN | NH₂ | NCOPh | O |
| CF₃ | CN | NH₂ | NSO₂Me | O |
| CF₃ | CN | NH₂ | NSO₂Et | O |
| CF₃ | CN | NH₂ | NSO₂Pr | O |
| CF₃ | CN | NH₂ | NSO₂Ph | O |
| CF₃ | CN | NH₂ | NSO₂iPr | O |
| CF₃ | CN | NH₂ | NNO₂ | O |

TABLE 3-continued

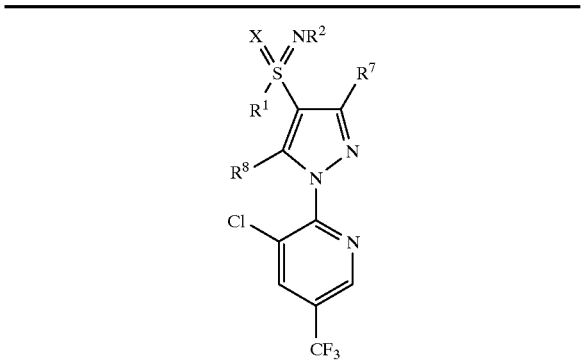

| R¹ | R⁷ | R⁸ | NR² | X |
|---|---|---|---|---|
| CF₃ | CN | NH₂ | NCOOMe | O |
| CF₃ | CN | NH₂ | NCOOEt | O |
| CF₃ | CN | NH₂ | NCOOPr | O |
| CF₃ | CN | NH₂ | NCOOiPr | O |
| CF₃ | CN | NH₂ | NCONHEt | O |
| CF₃ | CN | NH₂ | NCONHPr | O |
| CF₃ | CN | NH₂ | NCONH₂ | O |
| CF₃ | CN | NH₂ | NCONHMe | O |
| CF₃ | CN | NH₂ | NCN | O |
| CF₃ | CN | NH₂ | NCOSMe | O |
| CF₃ | CN | NH₂ | NCOSEt | O |
| CF₃ | CN | NH₂ | NCSOMe | O |
| CF₃ | CN | NH₂ | NCSOEt | O |
| CF₃ | CN | NH₂ | NCSOPr | O |
| CF₃ | CN | NH₂ | NSO₂NH₂ | O |
| CF₃ | CN | NH₂ | NSO₂NHMe | O |
| CF₃ | CN | NH₂ | NSO₂NMe₂ | O |
| CF₃ | CN | NH₂ | NP(O)(OMe)₂ | O |
| CF₃ | CN | NH₂ | NP(O)(OEt)₂ | O |
| CF₃ | CN | NH₂ | NP(O)Me₂ | O |
| CF₃ | CN | NH₂ | NP(O)Et₂ | O |
| CF₃ | CN | NH₂ | NP(O)Me(OMe) | O |
| CF₃ | CN | NH₂ | NP(O)(OPr)₂ | O |
| CF₃ | CN | NH₂ | NC(O)C(O)H | O |
| CF₃ | CN | NH₂ | NC(O)C(O)Me | O |
| CF₃ | CN | NH₂ | NC(O)C(O)OMe | O |
| CF₃ | CN | NH₂ | NC(O)C(O)OEt | O |
| CF₃ | CN | NH₂ | NC(O)C(O)NH₂ | O |
| CF₃ | CN | NH₂ | NC(O)C(O)OH | O |
| CF₃ | CN | NH₂ | NC(NH)NH₂ | O |
| CF₃ | CN | NH₂ | NC(NOH)NH₂ | O |
| CF₃ | CN | NH₂ | NC(NH)NHMe | O |
| CF₃ | CN | NH₂ | NC(NH)NMe₂ | O |
| CF₃ | CN | NH₂ | NC(NH)OMe | O |
| CF₃ | CN | NH₂ | NC(NH)OEt | O |
| CF₃ | CN | NH₂ | NCOMe | O |
| CF₃ | CN | NH₂ | NCOEt | O |
| CF₃ | CN | NH₂ | NCOPr | O |
| CF₃ | CN | NH₂ | NCHO | O |
| CF₃ | CN | NH₂ | NCOiPr | O |
| CF₃ | CN | NH₂ | NCOtBu | O |
| CF₃ | CN | NH₂ | NCOPh | O |
| CF₃ | CN | NH₂ | NSO₂Me | O |
| CF₃ | CN | NH₂ | NSO₂Et | O |
| CF₃ | CN | NH₂ | NSO₂Pr | O |
| CF₃ | CN | NH₂ | NSO₂Ph | O |
| CF₃ | CN | NH₂ | NSO₂iPr | O |
| CF₃ | CN | NH₂ | NNO₂ | O |
| CF₃ | CN | NH₂ | NCOOMe | O |
| CF₃ | CN | NH₂ | NCOOEt | O |
| CF₃ | CN | NH₂ | NCOOPr | O |
| CF₃ | CN | NH₂ | NCOOiPr | O |
| CF₃ | CN | NH₂ | NCONHEt | O |
| CF₃ | CN | NH₂ | NCONHPr | O |
| CF₃ | CN | NH₂ | NCONH₂ | O |
| CF₃ | CN | NH₂ | NCONHMe | O |
| CF₃ | CN | NH₂ | NCN | O |
| CF₃ | CN | NH₂ | NCOSMe | O |
| CF₃ | CN | NH₂ | NCOSEt | O |
| CF₃ | CN | NH₂ | NCSOMe | O |

| R¹ | R⁷ | R⁸ | NR² | X |
|---|---|---|---|---|
| CF₃ | CN | NH₂ | NCSOEt | O |
| CF₃ | CN | H | NCSOPr | " |
| CF₃ | CN | H | NSO₂NH₂ | " |
| CF₃ | CN | H | NSO₂NHMe | " |
| CF₃ | CN | H | NSO₂NMe₂ | " |
| CF₃ | CN | H | NP(O)(OMe)₂ | " |
| CF₃ | CN | H | NP(O)(OEt)₂ | " |
| CF₃ | CN | H | NP(O)Me₂ | " |
| CF₃ | CN | H | NP(O)Et₂ | " |
| CF₃ | CN | H | NP(O)Me(OMe) | " |
| CF₃ | CN | H | NP(O)(OPr)₂ | " |
| CF₃ | CN | H | NC(O)C(O)H | " |
| CF₃ | CN | H | NC(O)C(O)Me | " |
| CF₃ | CN | H | NC(O)C(O)OMe | " |
| CF₃ | CN | H | NC(O)C(O)OEt | " |
| CF₃ | CN | H | NC(O)C(O)NH₂ | " |
| CF₃ | CN | H | NC(O)C(O)OH | " |
| CF₃ | CN | H | NC(NH)NH₂ | " |
| CF₃ | CN | H | NC(NOH)NH₂ | " |
| CF₃ | CN | H | NC(NH)NHMe | " |
| CF₃ | CN | H | NC(NH)NMe₂ | " |
| CF₃ | CN | H | NC(NH)OMe | " |
| CF₃ | CN | H | NC(NH)OEt | " |
| CF₃ | CN | H | NH | O |
| CF₃ | CN | H | NCOMe | O |
| CF₃ | CN | H | NCOEt | O |
| CF₃ | CN | H | NCOPr | O |
| CF₃ | CN | H | NCHO | O |
| CF₃ | CN | H | NCOiPr | O |
| CF₃ | CN | H | NCOtBu | O |
| CF₃ | CN | H | NCOPh | O |
| CF₃ | CN | H | NSO₂Me | O |
| CF₃ | CN | H | NSO₂Et | O |
| CF₃ | CN | H | NSO₂Pr | O |
| CF₃ | CN | H | NSO₂Ph | O |
| CF₃ | CN | H | NSO₂iPr | O |
| CF₃ | CN | H | NNO₂ | O |
| CF₃ | CN | H | NCOOMe | O |
| CF₃ | CN | H | NCOOEt | O |
| CF₃ | CN | H | NCOOPr | O |
| CF₃ | CN | H | NCOOiPr | O |
| CF₃ | CN | H | NCONHEt | O |
| CF₃ | CN | H | NCONHPr | O |
| CF₃ | CN | H | NCONH₂ | O |
| CF₃ | CN | H | NCONHMe | O |
| CF₃ | CN | H | NCN | O |
| CF₃ | CN | H | NCOSMe | O |
| CF₃ | CN | H | NCOSEt | O |
| CF₃ | CN | H | NCSOMe | O |
| CF₃ | CN | H | NCSOEt | O |
| CF₃ | CN | H | NCSOPr | O |
| CF₃ | CN | H | NSO₂NH₂ | O |
| CF₃ | CN | H | NSO₂NHMe | O |
| CF₃ | CN | H | NSO₂NMe₂ | O |
| CF₃ | CN | H | NP(O)(OMe)₂ | O |
| CF₃ | CN | H | NP(O)(OEt)₂ | O |
| CF₃ | CN | H | NP(O)Me₂ | O |
| CF₃ | CN | H | NP(O)Et₂ | O |
| CF₃ | CN | H | NP(O)Me(OMe) | O |
| CF₃ | CN | H | NP(O)(OPr)₂ | O |

TABLE 3-continued

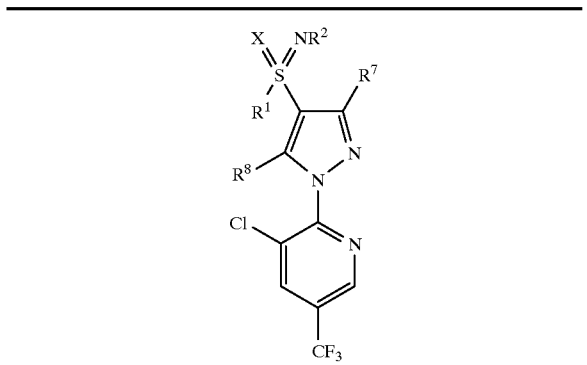

| R¹ | R⁷ | R⁸ | NR² | X |
|---|---|---|---|---|
| CF₃ | CN | H | NC(O)C(O)H | O |
| CF₃ | CN | H | NC(O)C(O)Me | O |
| CF₃ | CN | H | NC(O)C(O)OMe | O |
| CF₃ | CN | H | NC(O)C(O)OEt | O |
| CF₃ | CN | H | NC(O)C(O)NH₂ | O |
| CF₃ | CN | H | NC(O)C(O)OH | O |
| CF₃ | CN | H | NC(NH)NH₂ | O |
| CF₃ | CN | H | NC(NOH)NH₂ | O |
| CF₃ | CN | H | NC(NH)NHMe | O |
| CF₃ | CN | H | NC(NH)NMe₂ | O |
| CF₃ | CN | H | NC(NH)OMe | O |
| CF₃ | CN | H | NC(NH)OEt | O |
| CF₃ | CN | SMe | NCOMe | " |
| CF₃ | CN | SMe | NCOEt | " |
| CF₃ | CN | SMe | NCOPr | " |
| CF₃ | CN | SMe | NCHO | " |
| CF₃ | CN | SMe | NCOiPr | " |
| CF₃ | CN | SMe | NCOtBu | " |
| CF₃ | CN | SMe | NCOPh | " |
| CF₃ | CN | SMe | NSO₂Me | " |
| CF₃ | CN | SMe | NSO₂Et | " |
| CF₃ | CN | SMe | NSO₂Pr | " |
| CF₃ | CN | SMe | NSO₂Ph | " |
| CF₃ | CN | SMe | NSO₂iPr | " |
| CF₃ | CN | SMe | NNO₂ | " |
| CF₃ | CN | SMe | NCOOMe | " |
| CF₃ | CN | SMe | NCOOEt | " |
| CF₃ | CN | SMe | NCOOPr | " |
| CF₃ | CN | SMe | NCOOiPr | " |
| CF₃ | CN | SMe | NCONHEt | " |
| CF₃ | CN | SMe | NCONHPr | " |
| CF₃ | CN | SMe | NCONH₂ | " |
| CF₃ | CN | SMe | NCONHMe | " |
| CF₃ | CN | SMe | NCN | " |
| CF₃ | CN | SMe | NCOSMe | " |
| CF₃ | CN | SMe | NCOSEt | " |
| CF₃ | CN | SMe | NCSOMe | " |
| CF₃ | CN | SMe | NCSOEt | " |
| CF₃ | CN | SMe | NCSOPr | " |
| CF₃ | CN | SMe | NSO₂NH₂ | " |
| CF₃ | CN | SMe | NSO₂NHMe | O |
| CF₃ | CN | SMe | NSO₂NMe₂ | " |
| CF₃ | CN | SMe | NP(O)(OMe)₂ | " |
| CF₃ | CN | SMe | NP(O)(OEt)₂ | " |
| CF₃ | CN | SMe | NP(O)Me₂ | " |
| CF₃ | CN | SMe | NP(O)Et₂ | " |
| CF₃ | CN | SMe | NP(O)Me(OMe) | " |
| CF₃ | CN | SMe | NP(O)(OPr)₂ | " |
| CF₃ | CN | SMe | NC(O)C(O)H | " |
| CF₃ | CN | SMe | NC(O)C(O)Me | " |
| CF₃ | CN | SMe | NC(O)C(O)OMe | " |
| CF₃ | CN | SMe | NC(O)C(O)OEt | " |
| CF₃ | CN | SMe | NC(O)C(O)NH₂ | " |
| CF₃ | CN | SMe | NC(O)C(O)OH | " |
| CF₃ | CN | SMe | NC(NH)NH₂ | " |
| CF₃ | CN | SMe | NC(NOH)NH₂ | " |
| CF₃ | CN | SMe | NC(NH)NHMe | " |
| CF₃ | CN | SMe | NC(NH)NMe₂ | " |
| CF₃ | CN | SMe | NC(NH)OMe | " |
| CF₃ | CN | SMe | NC(NH)OEt | " |

TABLE 3-continued

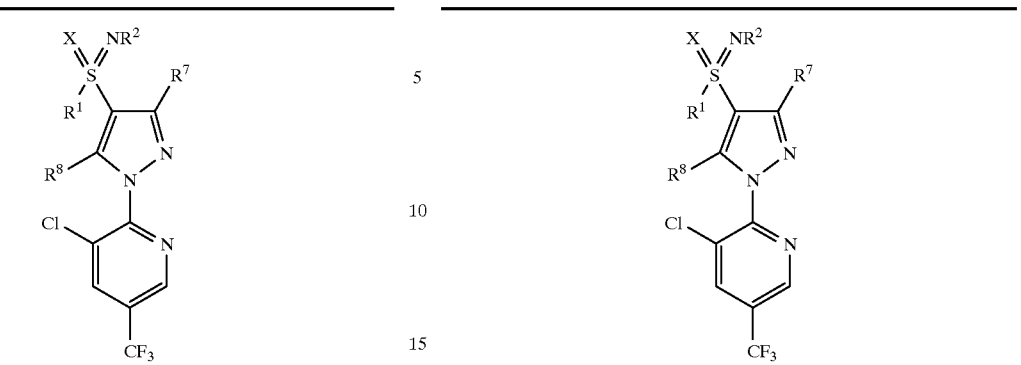

| R¹ | R⁷ | R⁸ | NR² | X |
|---|---|---|---|---|
| CF₃ | CN | SMe | NCOMe | O |
| CF₃ | CN | SMe | NCOEt | O |
| CF₃ | CN | SMe | NCOPr | O |
| CF₃ | CN | SMe | NCHO | O |
| CF₃ | CN | SMe | NCOiPr | O |
| CF₃ | CN | SMe | NCOtBu | O |
| CF₃ | CN | SMe | NCOPh | O |
| CF₃ | CN | SMe | NSO₂Me | O |
| CF₃ | CN | SMe | NSO₂Et | O |
| CF₃ | CN | SMe | NSO₂Pr | O |
| CF₃ | CN | SMe | NSO₂Ph | O |
| CF₃ | CN | SMe | NSO₂iPr | O |
| CF₃ | CN | SMe | NNO₂ | O |
| CF₃ | CN | SMe | NCOOMe | O |
| CF₃ | CN | SMe | NCOOEt | O |
| CF₃ | CN | SMe | NCOOPr | O |
| CF₃ | CN | SMe | NCOOiPr | O |
| CF₃ | CN | SMe | NCONHEt | O |
| CF₃ | CN | SMe | NCONHPr | O |
| CF₃ | CN | SMe | NCONH₂ | O |
| CF₃ | CN | SMe | NCONHMe | O |
| CF₃ | CN | SMe | NCN | O |
| CF₃ | CN | SMe | NCOSMe | O |
| CF₃ | CN | SMe | NCOSEt | O |
| CF₃ | CN | SMe | NCSOMe | O |
| CF₃ | CN | SMe | NCSOEt | O |
| CF₃ | CN | SMe | NCSOPr | O |
| CF₃ | CN | SMe | NSO₂NH₂ | O |
| CF₃ | CN | SMe | NSO₂NHMe | O |
| CF₃ | CN | SMe | NSO₂NMe₂ | O |
| CF₃ | CN | SMe | NP(O)(OMe)₂ | O |
| CF₃ | CN | SMe | NP(O)(OEt)₂ | O |
| CF₃ | CN | SMe | NP(O)Me₂ | O |
| CF₃ | CN | SMe | NP(O)Et₂ | O |
| CF₃ | CN | SMe | NP(O)Me(OMe) | O |
| CF₃ | CN | SMe | NP(O)(OPr)₂ | O |
| CF₃ | CN | SMe | NC(O)C(O)H | O |
| CF₃ | CN | SMe | NC(O)C(O)Me | O |
| CF₃ | CN | SMe | NC(O)C(O)OMe | O |
| CF₃ | CN | SMe | NC(O)C(O)OEt | O |
| CF₃ | CN | SMe | NC(O)C(O)NH₂ | O |
| CF₃ | CN | SMe | NC(O)C(O)OH | O |
| CF₃ | CN | SMe | NC(NH)NH₂ | O |
| CF₃ | CN | SMe | NC(NOH)NH₂ | O |
| CF₃ | CN | SMe | NC(NH)NHMe | O |
| CF₃ | CN | SMe | NC(NH)NMe₂ | O |
| CF₃ | CN | SMe | NC(NH)OMe | O |
| CF₃ | CN | SMe | NC(NH)OEt | O |
| CF₃ | CN | Cl | NCOMe | " |
| CF₃ | CN | Cl | NCOEt | " |
| CF₃ | CN | Cl | NCOPr | " |
| CF₃ | CN | Cl | NCHO | " |
| CF₃ | CN | Cl | NCOiPr | " |
| CF₃ | CN | Cl | NCOtBu | " |
| CF₃ | CN | Cl | NCOPh | " |
| CF₃ | CN | Cl | NSO₂Me | " |
| CF₃ | CN | Cl | NSO₂Et | " |
| CF₃ | CN | Cl | NSO₂Pr | " |
| CF₃ | CN | Cl | NSO₂Ph | " |
| CF₃ | CN | Cl | NSO₂iPr | " |

TABLE 3-continued

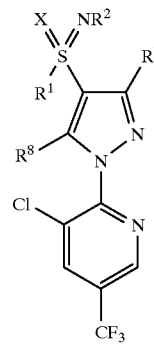

| R¹ | R⁷ | R⁸ | NR² | X |
|---|---|---|---|---|
| CF₃ | CN | Cl | NNO₂ | " |
| CF₃ | CN | Cl | NCOOMe | " |
| CF₃ | CN | Cl | NCOOEt | " |
| CF₃ | CN | Cl | NCOOPr | " |
| CF₃ | CN | Cl | NCOOiPr | " |
| CF₃ | CN | Cl | NCONHEt | " |
| CF₃ | CN | Cl | NCONHPr | " |
| CF₃ | CN | Cl | NCONH₂ | " |
| CF₃ | CN | Cl | NCONHMe | " |
| CF₃ | CN | Cl | NCN | " |
| CF₃ | CN | Cl | NCOSMe | " |
| CF₃ | CN | Cl | NCOSEt | " |
| CF₃ | CN | Cl | NCSOMe | " |
| CF₃ | CN | Cl | NCSOEt | " |
| CF₃ | CN | Cl | NCSOPr | " |
| CF₃ | CN | Cl | NSO₂NH₂ | " |
| CF₃ | CN | Cl | NSO₂NHMe | " |
| CF₃ | CN | Cl | NSO₂NMe₂ | " |
| CF₃ | CN | Cl | NP(O)(OMe)₂ | " |
| CF₃ | CN | Cl | NP(O)(OEt)₂ | " |
| CF₃ | CN | Cl | NP(O)Me₂ | " |
| CF₃ | CN | Cl | NP(O)Et₂ | " |
| CF₃ | CN | Cl | NP(O)Me(OMe) | " |
| CF₃ | CN | Cl | NP(O)(OPr)₂ | " |
| CF₃ | CN | Cl | NC(O)C(O)H | " |
| CF₃ | CN | Cl | NC(O)C(O)Me | " |
| CF₃ | CN | Cl | NC(O)C(O)OMe | " |
| CF₃ | CN | Cl | NC(O)C(O)OEt | " |
| CF₃ | CN | Cl | NC(O)C(O)NH₂ | " |
| CF₃ | CN | Cl | NC(O)C(O)OH | " |
| CF₃ | CN | Cl | NC(NH)NH₂ | " |
| CF₃ | CN | Cl | NC(NOH)NH₂ | " |
| CF₃ | CN | Cl | NC(NH)NHMe | " |
| CF₃ | CN | Cl | NC(NH)NMe₂ | " |
| CF₃ | CN | Cl | NC(NH)OMe | " |
| CF₃ | CN | Cl | NC(NH)OEt | " |
| CF₃ | CN | Cl | NCOMe | " |
| CF₃ | CN | Cl | NCOEt | " |
| CF₃ | CN | Cl | NCOPr | " |
| CF₃ | CN | Cl | NCHO | " |
| CF₃ | CN | Cl | NCOiPr | " |
| CF₃ | CN | Cl | NCOtBu | " |
| CF₃ | CN | Cl | NCOPh | " |
| CF₃ | CN | Cl | NSO₂Me | " |
| CF₃ | CN | Cl | NSO₂Et | " |
| CF₃ | CN | Cl | NSO₂Pr | " |
| CF₃ | CN | Cl | NSO₂Ph | " |
| CF₃ | CN | Cl | NSO₂iPr | " |
| CF₃ | CN | Cl | NNO₂ | " |
| CF₃ | CN | Cl | NCOOMe | " |
| CF₃ | CN | Cl | NCOOEt | " |
| CF₃ | CN | Cl | NCOOPr | " |
| CF₃ | CN | Cl | NCOOiPr | " |
| CF₃ | CN | Cl | NCONHEt | " |
| CF₃ | CN | Cl | NCONHPr | " |
| CF₃ | CN | Cl | NCONH₂ | " |
| CF₃ | CN | Cl | NCONHMe | " |
| CF₃ | CN | Cl | NCN | " |
| CF₃ | CN | Cl | NCOSMe | " |
| CF₃ | CN | Cl | NCOSEt | " |

TABLE 3-continued

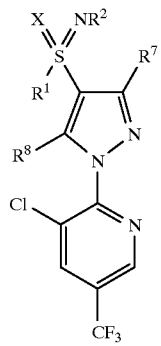

| R¹ | R⁷ | R⁸ | NR² | X |
|---|---|---|---|---|
| CF₃ | CN | Cl | NCSOMe | " |
| CF₃ | CN | Cl | NCSOEt | " |
| CF₃ | CN | Cl | NCSOPr | " |
| CF₃ | CN | Cl | NSO₂NH₂ | " |
| CF₃ | CN | Cl | NSO₂NHMe | " |
| CF₃ | CN | Cl | NSO₂NMe₂ | " |
| CF₃ | CN | Cl | NP(O)(OMe)₂ | " |
| CF₃ | CN | Cl | NP(O)(OEt)₂ | " |
| CF₃ | CN | Cl | NP(O)Me₂ | " |
| CF₃ | CN | Cl | NP(O)Et₂ | " |
| CF₃ | CN | Cl | NP(O)Me(OMe) | " |
| CF₃ | CN | Cl | NP(O)(OPr)₂ | " |
| CF₃ | CN | Cl | NC(O)C(O)H | " |
| CF₃ | CN | Cl | NC(O)C(O)Me | O |
| CF₃ | CN | Cl | NC(O)C(O)OMe | O |
| CF₃ | CN | Cl | NC(O)C(O)OEt | O |
| CF₃ | CN | Cl | NC(O)C(O)NH₂ | O |
| CF₃ | CN | Cl | NC(O)C(O)OH | O |
| CF₃ | CN | Cl | NC(NH)NH₂ | O |
| CF₃ | CN | Cl | NC(NOH)NH₂ | O |
| CF₃ | CN | Cl | NC(NH)NHMe | O |
| CF₃ | CN | Cl | NC(NH)NMe₂ | O |
| CF₃ | CN | Cl | NC(NH)OMe | O |
| CF₃ | CN | Cl | NC(NH)OEt | O |

TABLE 4

| R¹ | R⁹ | R¹¹ | NR² | X |
|---|---|---|---|---|
| CF₃ | H | H | NCOMe | — |
| CF₃ | H | H | NCOEt | — |
| CF₃ | H | H | NCOPr | — |
| CF₃ | H | H | NCHO | — |
| CF₃ | H | H | NCOiPr | — |
| CF₃ | H | H | NCOtBu | — |
| CF₃ | H | H | NCPh | — |
| CF₃ | H | H | NSO₂Me | — |
| CF₃ | H | H | NSO₂Et | — |
| CF₃ | H | H | NSO₂Pr | — |
| CF₃ | H | H | NSO₂Ph | — |

TABLE 4-continued

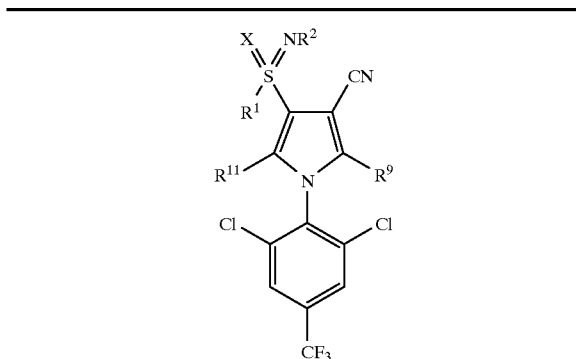

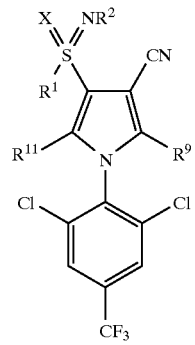

| R¹ | R⁹ | R¹¹ | NR² | X | R¹ | R⁹ | R¹¹ | NR² | X |
|---|---|---|---|---|---|---|---|---|---|
| CF₃ | H | H | NSO₂iPr | — | CF₃ | Cl | H | NCOSMe | — |
| CF₃ | H | H | NNO₂ | — | CF₃ | Cl | H | NCOSEt | — |
| CF₃ | H | H | NCOOMe | — | CF₃ | Cl | H | NCSOMe | — |
| CF₃ | H | H | NCOOEt | — | CF₃ | Cl | H | NCSOEt | — |
| CF₃ | H | H | NCOOPr | — | CF₃ | Cl | H | NCSOPr | — |
| CF₃ | H | H | NCOOiPr | — | CF₃ | Cl | H | NSO₂NH₂ | — |
| CF₃ | H | H | NCONHEt | — | CF₃ | Cl | H | NSO₂NHMe | — |
| CF₃ | H | H | NCONHPr | — | CF₃ | Cl | H | NSO₂NMe₂ | — |
| CF₃ | H | H | NCONH₂ | — | CF₃ | Cl | H | NP(O)(OMe)₂ | — |
| CF₃ | H | H | NCONHMe | — | CF₃ | Cl | H | NP(O)(OEt)₂ | — |
| CF₃ | H | H | NCN | — | CF₃ | Cl | H | NP(O)Me₂ | — |
| CF₃ | H | H | NCOSMe | — | CF₃ | Cl | H | NP(O)Et₂ | — |
| CF₃ | H | H | NCOSEt | — | CF₃ | Cl | H | NP(O)Me(OMe) | — |
| CF₃ | H | H | NCSOMe | — | CF₃ | Cl | H | NP(O)(OPr)₂ | — |
| CF₃ | H | H | NCSOEt | — | CF₃ | Cl | H | NC(O)C(O)H | — |
| CF₃ | H | H | NCSOPr | — | CF₃ | Cl | H | NC(O)C(O)Me | — |
| CF₃ | H | H | NSO₂NH₂ | — | CF₃ | Cl | H | NC(O)C(O)OMe | — |
| CF₃ | H | H | NSO₂NHMe | — | CF₃ | Cl | H | NC(O)C(O)OEt | — |
| CF₃ | H | H | NSO₂NMe₂ | — | CF₃ | Cl | H | NC(O)C(O)NH₂ | — |
| CF₃ | H | H | NP(O)(OMe)₂ | — | CF₃ | Cl | H | NC(O)C(O)OH | — |
| CF₃ | H | H | NP(O)(OEt)₂ | — | CF₃ | Cl | H | NC(NH)NH₂ | — |
| CF₃ | H | H | NP(O)Me₂ | — | CF₃ | Cl | H | NC(NOH)NH₂ | — |
| CF₃ | H | H | NP(O)Et₂ | — | CF₃ | Cl | H | NC(NH)NHMe | — |
| CF₃ | H | H | NP(O)Me(OMe) | — | CF₃ | Cl | H | NC(NH)NMe₂ | — |
| CF₃ | H | H | NP(O)(OPr)₂ | — | CF₃ | Cl | H | NC(NH)OMe | — |
| CF₃ | H | H | NC(O)C(O)H | — | CF₃ | Cl | H | NC(NH)OEt | — |
| CF₃ | H | H | NC(O)C(O)Me | — | CF₃ | Cl | Me | NCOMe | — |
| CF₃ | H | H | NC(O)C(O)OMe | — | CF₃ | Cl | Me | NCOEt | — |
| CF₃ | H | H | NC(O)C(O)OEt | — | CF₃ | Cl | Me | NCOPr | — |
| CF₃ | H | H | NC(O)C(O)NH₂ | — | CF₃ | Cl | Me | NCHO | — |
| CF₃ | H | H | NC(O)C(O)OH | — | CF₃ | Cl | Me | NCOiPr | — |
| CF₃ | H | H | NC(NH)NH₂ | — | CF₃ | Cl | Me | NCOtBu | — |
| CF₃ | H | H | NC(NOH)NH₂ | — | CF₃ | Cl | Me | NCOPh | — |
| CF₃ | H | H | NC(NH)NHMe | — | CF₃ | Cl | Me | NSO₂Me | — |
| CF₃ | H | H | NC(NH)NMe₂ | — | CF₃ | Cl | Me | NSO₂Et | — |
| CF₃ | H | H | NC(NH)OMe | — | CF₃ | Cl | Me | NSO₂Pr | — |
| CF₃ | H | H | NC(NH)OEt | — | CF₃ | Cl | Me | NSO₂Ph | — |
| CF₃ | Cl | H | NCOMe | — | CF₃ | Cl | Me | NSO₂iPr | — |
| CF₃ | Cl | H | NCOEt | — | CF₃ | Cl | Me | NNO₂ | — |
| CF₃ | Cl | H | NCOPr | — | CF₃ | Cl | Me | NCOOMe | — |
| CF₃ | Cl | H | NCHO | — | CF₃ | Cl | Me | NCOOEt | — |
| CF₃ | Cl | H | NCOiPr | — | CF₃ | Cl | Me | NCOOPr | — |
| CF₃ | Cl | H | NCOtBu | — | CF₃ | Cl | Me | NCOOiPr | — |
| CF₃ | Cl | H | NCOPh | — | CF₃ | Cl | Me | NCONHEt | — |
| CF₃ | Cl | H | NSO₂Me | — | CF₃ | Cl | Me | NCONHPr | — |
| CF₃ | Cl | H | NSO₂Et | — | CF₃ | Cl | Me | NCONH₂ | — |
| CF₃ | Cl | H | NSO₂Pr | — | CF₃ | Cl | Me | NCONHMe | — |
| CF₃ | Cl | H | NSO₂Ph | — | CF₃ | Cl | Me | NCN | — |
| CF₃ | Cl | H | NSO₂iPr | — | CF₃ | Cl | Me | NCOSMe | — |
| CF₃ | Cl | H | NNO₂ | — | CF₃ | Cl | Me | NCOSEt | — |
| CF₃ | Cl | H | NCOOMe | — | CF₃ | Cl | Me | NCSOMe | — |
| CF₃ | Cl | H | NCOOEt | — | CF₃ | Cl | Me | NCSOEt | — |
| CF₃ | Cl | H | NCOOPr | — | CF₃ | Cl | Me | NCSOPr | — |
| CF₃ | Cl | H | NCOOiPr | — | CF₃ | Cl | Me | NSO₂NH₂ | — |
| CF₃ | Cl | H | NCONHEt | — | CF₃ | Cl | Me | NSO₂NHMe | — |
| CF₃ | Cl | H | NCONHPr | — | CF₃ | Cl | Me | NSO₂NMe₂ | — |
| CF₃ | Cl | H | NCONH₂ | — | CF₃ | Cl | Me | NP(O)(OMe)₂ | — |
| CF₃ | Cl | H | NCONHMe | — | CF₃ | Cl | Me | NP(O)(OEt)₂ | — |
| CF₃ | Cl | H | NCN | — | CF₃ | Cl | Me | NP(O)Me₂ | — |

TABLE 4-continued

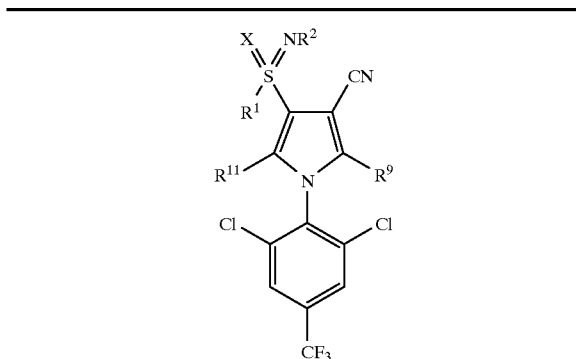

| R[1] | R[9] | R[11] | NR[2] | X |
|---|---|---|---|---|
| $CF_3$ | Cl | Me | NP(O)Et$_2$ | — |
| $CF_3$ | Cl | Me | NP(O)Me(OMe) | — |
| $CF_3$ | Cl | Me | NP(O)(OPr)$_2$ | — |
| $CF_3$ | Cl | Me | NC(O)C(O)H | — |
| $CF_3$ | Cl | Me | NC(O)C(O)Me | — |
| $CF_3$ | Cl | Me | NC(O)C(O)OMe | — |
| $CF_3$ | Cl | Me | NC(O)C(O)OEt | — |
| $CF_3$ | Cl | Me | NC(O)C(O)NH$_2$ | — |
| $CF_3$ | Cl | Me | NC(O)C(O)OH | — |
| $CF_3$ | Cl | Me | NC(NH)NH$_2$ | — |
| $CF_3$ | Cl | Me | NC(NOH)NH$_2$ | — |
| $CF_3$ | Cl | Me | NC(NH)NHMe | — |
| $CF_3$ | Cl | Me | NC(NH)NMe$_2$ | — |
| $CF_3$ | Cl | Me | NC(NH)OMe | — |
| $CF_3$ | Cl | Me | NC(NH)OEt | — |
| $CF_3$ | Cl | SMe | NCOMe | — |
| $CF_3$ | Cl | SMe | NCOEt | — |
| $CF_3$ | Cl | SMe | NCOPr | — |
| $CF_3$ | Cl | SMe | NCHO | — |
| $CF_3$ | Cl | SMe | NCOiPr | — |
| $CF_3$ | Cl | SMe | NCOtBu | — |
| $CF_3$ | Cl | SMe | NCOPh | — |
| $CF_3$ | Cl | SMe | NSO$_2$Me | — |
| $CF_3$ | Cl | SMe | NSO$_2$Et | — |
| $CF_3$ | Cl | SMe | NSO$_2$Pr | — |
| $CF_3$ | Cl | SMe | NSO$_2$Ph | — |
| $CF_3$ | Cl | SMe | NSO$_2$iPr | — |
| $CF_3$ | Cl | SMe | NNO$_2$ | — |
| $CF_3$ | Cl | SMe | NCOOMe | — |
| $CF_3$ | Cl | SMe | NCOOEt | — |
| $CF_3$ | Cl | SMe | NCOOPr | — |
| $CF_3$ | Cl | SMe | NCOOiPr | — |
| $CF_3$ | Cl | SMe | NCONHEt | — |
| $CF_3$ | Cl | SMe | NCONHPr | — |
| $CF_3$ | Cl | SMe | NCONH$_2$ | — |
| $CF_3$ | Cl | SMe | NCONHMe | — |
| $CF_3$ | Cl | SMe | NCN | — |
| $CF_3$ | Cl | SMe | NCOSMe | — |
| $CF_3$ | Cl | SMe | NCOSEt | — |
| $CF_3$ | Cl | SMe | NCSOMe | — |
| $CF_3$ | Cl | SMe | NCSOEt | — |
| $CF_3$ | Cl | SMe | NCSOPr | — |
| $CF_3$ | Cl | SMe | NSO$_2$NH$_2$ | — |
| $CF_3$ | Cl | SMe | NSO$_2$NHMe | — |
| $CF_3$ | Cl | SMe | NSO$_2$NMe$_2$ | — |
| $CF_3$ | Cl | SMe | NP(O)(OMe)$_2$ | — |
| $CF_3$ | Cl | SMe | NP(O)(OEt)$_2$ | — |
| $CF_3$ | Cl | SMe | NP(O)Me$_2$ | — |
| $CF_3$ | Cl | SMe | NP(O)Et$_2$ | — |
| $CF_3$ | Cl | SMe | NP(O)Me(OMe) | — |
| $CF_3$ | Cl | SMe | NP(O)(OPr)$_2$ | — |
| $CF_3$ | Cl | SMe | NC(O)C(O)H | — |
| $CF_3$ | Cl | SMe | NC(O)C(O)Me | — |
| $CF_3$ | Cl | SMe | NC(O)C(O)OMe | — |
| $CF_3$ | Cl | SMe | NC(O)C(O)OEt | — |
| $CF_3$ | Cl | SMe | NC(O)C(O)NH$_2$ | — |
| $CF_3$ | Cl | SMe | NC(O)C(O)OH | — |
| $CF_3$ | Cl | SMe | NC(NH)NH$_2$ | — |
| $CF_3$ | Cl | SMe | NC(NOH)NH$_2$ | — |

TABLE 4-continued

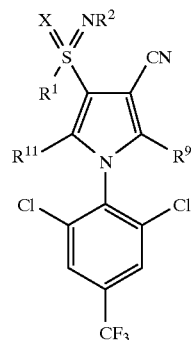

| R[1] | R[9] | R[11] | NR[2] | X |
|---|---|---|---|---|
| $CF_3$ | Cl | SMe | NC(NH)NHMe | — |
| $CF_3$ | Cl | SMe | NC(NH)NMe$_2$ | — |
| $CF_3$ | Cl | SMe | NC(NH)OMe | — |
| $CF_3$ | Cl | SMe | NC(NH)OEt | — |
| $CF_3$ | H | Me | NCOMe | — |
| $CF_3$ | H | Me | NCOEt | — |
| $CF_3$ | H | Me | NCOPr | — |
| $CF_3$ | H | Me | NCHO | — |
| $CF_3$ | H | Me | NCOiPr | — |
| $CF_3$ | H | Me | NCOtBu | — |
| $CF_3$ | H | Me | NCOPh | — |
| $CF_3$ | H | Me | NSO$_2$Me | — |
| $CF_3$ | H | Me | NSO$_2$Et | — |
| $CF_3$ | H | Me | NSO$_2$Pr | — |
| $CF_3$ | H | Me | NSO$_2$Ph | — |
| $CF_3$ | H | Me | NSO$_2$iPr | — |
| $CF_3$ | H | Me | NNO$_2$ | — |
| $CF_3$ | H | Me | NCOOMe | — |
| $CF_3$ | H | Me | NCOOEt | — |
| $CF_3$ | H | Me | NCOOPr | — |
| $CF_3$ | H | Me | NCOOiPr | — |
| $CF_3$ | H | Me | NCONHEt | — |
| $CF_3$ | H | Me | NCONHPr | — |
| $CF_3$ | H | Me | NCONH$_2$ | — |
| $CF_3$ | H | Me | NCONHMe | — |
| $CF_3$ | H | Me | NCN | — |
| $CF_3$ | H | Me | NCOSMe | — |
| $CF_3$ | H | Me | NCOSEt | — |
| $CF_3$ | H | Me | NCSOMe | — |
| $CF_3$ | H | Me | NCSOEt | — |
| $CF_3$ | H | Me | NCSOPr | — |
| $CF_3$ | H | Me | NSO$_2$NH$_2$ | — |
| $CF_3$ | H | Me | NSO$_2$NHMe | — |
| $CF_3$ | H | Me | NSO$_2$NMe$_2$ | — |
| $CF_3$ | H | Me | NP(O)(OMe)$_2$ | — |
| $CF_3$ | H | Me | NP(O)(OEt)$_2$ | — |
| $CF_3$ | H | Me | NP(O)Me$_2$ | — |
| $CF_3$ | H | Me | NP(O)Et$_2$ | — |
| $CF_3$ | H | Me | NP(O)Me(OMe) | — |
| $CF_3$ | H | Me | NP(O)(OPr)$_2$ | — |
| $CF_3$ | H | Me | NC(O)C(O)H | — |
| $CF_3$ | H | Me | NC(O)C(O)Me | — |
| $CF_3$ | H | Me | NC(O)C(O)OMe | — |
| $CF_3$ | H | Me | NC(O)C(O)OEt | — |
| $CF_3$ | H | Me | NC(O)C(O)NH$_2$ | — |
| $CF_3$ | H | Me | NC(O)C(O)OH | — |
| $CF_3$ | H | Me | NC(NH)NH$_2$ | — |
| $CF_3$ | H | Me | NC(NOH)NH$_2$ | — |
| $CF_3$ | H | Me | NC(NH)NHMe | — |
| $CF_3$ | H | Me | NC(NH)NMe$_2$ | — |
| $CF_3$ | H | Me | NC(NH)OMe | — |
| $CF_3$ | H | Me | NC(NH)OEt | — |
| $CF_3$ | H | SMe | NCOMe | — |
| $CF_3$ | H | SMe | NCOEt | — |
| $CF_3$ | H | SMe | NCOPr | — |
| $CF_3$ | H | SMe | NCHO | — |
| $CF_3$ | H | SMe | NCOiPr | — |
| $CF_3$ | H | SMe | NCOtBu | — |
| $CF_3$ | H | SMe | NCOPh | — |

TABLE 4-continued

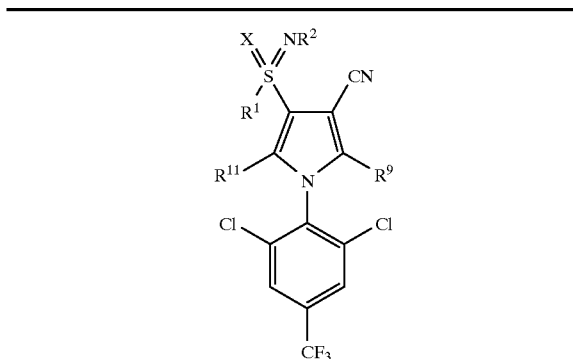

| R¹ | R⁹ | R¹¹ | NR² | X |
|---|---|---|---|---|
| CF₃ | H | SMe | NSO₂Me | — |
| CF₃ | H | SMe | NSO₂Et | — |
| CF₃ | H | SMe | NSO₂Pr | — |
| CF₃ | H | SMe | NSO₂Ph | — |
| CF₃ | H | SMe | NSO₂iPr | — |
| CF₃ | H | SMe | NNO₂ | — |
| CF₃ | H | SMe | NCOOMe | — |
| CF₃ | H | SMe | NCOOEt | — |
| CF₃ | H | SMe | NCOOPr | — |
| CF₃ | H | SMe | NCOOiPr | — |
| CF₃ | H | SMe | NCONHEt | — |
| CF₃ | H | SMe | NCONHPr | — |
| CF₃ | H | SMe | NCONH₂ | — |
| CF₃ | H | SMe | NCONHMe | — |
| CF₃ | H | SMe | NCN | — |
| CF₃ | H | SMe | NCOSMe | — |
| CF₃ | H | SMe | NCOSEt | — |
| CF₃ | H | SMe | NCSOMe | — |
| CF₃ | H | SMe | NCSOEt | — |
| CF₃ | H | SMe | NCSOPr | — |
| CF₃ | H | SMe | NSO₂NH₂ | — |
| CF₃ | H | SMe | NSO₂NHMe | — |
| CF₃ | H | SMe | NSO₂NMe₂ | — |
| CF₃ | H | SMe | NP(O)(OMe)₂ | — |
| CF₃ | H | SMe | NP(O)(OEt)₂ | — |
| CF₃ | H | SMe | NP(O)Me₂ | — |
| CF₃ | H | SMe | NP(O)Et₂ | — |
| CF₃ | H | SMe | NP(O)Me(OMe) | — |
| CF₃ | H | SMe | NP(O)(OPr)₂ | — |
| CF₃ | H | SMe | NC(O)C(O)H | — |
| CF₃ | H | SMe | NC(O)C(O)Me | — |
| CF₃ | H | SMe | NC(O)C(O)OMe | — |
| CF₃ | H | SMe | NC(O)C(O)OEt | — |
| CF₃ | H | SMe | NC(O)C(O)NH₂ | — |
| CF₃ | H | SMe | NC(O)C(O)OH | — |
| CF₃ | H | SMe | NC(NH)NH₂ | — |
| CF₃ | H | SMe | NC(NOH)NH₂ | — |
| CF₃ | H | SMe | NC(NH)NHMe | — |
| CF₃ | H | SMe | NC(NH)NMe₂ | — |
| CF₃ | H | SMe | NC(NH)OMe | — |
| CF₃ | H | SMe | NC(NH)OEt | — |
| CF₃ | Me | H | NCOMe | — |
| CF₃ | Me | H | NCOEt | — |
| CF₃ | Me | H | NCOPr | — |
| CF₃ | Me | H | NCHO | — |
| CF₃ | Me | H | NCOiPr | — |
| CF₃ | Me | H | NCOtBu | — |
| CF₃ | Me | H | NCOPh | — |
| CF₃ | Me | H | NSO₂Me | — |
| CF₃ | Me | H | NSO₂Et | — |
| CF₃ | Me | H | NSO₂Pr | — |
| CF₃ | Me | H | NSO₂Ph | — |
| CF₃ | Me | H | NSO₂iPr | — |
| CF₃ | Me | H | NNO₂ | — |
| CF₃ | Me | H | NCOOMe | — |
| CF₃ | Me | H | NCOOEt | — |
| CF₃ | Me | H | NCOOPr | — |
| CF₃ | Me | H | NCOOiPr | — |
| CF₃ | Me | H | NCONHEt | — |

TABLE 4-continued

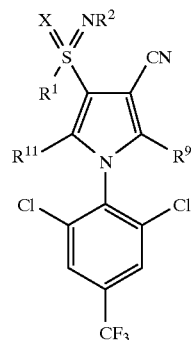

| R¹ | R⁹ | R¹¹ | NR² | X |
|---|---|---|---|---|
| CF₃ | Me | H | NCONHPr | — |
| CF₃ | Me | H | NCONH₂ | — |
| CF₃ | Me | H | NCONHMe | — |
| CF₃ | Me | H | NCN | — |
| CF₃ | Me | H | NCOSMe | — |
| CF₃ | Me | H | NCOSEt | — |
| CF₃ | Me | H | NCSOMe | — |
| CF₃ | Me | H | NCSOEt | — |
| CF₃ | Me | H | NCSOPr | — |
| CF₃ | Me | H | NSO₂NH₂ | — |
| CF₃ | Me | H | NSO₂NHMe | — |
| CF₃ | Me | H | NSO₂NMe₂ | — |
| CF₃ | Me | H | NP(O)(OMe)₂ | — |
| CF₃ | Me | H | NP(O)(OEt)₂ | — |
| CF₃ | Me | H | NP(O)Me₂ | — |
| CF₃ | Me | H | NP(O)Et₂ | — |
| CF₃ | Me | H | NP(O)Me(OMe) | — |
| CF₃ | Me | H | NP(O)(OPr)₂ | — |
| CF₃ | Me | H | NC(O)C(O)H | — |
| CF₃ | Me | H | NC(O)C(O)Me | — |
| CF₃ | Me | H | NC(O)C(O)OMe | — |
| CF₃ | Me | H | NC(O)C(O)OEt | — |
| CF₃ | Me | H | NC(O)C(O)NH₂ | — |
| CF₃ | Me | H | NC(O)C(O)OH | — |
| CF₃ | Me | H | NC(NH)NH₂ | — |
| CF₃ | Me | H | NC(NOH)NH₂ | — |
| CF₃ | Me | H | NC(NH)NHMe | — |
| CF₃ | Me | H | NC(NH)NMe₂ | — |
| CF₃ | Me | H | NC(NH)OMe | — |
| CF₃ | Me | H | NC(NH)OEt | — |
| CF₃ | Me | Me | NCOMe | — |
| CF₃ | Me | Me | NCOEt | — |
| CF₃ | Me | Me | NCOPr | — |
| CF₃ | Me | Me | NCHO | — |
| CF₃ | Me | Me | NCOiPr | — |
| CF₃ | Me | Me | NCOtBu | — |
| CF₃ | Me | Me | NCOPh | — |
| CF₃ | Me | Me | NSO₂Me | — |
| CF₃ | Me | Me | NSO₂Et | — |
| CF₃ | Me | Me | NSO₂Pr | — |
| CF₃ | Me | Me | NSO₂Ph | — |
| CF₃ | Me | Me | NSO₂iPr | — |
| CF₃ | Me | Me | NNO₂ | — |
| CF₃ | Me | Me | NCOOMe | — |
| CF₃ | Me | Me | NCOOEt | — |
| CF₃ | Me | Me | NCOOPr | — |
| CF₃ | Me | Me | NCOOiPr | — |
| CF₃ | Me | Me | NCONHEt | — |
| CF₃ | Me | Me | NCONHPr | — |
| CF₃ | Me | Me | NCONH₂ | — |
| CF₃ | Me | Me | NCONHMe | — |
| CF₃ | Me | Me | NCN | — |
| CF₃ | Me | Me | NCOSMe | — |
| CF₃ | Me | Me | NCOSEt | — |
| CF₃ | Me | Me | NCSOMe | — |
| CF₃ | Me | Me | NCSOEt | — |
| CF₃ | Me | Me | NCSOPr | — |
| CF₃ | Me | Me | NSO₂NH₂ | — |
| CF₃ | Me | Me | NSO₂NHMe | — |

TABLE 4-continued

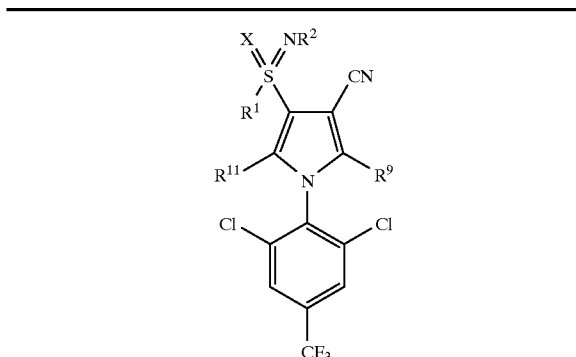

| R¹ | R⁹ | R¹¹ | NR² | X |
|---|---|---|---|---|
| CF₃ | Me | Me | NSO₂NMe₂ | — |
| CF₃ | Me | Me | NP(O)(OMe)₂ | — |
| CF₃ | Me | Me | NP(O)(OEt)₂ | — |
| CF₃ | Me | Me | NP(O)Me₂ | — |
| CF₃ | Me | Me | NP(O)Et₂ | — |
| CF₃ | Me | Me | NP(O)Me(OMe) | — |
| CF₃ | Me | Me | NP(O)(OPr)₂ | — |
| CF₃ | Me | Me | NC(O)C(O)H | — |
| CF₃ | Me | Me | NC(O)C(O)Me | — |
| CF₃ | Me | Me | NC(O)C(O)OMe | — |
| CF₃ | Me | Me | NC(O)C(O)OEt | — |
| CF₃ | Me | Me | NC(O)C(O)NH₂ | — |
| CF₃ | Me | Me | NC(O)C(O)OH | — |
| CF₃ | Me | Me | NC(NH)NH₂ | — |
| CF₃ | Me | Me | NC(NOH)NH₂ | — |
| CF₃ | Me | Me | NC(NH)NHMe | — |
| CF₃ | Me | Me | NC(NH)NMe₂ | — |
| CF₃ | Me | Me | NC(NH)OMe | — |
| CF₃ | Me | Me | NC(NH)OEt | — |
| Me | H | H | NCOMe | — |
| Me | H | H | NCOEt | — |
| Me | H | H | NCOPr | — |
| Me | H | H | NCHO | — |
| Me | H | H | NCOiPr | — |
| Me | H | H | NCOtBu | — |
| Me | H | H | NCOPh | — |
| Me | H | H | NSO₂Me | — |
| Me | H | H | NSO₂Et | — |
| Me | H | H | NSO₂Pr | — |
| Me | H | H | NSO₂Ph | — |
| Me | H | H | NSO₂iPr | — |
| Me | H | H | NNO₂ | — |
| Me | H | H | NCOOMe | — |
| Me | H | H | NCOOEt | — |
| Me | H | H | NCOOPr | — |
| Me | H | H | NCOOiPr | — |
| Me | H | H | NCONHEt | — |
| Me | H | H | NCONHPr | — |
| Me | H | H | NCONH₂ | — |
| Me | H | H | NCONHMe | — |
| Me | H | H | NCN | — |
| Me | H | H | NCOSMe | — |
| Me | H | H | NCOSEt | — |
| Me | H | H | NCSOMe | — |
| Me | H | H | NCSOEt | — |
| Me | H | H | NCSOPr | — |
| Me | H | H | NSO₂NH₂ | — |
| Me | H | H | NSO₂NHMe | — |
| Me | H | H | NSO₂NMe₂ | — |
| Me | H | H | NP(O)(OMe)₂ | — |
| Me | H | H | NP(O)(OEt)₂ | — |
| Me | H | H | NP(O)Me₂ | — |
| Me | H | H | NP(O)Et₂ | — |
| Me | H | H | NP(O)Me(OMe) | — |
| Me | H | H | NP(O)(OPr)₂ | — |
| Me | H | H | NC(O)C(O)H | — |
| Me | H | H | NC(O)C(O)Me | — |
| Me | H | H | NC(O)C(O)OMe | — |
| Me | H | H | NC(O)C(O)OEt | — |

TABLE 4-continued

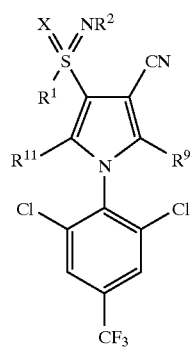

| R¹ | R⁹ | R¹¹ | NR² | X |
|---|---|---|---|---|
| Me | H | H | NC(O)C(O)NH₂ | — |
| Me | H | H | NC(O)C(O)OH | — |
| Me | H | H | NC(NH)NH₂ | — |
| Me | H | H | NC(NOH)NH₂ | — |
| Me | H | H | NC(NH)NHMe | — |
| Me | H | H | NC(NH)NMe₂ | — |
| Me | H | H | NC(NH)OMe | — |
| Me | H | H | NC(NH)OEt | — |
| Me | Cl | H | NCOMe | — |
| Me | Cl | H | NCOEt | — |
| Me | Cl | H | NCOPr | — |
| Me | Cl | H | NCHO | — |
| Me | Cl | H | NCOiPr | — |
| Me | Cl | H | NCOtBu | — |
| Me | Cl | H | NCOPh | — |
| Me | Cl | H | NSO₂Me | — |
| Me | Cl | H | NSO₂Et | — |
| Me | Cl | H | NSO₂Pr | — |
| Me | Cl | H | NSO₂Ph | — |
| Me | Cl | H | NSO₂iPr | — |
| Me | Cl | H | NNO₂ | — |
| Me | Cl | H | NCOOMe | — |
| Me | Cl | H | NCOOEt | — |
| Me | Cl | H | NCOOPr | — |
| Me | Cl | H | NCOOiPr | — |
| Me | Cl | H | NCONHEt | — |
| Me | Cl | H | NCONHPr | — |
| Me | Cl | H | NCONH₂ | — |
| Me | Cl | H | NCONHMe | — |
| Me | Cl | H | NCN | — |
| Me | Cl | H | NCOSMe | — |
| Me | Cl | H | NCOSEt | — |
| Me | Cl | H | NCSOMe | — |
| Me | Cl | H | NCSOEt | — |
| Me | Cl | H | NCSOPr | — |
| Me | Cl | H | NSO₂NH₂ | — |
| Me | Cl | H | NSO₂NHMe | — |
| Me | Cl | H | NSO₂NMe₂ | — |
| Me | Cl | H | NP(O)(OMe)₂ | — |
| Me | Cl | H | NP(O)(OEt)₂ | — |
| Me | Cl | H | NP(O)Me₂ | — |
| Me | Cl | H | NP(O)Et₂ | — |
| Me | Cl | H | NP(O)Me(OMe) | — |
| Me | Cl | H | NP(O)(OPr)₂ | — |
| Me | Cl | H | NC(O)C(O)H | — |
| Me | Cl | H | NC(O)C(O)Me | — |
| Me | Cl | H | NC(O)C(O)OMe | — |
| Me | Cl | H | NC(O)C(O)OEt | — |
| Me | Cl | H | NC(O)C(O)NH₂ | — |
| Me | Cl | H | NC(O)C(O)OH | — |
| Me | Cl | H | NC(NH)NH₂ | — |
| Me | Cl | H | NC(NOH)NH₂ | — |
| Me | Cl | H | NC(NH)NHMe | — |
| Me | Cl | H | NC(NH)NMe₂ | — |
| Me | Cl | H | NC(NH)OMe | — |
| Me | Cl | H | NC(NH)OEt | — |
| Me | Cl | Me | NCOMe | — |
| Me | Cl | Me | NCOEt | — |
| Me | Cl | Me | NCOPr | — |

TABLE 4-continued

| R¹ | R⁹ | R¹¹ | NR² | X |
|---|---|---|---|---|
| Me | Cl | Me | NCHO | — |
| Me | Cl | Me | NCOiPr | — |
| Me | Cl | Me | NCOtBu | — |
| Me | Cl | Me | NCOPh | — |
| Me | Cl | Me | NSO₂Me | — |
| Me | Cl | Me | NSO₂Et | — |
| Me | Cl | Me | NSO₂Pr | — |
| Me | Cl | Me | NSO₂Ph | — |
| Me | Cl | Me | NSO₂iPr | — |
| Me | Cl | Me | NNO₂ | — |
| Me | Cl | Me | NCOOMe | — |
| Me | Cl | Me | NCOOEt | — |
| Me | Cl | Me | NCOOPr | — |
| Me | Cl | Me | NCOOiPr | — |
| Me | Cl | Me | NCONHEt | — |
| Me | Cl | Me | NCONHPr | — |
| Me | Cl | Me | NCONH₂ | — |
| Me | Cl | Me | NCONHMe | — |
| Me | Cl | Me | NCN | — |
| Me | Cl | Me | NCOSMe | — |
| Me | Cl | Me | NCOSEt | — |
| Me | Cl | Me | NCSOMe | — |
| Me | Cl | Me | NCSOEt | — |
| Me | Cl | Me | NCSOPr | — |
| Me | Cl | Me | NSO₂NH₂ | — |
| Me | Cl | Me | NSO₂NHMe | — |
| Me | Cl | Me | NSO₂NMe₂ | — |
| Me | Cl | Me | NP(O)(OMe)₂ | — |
| Me | Cl | Me | NP(O)(OEt)₂ | — |
| Me | Cl | Me | NP(O)Me₂ | — |
| Me | Cl | Me | NP(O)Et₂ | — |
| Me | Cl | Me | NP(O)Me(OMe) | — |
| Me | Cl | Me | NP(O)(OPr)₂ | — |
| Me | Cl | Me | NC(O)C(O)H | — |
| Me | Cl | Me | NC(O)C(O)Me | — |
| Me | Cl | Me | NC(O)C(O)OMe | — |
| Me | Cl | Me | NC(O)C(O)OEt | — |
| Me | Cl | Me | NC(O)C(O)NH₂ | — |
| Me | Cl | Me | NC(O)C(O)OH | — |
| Me | Cl | Me | NC(NH)NH₂ | — |
| Me | Cl | Me | NC(NOH)NH₂ | — |
| Me | Cl | Me | NC(NH)NHMe | — |
| Me | Cl | Me | NC(NH)NMe₂ | — |
| Me | Cl | Me | NC(NH)OMe | — |
| Me | Cl | Me | NC(NH)OEt | — |
| Me | Cl | SMe | NCOMe | — |
| Me | Cl | SMe | NCOEt | — |
| Me | Cl | SMe | NCOPr | — |
| Me | Cl | SMe | NCHO | — |
| Me | Cl | SMe | NCOiPr | — |
| Me | Cl | SMe | NCOtBu | — |
| Me | Cl | SMe | NCOPh | — |
| Me | Cl | SMe | NSO₂Me | — |
| Me | Cl | SMe | NSO₂Et | — |
| Me | Cl | SMe | NSO₂Pr | — |
| Me | Cl | SMe | NSO₂Ph | — |
| Me | Cl | SMe | NSO₂iPr | — |
| Me | Cl | SMe | NNO₂ | — |
| Me | Cl | SMe | NCOOMe | — |
| Me | Cl | SMe | NCOOEt | — |
| Me | Cl | SMe | NCOOPr | — |
| Me | Cl | SMe | NCOOiPr | — |
| Me | Cl | SMe | NCONHEt | — |
| Me | Cl | SMe | NCONHPr | — |
| Me | Cl | SMe | NCONH₂ | — |
| Me | Cl | SMe | NCONHMe | — |
| Me | Cl | SMe | NCN | — |
| Me | Cl | SMe | NCOSMe | — |
| Me | Cl | SMe | NCOSEt | — |
| Me | Cl | SMe | NCSOMe | — |
| Me | Cl | SMe | NCSOEt | — |
| Me | Cl | SMe | NCSOPr | — |
| Me | Cl | SMe | NSO₂NH₂ | — |
| Me | Cl | SMe | NSO₂NHMe | — |
| Me | Cl | SMe | NSO₂NMe₂ | — |
| Me | Cl | SMe | NP(O)(OMe)₂ | — |
| Me | Cl | SMe | NP(O)(OEt)₂ | — |
| Me | Cl | SMe | NP(O)Me₂ | — |
| Me | Cl | SMe | NP(O)Et₂ | — |
| Me | Cl | SMe | NP(O)Me(OMe) | — |
| Me | Cl | SMe | NP(O)(OPr)₂ | — |
| Me | Cl | SMe | NC(O)C(O)H | — |
| Me | Cl | SMe | NC(O)C(O)Me | — |
| Me | Cl | SMe | NC(O)C(O)OMe | — |
| Me | Cl | SMe | NC(O)C(O)OEt | — |
| Me | Cl | SMe | NC(O)C(O)NH₂ | — |
| Me | Cl | SMe | NC(O)C(O)OH | — |
| Me | Cl | SMe | NC(NH)NH₂ | — |
| Me | Cl | SMe | NC(NOH)NH₂ | — |
| Me | Cl | SMe | NC(NH)NHMe | — |
| Me | Cl | SMe | NC(NH)NMe₂ | — |
| Me | Cl | SMe | NC(NH)OMe | — |
| Me | Cl | SMe | NC(NH)OEt | — |
| Me | H | Me | NCOMe | — |
| Me | H | Me | NCOEt | — |
| Me | H | Me | NCOPr | — |
| Me | H | Me | NCHO | — |
| Me | H | Me | NCOiPr | — |
| Me | H | Me | NCOtBu | — |
| Me | H | Me | NCOPh | — |
| Me | H | Me | NSO₂Me | — |
| Me | H | Me | NSO₂Et | — |
| Me | H | Me | NSO₂Pr | — |
| Me | H | Me | NSO₂Ph | — |
| Me | H | Me | NSO₂iPr | — |
| Me | H | Me | NNO₂ | — |
| Me | H | Me | NCOOMe | — |
| Me | H | Me | NCOOEt | — |
| Me | H | Me | NCOOPr | — |
| Me | H | Me | NCOOiPr | — |
| Me | H | Me | NCONHEt | — |
| Me | H | Me | NCONHPr | — |
| Me | H | Me | NCONH₂ | — |
| Me | H | Me | NCONHMe | — |
| Me | H | Me | NCN | — |
| Me | H | Me | NCOSMe | — |
| Me | H | Me | NCOSEt | — |
| Me | H | Me | NCSOMe | — |

TABLE 4-continued

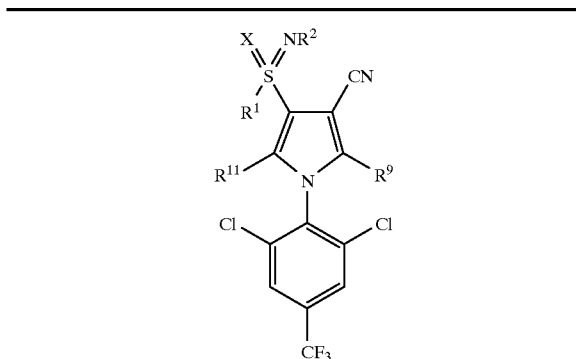

| R¹ | R⁹ | R¹¹ | NR² | X |
|---|---|---|---|---|
| Me | H | Me | NCSOEt | — |
| Me | H | Me | NCSOPr | — |
| Me | H | Me | NSO₂NH₂ | — |
| Me | H | Me | NSO₂NHMe | — |
| Me | H | Me | NSO₂NMe₂ | — |
| Me | H | Me | NP(O)(OMe)₂ | — |
| Me | H | Me | NP(O)(OEt)₂ | — |
| Me | H | Me | NP(O)Me₂ | — |
| Me | H | Me | NP(O)Et₂ | — |
| Me | H | Me | NP(O)Me(OMe) | — |
| Me | H | Me | NP(O)(OPr)₂ | — |
| Me | H | Me | NC(O)C(O)H | — |
| Me | H | Me | NC(O)C(O)Me | — |
| Me | H | Me | NC(O)C(O)OMe | — |
| Me | H | Me | NC(O)C(O)OEt | — |
| Me | H | Me | NC(O)C(O)NH₂ | — |
| Me | H | Me | NC(O)C(O)OH | — |
| Me | H | Me | NC(NH)NH₂ | — |
| Me | H | Me | NC(NOH)NH₂ | — |
| Me | H | Me | NC(NH)NHMe | — |
| Me | H | Me | NC(NH)NMe₂ | — |
| Me | H | Me | NC(NH)OMe | — |
| Me | H | Me | NC(NH)OEt | — |
| Me | H | SMe | NCOMe | — |
| Me | H | SMe | NCOEt | — |
| Me | H | SMe | NCOPr | — |
| Me | H | SMe | NCHO | — |
| Me | H | SMe | NCOiPr | — |
| Me | H | SMe | NCOtBu | — |
| Me | H | SMe | NCOPh | — |
| Me | H | SMe | NSO₂Me | — |
| Me | H | SMe | NSO₂Et | — |
| Me | H | SMe | NSO₂Pr | — |
| Me | H | SMe | NSO₂Ph | — |
| Me | H | SMe | NSO₂iPr | — |
| Me | H | SMe | NNO₂ | — |
| Me | H | SMe | NCOOMe | — |
| Me | H | SMe | NCOOEt | — |
| Me | H | SMe | NCOOPr | — |
| Me | H | SMe | NCOOiPr | — |
| Me | H | SMe | NCONHEt | — |
| Me | H | SMe | NCONHPr | — |
| Me | H | SMe | NCONH₂ | — |
| Me | H | SMe | NCONHMe | — |
| Me | H | SMe | NCN | — |
| Me | H | SMe | NCOSMe | — |
| Me | H | SMe | NCOSEt | — |
| Me | H | SMe | NCSOMe | — |
| Me | H | SMe | NCSOEt | — |
| Me | H | SMe | NCSOPr | — |
| Me | H | SMe | NSO₂NH₂ | — |
| Me | H | SMe | NSO₂NHMe | — |
| Me | H | SMe | NSO₂NMe₂ | — |
| Me | H | SMe | NP(O)(OMe)₂ | — |
| Me | H | SMe | NP(O)(OEt)₂ | — |
| Me | H | SMe | NP(O)Me₂ | — |
| Me | H | SMe | NP(O)Et₂ | — |
| Me | H | SMe | NP(O)Me(OMe) | — |
| Me | H | SMe | NP(O)(OPr)₂ | — |

TABLE 4-continued

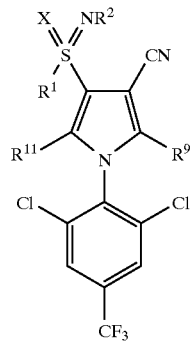

| R¹ | R⁹ | R¹¹ | NR² | X |
|---|---|---|---|---|
| Me | H | SMe | NC(O)C(O)H | — |
| Me | H | SMe | NC(O)C(O)Me | — |
| Me | H | SMe | NC(O)C(O)OMe | — |
| Me | H | SMe | NC(O)C(O)OEt | — |
| Me | H | SMe | NC(O)C(O)NH₂ | — |
| Me | H | SMe | NC(O)C(O)OH | — |
| Me | H | SMe | NC(NH)NH₂ | — |
| Me | H | SMe | NC(NOH)NH₂ | — |
| Me | H | SMe | NC(NH)NHMe | — |
| Me | H | SMe | NC(NH)NMe₂ | — |
| Me | H | SMe | NC(NH)OMe | — |
| Me | H | SMe | NC(NH)OEt | — |
| Me | Me | H | NCOMe | — |
| Me | Me | H | NCOEt | — |
| Me | Me | H | NCOPr | — |
| Me | Me | H | NCHO | — |
| Me | Me | H | NCOiPr | — |
| Me | Me | H | NCOtBu | — |
| Me | Me | H | NCOPh | — |
| Me | Me | H | NSO₂Me | — |
| Me | Me | H | NSO₂Et | — |
| Me | Me | H | NSO₂Pr | — |
| Me | Me | H | NSO₂Ph | — |
| Me | Me | H | NSO₂iPr | — |
| Me | Me | H | NNO₂ | — |
| Me | Me | H | NCOOMe | — |
| Me | Me | H | NCOOEt | — |
| Me | Me | H | NCOOPr | — |
| Me | Me | H | NCOOiPr | — |
| Me | Me | H | NCONHEt | — |
| Me | Me | H | NCONHPr | — |
| Me | Me | H | NCONH₂ | — |
| Me | Me | H | NCONHMe | — |
| Me | Me | H | NCN | — |
| Me | Me | H | NCOSMe | — |
| Me | Me | H | NCOSEt | — |
| Me | Me | H | NCSOMe | — |
| Me | Me | H | NCSOEt | — |
| Me | Me | H | NCSOPr | — |
| Me | Me | H | NSO₂NH₂ | — |
| Me | Me | H | NSO₂NHMe | — |
| Me | Me | H | NSO₂NMe₂ | — |
| Me | Me | H | NP(O)(OMe)₂ | — |
| Me | Me | H | NP(O)(OEt)₂ | — |
| Me | Me | H | NP(O)Me₂ | — |
| Me | Me | H | NP(O)Et₂ | — |
| Me | Me | H | NP(O)Me(OMe) | — |
| Me | Me | H | NP(O)(OPr)₂ | — |
| Me | Me | H | NC(O)C(O)H | — |
| Me | Me | H | NC(O)C(O)Me | — |
| Me | Me | H | NC(O)C(O)OMe | — |
| Me | Me | H | NC(O)C(O)OEt | — |
| Me | Me | H | NC(O)C(O)NH₂ | — |
| Me | Me | H | NC(O)C(O)OH | — |
| Me | Me | H | NC(NH)NH₂ | — |
| Me | Me | H | NC(NOH)NH₂ | — |
| Me | Me | H | NC(NH)NHMe | — |
| Me | Me | H | NC(NH)NMe₂ | — |
| Me | Me | H | NC(NH)OMe | — |

TABLE 4-continued

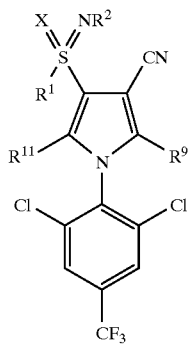

| R¹ | R⁹ | R¹¹ | NR² | X |
|---|---|---|---|---|
| Me | Me | H | NC(NH)OEt | — |
| Me | Me | Me | NCOMe | — |
| Me | Me | Me | NCOEt | — |
| Me | Me | Me | NCOPr | — |
| Me | Me | Me | NCHO | — |
| Me | Me | Me | NCOiPr | — |
| Me | Me | Me | NCOtBu | — |
| Me | Me | Me | NCOPh | — |
| Me | Me | Me | NSO₂Me | — |
| Me | Me | Me | NSO₂Et | — |
| Me | Me | Me | NSO₂Pr | — |
| Me | Me | Me | NSO₂Ph | — |
| Me | Me | Me | NSO₂iPr | — |
| Me | Me | Me | NNO₂ | — |
| Me | Me | Me | NCOOMe | — |
| Me | Me | Me | NCOOEt | — |
| Me | Me | Me | NCOOPr | — |
| Me | Me | Me | NCOOiPr | — |
| Me | Me | Me | NCONHEt | — |
| Me | Me | Me | NCONHPr | — |
| Me | Me | Me | NCONH₂ | — |
| Me | Me | Me | NCONHMe | — |
| Me | Me | Me | NCN | — |
| Me | Me | Me | NCOSMe | — |
| Me | Me | Me | NCOSEt | — |
| Me | Me | Me | NCSOMe | — |
| Me | Me | Me | NCSOEt | — |
| Me | Me | Me | NCSOPr | — |
| Me | Me | Me | NSO₂NH₂ | — |
| Me | Me | Me | NSO₂NHMe | — |
| Me | Me | Me | NSO₂NMe₂ | — |
| Me | Me | Me | NP(O)(OMe)₂ | — |
| Me | Me | Me | NP(O)(OEt)₂ | — |
| Me | Me | Me | NP(O)Me₂ | — |
| Me | Me | Me | NP(O)Et₂ | — |
| Me | Me | Me | NP(O)Me(OMe) | — |
| Me | Me | Me | NP(O)(OPr)₂ | — |
| Me | Me | Me | NC(O)C(O)H | — |
| Me | Me | Me | NC(O)C(O)Me | — |
| Me | Me | Me | NC(O)C(O)OMe | — |
| Me | Me | Me | NC(O)C(O)OEt | — |
| Me | Me | Me | NC(O)C(O)NH₂ | — |
| Me | Me | Me | NC(O)C(O)OH | — |
| Me | Me | Me | NC(NH)NH₂ | — |
| Me | Me | Me | NC(NOH)NH₂ | — |
| Me | Me | Me | NC(NH)NHMe | — |
| Me | Me | Me | NC(NH)NMe₂ | — |
| Me | Me | Me | NC(NH)OMe | — |
| Me | Me | Me | NC(NH)OEt | — |

TABLE 5

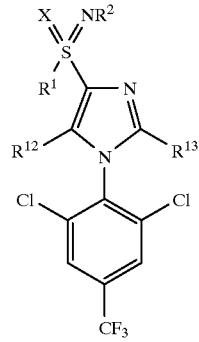

| R¹ | R¹² | R¹³ | NR² | X |
|---|---|---|---|---|
| CF₃ | Cl | Me | NCOMe | " |
| CF₃ | Cl | Me | NCOEt | " |
| CF₃ | Cl | Me | NCOPr | " |
| CF₃ | Cl | Me | NCHO | " |
| CF₃ | Cl | Me | NCOiPr | " |
| CF₃ | Cl | Me | NCOtBu | " |
| CF₃ | Cl | Me | NCOPh | " |
| CF₃ | Cl | Me | NSO₂Me | " |
| CF₃ | Cl | Me | NSO₂Et | " |
| CF₃ | Cl | Me | NSO₂Pr | " |
| CF₃ | Cl | Me | NSO₂Ph | " |
| CF₃ | Cl | Me | NSO₂iPr | " |
| CF₃ | Cl | Me | NNO₂ | " |
| CF₃ | Cl | Me | NCOOMe | " |
| CF₃ | Cl | Me | NCOOEt | " |
| CF₃ | Cl | Me | NCOOPr | " |
| CF₃ | Cl | Me | NCOOiPr | " |
| CF₃ | Cl | Me | NCONHEt | " |
| CF₃ | Cl | Me | NCONHPr | " |
| CF₃ | Cl | Me | NCONH₂ | " |
| CF₃ | Cl | Me | NCONHMe | " |
| CF₃ | Cl | Me | NCN | " |
| CF₃ | Cl | Me | NCOSMe | " |
| CF₃ | Cl | Me | NCOSEt | " |
| CF₃ | Cl | Me | NCSOMe | " |
| CF₃ | Cl | Me | NCSOEt | " |
| CF₃ | Cl | Me | NCSOPr | " |
| CF₃ | Cl | Me | NSO₂NH₂ | " |
| CF₃ | Cl | Me | NSO₂NHMe | " |
| CF₃ | Cl | Me | NSO₂NMe₂ | " |
| CF₃ | Cl | Me | NP(O)(OMe)₂ | " |
| CF₃ | Cl | Me | NP(O)(OEt)₂ | " |
| CF₃ | Cl | Me | NP(O)Me₂ | " |
| CF₃ | Cl | Me | NP(O)Et₂ | " |
| CF₃ | Cl | Me | NP(O)Me(OMe) | " |
| CF₃ | Cl | Me | NP(O)(OPr)₂ | " |
| CF₃ | Cl | Me | NC(O)C(O)H | " |
| CF₃ | Cl | Me | NC(O)C(O)Me | " |
| CF₃ | Cl | Me | NC(O)C(O)OMe | " |
| CF₃ | Cl | Me | NC(O)C(O)OEt | " |
| CF₃ | Cl | Me | NC(O)C(O)NH₂ | " |
| CF₃ | Cl | Me | NC(O)C(O)OH | " |
| CF₃ | Cl | Me | NC(NH)NH₂ | " |
| CF₃ | Cl | Me | NC(NOH)NH₂ | " |
| CF₃ | Cl | Me | NC(NH)NHMe | " |
| CF₃ | Cl | Me | NC(NH)NMe₂ | " |
| CF₃ | Cl | Me | NC(NH)OMe | " |
| CF₃ | Cl | Me | NC(NH)OEt | " |
| CF₃ | Cl | Me | NCOMe | O |
| CF₃ | Cl | Me | NCOEt | O |
| CF₃ | Cl | Me | NCOPr | O |
| CF₃ | Cl | Me | NCHO | O |
| CF₃ | Cl | Me | NCOiPr | O |
| CF₃ | Cl | Me | NCOtBu | O |
| CF₃ | Cl | Me | NCOPh | O |
| CF₃ | Cl | Me | NSO₂Me | O |
| CF₃ | Cl | Me | NSO₂Et | O |
| CF₃ | Cl | Me | NSO₂Pr | O |
| CF₃ | Cl | Me | NSO₂Ph | O |

TABLE 5-continued

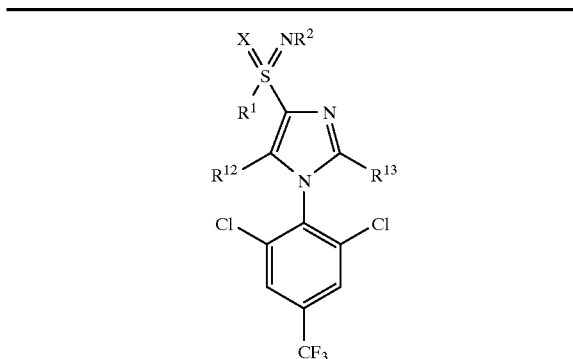

| R¹ | R¹² | R¹³ | NR² | X |
|---|---|---|---|---|
| CF₃ | Cl | Me | NSO₂iPr | O |
| CF₃ | Cl | Me | NNO₂ | O |
| CF₃ | Cl | Me | NCOOMe | O |
| CF₃ | Cl | Me | NCOOEt | O |
| CF₃ | Cl | Me | NCOOPr | O |
| CF₃ | Cl | Me | NCOOiPr | O |
| CF₃ | Cl | Me | NCONHEt | O |
| CF₃ | Cl | Me | NCONHPr | O |
| CF₃ | Cl | Me | NCONH₂ | O |
| CF₃ | Cl | Me | NCONHMe | O |
| CF₃ | Cl | Me | NCN | O |
| CF₃ | Cl | Me | NCOSMe | O |
| CF₃ | Cl | Me | NCOSEt | O |
| CF₃ | Cl | Me | NCSOMe | O |
| CF₃ | Cl | Me | NCSOEt | O |
| CF₃ | Cl | Me | NCSOPr | O |
| CF₃ | Cl | Me | NSO₂NH₂ | O |
| CF₃ | Cl | Me | NSO₂NHMe | O |
| CF₃ | Cl | Me | NSO₂NMe₂ | O |
| CF₃ | Cl | Me | NP(O)(OMe)₂ | O |
| CF₃ | Cl | Me | NP(O)(OEt)₂ | O |
| CF₃ | Cl | Me | NP(O)Me₂ | O |
| CF₃ | Cl | Me | NP(O)Et₂ | O |
| CF₃ | Cl | Me | NP(O)Me(OMe) | O |
| CF₃ | Cl | Me | NP(O)(OPr)₂ | O |
| CF₃ | Cl | Me | NC(O)C(O)H | O |
| CF₃ | Cl | Me | NC(O)C(O)Me | O |
| CF₃ | Cl | Me | NC(O)C(O)OMe | O |
| CF₃ | Cl | Me | NC(O)C(O)OEt | O |
| CF₃ | Cl | Me | NC(O)C(O)NH₂ | O |
| CF₃ | Cl | Me | NC(O)C(O)OH | O |
| CF₃ | Cl | Me | NC(NH)NH₂ | O |
| CF₃ | Cl | Me | NC(NOH)NH₂ | O |
| CF₃ | Cl | Me | NC(NH)NHMe | O |
| CF₃ | Cl | Me | NC(NH)NMe₂ | O |
| CF₃ | Cl | Me | NC(NH)OMe | O |
| CF₃ | Cl | Me | NC(NH)OEt | O |
| CF₃ | H | Me | NCOMe | " |
| CF₃ | H | Me | NCOEt | " |
| CF₃ | H | Me | NCOPr | " |
| CF₃ | H | Me | NCHO | " |
| CF₃ | H | Me | NCOiPr | " |
| CF₃ | H | Me | NCOtBu | " |
| CF₃ | H | Me | NCOPh | " |
| CF₃ | H | Me | NSO₂Me | " |
| CF₃ | H | Me | NSO₂Et | " |
| CF₃ | H | Me | NSO₂Pr | " |
| CF₃ | H | Me | NSO₂Ph | " |
| CF₃ | H | Me | NSO₂iPr | " |
| CF₃ | H | Me | NNO₂ | " |
| CF₃ | H | Me | NCOOMe | " |
| CF₃ | H | Me | NCOOEt | " |
| CF₃ | H | Me | NCOOPr | " |
| CF₃ | H | Me | NCOOiPr | " |
| CF₃ | H | Me | NCONHEt | " |
| CF₃ | H | Me | NCONHPr | " |
| CF₃ | H | Me | NCONH₂ | " |
| CF₃ | H | Me | NCONHMe | " |
| CF₃ | H | Me | NCN | " |
| CF₃ | H | Me | NCOSMe | " |
| CF₃ | H | Me | NCOSEt | " |
| CF₃ | H | Me | NCSOMe | " |
| CF₃ | H | Me | NCSOEt | " |
| CF₃ | H | Me | NCSOPr | " |
| CF₃ | H | Me | NSO₂NH₂ | " |
| CF₃ | H | Me | NSO₂NHMe | " |
| CF₃ | H | Me | NSO₂NMe₂ | " |
| CF₃ | H | Me | NP(O)(OMe)₂ | " |
| CF₃ | H | Me | NP(O)(OEt)₂ | " |
| CF₃ | H | Me | NP(O)Me₂ | " |
| CF₃ | H | Me | NP(O)Et₂ | " |
| CF₃ | H | Me | NP(O)Me(OMe) | " |
| CF₃ | H | Me | NP(O)(OPr)₂ | " |
| CF₃ | H | Me | NC(O)C(O)H | " |
| CF₃ | H | Me | NC(O)C(O)Me | " |
| CF₃ | H | Me | NC(O)C(O)OMe | " |
| CF₃ | H | Me | NC(O)C(O)OEt | " |
| CF₃ | H | Me | NC(O)C(O)NH₂ | " |
| CF₃ | H | Me | NC(O)C(O)OH | " |
| CF₃ | H | Me | NC(NH)NH₂ | " |
| CF₃ | H | Me | NC(NOH)NH₂ | " |
| CF₃ | H | Me | NC(NH)NHMe | " |
| CF₃ | H | Me | NC(NH)NMe₂ | " |
| CF₃ | H | Me | NC(NH)OMe | " |
| CF₃ | H | Me | NC(NH)OEt | " |
| CF₃ | H | Me | NCOMe | O |
| CF₃ | H | Me | NCOEt | O |
| CF₃ | H | Me | NCOPr | O |
| CF₃ | H | Me | NCHO | O |
| CF₃ | H | Me | NCOiPr | O |
| CF₃ | H | Me | NCOtBu | O |
| CF₃ | H | Me | NCOPh | O |
| CF₃ | H | Me | NSO₂Me | O |
| CF₃ | H | Me | NSO₂Et | O |
| CF₃ | H | Me | NSO₂Pr | O |
| CF₃ | H | Me | NSO₂Ph | O |
| CF₃ | H | Me | NSO₂iPr | O |
| CF₃ | H | Me | NNO₂ | O |
| CF₃ | H | Me | NCOOMe | O |
| CF₃ | H | Me | NCOOEt | O |
| CF₃ | H | Me | NCOOPr | O |
| CF₃ | H | Me | NCOOiPr | O |
| CF₃ | H | Me | NCONHEt | O |
| CF₃ | H | Me | NCONHPr | O |
| CF₃ | H | Me | NCONH₂ | O |
| CF₃ | H | Me | NCONHMe | O |
| CF₃ | H | Me | NCN | O |
| CF₃ | H | Me | NCOSMe | O |
| CF₃ | H | Me | NCOSEt | O |
| CF₃ | H | Me | NCSOMe | O |
| CF₃ | H | Me | NCSOEt | O |
| CF₃ | H | Me | NCSOPr | O |
| CF₃ | H | Me | NSO₂NH₂ | O |
| CF₃ | H | Me | NSO₂NHMe | O |
| CF₃ | H | Me | NSO₂NMe₂ | O |
| CF₃ | H | Me | NP(O)(OMe)₂ | O |
| CF₃ | H | Me | NP(O)(OEt)₂ | O |
| CF₃ | H | Me | NP(O)Me₂ | O |

TABLE 5-continued

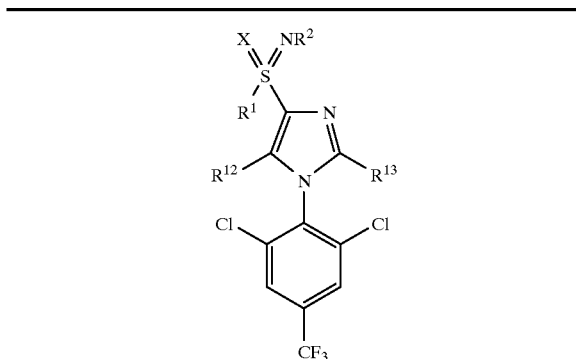

| R¹ | R¹² | R¹³ | NR² | X |
|---|---|---|---|---|
| CF₃ | H | Me | NP(O)Et₂ | O |
| CF₃ | H | Me | NP(O)Me(OMe) | O |
| CF₃ | H | Me | NP(O)(OPr)₂ | O |
| CF₃ | H | Me | NC(O)C(O)H | O |
| CF₃ | H | Me | NC(O)C(O)Me | O |
| CF₃ | H | Me | NC(O)C(O)OMe | O |
| CF₃ | H | Me | NC(O)C(O)OEt | O |
| CF₃ | H | Me | NC(O)C(O)NH₂ | O |
| CF₃ | H | Me | NC(O)C(O)OH | O |
| CF₃ | H | Me | NC(NH)NH₂ | O |
| CF₃ | H | Me | NC(NOH)NH₂ | O |
| CF₃ | H | Me | NC(NH)NHMe | O |
| CF₃ | H | Me | NC(NH)NMe₂ | O |
| CF₃ | H | Me | NC(NH)OMe | O |
| CF₃ | H | Me | NC(NH)OEt | O |
| CF₃ | Me | Me | NCOMe | " |
| CF₃ | Me | Me | NCOEt | " |
| CF₃ | Me | Me | NCOPr | " |
| CF₃ | Me | Me | NCHO | " |
| CF₃ | Me | Me | NCOiPr | " |
| CF₃ | Me | Me | NCOtBu | " |
| CF₃ | Me | Me | NCOPh | " |
| CF₃ | Me | Me | NSO₂Me | " |
| CF₃ | Me | Me | NSO₂Et | " |
| CF₃ | Me | Me | NSO₂Pr | " |
| CF₃ | Me | Me | NSO₂Ph | " |
| CF₃ | Me | Me | NSO₂iPr | " |
| CF₃ | Me | Me | NNO₂ | " |
| CF₃ | Me | Me | NCOOMe | " |
| CF₃ | Me | Me | NCOOEt | " |
| CF₃ | Me | Me | NCOOPr | " |
| CF₃ | Me | Me | NCOOiPr | " |
| CF₃ | Me | Me | NCONHEt | " |
| CF₃ | Me | Me | NCONHPr | " |
| CF₃ | Me | Me | NCONH₂ | " |
| CF₃ | Me | Me | NCONHMe | " |
| CF₃ | Me | Me | NCN | " |
| CF₃ | Me | Me | NCOSMe | " |
| CF₃ | Me | Me | NCOSEt | " |
| CF₃ | Me | Me | NCSOMe | " |
| CF₃ | Me | Me | NCSOEt | " |
| CF₃ | Me | Me | NCSOPr | " |
| CF₃ | Me | Me | NSO₂NH₂ | " |
| CF₃ | Me | Me | NSO₂NHMe | " |
| CF₃ | Me | Me | NSO₂NMe₂ | " |
| CF₃ | Me | Me | NP(O)(OMe)₂ | " |
| CF₃ | Me | Me | NP(O)(OEt)₂ | " |
| CF₃ | Me | Me | NP(O)Me₂ | " |
| CF₃ | Me | Me | NP(O)Et₂ | " |
| CF₃ | Me | Me | NP(O)Me(OMe) | " |
| CF₃ | Me | Me | NP(O)(OPr)₂ | " |
| CF₃ | Me | Me | NC(O)C(O)H | " |
| CF₃ | Me | Me | NC(O)C(O)Me | " |
| CF₃ | Me | Me | NC(O)C(O)OMe | " |
| CF₃ | Me | Me | NC(O)C(O)OEt | " |
| CF₃ | Me | Me | NC(O)C(O)NH₂ | " |
| CF₃ | Me | Me | NC(O)C(O)OH | " |
| CF₃ | Me | Me | NC(NH)NH₂ | " |
| CF₃ | Me | Me | NC(NOH)NH₂ | " |
| CF₃ | Me | Me | NC(NH)NHMe | " |
| CF₃ | Me | Me | NC(NH)NMe₂ | " |
| CF₃ | Me | Me | NC(NH)OMe | " |
| CF₃ | Me | Me | NC(NH)OEt | " |
| CF₃ | Me | Me | NCOMe | O |
| CF₃ | Me | Me | NCOEt | O |
| CF₃ | Me | Me | NCOPr | O |
| CF₃ | Me | Me | NCHO | O |
| CF₃ | Me | Me | NCOiPr | O |
| CF₃ | Me | Me | NCOtBu | O |
| CF₃ | Me | Me | NCOPh | O |
| CF₃ | Me | Me | NSO₂Me | O |
| CF₃ | Me | Me | NSO₂Et | O |
| CF₃ | Me | Me | NSO₂Pr | O |
| CF₃ | Me | Me | NSO₂Ph | O |
| CF₃ | Me | Me | NSO₂iPr | O |
| CF₃ | Me | Me | NNO₂ | O |
| CF₃ | Me | Me | NCOOMe | O |
| CF₃ | Me | Me | NCOOEt | O |
| CF₃ | Me | Me | NCOOPr | O |
| CF₃ | Me | Me | NCOOiPr | O |
| CF₃ | Me | Me | NCONHEt | O |
| CF₃ | Me | Me | NCONHPr | O |
| CF₃ | Me | Me | NCONH₂ | O |
| CF₃ | Me | Me | NCONHMe | O |
| CF₃ | Me | Me | NCN | O |
| CF₃ | Me | Me | NCOSMe | O |
| CF₃ | Me | Me | NCOSEt | O |
| CF₃ | Me | Me | NCSOMe | O |
| CF₃ | Me | Me | NCSOEt | O |
| CF₃ | Me | Me | NCSOPr | O |
| CF₃ | Me | Me | NSO₂NH₂ | O |
| CF₃ | Me | Me | NSO₂NHMe | O |
| CF₃ | Me | Me | NSO₂NMe₂ | O |
| CF₃ | Me | Me | NP(O)(OMe)₂ | O |
| CF₃ | Me | Me | NP(O)(OEt)₂ | O |
| CF₃ | Me | Me | NP(O)Me₂ | O |
| CF₃ | Me | Me | NP(O)Et₂ | O |
| CF₃ | Me | Me | NP(O)Me(OMe) | O |
| CF₃ | Me | Me | NP(O)(OPr)₂ | O |
| CF₃ | Me | Me | NC(O)C(O)H | O |
| CF₃ | Me | Me | NC(O)C(O)Me | O |
| CF₃ | Me | Me | NC(O)C(O)OMe | O |
| CF₃ | Me | Me | NC(O)C(O)OEt | O |
| CF₃ | Me | Me | NC(O)C(O)NH₂ | O |
| CF₃ | Me | Me | NC(O)C(O)OH | O |
| CF₃ | Me | Me | NC(NH)NH₂ | O |
| CF₃ | Me | Me | NC(NOH)NH₂ | O |
| CF₃ | Me | Me | NC(NH)NHMe | O |
| CF₃ | Me | Me | NC(NH)NMe₂ | O |
| CF₃ | Me | Me | NC(NH)OMe | O |
| CF₃ | Me | Me | NC(NH)OEt | O |
| CF₃ | Cl | Cl | NCOMe | " |
| CF₃ | Cl | Cl | NCOEt | " |
| CF₃ | Cl | Cl | NCOPr | " |
| CF₃ | Cl | Cl | NCHO | " |
| CF₃ | Cl | Cl | NCOiPr | " |
| CF₃ | Cl | Cl | NCOtBu | " |
| CF₃ | Cl | Cl | NCOPh | " |

TABLE 5-continued

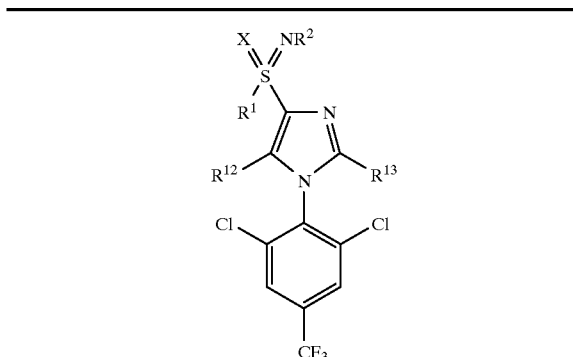

| R¹ | R¹² | R¹³ | NR² | X |
|---|---|---|---|---|
| CF₃ | Cl | Cl | NSO₂Me | " |
| CF₃ | Cl | Cl | NSO₂Et | " |
| CF₃ | Cl | Cl | NSO₂Pr | " |
| CF₃ | Cl | Cl | NSO₂Ph | " |
| CF₃ | Cl | Cl | NSO₂iPr | " |
| CF₃ | Cl | Cl | NNO₂ | " |
| CF₃ | Cl | Cl | NCOOMe | " |
| CF₃ | Cl | Cl | NCOOEt | " |
| CF₃ | Cl | Cl | NCOOPr | " |
| CF₃ | Cl | Cl | NCOOiPr | " |
| CF₃ | Cl | Cl | NCONHEt | " |
| CF₃ | Cl | Cl | NCONHPr | " |
| CF₃ | Cl | Cl | NCONH₂ | " |
| CF₃ | Cl | Cl | NCONHMe | " |
| CF₃ | Cl | Cl | NCN | " |
| CF₃ | Cl | Cl | NCOSMe | " |
| CF₃ | Cl | Cl | NCOSEt | " |
| CF₃ | Cl | Cl | NCSOMe | " |
| CF₃ | Cl | Cl | NCSOEt | " |
| CF₃ | Cl | Cl | NCSOPr | " |
| CF₃ | Cl | Cl | NSO₂NH₂ | " |
| CF₃ | Cl | Cl | NSO₂NHMe | " |
| CF₃ | Cl | Cl | NSO₂NMe₂ | " |
| CF₃ | Cl | Cl | NP(O)(OMe)₂ | " |
| CF₃ | Cl | Cl | NP(O)(OEt)₂ | " |
| CF₃ | Cl | Cl | NP(O)Me₂ | " |
| CF₃ | Cl | Cl | NP(O)Et₂ | " |
| CF₃ | Cl | Cl | NP(O)Me(OMe) | " |
| CF₃ | Cl | Cl | NP(O)(OPr)₂ | " |
| CF₃ | Cl | Cl | NC(O)C(O)H | " |
| CF₃ | Cl | Cl | NC(O)C(O)Me | " |
| CF₃ | Cl | Cl | NC(O)C(O)OMe | " |
| CF₃ | Cl | Cl | NC(O)C(O)OEt | " |
| CF₃ | Cl | Cl | NC(O)C(O)NH₂ | " |
| CF₃ | Cl | Cl | NC(O)C(O)OH | " |
| CF₃ | Cl | Cl | NC(NH)NH₂ | " |
| CF₃ | Cl | Cl | NC(NOH)NH₂ | " |
| CF₃ | Cl | Cl | NC(NH)NHMe | " |
| CF₃ | Cl | Cl | NC(NH)NMe₂ | " |
| CF₃ | Cl | Cl | NC(NH)OMe | " |
| CF₃ | Cl | Cl | NC(NH)OEt | " |
| CF₃ | Cl | Cl | NCOMe | O |
| CF₃ | Cl | Cl | NCOEt | O |
| CF₃ | Cl | Cl | NCOPr | O |
| CF₃ | Cl | Cl | NCHO | O |
| CF₃ | Cl | Cl | NCOiPr | O |
| CF₃ | Cl | Cl | NCOtBu | O |
| CF₃ | Cl | Cl | NCOPh | O |
| CF₃ | Cl | Cl | NSO₂Me | O |
| CF₃ | Cl | Cl | NSO₂Et | O |
| CF₃ | Cl | Cl | NSO₂Pr | O |
| CF₃ | Cl | Cl | NSO₂Ph | O |
| CF₃ | Cl | Cl | NSO₂iPr | O |
| CF₃ | Cl | Cl | NNO₂ | O |
| CF₃ | Cl | Cl | NCOOMe | O |
| CF₃ | Cl | Cl | NCOOEt | O |
| CF₃ | Cl | Cl | NCOOPr | O |
| CF₃ | Cl | Cl | NCOOiPr | O |
| CF₃ | Cl | Cl | NCONHEt | O |

TABLE 5-continued

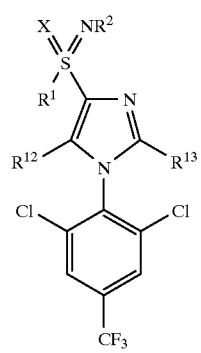

| R¹ | R¹² | R¹³ | NR² | X |
|---|---|---|---|---|
| CF₃ | Cl | Cl | NCONHPr | O |
| CF₃ | Cl | Cl | NCONH₂ | O |
| CF₃ | Cl | Cl | NCONHMe | O |
| CF₃ | Cl | Cl | NCN | O |
| CF₃ | Cl | Cl | NCOSMe | O |
| CF₃ | Cl | Cl | NCOSEt | O |
| CF₃ | Cl | Cl | NCSOMe | O |
| CF₃ | Cl | Cl | NCSOEt | O |
| CF₃ | Cl | Cl | NCSOPr | O |
| CF₃ | Cl | Cl | NSO₂NH₂ | O |
| CF₃ | Cl | Cl | NSO₂NHMe | O |
| CF₃ | Cl | Cl | NSO₂NMe₂ | O |
| CF₃ | Cl | Cl | NP(O)(OMe)₂ | O |
| CF₃ | Cl | Cl | NP(O)(OEt)₂ | O |
| CF₃ | Cl | Cl | NP(O)Me₂ | O |
| CF₃ | Cl | Cl | NP(O)Et₂ | O |
| CF₃ | Cl | Cl | NP(O)Me(OMe) | O |
| CF₃ | Cl | Cl | NP(O)(OPr)₂ | O |
| CF₃ | Cl | Cl | NC(O)C(O)H | O |
| CF₃ | Cl | Cl | NC(O)C(O)Me | O |
| CF₃ | Cl | Cl | NC(O)C(O)OMe | O |
| CF₃ | Cl | Cl | NC(O)C(O)OEt | O |
| CF₃ | Cl | Cl | NC(O)C(O)NH₂ | O |
| CF₃ | Cl | Cl | NC(O)C(O)OH | O |
| CF₃ | Cl | Cl | NC(NH)NH₂ | O |
| CF₃ | Cl | Cl | NC(NOH)NH₂ | O |
| CF₃ | Cl | Cl | NC(NH)NHMe | O |
| CF₃ | Cl | Cl | NC(NH)NMe₂ | O |
| CF₃ | Cl | Cl | NC(NH)OMe | O |
| CF₃ | Cl | Cl | NC(NH)OEt | O |
| CF₃ | Cl | H | NCOMe | " |
| CF₃ | Cl | H | NCOEt | " |
| CF₃ | Cl | H | NCOPr | " |
| CF₃ | Cl | H | NCHO | " |
| CF₃ | Cl | H | NCOiPr | " |
| CF₃ | Cl | H | NCOtBu | " |
| CF₃ | Cl | H | NCOPh | " |
| CF₃ | Cl | H | NSO₂Me | " |
| CF₃ | Cl | H | NSO₂Et | " |
| CF₃ | Cl | H | NSO₂Pr | " |
| CF₃ | Cl | H | NSO₂Ph | " |
| CF₃ | Cl | H | NSO₂iPr | " |
| CF₃ | Cl | H | NNO₂ | " |
| CF₃ | Cl | H | NCOOMe | " |
| CF₃ | Cl | H | NCOOEt | " |
| CF₃ | Cl | H | NCOOPr | " |
| CF₃ | Cl | H | NCOOiPr | " |
| CF₃ | Cl | H | NCONHEt | " |
| CF₃ | Cl | H | NCONHPr | " |
| CF₃ | Cl | H | NCONH₂ | " |
| CF₃ | Cl | H | NCONHMe | " |
| CF₃ | Cl | H | NCOEt | O |
| CF₃ | Cl | H | NCOPr | O |
| CF₃ | Cl | H | NCHO | O |
| CF₃ | Cl | H | NCOiPr | O |
| CF₃ | Cl | H | NCOtBu | O |
| CF₃ | Cl | H | NCOPh | O |
| CF₃ | Cl | H | NSO₂Me | O |
| CF₃ | Cl | H | NSO₂Et | O |

TABLE 5-continued $$\underset{\underset{\underset{CF_3}{\bigoplus}}{Cl\diagdown\diagup Cl}}{\overset{X\diagdown\diagup NR^2}{\underset{R^1}{\overset{S}{\bigoplus}}\diagdown\underset{R^{12}\diagdown N\diagup R^{13}}{\bigoplus}}}$$

| $R^1$ | $R^{12}$ | $R^{13}$ | $NR^2$ | X |
|---|---|---|---|---|
| $CF_3$ | Cl | H | $NSO_2Pr$ | O |
| $CF_3$ | Cl | H | $NSO_2Ph$ | O |
| $CF_3$ | Cl | H | $NSO_2iPr$ | O |
| $CF_3$ | Cl | H | $NNO_2$ | O |
| $CF_3$ | Cl | H | NCOOMe | O |
| $CF_3$ | Cl | H | NCOOEt | O |
| $CF_3$ | Cl | H | NCOOPr | O |
| $CF_3$ | Cl | H | NCOOiPr | O |
| $CF_3$ | Cl | H | NCONHEt | O |
| $CF_3$ | Cl | H | NCONHPr | O |
| $CF_3$ | Cl | H | $NCONH_2$ | O |
| $CF_3$ | Cl | H | NCONHMe | O |
| $CF_3$ | Cl | H | NCN | O |
| $CF_3$ | Cl | H | NCOSMe | O |
| $CF_3$ | Cl | H | NCOSEt | O |
| $CF_3$ | Cl | H | NCSOMe | O |
| $CF_3$ | Cl | H | NCSOEt | O |
| $CF_3$ | Cl | H | NCSOPr | O |
| $CF_3$ | Cl | H | $NSO_2NH_2$ | O |
| $CF_3$ | Cl | H | $NSO_2NHMe$ | O |
| $CF_3$ | Cl | H | $NSO_2NMe_2$ | O |
| $CF_3$ | Cl | H | $NP(O)(OMe)_2$ | O |
| $CF_3$ | Cl | H | $NP(O)(OEt)_2$ | O |
| $CF_3$ | Cl | H | $NP(O)Me_2$ | O |
| $CF_3$ | Cl | H | $NP(O)Et_2$ | O |
| $CF_3$ | Cl | H | NP(O)Me(OMe) | O |
| $CF_3$ | Cl | H | $NP(O)(OPr)_2$ | O |
| $CF_3$ | Cl | H | NC(O)C(O)H | O |
| $CF_3$ | Cl | H | NC(O)C(O)Me | O |
| $CF_3$ | Cl | H | NC(O)C(O)OMe | O |
| $CF_3$ | Cl | H | NC(O)C(O)OEt | O |
| $CF_3$ | Cl | H | $NC(O)C(O)NH_2$ | O |
| $CF_3$ | Cl | H | NC(O)C(O)OH | O |
| $CF_3$ | Cl | H | $NC(NH)NH_2$ | O |
| $CF_3$ | Cl | H | $NC(NOH)NH_2$ | O |
| $CF_3$ | Cl | H | NC(NH)NHMe | O |
| $CF_3$ | Cl | H | $NC(NH)NMe_2$ | O |
| $CF_3$ | Cl | H | NC(NH)OMe | O |
| $CF_3$ | Cl | H | NC(NH)OEt | O |

COMPOSITIONS AND METHODS OF USE

The present invention provides pesticidal compositions and methods of controlling arthropod, nematode, helminth and protozoan pests, using the compounds of formulas (I) and (II), as set forth in the Summary of the Invention hereinabove. In a preferred aspect, the present invention provides a method for controlling arthropods or nematodes at a locus comprising applying to said locus an arthropodicidally or nematocidally effective amount of a compound of either formula (I) or formula (II) or a composition comprising said compound and an agriculturally acceptable inert carrier therefor. In a more preferred embodiment, the arthropods whose control is desired are insects, and to that end the invention provides a method for controlling insects at a locus comprising applying to said locus an insecticidally effective amount of a compound of either formula (I) or (II), or an insecticidally effective amount of an insecticidal composition comprising an insecticidally effective amount of a compound of either formula (I) or (II) and an agriculturally acceptable inert carrier therefor. In another preferred embodiment, control of nematodes is desired, and to that end the invention provides a method of controlling nematodes at a locus comprising applying to said locus a nematocidally effective amount of a compound of either formula (I) or (II), or a nematocidally effective amount of a nematocidal composition comprising a nematocidally effective amount of a compound of either formula (I) or (II) and an agriculturally acceptable inert carrier therefor. Preferably, the locus to which the arthropodicidally (especially insecticidally) or nematocidally effective amount is applied is a crop-growing area, that is, an area in which a crop is growing or in which a crop has been planted, or an area in which a crop will be planted/grown.

The compositions which can be used in the invention for the pesticidal, particularly the arthropodicidal (especially insecticidal) or nematocidal, treatment of the invention can comprise from about 0.001 to about 95% of the active ingredient of either formula (I) or (II). The term "active ingredient of either formula (I) or (II)" or "active ingredient" as used herein refers to a compound of either formula (I) or (II) or salt thereof. The expression "compound of either formula (I) or (II)" is also used herein to mean the compound or its salt.

The diluted liquid formulations, as applied to the locus to be treated or crop, generally comprise from about 0.001 to about 3% of active ingredient of either formula (I) or (II), preferably from about 0.1 to about 0.5%.

The solid formulations as applied to the locus or crop generally comprise from about 0.1 to about 8% of active ingredient of either formula (I) or (II), preferably from about 0.5 to about 1.5%.

The concentrated compositions are compositions which are commercialized or transported or stored. For application to plants, they are normally diluted in water and applied in such diluted form. The diluted forms are part of the invention as well as the concentrated forms.

The concentrated formulations generally comprise from about 5 to about 95% of active ingredient of either formula (I) or (II), preferably from about 10 to about 50%.

The insecticidal compositions of the invention can be applied once, or more than once, throughout the whole insect season. Insecticidal compositions according to the invention are usually applied to the locus to be treated or crop area at a rate of from about 0.04 to about 2 kg/ha of active ingredient, preferably from about 0.1 to about 1 kg/ha.

The concentrated insecticidal compositions according to the invention can be in the form of a solid, e.g., dusts or granules or wettable powders, or, preferably, in the form of a liquid, such as an emulsifiable concentrate or a true solution.

The compositions according to the instant invention generally comprise from about 0.5 to about 95% of active ingredient. The remainder of the composition up to 100% comprises a carrier as well as various additives such as those hereafter indicated.

By "carrier", there is meant herein an organic or inorganic material, which can be natural or synthetic, and which is associated with the active ingredient and which facilitates its application to the locus to be treated or crop. This carrier is thus generally inert and should be agriculturally acceptable, especially on the contemplated or treated locus or crop. The carrier can be solid (clay, silicates, silica, resins, wax, fertilizers, etc.) or liquid (water, alcohols, ketones, oil solvents, saturated or unsaturated hydrocarbons, chlorinated hydrocarbons, liquified petroleum gas, etc.).

Among the many additives, the compositions of the invention can comprise surfactants as well as other ingredients such as dispersants, stickers, antifoam agents, antifreezing agents, dyestuffs, thickeners, adhesives, protective colloids, penetrating agents, stabilizing agents, sequestering agents, antiflocculating agents, corrosion inhibitors, pigments and polymers.

More generally, the compositions of the invention can comprise all kinds of solid or liquid additives which are known in the art of insecticides and insecticidal treatments.

The surfactants can be of the emulsifying or wetting type, ionic or non-ionic. Possible surfactants are salts of polyacrylic or lignosulfonic acids; salts of phenolsulfonic or naphthalenesulfonic acids; polycondensates of ethylene oxide with fatty alcohols or fatty acids or fatty amines or substituted phenols (particularly alkylphenols or arylphenols); ester-salts of sulfosuccinic acids; taurine derivatives such as alkyl taurates; phosphoric esters; or esters of alcohols or polyoxyethylated phenols. When the spraying vehicle is water, the use of at least one surfactant is generally required because the active ingredients are not water-soluble.

The method of application of the compositions of the invention is generally the spraying of a mixture which has been previously made by dilution of more concentrated formulations according to the invention.

Solid compositions can be powders for dusting or for dispersion (wherein the content of active ingredient can be up to 100%) and granules, especially extruded or compacted granules, or granules which have been made by impregnation of a powder (the content of active ingredient in such powders can then be between about 1 and about 80%).

Liquid compositions or compositions which have to be liquid when applied include solutions, water-soluble concentrates, emulsifiable concentrates, emulsions, wettable powders or pastes or water-dispersible granules.

Emulsifiable concentrates generally comprise from about 10 to about 80% of active ingredient; the emulsions when applied generally comprise from about 0.01 to about 20% of active ingredient.

For example, the emulsifiable concentrates can comprise the solvent and, to the extent needed, from about 2 to about 20% of suitable additives as stabilizers, surfactants, penetrating agents, corrosion inhibitors or other additives already recited.

These concentrates are usually diluted in tank water so as to obtain the dilution appropriate for spraying.

The concentrated suspensions can also be applied by spraying and have to be fluid without allowing any solid to separate and fall to the bottom. Generally they comprise from about 1 to about 75% of active ingredient (preferably from about 2 to about 50%), from about 0.5 to about 15% of surfactants, from about 0.1 to about 10% of thickener, and from 0 to about 10% of other suitable additives as already indicated, the remainder being water or an organic liquid wherein the active ingredient is insoluble or has a low solubility.

The wettable powders generally comprise the active ingredient (from about 1 to about 95%, preferably from about 2 to about 80%), the solid carrier, a wetting agent (from 0 to about 5%), a dispersing agent (from about 3 to about 10%) and, to the extent needed, from 0 to about 10% of other additives such as stabilizers and others as already listed.

In order to obtain these wettable powders or dusting powders, it is appropriate to intimately mix the active ingredients and the additives, as by grinding in a mill or similar device.

Dispersible granules are generally made by agglomeration of a powder followed by an appropriate granulation process.

The emulsions herein described can be of the oil-in-water or water-in-oil types. Fluidity of the emulsions can range from low viscosities up to high viscosities approaching those of gels.

Among these many compositions or formulations, one skilled in the art can choose the one most appropriate, according to the specific conditions of the treatment problem.

The compounds and compositions of the invention can also be used in admixtures with another pesticide e.g., an insecticide, acaricide or herbicide.

The invention is further illustrated by the following examples which are not considered as limiting the invention but are given to better enable use of it.

BIOLOGICAL EFFICACY

The following representative methods were used to apply the compounds of the invention and to observe the biological activity obtained therefrom: a soil drench on aphid-infested plants; a bait application on flies.

The species used were as follows:

| GENUS, SPECIES | COMMON NAME |
| --- | --- |
| Aphis gossypii | cotton leaf aphid |
| Schizaphis graminum | greenbug |
| Musca domestica | housefly |

The Soil Drench Test (systemic activity: aphids)

Cotton and sorghum plants were established in pots. One day prior to treatment, each pot was infested with about 25 aphids of a mixed population. Cotton plants were infested with aphids and sorghum plants were infested with the greenbug. The selected compound of formula (I) or formula (II) was applied to the soil surface in a dilution that delivered the equivalent of 10.0 ppm soil concentration by weight. Aphid counts were obtained at 5 DAT (ie. days after treatment). The number of aphids on the treated plants was compared to the number of those on the untreated control plants. Compounds that showed greater than 30% mortality on either aphid or greenbug were the following: 1a, 1b, 3–29, 30a, 31–32

The Housefly Bait/Contact Test

About 25 four to six-day-old adult houseflies (Musca domestica) were anesthetized and placed in a cage with a sugar water bait solution containing the compound. The compound concentration in the bait solution was 100 ppm. After 24 hours, flies which showed no movement on stimulation were considered dead. Compounds that showed greater than 30% mortality on housefly were the following: 1 , 1a, 1b, 2, 3–10, 12–14, 16, 18–20, 22, 25, 26, 28–30, 30a, 31,32

While the invention has been described in terms of various preferred embodiments, the skilled artisan will appreciate that various modifications, substitutions, omissions and changes can be made without departing from the spirit thereof. Accordingly, it is intended that the scope of the present invention be limited solely by the scope of the following claims, including equivalents thereof.

We claim:

1. A compound having the formula

(I)

or

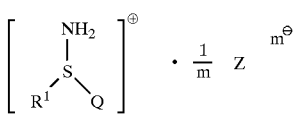
(II)

wherein:

=X is $NR^3$, =O or an electron pair;

$R^1$ is $C_1$–$C_6$ alkyl, $C_3$–$C_6$ cycloalkyl, or $C_4$–$C_8$ (cycloalkyl)alkyl, each of which is optionally substituted by one or more halogen;

$R^2$ and $R^3$ are independantly selected from H; $C_1$–$C_6$ alkyl; $C_1$–$C_6$ haloalkyl; $COR^4$; $S(O)_pR^4$; CN; $NO_2$; $COOR^4$; $CONR^4R^5$; $C(O)SR^4$; $C(S)OR^4$; $SO_2NR^4R^5$; $P(O)_q(R^4)(R^5)$; $P(O)_q(OR^4)(R^5)$; $P(O)_q(OR^4)(OR^5)$; $C-(NR^4)NR^5R^6$; $CH=NR^4$; $C=(NR^4)(OR^5)$; $C(S)N(R^4)(R^5)$; $C(O)C(O)R^4$; $C(O)C(O)OR^4$; $C(O)C(O)NR^4R^5$; and $CONR^4SO_2R^5$:

m is 1 or 2;

p is 0, 1 or 2;

q is 0 or 1;

$R^4$, $R^5$ and $R^6$ are independently selected from H; $NO_2$; CN; CHO; $R^{14}$; phenyl optionally substituted by one or more $R^{14}$, halogen, CN, $NO_2$, $OR^{14}$, $SR^{14}$, $COR^{14}$, $COOR^{14}$, or $OR^{14}$; halogen; $COR^{14}$; $COOR^{14}$; CHO; and OH;

Q is Q-1 as designated below:

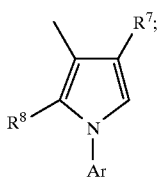
Q-1

$R^7$ is CN, $NO_2$, H, $C_1$–$C_4$ alkyl, $C_1$–$C_4$ haloalkyl, halogen, CHO, $COR^{20}$;

$R^8$ is H, halogen, CN, $S(O)_pR^{14}$, $OR^4$, $NR^{16}R^{17}$, $N(R^{16})CON(R^{17})(R^{18})$, $N_3$ or $NH(C_1$–$C_5$ alkyl) substituted by one or more OH, $OR^{14}$, $S(O)_pR^{14}$, CN, $NO_2$, $COOR^{14}$ or $CON(R^{16})(R^{17})$;

Ar is phenyl, optionally bearing one or more substituents selected from the group consisting of halogen, $R^{15}$, $OR^{15}$, $SF_5$ and $S(O)_pR^{15}$; or Ar is 2-pyrldyl, optionally bearing one or more substituents selected from the group consisting of halogen, $R^{15}$, $OR^{15}$, $SF_5$ and $S(O)_pR^{14}$;

$R^{14}$ and $R^{19}$ are independently selected from $C_1$–$C_6$ alkyl, $C_3$–$C_6$ cycloalkyl, and $C_4$–$C_8$ (cycloalkyl)alkyl, each of which is optionally substituted by one or more halogen;

$R^{15}$ is $C_1$–$C_6$ alkyl, optionally substituted by one or more halogen;

$R^{16}$, $R^{17}$ and $R^{18}$ are independently selected from H, $NO_2$, CN, CHO, $R^{19}$, $COR^{19}$, and $COOR^{19}$;

$R^{20}$ is $C_1$–$C_6$ alkyl, optionally substituted by one or more halogen; and Z is an anionic counter ion.

2. A compound according to claim 1, having formula (I).

3. A compound according to claim 2, wherein =X is =NH, —O or an electron pair.

4. A compound according to claim 3, wherein =X is =O or an electron pair.

5. A compound according to claim 1, wherein $R^1$ is $C_1$–$C_6$ alkyl, optionally substituted by one or more halogen.

6. A compound according to claim 5, wherein $R^1$ is methyl or ethyl.

7. A compound according to claim 1, wherein $R^2$ is H.

8. A compound according to claim 1, wherein $R^2$ is $COOR^4$.

9. A compound according to claim 8, wherein $R^4$ is $C_1$–$C_6$ alkyl.

10. A compound according to claim 1, wherein $R^2$ is $S(O)_pR^4$.

11. A compound according to claim 10 wherein p is two and $R^4$ is $C_1$–$C_6$ alkyl or phenyl optionally substituted by one or more $R^{14}$.

12. A compound according to claim 1 wherein $R^2$ is CN.

13. A compound according to claim 1, wherein $R^2$ is $CONR^4R^5$.

14. A compound according to claim 13, wherein $R^4$ is H or $C_1$–$C_6$ alkyl and $R^5$ is $C_1$–$C_6$ alkyl, or wherein $R^4$ is H and $R^5$ is $COR^{14}$ wherein $R^{14}$ is $C_1$–$C_6$ alkyl, optionally substituted by one or more halogen.

15. A compound according to claim 1, wherein $R^2$ is $COR^4$.

16. A compound according to claim 15, wherein $R^4$ is H or $C_1$–$C_6$ alkyl.

17. A compound according to claim 1, wherein $R^2$ is $P(O)_q(OR^4)(OR^5)$ or $P(O)_q(R^4)(R^5)$.

18. A compound according to claim 17, wherein q is one and $R^4$ and $R^5$ are each $C_1$–$C_6$ alkyl.

19. A compound according to claim 1 wherein $R^7$ is CN, H or $C_1$–$C_4$ alkyl.

20. A compound according to claim 19, wherein $R^7$ is CN.

21. A compound according to claim 1, wherein $R^8$ is $N(R^{16})(R^{17})$.

22. A compound according to claim 21, wherein $R^8$ is $NH_2$.

23. A compound according to claim 22, wherein $R^7$ is CN.

24. A compound according to claim 1, wherein Ar is phenyl, substituted in the 2 and 6 positions by halogen and in the 4-position by halogenated $C_1$–$C_6$ alkyl or $SF_5$ or $OR^{15}$.

25. A compound according to claim 24, wherein Ar is 2,6-dichloro 4 trifluoromethylphenyl.

26. A compound according to claim 1, wherein Ar is 2-pyridyl substituted in the 3 position by halogen and in the 5-position by halogenated $C_1$–$C_6$ alkyl or $SF_5$ or $OR^{15}$.

27. A compound according to claim 26, wherein Ar is 3-chloro-5-trifluoromethylpyrid-2-yl.

28. A compound according to claim 1, wherein Z is $Cl^-$, $Br^-$, $I^-$, $P^-$, $OSO_2R^1$, $ClO_4^-$, $OCOR^{4-}$, $BF_4^-$, $SbF_6^-$, $SO_3^-$ $HSO_4^-$, a phosphate anion or a hydrogenophosphate anion.

29. The compound according to claim 1, having the formula:

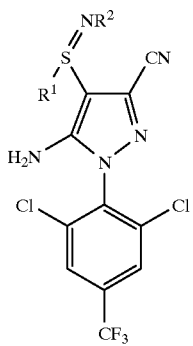

wherein:
(a) $R^1$ is ethyl and $R^2$ is COO(tert-butyl);
(b) $R^1$ is ethyl and $R^2$ is $COCH_3$;
(c) $R^1$ is ethyl and $R^2$ is $COOCH_3$;
(d) $R^1$ is ethyl and $R^2$ is $SO_2CH_3$;
(e) $R^1$ is ethyl and $R^2$ is $CONHCH_3$;
(f) $R^1$ is ethyl and $R^2$ is CN;
(g) $R^1$ is ethyl and $R^2$ is CHO;
(h) $R^1$ is methyl and $R^2$ is $COCH_3$;
(i) $R^1$ is ethyl and $R^2$ is $PO(OC_2H_5)_2$;
(j) $R^1$ is ethyl and $R^2$ is $CON(CH_3)_2$;
(k) $R^1$ is ethyl and $R^2$ is $PO(CH_3)_2$;
(l) $R^1$ is ethyl and $R^2$ is $CONHCOCCl_3$;
(m) $R^1$ is ethyl and $R^2$ is $CONHCOCH_2Cl$; or
(n) $R^1$ is methyl and $R^2$ is

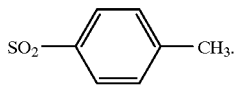

30. The compound according to claim 1, having the formula:

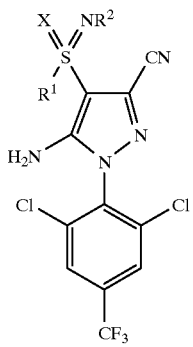

wherein:
(a) $R^1$ is ethyl, X is O and $R^2$ is COO(tert-butyl);
(b) $R^1$ is ethyl, X is O and $R^2$ is $COOCH_3$; or
(c) $R^1$ is ethyl, X is O and $R^2$ is H.

31. The compound according to claim 1, which is;

2,4,6-trimethylbenzenesulfonic acid, compound with S-4-[5-amino-3-cyano-1-(2,6-dichloro-4-trifluoromethyl)phenyl]pyrazolyl-S-ethylsulfilimine;

2,4,6-trimethlylbenzenesulfonic acid, compound with S-4-[5- amino-3-cyano-1-(2,6-dichloro-4-trifluoromethyl)phenyl]pyrazolyl-S-methylsulfimine;

2,4,6-trimethylbenzenesulfonic acid, compound with S-4-[5amino-1-(2,6-dichloro-4-trifluoromethyl)phenyl]pyrazolyl-S-methylsulfilimine;

2,4,6-trimethylbenzenesulfonic acid, compound with S4-[5amino-1-(2,6-dichloro-4-trifluoromethyl)phenyl-3-methyl]pyrazolyl-S-methylsulfilimine;

2,4,6-trimethylbenzenesulfonic acid, compound with S4-[5-amino-1-(2,6dichloro-4-trifluoromethyl)phenyl-3-ethyl]pyrazolyl-S-ethylsulfilimine;

S {[5-amino-3-cyano-1-(2,6-dichloro-4-trifluoromethyl)phenyl]4-(1H-pyrazolyl)}-S-ethyl-N-(tert-butoxycarbonyl)sulfilimine;

S-{[5-amino-3-cyano-1-(2,6-dichloro-4-trifluoromethyl)phenyl]-4-(1H-pyrazolyl)}-S-ethyl-N-acetylsulfilimine:

S-{[5-amino-3-cyano-1-(2,6-dichloro-4-trifluoromethyl)phenyl]-4-(1H-pyrazolyl)}-S-ethyl-N-(methoxycarbonyl)sulfilimine;

S-{[5-amino-3-cyano-1-(2,6-dichloro-4-trifluoromethyl)phenyl]-4-(1H-pyrazolyl)}-S-ethyl-N-(methylsulfonyl)sulfilimine;

S-{[5-amino-3-cyano-1-(2,6-dichloro-4-trifluoromethyl)phenyl]-4-(1H-pyrazolyl)}-S-ethyl-N-(methoxycarbonyl)sulfilimine;

S-{[5-amino-3-cyano-1-(2,6-dichloro-4-trifluoromethyl)phenyl]-4-(1H-pyrazolyl)}-S-ethyl-N-(cyanol)sulfilimine;

S-{[5-amino-3-cyano-1-(2,6-dichloro-4-trifluoromethyl)phenyl]-4-(1H-pyrazolyl)}-S-ethyl-N-(formyl)sulfilimine;

S-{[5-amino-3-cyano-1-(2,6-dichloro-4-trifluoromethyl)phenyl]-4-(1H-pyrazolyl)}-S-methyl-N-acetylsulfilimine;

S {[5-amino-3-cyano-1-(2,6-dichloro-4-trifluoromethyl)phenyl]4-(1H-pyrazolyl)}ethyl-N-(diethylphosphoryl)sulfilimine;

S-{[5-amino-3-cyano-1-(2,6-dichloro-4-trifluoromethyl)phenyl]-4-(1H-pyrazolyl)}-S-ethyl-N-(dimethylcarbonyl)sulfilimine;

S-{[5-amino-3-cyano-1-(2,6-dichloro-4-trifluoromethyl)phenyl]-4-(1H-pyrazolyl)}-S-ethyl-N-(dimethylcarbonyl)sulfilimine;

S-{[5-amino-3-cyano-1-(2,6-dichloro-4-trifluoromethyl)phenyl]-4-(1H-pyrazolyl)}-S-ethyl-N-(trichloroacetylamino)carbonyl)sulfilimine;

S-{[5-amino-3-cyano-1-(2,6-dichloro-4-trifluoromethyl)phenyl]-4-(1H-pyrazolyl)}-S-ethyl-N-(chloroacetylamino)carbonyl)sulfilimine;

S-{[5-amino-3-cyano-1-(2,6-dichloro-4-trifluoromethyl)phenyl]-4-(1H-pyrazolyl)}-S-ethyl-N-(methylthiocarbonyl)sulfilimine;

S-{[5-amino-3-cyano-1-(2,6-dichloro-4-trifluoromethyl)phenyl]-4-(1H-pyrazolyl)}-S-ethyl-N-(ethoxycarbonylmethyl)aminocarbonyl)sulfilimine;

S-{[5-amino-3-cyano-1-(2,6-dichloro-4-trifluoromethyl)phenyl]-4-(1H-pyrazolyl)}-S-methyl-N-methylthiocarbonyl)sulfilimine;

S-{[5-amino-3-cyano-1-(2,6-dichloro-4-trifluoromethyl)phenyl]-4-(1H-pyrazolyl)}-S-methyl-N-ethoxycarbonylaminocarbonyl)sulfilimine;

S-{[5-amino-3-cyano-1-(2,6-dichloro-4-trifluoromethyl)phenyl]-4-(1H-pyrazolyl)}-S-methyl-N-(formyl)sulfilimine;

S-{[5-amino-3-cyano-1-(2,6-dichloro-4-trifluoromethyl)phenyl]-4-(1H-pyrazolyl)}-S-methyl-N-(cyano)sulfilimine;

S-{[5-amino-3-cyano-1-(2,6-dichloro-4-trifluoromethyl)phenyl]-4-(1H-pyrazolyl)}-S-methyl-N-(1,2 dioxopropy)sulfilimine;

S-{[5-amino-3-cyano-1-(2,6-dichloro-4-trifluoromethyl)phenyl]-4-(1H-pyrazolyl)}-S-methyl-N-(tert-buloxycarbony)sulfilimine;

S-{[5-amino-1-(2,6-dichloro-4-trifluoromethyl)phenyl]-4-(1H-pyrazolyl)}-S-methyl-N-(formyl)sulfilimine;

S-{[5-amino-1-(2,6-dichloro-4-trifluoromethyl)phenyl]-4-(1H-pyrazolyl)}-S-methyl-N-(acetyl)sulfilimine;

S-{[5-amino-1-(2,6-dichloro-4-trifluoromethyl)phenyl]-4-(1H-pyrazolyl)}-S-methyl-N-(cyano)sulfilimine;

S-{[5-amino-1-(2,6-dichloro-4-trifluoromethyl)phenyl]-4-(1H-pyrazolyl)}-S-methyl-N-(formyl)sulfilimine;

S-{[5-amino-1-(2,6-dichloro-4-trifluoromethyl)phenyl]-4-(1H-pyrazolyl)}-S-methyl-N-(cyano)sulfilimine;

S-{[5-amino-1-(2,6-dichloro-4-trifluoromethyl)phenyl]-4-(1H-pyrazolyl)}-S-methyl-N-(formyl)sulfilimine;

S-{[5-amino-1-(2,6-dichloro-4-trifluoromethyl)phenyl]-4-(1H-pyrazolyl)}-S-methyl-N-(cyano)sulfilimine;

N-(tert-butoxycarbonyl)S-4-[5amino-3-cyano-1-(2,6-dichloro-4-trifluoromethyl)phenylpyrazolyl]-S-ethylsulfoximine;

N-acetyl S-4-[5-amino-3-cyano-1-(2,6-dichloro-4trifluoromethyl)phenylpyrazolyl]-S-ethylsulfoximine;

S-4-[5-amino-3-cyano-1-(2,6-dichloro-4-trifluoromethyl)phenylpyrazolyl]-S-ethylsulfoximine;

S-[5-amino-3-cyano-1-(2,6-dichloro-4-trifluoromethyl)phenyl-4-(1H-pyrazolyl)]-S-methyl-N-[(4-methylphenyl)sulfonyl]sulfilimine; or S-4-[5-amino-3-cyano-1-(2-(3-chloro-5-trifluoromethyl)pyridyl)pyrazolyl]-S-ethylsulfoxide.

32. A pesticidal composition comprising a pesticidally effective amount of a compound of formula (I) or (II) as claimed in claim 1 and an agriculturally acceptable inert carrier therefor.

33. A composition according to claim 32, wherein the pesticidally effective amount is an arthropodicidally effective amount.

34. A composition according to claim 33, wherein the arthropodicidally effective amount is an insecticidally effective amount.

35. A composition according to claim 32, wherein the pesticidally effective amount is a nematocidally effective amount.

36. A composition according to claim 32, further comprising an agriculturally acceptable surfactant.

37. A method for controlling pests at a locus, said method comprising applying to said locus a pesticidally effective amount of a compound of formula (I) or (II) as claimed in claim 1.

38. A method according to claim 37 for controlling arthropods at a locus, said method comprising applying said locus an arthropodicidally effective amount of a compound of formula (I) or (II).

39. A method according to claim 38 for controlling insects at a locus, said method comprising applying to said locus an insecticidally effective amount of a compound of formula (I) or (II).

40. A method according to claim 37 for controlling nematodes at a locus, said method comprising applying to said locus a nematocidally effective amount of a compound of formula (I) or (II).

* * * * *